United States Patent
Gray et al.

(10) Patent No.: US 8,394,818 B2
(45) Date of Patent: Mar. 12, 2013

(54) SOLUBLE MTOR COMPLEXES AND MODULATORS THEREOF

(75) Inventors: Nathanael Gray, Boston, MA (US); Jae Won Chang, Boston, MA (US); Jianming Zhang, Cambridge, MA (US); Carson C. Thoreen, Jamaica Plain, MA (US); Seong Woo Anthony Kang, Cambridge, MA (US); David M. Sabatini, Cambridge, MA (US); Qingsong Liu, Jamaica Plain, MA (US)

(73) Assignees: Dana-Farber Cancer Institute, Inc., Boston, MA (US); Whitehead Institute for Biomedical Research, Cambridge, MA (US)

( * ) Notice: Subject to any disclaimer, the term of this patent is extended or adjusted under 35 U.S.C. 154(b) by 12 days.

(21) Appl. No.: 13/124,159

(22) PCT Filed: Oct. 16, 2009

(86) PCT No.: PCT/US2009/005656
§ 371 (c)(1),
(2), (4) Date: Aug. 8, 2011

(87) PCT Pub. No.: WO2010/044885
PCT Pub. Date: Apr. 22, 2010

(65) Prior Publication Data
US 2011/0288091 A1 Nov. 24, 2011

Related U.S. Application Data

(60) Provisional application No. 61/106,411, filed on Oct. 17, 2008, provisional application No. 61/196,772, filed on Oct. 20, 2008, provisional application No. 61/185,923, filed on Jun. 10, 2009.

(51) Int. Cl.
*A61K 31/4375* (2006.01)
*C07D 471/06* (2006.01)
(52) U.S. Cl. ......................................... 514/292; 546/81
(58) Field of Classification Search ............... 546/81; 514/292
See application file for complete search history.

(56) References Cited

U.S. PATENT DOCUMENTS

| 6,992,089 B2 | 1/2006 | LaVoie et al. |
| 7,319,105 B2 | 1/2008 | LaVoie et al. |
| 2004/0102443 A1 | 5/2004 | LaVoie et al. |
| 2006/0199804 A1 | 9/2006 | Hummersone et al. |
| 2008/0045538 A1 | 2/2008 | LaVoie et al. |

FOREIGN PATENT DOCUMENTS

| WO | WO 03/041660 A2 | 5/2003 |
| WO | WO 2004/014906 A2 | 2/2004 |
| WO | WO 2004/014918 A1 | 2/2004 |
| WO | WO 2006/065448 A2 | 6/2006 |
| WO | WO 2006/122806 A2 | 11/2006 |
| WO | WO 2007/002931 A2 | 1/2007 |
| WO | WO 2007/087395 A2 | 8/2007 |
| WO | WO 2007/106503 A2 | 9/2007 |

OTHER PUBLICATIONS

W. Feng et al, Bioorganic and Medicinal Chemistry (2008), vol. 16, pp. 9295-9301.*
International Preliminary Report on Patentability for PCT/US2009/005656 mailed Apr. 28, 2011.
International Search Report and Written Opinion for PCT/US2009/005656 mailed Jul. 5, 2010.
Invitation to Pay Additional Fees for PCT/US2009/005656 mailed May 25, 2010.
Berge et al., Pharmaceutical salts. J Pharm Sci. Jan. 1977;66(1);1-19.
Carter et al., Inhibition of drug-resistant mutants of ABL, KIT, and EGF receptor kinases. Proc Natl Acad Sci U S A. Aug. 2, 2005;102(31):11011-6. Epub Jul. 26, 2005.
Chiang et al., Targeting the mTOR signaling network in cancer. Trends Mol Med. Oct. 2007;13(10):433-42. Epub Oct. 1, 2007.
Cohen et al., Approval summary for imatinib mesylate capsules in the treatment of chronic myelogenous leukemia. Clin Cancer Res. May 2002;8(5):935-42.
Dancey, Therapeutic targets: MTOR and related pathways. Cancer Biol Ther. Sep. 2006;5(9):1065-73. Epub Sep. 6, 2006.
Feng et al., Synthesis of N-substituted 5-[2-(N alkylamino)ethyl]dihenzo[c,h][1.6]naphthyridines as novel topoisomerase 1-targeting antitumor agents, Bioorg Med Chem. Oct. 15, 2008;16(20):9295-301. Epub Sep. 5, 2008.
Huang et al., Finding new components of the target of rapamycin (TOR) signaling network through chemical genetics and proteome chips. Proc Natl Acad Sci U S A. Nov. 23, 2004;101(47):16594-9. Epub Nov. 11, 2004.
Kontopidis et al., Differential binding of inhibitors to active and inactive CDK2 provides insights for drug design. Chem Biol, Feb. 2006;13(2):201-11.
Kwak et al., Irreversible inhibitors of the EGF receptor may circumvent acquired resistance to gefitinib, Proc Natl Acad Sci U S A. May 24, 2005;102(21):7665-70. Epub May 16, 2005.
Liu et al., Rational design of inhibitors that bind to inactive kinase conformations. Nat Chem Biol. Jul. 2006;2(7):358-64.
Pelech, Hitting the right kinase targets: protein kinase selection for drug discovery. Bioforum Eur. 2008:12(6):36-8.
Ranson, ZD1839 (Iressa): for more than just non-small cell lung cancer, Oncologist. 2002;7 Suppl 4:16-24.

(Continued)

*Primary Examiner* — Kamal Saeed
*Assistant Examiner* — Janet L Coppins
(74) *Attorney, Agent, or Firm* — Wolf, Greenfield & Sacks, P.C.

(57) ABSTRACT

The present invention relates to small molecule modulators of mTORC1 and mTORC2, syntheses thereof, and intermediates thereto. Such small molecule modulators are useful in the treatment of proliferative diseases (e.g., benign neoplasms, cancers, inflammatory diseases, autoimmune diseases, diabetic retinopathy) and metabolic diseases. Novel small molecules are provided that inhibit one or more of mTORC1, mTORC2, and PI3K-related proteins. Novel methods of providing soluble mTORC1 and mTORC2 complexes are discussed, as well as methods of using the soluble complexes in a high-throughput manner to screen for inhibitory compounds.

31 Claims, 3 Drawing Sheets

OTHER PUBLICATIONS

Reid et al., Dual inhibition of ErbB1 (EGFR/HER1) and ErbB2 (HER2/neu). Eur J Cancer. Feb. 2007;43(3);481-9. Epub Jan. 8, 2007.

Rewcastle et al., Tyrosine kinase inhibitors. 5. Synthesis and structure-activity relationships for 4-[(phenylmethyl)amino]-and 4-(phenylamino)quinazolines as potent adenosine 5'-triphosphate binding site inhibitors of the tyrosine kinase domain of the epidermal growth factory receptor. J Med Chem. Sep. 1, 1995;38(18):3482-7.

Sabatini, mTOR and cancer: insights into a complex relationship. Nat Rev Cancer. Sep. 2006;6(9):729-34, Epub Aug. 17, 2006. p. 1-6.

Savage et al., Imatinib mesylate—a new oral targeted therapy. N Engl J Med. Feb. 28, 2002;346(9):683-93.

Schirmer et al., Targeted covalent inactivation of protein kinases by resorcylic acid lactone polyketides. Proc Natl Acad Sci U S A. Mar. 14, 2006;103(11):4234-9. Epub Mar. 6, 2006.

Smaill et al., Tyrosine Kinase inhibitors. 17. Irreversible inhibitors of the epidermal growth factor receptor: 4-(phenylamino)quinazoline- and 4-(phenylamino)pyrido[3,2-d]pyrimidine-6-acrylamides bearing additional solubilizing functions. J Med Chem. Apr. 6, 2000;43(7):1380-97.

Stauffer et al., Blocking the P13K-PKB pathway in tumor cells. Curr Med Chem Anticancer Agents. Sep. 2005;5(5):449-62.

Verheijen et al., Phosphatidylinositol 3-kinase (P13K) inhibitors as anticancer drugs. Drugs Fut. 2007;32(6):537-47.

Wang et al., 2-Anilino-4-(thiazol-5-yl)pyrimidine (CDK) inhibitors: synthesis, SAR analysis. X-ray crystallography, and biological activity. J Med Chem. Mar. 25, 2004;47(7):1662-75.

* cited by examiner

A

B

PI-103            Kin001-084

SOLUBLE MTOR COMPLEXES AND MODULATORS THEREOF

The present application is a national stage filing under 35 U.S.C. §371 of international PCT application, PCT/US2009/005656, filed Oct. 16, 2009, which claims priority under 35 U.S.C. §119(e) to U.S. provisional applications, U.S. Ser. No. 61/106,411, filed Oct. 17, 2008, U.S. Ser. No. 61/196,772, filed Oct. 20, 2008, and U.S. Ser. No. 61/185,923, filed Jun. 10, 2009; each of which is incorporated herein by reference.

GOVERNMENT SUPPORT

This invention was made with U.S. government support under grants CA103866, CA129105, GM072555, and AI04389 awarded by the National Institutes of Health, and grant W81XWH-07-1-0448 awarded by the Department of Defense. The U.S. government has certain rights in the invention.

FIELD OF THE INVENTION

The present invention relates to small molecule inhibitors of mTORC1 and mTORC2, syntheses thereof, and intermediates thereto. The invention also provides pharmaceutical compositions comprising compounds of the present invention and methods of using the compounds in the treatment of proliferative diseases (e.g., benign neoplasms, cancers, inflammatory diseases, autoimmune diseases, diabetic retinopathy) and metabolic diseases. The invention further provides methods of providing soluble mTORC1 and mTORC2 complexes, and methods of using the complexes in biological assays, including high-throughput screens.

BACKGROUND OF THE INVENTION

There has been considerable interest in the mTOR signaling pathway because of its role in many processes that have been implicated in both cancer and metabolic diseases. The mTOR protein is a large serine/threonine kinase that acts as the catalytic subunit of two functionally independent complexes called mTORC1 and mTORC2. The mTORC1 complex also contains the proteins Raptor and mLST8 and is regulated by nutrient availability, such as amino acids and glucose, and growth factor signaling. Many, though not all, of these signals are transduced to mTOR through the small G-protein rheb, which associates with and activates mTORC1 directly. The best-characterized downstream substrates are the AGC kinases S6K1 and S6K2 and the translation initiation inhibitor 4EBP1. Through these components, and possibly additional unidentified targets, mTORC1 broadly controls the rate of protein synthesis, sensitivity to insulin through negative feedback signaling, and ribosome biogenesis. mTORC1 is also the target of the FDA approved drug rapamycin, which inhibits the complex by first associating with the cellular protein FKBP12, and then binding to an mTOR domain known as the FKBP12-rapamycin binding domain (FRB).

The mTORC2 complex also contains mTOR and mLST8, but includes the proteins Rictor and mSIN1 instead of Raptor. Like mTORC1, mTORC2 is activated by insulin and other growth factors that activate the PI3K/PTEN pathway but is not affected by nutrient levels. mTORC2 is generally considered to be insensitive to rapamycin, though this may not be true under some circumstances. This complex was recently shown to phosphorylate the hydrophobic motif of the AGC kinase Akt/PKB, which is a key event in the activation of Akt/PKB kinase activity. Akt/PKB is considered a key regulator of cell proliferation, survival, and nutrient uptake and is thought to be the primary downstream effector of PI3K/PTEN signaling. Akt/PKB is also known to be hyper-activated in a wide variety of cancers, particularly in those in which the tumor suppressor PTEN is inactivated or PI3K is mutationally activated. It is also likely that mTORC2 phosphorylates the analogous site on the AGC kinases SGK1/2/3, which show considerable sequence similarity to Akt/PKB and are known to participate in similar processes. Efforts using cell-based screens to discover mTOR inhibitors are often hampered by difficulties in the unambiguous identification of the inhibited species. Due to the independent functions of mTORC1 and mTORC2 and their biological and medical relevance, it would be useful to find modulators of each of these complexes.

SUMMARY OF THE INVENTION

The present invention encompasses the recognition that small molecule modulators of mTOR are useful in the treatment of proliferative diseases and metabolic diseases. Novel compounds are provided that inhibit one or both of mTORC1 and mTORC2. The compounds may inhibit mTORC1 or mTORC2 in an ATP competitive manner.

In one aspect, the invention provides compound of formula I:

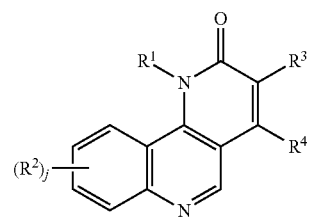

wherein:
R$^1$ is an optionally substituted group selected from the group consisting of 6-10-membered aryl; C$_{7-15}$ arylalkyl; C$_{6-15}$ heteroarylalkyl; C$_{1-12}$ heteroaliphatic; C$_{1-12}$ aliphatic; 5-10-membered heteroaryl having 1-4 heteroatoms independently selected from the group consisting of nitrogen, oxygen, and sulfur; and 4-7-membered heterocyclic having 1-2 heteroatoms independently selected from the group consisting of nitrogen, oxygen, and sulfur;

each occurrence of R$^2$ is independently halogen, —NR$_2$—OR, —SR, or an optionally substituted group selected from the group consisting of C$_{1-12}$ acyl; 6-10-membered aryl; C$_{7-15}$ arylalkyl; C$_{6-15}$ heteroarylalkyl; C$_{1-12}$ heteroaliphatic; C$_{1-12}$ aliphatic; 5-10-membered heteroaryl having 1-4 heteroatoms independently selected from the group consisting of nitrogen, oxygen, and sulfur; and 4-7-membered heterocyclic having 1-2 heteroatoms independently selected from the group consisting of nitrogen, oxygen, and sulfur;

j is an integer from 1 to 4, inclusive;

R$^3$ and R$^4$ are independently hydrogen, halogen, or optionally substituted C$_{1-6}$ aliphatic, with the proviso that R$^3$ and R$^4$ are not taken together to form a ring; and each R is independently hydrogen, an optionally substituted group selected from the group consisting of C$_{1-12}$ acyl; 6-10-membered aryl; C$_{7-15}$ arylalkyl; C$_{6-15}$ heteroarylalkyl; C$_{1-12}$ aliphatic; 5-10-membered heteroaryl having 1-4 heteroatoms independently selected from the group consisting of nitrogen, oxygen, and sulfur; 4-7-membered heterocyclic having 1-2 heteroatoms independently selected from the group consisting of nitrogen, oxygen, and sulfur; and $C_{1-12}$ heteroaliphatic having 1-2 heteroatoms independently selected from the group consisting of nitrogen, oxygen, and sulfur; or two R on the same nitrogen atom are taken with the nitrogen to form a 4-7-membered heterocyclic ring having 1-2 heteroatoms independently selected from the group consisting of nitrogen, oxygen, and sulfur.

In one aspect, the invention provides compound of formula IV:

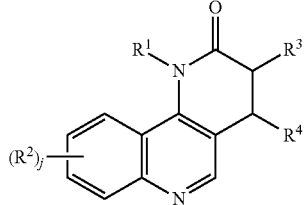

IV wherein:

$R^1$ is an optionally substituted group selected from the group consisting of 6-10-membered aryl; $C_{7-15}$ arylalkyl; $C_{6-15}$ heteroarylalkyl; $C_{1-12}$ heteroaliphatic; $C_{1-12}$ aliphatic; 5-10-membered heteroaryl having 1-4 heteroatoms independently selected from the group consisting of nitrogen, oxygen, and sulfur; and 4-7-membered heterocyclic having 1-2 heteroatoms independently selected from the group consisting of nitrogen, oxygen, and sulfur;

each occurrence of $R^2$ is independently halogen, —$NR_2$— OR, —SR, or an optionally substituted group selected from the group consisting of $C_{1-12}$ acyl; 6-10-membered aryl; $C_{7-15}$ arylalkyl; $C_{6-15}$ heteroarylalkyl; $C_{1-12}$ heteroaliphatic; $C_{1-12}$ aliphatic; 5-10-membered heteroaryl having 1-4 heteroatoms independently selected from the group consisting of nitrogen, oxygen, and sulfur; and 4-7-membered heterocyclic having 1-2 heteroatoms independently selected from the group consisting of nitrogen, oxygen, and sulfur;

j is an integer from 1 to 4, inclusive;

$R^3$ and $R^4$ are independently hydrogen, halogen, or optionally substituted $C_{1-6}$ aliphatic, with the proviso that $R^3$ and $R^4$ are not taken together to form a ring; and each R is independently hydrogen, an optionally substituted group selected from the group consisting of $C_{1-12}$ acyl; 6-10-membered aryl; $C_{7-15}$ arylalkyl; $C_{6-15}$ heteroarylalkyl; $C_{1-12}$ aliphatic; 5-10-membered heteroaryl having 1-4 heteroatoms independently selected from the group consisting of nitrogen, oxygen, and sulfur; 4-7-membered heterocyclic having 1-2 heteroatoms independently selected from the group consisting of nitrogen, oxygen, and sulfur; and $C_{1-12}$ heteroaliphatic having 1-2 heteroatoms independently selected from the group consisting of nitrogen, oxygen, and sulfur; or two R on the same nitrogen atom are taken with the nitrogen to form a 4-7-membered heterocyclic ring having 1-2 heteroatoms independently selected from the group consisting of nitrogen, oxygen, and sulfur.

In one aspect, the invention provides compound of formula V:

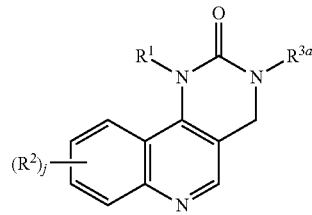

V wherein:

$R^1$ is an optionally substituted group selected from the group consisting of 6-10-membered aryl; $C_{7-15}$ arylalkyl; $C_{6-15}$ heteroarylalkyl; $C_{1-12}$ heteroaliphatic; $C_{1-12}$ aliphatic; 5-10-membered heteroaryl having 1-4 heteroatoms independently selected from the group consisting of nitrogen, oxygen, and sulfur; and 4-7-membered heterocyclic having 1-2 heteroatoms independently selected from the group consisting of nitrogen, oxygen, and sulfur;

each occurrence of $R^2$ is independently halogen, —$NR_2$— OR, —SR, or an optionally substituted group selected from the group consisting of $C_{1-12}$ acyl; 6-10-membered aryl; $C_{7-15}$ arylalkyl; $C_{6-15}$ heteroarylalkyl; $C_{1-12}$ heteroaliphatic; $C_{1-12}$ aliphatic; 5-10-membered heteroaryl having 1-4 heteroatoms independently selected from the group consisting of nitrogen, oxygen, and sulfur; and 4-7-membered heterocyclic having 1-2 heteroatoms independently selected from the group consisting of nitrogen, oxygen, and sulfur;

j is an integer from 1 to 4, inclusive;

$R^{3a}$ is hydrogen or optionally substituted $C_{1-6}$ aliphatic; and each R is independently hydrogen, an optionally substituted group selected from the group consisting of $C_{1-12}$ acyl; 6-10-membered aryl; $C_{7-15}$ arylalkyl; $C_{6-15}$ heteroarylalkyl; $C_{1-12}$ aliphatic; 5-10-membered heteroaryl having 1-4 heteroatoms independently selected from the group consisting of nitrogen, oxygen, and sulfur; 4-7-membered heterocyclic having 1-2 heteroatoms independently selected from the group consisting of nitrogen, oxygen, and sulfur; and $C_{1-12}$ heteroaliphatic having 1-2 heteroatoms independently selected from the group consisting of nitrogen, oxygen, and sulfur; or two R on the same nitrogen atom are taken with the nitrogen to form a 4-7-membered heterocyclic ring having 1-2 heteroatoms independently selected from the group consisting of nitrogen, oxygen, and sulfur.

In one aspect, the invention provides compound of formula VI:

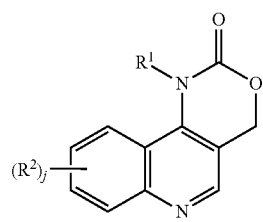

VI wherein:

$R^1$ is an optionally substituted group selected from the group consisting of 6-10-membered aryl; $C_{7-15}$ arylalkyl; $C_{6-15}$ heteroarylalkyl; $C_{1-12}$ heteroaliphatic; $C_{1-12}$ aliphatic; 5-10-membered heteroaryl having 1-4 heteroatoms independently selected from the group consisting of nitrogen, oxygen, and sulfur; and 4-7-membered heterocyclic having 1-2 heteroatoms independently selected from the group consisting of nitrogen, oxygen, and sulfur;

each occurrence of $R^2$ is independently halogen, —$NR_2$— OR, —SR, or an optionally substituted group selected from the group consisting of $C_{1-12}$ acyl; 6-10-membered aryl; $C_{7-15}$ arylalkyl; $C_{6-15}$ heteroarylalkyl; $C_{1-12}$ heteroaliphatic; $C_{1-12}$ aliphatic; 5-10-membered heteroaryl having 1-4 heteroatoms independently selected from the group consisting of nitrogen, oxygen, and sulfur; and 4-7-membered heterocyclic having 1-2 heteroatoms independently selected from the group consisting of nitrogen, oxygen, and sulfur;

j is an integer from 1 to 4, inclusive; and each R is independently hydrogen, an optionally substituted group selected from the group consisting of $C_{1-12}$ acyl; 6-10-membered aryl; $C_{7-15}$ arylalkyl; $C_{6-15}$ heteroarylalkyl; $C_{1-12}$ aliphatic; 5-10-membered heteroaryl having 1-4 heteroatoms independently selected from the group consisting of nitrogen, oxygen, and sulfur; 4-7-membered heterocyclic having 1-2 heteroatoms independently selected from the group consisting of nitrogen, oxygen, and sulfur; and $C_{1-12}$ heteroaliphatic having 1-2 heteroatoms independently selected from the group consisting of nitrogen, oxygen, and sulfur; or two R on the same nitrogen atom are taken with the nitrogen to form a 4-7-membered heterocyclic ring having 1-2 heteroatoms independently selected from the group consisting of nitrogen, oxygen, and sulfur.

In one aspect, the invention provides compound of formula VII:

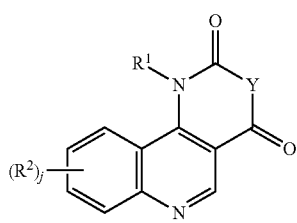

VII wherein:

$R^1$ is an optionally substituted group selected from the group consisting of 6-10-membered aryl; $C_{7-15}$ arylalkyl; $C_{6-15}$ heteroarylalkyl; $C_{1-12}$ heteroaliphatic; $C_{1-12}$ aliphatic; 5-10-membered heteroaryl having 1-4 heteroatoms independently selected from the group consisting of nitrogen, oxygen, and sulfur; and 4-7-membered heterocyclic having 1-2 heteroatoms independently selected from the group consisting of nitrogen, oxygen, and sulfur;

each occurrence of $R^2$ is independently halogen, —$NR_2$— OR, —SR, or an optionally substituted group selected from the group consisting of $C_{1-12}$ acyl; 6-10-membered aryl; $C_{7-15}$ arylalkyl; $C_{6-15}$ heteroarylalkyl; $C_{1-12}$ heteroaliphatic; $C_{1-12}$ aliphatic; 5-10-membered heteroaryl having 1-4 heteroatoms independently selected from the group consisting of nitrogen, oxygen, and sulfur; and 4-7-membered heterocyclic having 1-2 heteroatoms independently selected from the group consisting of nitrogen, oxygen, and sulfur;

j is an integer from 1 to 4, inclusive; and each R is independently hydrogen, an optionally substituted group selected from the group consisting of $C_{1-12}$ acyl; 6-10-membered aryl; $C_{7-15}$ arylalkyl; $C_{6-15}$ heteroarylalkyl; $C_{1-12}$ aliphatic; 5-10-membered heteroaryl having 1-4 heteroatoms independently selected from the group consisting of nitrogen, oxygen, and sulfur; 4-7-membered heterocyclic having 1-2 heteroatoms independently selected from the group consisting of nitrogen, oxygen, and sulfur; and $C_{1-12}$ heteroaliphatic having 1-2 heteroatoms independently selected from the group consisting of nitrogen, oxygen, and sulfur; or two R on the same nitrogen atom are taken with the nitrogen to form a 4-7-membered heterocyclic ring having 1-2 heteroatoms independently selected from the group consisting of nitrogen, oxygen, and sulfur; and Y is O or $NR^{3a}$; and $R^{3a}$ is hydrogen or optionally substituted $C_{1-6}$ aliphatic.

In one aspect, the invention provides compound of formula VIII:

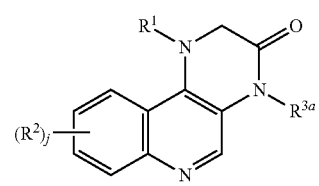

VIII wherein:

$R^1$ is an optionally substituted group selected from the group consisting of 6-10-membered aryl; $C_{7-15}$ arylalkyl; $C_{6-15}$ heteroarylalkyl; $C_{1-12}$ heteroaliphatic; $C_{1-12}$ aliphatic; 5-10-membered heteroaryl having 1-4 heteroatoms independently selected from the group consisting of nitrogen, oxygen, and sulfur; and 4-7-membered heterocyclic having 1-2 heteroatoms independently selected from the group consisting of nitrogen, oxygen, and sulfur;

each occurrence of $R^2$ is independently halogen, —$NR_2$— OR, —SR, or an optionally substituted group selected from the group consisting of $C_{1-12}$ acyl; 6-10-membered aryl; $C_{7-15}$ arylalkyl; $C_{6-15}$ heteroarylalkyl; $C_{1-12}$ heteroaliphatic; $C_{1-12}$ aliphatic; 5-10-membered heteroaryl having 1-4 heteroatoms independently selected from the group consisting of nitrogen, oxygen, and sulfur; and 4-7-membered heterocyclic having 1-2 heteroatoms independently selected from the group consisting of nitrogen, oxygen, and sulfur;

j is an integer from 1 to 4, inclusive; and each R is independently hydrogen, an optionally substituted group selected from the group consisting of $C_{1-12}$ acyl; 6-10-membered aryl; $C_{7-15}$ arylalkyl; $C_{6-15}$ heteroarylalkyl; $C_{1-12}$ aliphatic; 5-10-membered heteroaryl having 1-4 heteroatoms independently selected from the group consisting of nitrogen, oxygen, and sulfur; 4-7-membered heterocyclic having 1-2 heteroatoms independently selected from the group consisting of nitrogen, oxygen, and sulfur; and $C_{1-12}$ heteroaliphatic having 1-2 heteroatoms independently selected from the group consisting of nitrogen, oxygen, and sulfur; or two R on the same nitrogen atom are taken with the nitrogen to form a 4-7-membered heterocyclic ring having 1-2 heteroatoms independently selected from the group consisting of nitrogen, oxygen, and sulfur; and $R^{3a}$ is hydrogen or optionally substituted $C_{1-6}$ aliphatic.

In one aspect, the invention provides compound of formula IX:

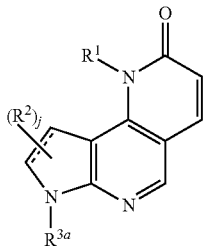

wherein:
--- denotes a single or double bond;
$R^1$ is an optionally substituted group selected from the group consisting of 6-10-membered aryl; $C_{7-15}$ arylalkyl; $C_{6-15}$ heteroarylalkyl; $C_{1-12}$ heteroaliphatic; $C_{1-12}$ aliphatic; 5-10-membered heteroaryl having 1-4 heteroatoms independently selected from the group consisting of nitrogen, oxygen, and sulfur; and 4-7-membered heterocyclic having 1-2 heteroatoms independently selected from the group consisting of nitrogen, oxygen, and sulfur;
each occurrence of $R^2$ is independently halogen, —$NR_2$—OR, —SR, or an optionally substituted group selected from the group consisting of $C_{1-12}$ acyl; 6-10-membered aryl; $C_{7-15}$ arylalkyl; $C_{6-15}$ heteroarylalkyl; $C_{1-12}$ heteroaliphatic; $C_{1-12}$ aliphatic; 5-10-membered heteroaryl having 1-4 heteroatoms independently selected from the group consisting of nitrogen, oxygen, and sulfur; and 4-7-membered heterocyclic having 1-2 heteroatoms independently selected from the group consisting of nitrogen, oxygen, and sulfur;
j is an integer from 0 to 2, inclusive; and
each R is independently hydrogen, an optionally substituted group selected from the group consisting of $C_{1-12}$ acyl; 6-10-membered aryl; $C_{7-15}$ arylalkyl; $C_{6-15}$ heteroarylalkyl; $C_{1-12}$ aliphatic; 5-10-membered heteroaryl having 1-4 heteroatoms independently selected from the group consisting of nitrogen, oxygen, and sulfur; 4-7-membered heterocyclic having 1-2 heteroatoms independently selected from the group consisting of nitrogen, oxygen, and sulfur; and $C_{1-12}$ heteroaliphatic having 1-2 heteroatoms independently selected from the group consisting of nitrogen, oxygen, and sulfur; or
two R on the same nitrogen atom are taken with the nitrogen to form a 4-7-membered heterocyclic ring having 1-2 heteroatoms independently selected from the group consisting of nitrogen, oxygen, and sulfur; and
$R^{3a}$ is hydrogen or optionally substituted $C_{1-6}$ aliphatic.

According to one aspect, the invention provides pharmaceutical compositions comprising a compound of the invention and a pharmaceutically acceptable excipient. In certain embodiments, the pharmaceutical composition comprises a therapeutically effective amount of the compound to treat a proliferative disease or a metabolic disease. In some embodiments, the composition comprises a compound of the invention and another anti-neoplastic agent. In some embodiments, the pharmaceutical composition further comprises an allosteric mTOR inhibitor. In certain embodiments, the allosteric mTOR inhibitor is a rapalog.

According to one aspect, the invention provides a method of treating a subject with a proliferative disease comprising administering to the subject a therapeutically effective amount of a compound of formula I. In certain embodiments, the proliferative disease is selected from the group consisting of benign neoplasms, cancer, inflammatory disease, autoimmune disease, and diabetic retinopathy. In some embodiments, the proliferative disease is a solid tumor. In some embodiments, the proliferative disease is a hematological malignancy.

According to one aspect, the invention provides a method of treating a metabolic disease in a subject suffering therefrom comprising administering to the subject a therapeutically effective amount of a compound of formula I. In certain embodiments, the metabolic disease is diabetes. In some embodiments, the metabolic disease is metabolic syndrome, insulin resistance, obesity, or a combination thereof.

According to one aspect, the invention provides a method for the modulation of one or both of mTORC1 and mTORC2, the method comprising contacting said mTORC1 and/or mTORC2 with an effective amount of an inventive compound. In some embodiments, the modulating agent acts as an agonist. In some embodiments, the modulating agent acts as a partial agonist. In some embodiments, the modulating agent acts as an antagonist. In some embodiments, the modulation of mTORC1/2 occurs in a cell. In some embodiments, both mTORC1 and mTORC2 are inhibited. In certain embodiments, mTORC1 is selectively inhibited. In certain embodiments, mTORC2 is selectively inhibited. In certain embodiments, the inhibition occurs via an ATP-competitive mechanism. In certain embodiments, an effective amount of an inventive compound also inhibits one or more protein kinases, wherein said protein kinase comprises a kinase domain with similarity to Pi3K (the PIKK family of kinases). In some embodiments, a compound of the invention does not inhibit or affect other protein kinases.

According to one aspect, the present disclosure provides a high-throughput method for screening one or more test compounds to identify those that exert an effect on mTORC1, the method comprising the steps of:
a) introducing into each of a plurality of reaction vessels:
purified mTORC1; mTORC1 substrate; ATP; and
one or more test compounds whose effect on mTORC1 is to be evaluated;
b) incubating the vessels under suitable conditions and for a time sufficient to allow phosphorylation of the mTORC1 substrate; and
c) assaying for the presence or amount of the phosphorylated mTORC1 substrate, thereby revealing the effect of the test compound on mTORC1.

In some embodiments, a purified mTORC1 substrate is S6K and the phosphorylated substrate is phospho-S6K. In some embodiments, the method further comprises the step of removing unassociated antibody from each reaction vessel. In certain embodiments, the antibody is conjugated to an enzyme. In some embodiments, the method further comprises introducing a secondary ligand that binds specifically to said antibody, and wherein the step of assaying comprises assaying for bound secondary ligand. In some embodiments, the step of assaying utilizes a detection technique selected from the group consisting of chemiluminescence, fluorescence, phosphorescence, radioactivity, colorimetry, ultra-violet spectroscopy, and infra-red spectroscopy.

According to one aspect, the present disclosure provides a high-throughput method for screening one or more test compounds to identify those that exert an effect on mTORC2, the method comprising the steps of:
a) introducing into each of a plurality of reaction vessels:
purified mTORC2; mTORC2 substrate; ATP; and
one or more test compounds whose effect on mTORC2 is to be evaluated;

b) incubating the vessels under suitable conditions and for a time sufficient to allow phosphorylation of the mTORC2 substrate; and c) assaying for the presence or amount of the phosphorylated mTORC2 substrate, thereby revealing the effect of the test compound on mTORC2.

In some embodiments, a purified mTORC2 substrate is Akt/PKB and the phosphorylated substrate is phospho-Akt/PKB. In some embodiments, the method further comprises the step of removing unassociated antibody from each reaction vessel. In certain embodiments, the antibody is conjugated to an enzyme. In some embodiments, the method further comprises introducing a secondary ligand that binds specifically to said antibody, and wherein the step of assaying comprises assaying for bound secondary ligand. In some embodiments, the step of assaying utilizes a detection technique selected from the group consisting of chemiluminescence, fluorescence, phosphorescence, radioactivity, colorimetry, ultra-violet spectroscopy, and infra-red spectroscopy.

According to one aspect, the invention provides a method for the preparation of a compound of formula I':

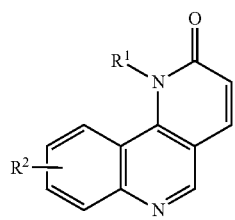

I' wherein:

R$^1$ is an optionally substituted group selected from the group consisting of 6-10-membered aryl; C$_{7-15}$ arylalkyl; C$_{6-15}$ heteroarylalkyl; C$_{1-12}$ heteroaliphatic; C$_{1-12}$ aliphatic; 5-10-membered heteroaryl having 1-4 heteroatoms independently selected from the group consisting of nitrogen, oxygen, and sulfur; and 4-7-membered heterocyclic having 1-2 heteroatoms independently selected from the group consisting of nitrogen, oxygen, and sulfur;

each occurrence of R$^2$ is independently halogen, —NR$_2$— OR, —SR, or an optionally substituted group selected from the group consisting of C$_{1-12}$ acyl; 6-10-membered aryl; C$_{7-15}$ arylalkyl; C$_{6-15}$ heteroarylalkyl; C$_{1-12}$ heteroaliphatic; C$_{1-12}$ aliphatic; 5-10-membered heteroaryl having 1-4 heteroatoms independently selected from the group consisting of nitrogen, oxygen, and sulfur; and 4-7-membered heterocyclic having 1-2 heteroatoms independently selected from the group consisting of nitrogen, oxygen, and sulfur; and each R is independently hydrogen, an optionally substituted group selected from the group consisting of C$_{1-12}$ acyl; 6-10-membered aryl; C$_{7-15}$ arylalkyl; C$_{6-15}$ heteroarylalkyl; C$_{1-12}$ aliphatic; 5-10-membered heteroaryl having 1-4 heteroatoms independently selected from the group consisting of nitrogen, oxygen, and sulfur; 4-7-membered heterocyclic having 1-2 heteroatoms independently selected from the group consisting of nitrogen, oxygen, and sulfur; and C$_{1-12}$ heteroaliphatic having 1-2 heteroatoms independently selected from the group consisting of nitrogen, oxygen, and sulfur; or:

two R on the same nitrogen atom are taken with the nitrogen to form a 4-7-membered heterocyclic ring having 1-2 heteroatoms independently selected from the group consisting of nitrogen, oxygen, and sulfur; comprising the steps of:

(a) providing an aniline of formula A:

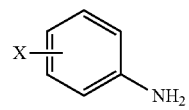

A wherein X is halogen, -Otf, or -OTs; and (b) reacting the aniline of formula A with ethyl ethoxymethylenemalonate to form a compound of formula B:

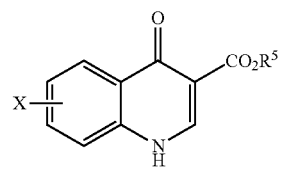

B wherein
X is halogen, -Otf, or -OTs;
R$^5$ is C$_{1-6}$ aliphatic; and (c) chlorinating the compound of formula B with a suitable chlorinating reagent to form quinoline C:

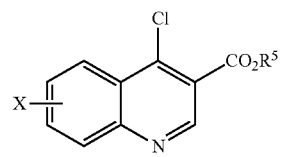

C wherein X is halogen, -Otf, or -OTs;
R$^5$ is C$_{1-6}$ aliphatic; and (d) substituting the quinoline C with an amine of formula D:

D wherein R$^1$ is an optionally substituted group selected from the group consisting of 6-10-membered aryl; C$_{7-15}$ arylalkyl; C$_{6-15}$ heteroarylalkyl; C$_{1-12}$ heteroaliphatic; C$_{1-12}$ aliphatic; 5-10-membered heteroaryl having 1-4 heteroatoms independently selected from the group consisting of nitrogen, oxygen, and sulfur; and 4-7-membered heterocyclic having 1-2 heteroatoms independently selected from the group consisting of nitrogen, oxygen, and sulfur;

to form an ester E:

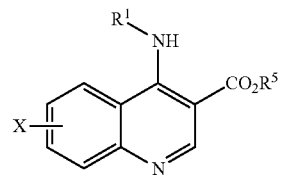

E wherein:
X is halogen, -Otf, or -OTs;
R$^1$ is an optionally substituted group selected from the group consisting of 6-10-membered aryl; C$_{7-15}$ arylalkyl;

$C_{6-15}$ heteroarylalkyl; $C_{1-12}$ heteroaliphatic; $C_{1-12}$ aliphatic; 5-10-membered heteroaryl having 1-4 heteroatoms independently selected from the group consisting of nitrogen, oxygen, and sulfur; and 4-7-membered heterocyclic having 1-2 heteroatoms independently selected from the group consisting of nitrogen, oxygen, and sulfur;

$R^5$ is $C_{1-6}$ aliphatic; and (e) reducing the ester E under suitable conditions to provide a (quinoline-3-yl)methanol of formula F:

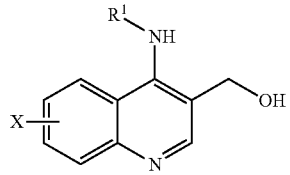

F wherein:

X is halogen, -Otf, or -OTs;

$R^1$ is an optionally substituted group selected from the group consisting of 6-10-membered aryl; $C_{7-15}$ arylalkyl; $C_{6-15}$ heteroarylalkyl; $C_{1-12}$ heteroaliphatic; $C_{1-12}$ aliphatic; 5-10-membered heteroaryl having 1-4 heteroatoms independently selected from the group consisting of nitrogen, oxygen, and sulfur; and 4-7-membered heterocyclic having 1-2 heteroatoms independently selected from the group consisting of nitrogen, oxygen, and sulfur; and (f) oxidizing a (quinoline-3-yl)methanol of formula F under suitable conditions to provide a quinoline-3-carbaldehyde of formula G:

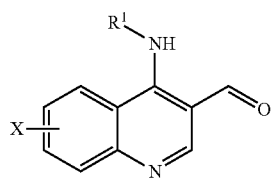

G wherein:

X is halogen, -Otf, or -OTs;

$R^1$ is an optionally substituted group selected from the group consisting of 6-10-membered aryl; $C_{7-15}$ arylalkyl; $C_{6-15}$ heteroarylalkyl; $C_{1-12}$ heteroaliphatic; $C_{1-12}$ aliphatic; 5-10-membered heteroaryl having 1-4 heteroatoms independently selected from the group consisting of nitrogen, oxygen, and sulfur; and 4-7-membered heterocyclic having 1-2 heteroatoms independently selected from the group consisting of nitrogen, oxygen, and sulfur; and (g) cyclizing the quinoline-3-carbaldehyde of formula G with triethyl phosphonoacetate to form a tricyclic compound of formula H:

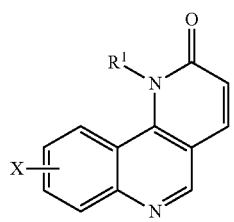

H wherein:

X is halogen, -Otf, or -OTs;

$R^1$ is an optionally substituted group selected from the group consisting of 6-10-membered aryl; $C_{7-15}$ arylalkyl; $C_{6-15}$ heteroarylalkyl; $C_{1-12}$ heteroaliphatic; $C_{1-12}$ aliphatic; 5-10-membered heteroaryl having 1-4 heteroatoms independently selected from the group consisting of nitrogen, oxygen, and sulfur; and 4-7-membered heterocyclic having 1-2 heteroatoms independently selected from the group consisting of nitrogen, oxygen, and sulfur; and (h) conjugating a tricyclic compound of formula H with a boronate of formula J:

$$R^2\text{---}B(OR^y)_2 \qquad J$$

wherein $R^2$ is an optionally substituted group selected from the group consisting of $C_{1-12}$ acyl; 6-10-membered aryl; $C_{7-15}$ arylalkyl; $C_{6-15}$ heteroarylalkyl; $C_{1-12}$ heteroaliphatic; $C_{1-12}$ aliphatic; 5-10-membered heteroaryl having 1-4 heteroatoms independently selected from the group consisting of nitrogen, oxygen, and sulfur; and 4-7-membered heterocyclic having 1-2 heteroatoms independently selected from the group consisting of nitrogen, oxygen, and sulfur; and $R^y$ is hydrogen or optionally substituted, straight or branched, $C_{1-12}$-aliphatic; or two $R^y$ attached to the same oxygen are taken together with their intervening atoms to form a monocyclic or bicyclic 5-8-membered ring;

in the presence of a suitable metal complex to form a compound of formula I'.

DETAILED DESCRIPTION OF CERTAIN EMBODIMENTS

Figure 1:
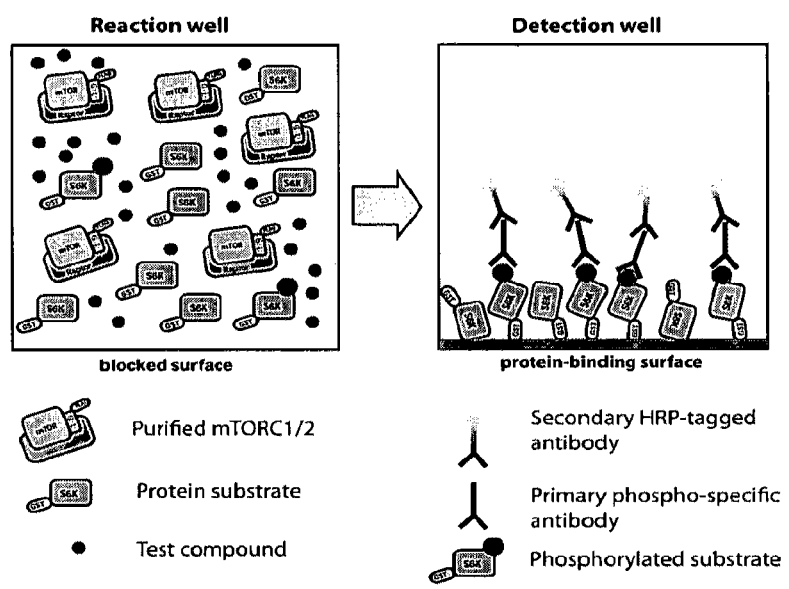
FIG. 1A is an illustration of mTORC1/2 high-throughput screening method. Reaction vessels containing soluble mTORC1 or mTORC2, full-length p70 S6K or AKT1, ATP and test compound in micro-well plates are incubated under suitable conditions to allow phosphorylation of S6K or AKT1 by mTORC1 or mTORC2, respectively. Terminated reactions are then transferred to high-protein binding wells and probed with antibodies specific for phosphorylated S6K (T389) or AKT1 (S473). Wells are then incubated with an HRP-tagged secondary antibody. The amount of bound secondary antibody is then measured by chemi-luminescence.
FIG. 1B shows sample data from a mTORC1 screen. Control compound (PI-103) and test compound (Kin001-084) were assayed at eight concentrations to determine IC50s against mTORC1.
Figure 1:
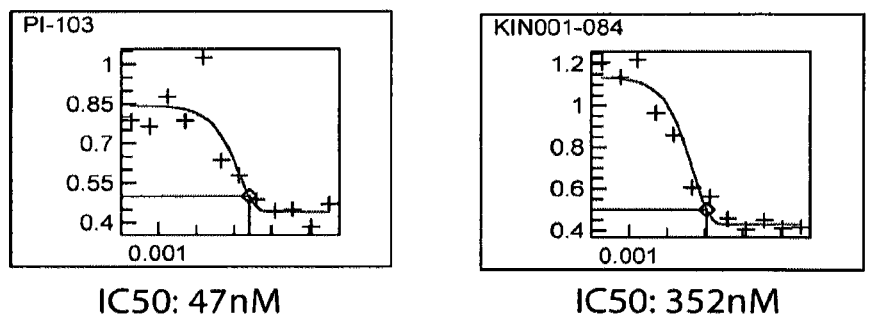

The mammalian target of rapamycin (mTOR) is a protein kinase that integrates nutrient and growth factor-derived signals to regulate cellular growth and survival processes. Rapamycin is a natural product that specifically inhibits mTOR signaling in a variety of cell types, resulting in immunosuppressant and antiproliferative activities. mTOR has been shown to exist in at least two separate complexes that differ in the composition of protein factors and in their sensitivity to inhibition by rapamycin. The first complex, mTOR complex 1 (mTORC1) is sensitive to inhibition by rapamycin and contains mTOR, mLST8/GβL, and raptor. The second complex, mTOR complex 2 (mTORC2), contains mTOR, mLST8/GβL, rictor, and mSin1, and was originally thought to be insensitive to rapamycin. As discussed below, more recent results showed that rapamycin inhibits the assembly of mTORC2 and that, in a number of cell types, prolonged rapamycin treatment reduces the levels of mTORC2. The present disclosure describes purified mTORC1 and mTORC2 complexes, assays to screen for modulators of these complexes, and a new class of small molecule modulators of mTORC1 and/or mTORC2.

Compounds

Compounds of this invention include those described generally herein and those further illustrated by the classes, subclasses, and species disclosed herein. In some embodiments, provided compounds are small molecule modulators of mTORC1, mTORC2, or other proteins that contain a kinase domain with similarity to PI3K. For purposes of this invention, the chemical elements are identified in accordance with the Periodic Table of the Elements, CAS version, *Handbook of Chemistry and Physics*, 75$^{th}$ Ed. Additionally, general principles of organic chemistry are described in *Organic Chemistry*, Thomas Sorrell, University Science Books, Sausalito: 1999, and *March's Advanced Organic Chemistry*, 5$^{th}$ Ed., Ed.: Smith, M. B. and March, J., John Wiley & Sons, New York: 2001, the entire contents of which are hereby incorporated by reference.

In certain embodiments, the present invention provides compounds of formula I:

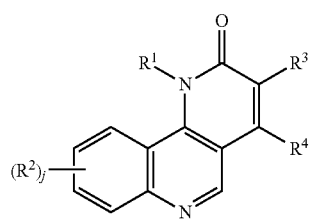

wherein:

$R^1$ is an optionally substituted group selected from the group consisting of 6-10-membered aryl; $C_{7-15}$ arylalkyl; $C_{6-15}$ heteroarylalkyl; $C_{1-12}$ heteroaliphatic; $C_{1-12}$ aliphatic; 5-10-membered heteroaryl having 1-4 heteroatoms independently selected from the group consisting of nitrogen, oxygen, and sulfur; and 4-7-membered heterocyclic having 1-2 heteroatoms independently selected from the group consisting of nitrogen, oxygen, and sulfur;

each occurrence of $R^2$ is independently halogen, —NR$_2$—OR, —SR, or an optionally substituted group selected from the group consisting of $C_{1-12}$ acyl; 6-10-membered aryl; $C_{7-15}$ arylalkyl; $C_{6-15}$ heteroarylalkyl; $C_{1-12}$ heteroaliphatic; $C_{1-12}$ aliphatic; 5-10-membered heteroaryl having 0-4 heteroatoms independently selected from the group consisting of nitrogen, oxygen, and sulfur; and 4-7-membered heterocyclic having 1-2 heteroatoms independently selected from the group consisting of nitrogen, oxygen, and sulfur;

j is an integer from 1 to 4, inclusive;

$R^3$ and $R^4$ are independently hydrogen, hydroxyl, alkoxy, halogen, or optionally substituted $C_{1-6}$ aliphatic, with the proviso that $R^3$ and $R^4$ are not taken together to form a ring; and each R is independently hydrogen, an optionally substituted group selected from the group consisting of $C_{1-12}$ acyl; 6-10-membered aryl; $C_{7-15}$ arylalkyl; $C_{6-15}$ heteroarylalkyl; $C_{1-12}$ aliphatic; 5-10-membered heteroaryl having 1-4 heteroatoms independently selected from the group consisting of nitrogen, oxygen, and sulfur; 4-7-membered heterocyclic having 1-2 heteroatoms independently selected from the group consisting of nitrogen, oxygen, and sulfur; and $C_{1-12}$ heteroaliphatic having 1-2 heteroatoms independently selected from the group consisting of nitrogen, oxygen, and sulfur; or:

two R on the same nitrogen atom are taken with the nitrogen to form a 4-7-membered heterocyclic ring having 1-2 heteroatoms independently selected from the group consisting of nitrogen, oxygen, and sulfur.

In some embodiments, $R^1$ is an optionally substituted group selected from 6-10-membered aryl or 5-10-membered heteroaryl having 1-4 heteroatoms independently selected from the group consisting of nitrogen, oxygen, and sulfur. In certain embodiments, $R^1$ is an optionally substituted 6-10-membered aryl group. In certain embodiments, $R^1$ is an optionally substituted $C_{7-15}$ arylalkyl group. In certain embodiments, $R^1$ is an optionally substituted $C_{6-15}$ heteroarylalkyl group. In certain embodiments, $R^1$ is an optionally substituted $C_{1-12}$ aliphatic group. In some embodiments, $R^1$ is an optionally substituted $C_{1-12}$ heteroaliphatic group. In certain embodiments, $R^1$ is an optionally substituted 5-10-membered heteroaryl group having 1-4 heteroatoms independently selected from the group consisting of nitrogen, oxygen, and sulfur. In certain embodiments, $R^1$ is an optionally substituted 6-10-membered aryl or 4-7-membered heterocyclic group having 1-2 heteroatoms independently selected from the group consisting of nitrogen, oxygen, and sulfur. In certain embodiments, $R^1$ is an optionally substituted monocyclic aryl group. In certain embodiments, $R^1$ is an optionally substituted bicyclic aryl group. In certain embodiments, R' is an optionally substituted monocyclic heteroaryl group. In certain embodiments, $R^1$ is an optionally substituted bicyclic heteroaryl group.

In certain embodiments, $R^1$ is an optionally substituted group selected from 6-membered aryl or 6-membered heteroaryl having 1-4 heteroatoms independently selected from the group consisting of nitrogen, oxygen, and sulfur. In certain embodiments, $R^1$ is optionally substituted phenyl or pyridyl. In some embodiments, $R^1$ is monosubstituted phenyl. In some embodiments, $R^1$ is disubstituted phenyl. In some embodiments, $R^1$ is trisubstituted phenyl. In some embodiments, $R^1$ is optionally substituted phenyl.

In some embodiments, $R^1$ is selected from the group consisting of:

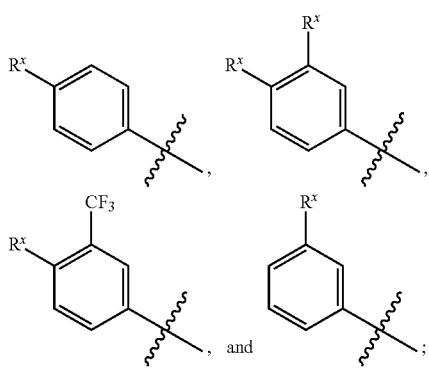

wherein each occurrence of $R^x$ is independently halogen, —$NR_2$, —OR, —SR, —$SO_2R$, or an optionally substituted group selected from the group consisting of 6-10-membered aryl; $C_{7-15}$ arylalkyl; $C_{6-15}$ heteroarylalkyl; $C_{1-12}$ aliphatic; 5-10-membered heteroaryl having 1-4 heteroatoms independently selected from the group consisting of nitrogen, oxygen, and sulfur; and 4-7-membered heterocyclic having 1-2 heteroatoms independently selected from the group consisting of nitrogen, oxygen, and sulfur.

In some embodiments, $R^1$ is

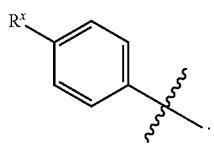

In some embodiments, $R^1$ is

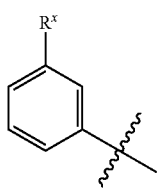

In some embodiments, $R^1$ is

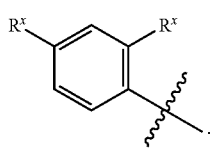

In some embodiments, $R^1$ is

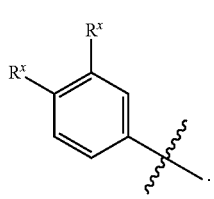

In some embodiments, $R^1$ is

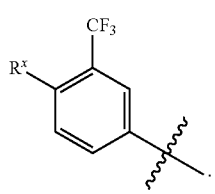

In some embodiments, $R^1$ is

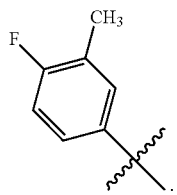

In some embodiments, $R^1$ is

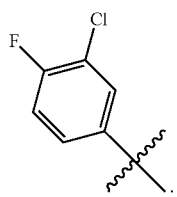

In some embodiments, $R^1$ is

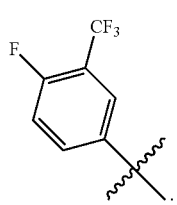

In some embodiments, $R^1$ is

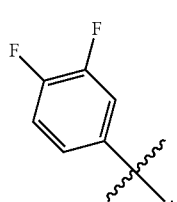

In some embodiments, R¹ is

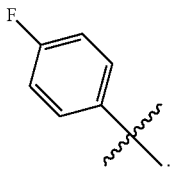

In some embodiments, R¹ is

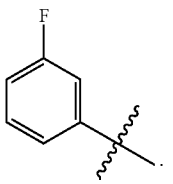 [SMILES: *c1cccc(F)c1]

In some embodiments, R¹ is

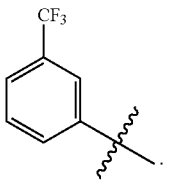

In some embodiments, R¹ is

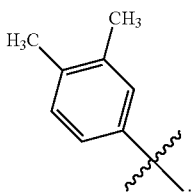

In some embodiments, R¹ is

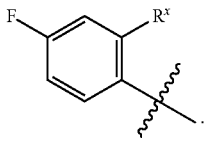

In some embodiments, R¹ is

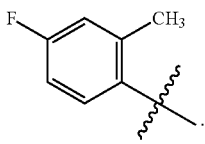

In some embodiments, R¹ is

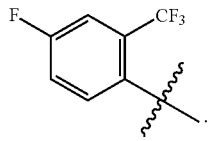

In some embodiments, R¹ is

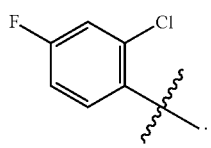

In some embodiments, R¹ is monosubstituted pyridyl. In some embodiments, R¹ is disubstituted pyridyl. In some embodiments, R¹ is trisubstituted pyridyl. In some embodiments, R¹ is optionally substituted pyridyl. In certain embodiments, R¹ is selected from the group consisting of

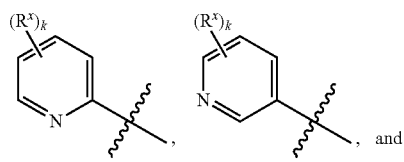

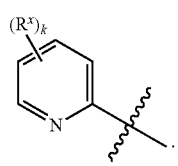

wherein k is an integer from 1 to 4.

In some embodiments, R¹ is

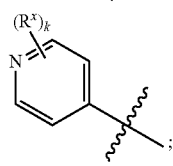

In some embodiments, R¹ is

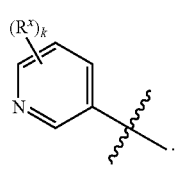

In some embodiments, $R^1$ is
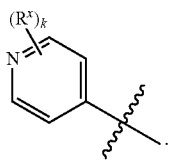
In some embodiments, $R^1$ is bicyclic. In some embodiments, $R^1$ is
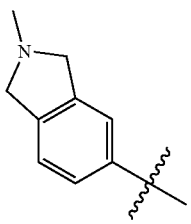
Exemplary $R^1$ groups are set forth in Table 1, below.
TABLE 1
Exemplary $R^1$ groups: a1, b1, c1, d1, e1, f1, g1, h1, i1, j1, k1, l1, m1

TABLE 1-continued
Exemplary R¹ groups
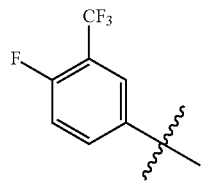 [SMILES: *c1ccc(F)c(C(F)(F)F)c1] n1
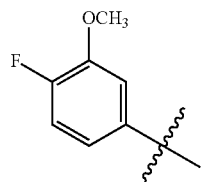 [SMILES: *c1ccc(F)c(OC)c1] o1
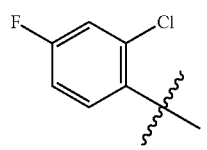 [SMILES: *c1ccc(F)cc1Cl] p1
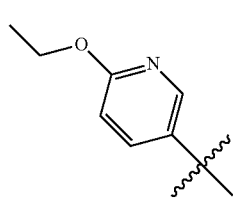 [SMILES: *c1ccc(OCC)nc1] q1
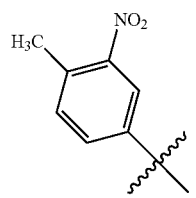 r1
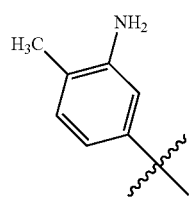 s1
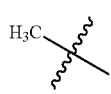
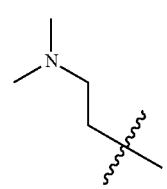 [SMILES: *CCN(C)C] t1
TABLE 1-continued
Exemplary R¹ groups
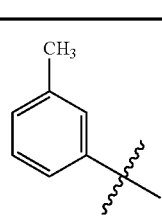 u1
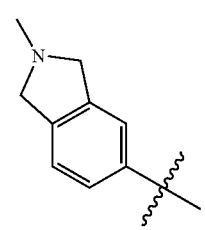 [SMILES: *c1ccc2c(c1)CN(C)C2] v1
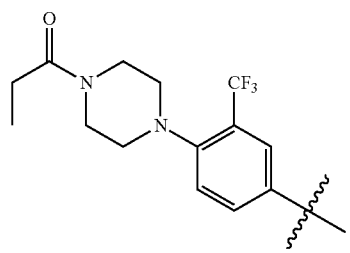 [SMILES: *c1ccc(N2CCN(C(=O)CC)CC2)c(C(F)(F)F)c1] w1
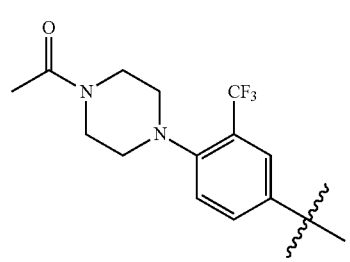 [SMILES: *c1ccc(N2CCN(C(C)=O)CC2)c(C(F)(F)F)c1] x1
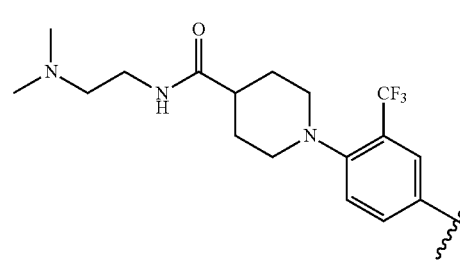 y1
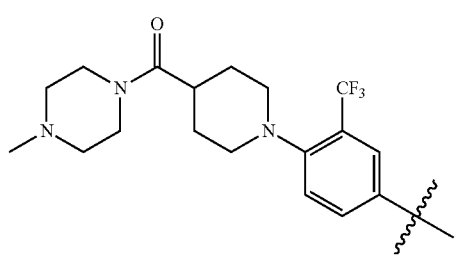 [SMILES: *c1ccc(N2CCC(C(=O)N3CCN(C)CC3)CC2)c(C(F)(F)F)c1] z1

TABLE 1-continued
Exemplary R¹ groups
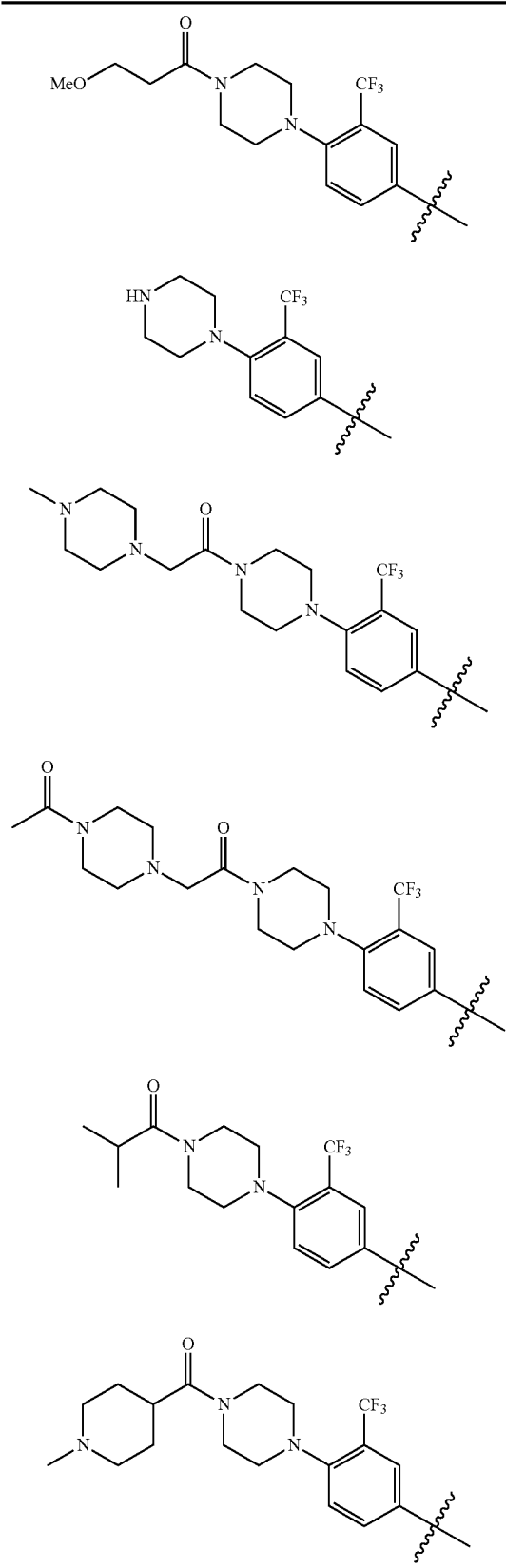
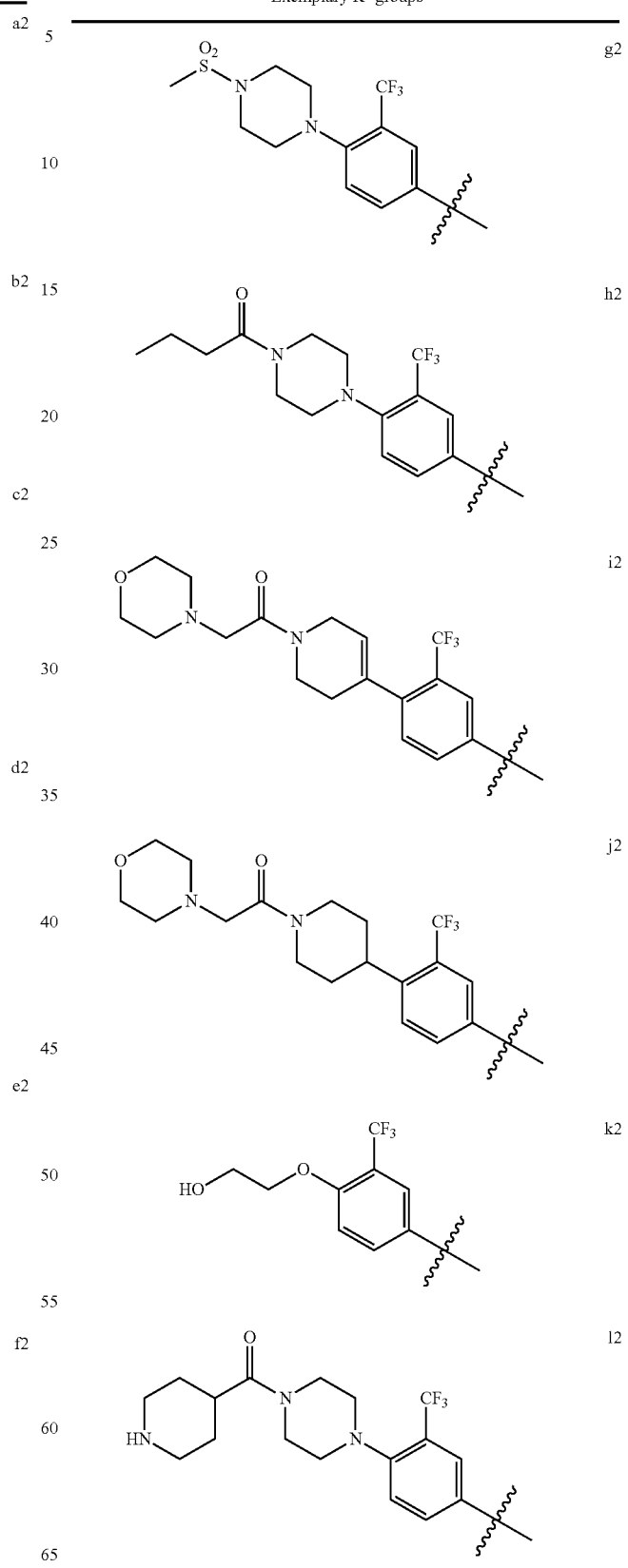

TABLE 1-continued
Exemplary R¹ groups
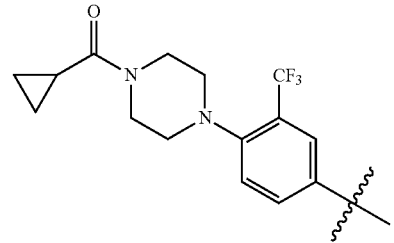 [SMILES: *c1ccc(N2CCN(C(=O)C3CC3)CC2)c(C(F)(F)F)c1] m2
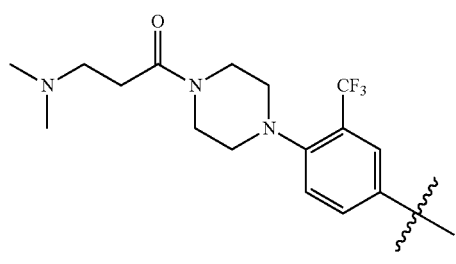 [SMILES: *c1ccc(N2CCN(C(=O)CCN(C)C)CC2)c(C(F)(F)F)c1] n2
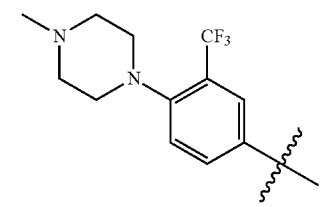 [SMILES: *c1ccc(N2CCN(C)CC2)c(C(F)(F)F)c1] o2
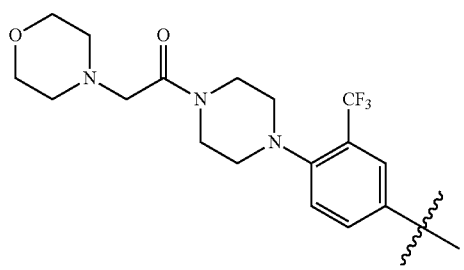 [SMILES: *c1ccc(N2CCN(C(=O)CN3CCOCC3)CC2)c(C(F)(F)F)c1] p2
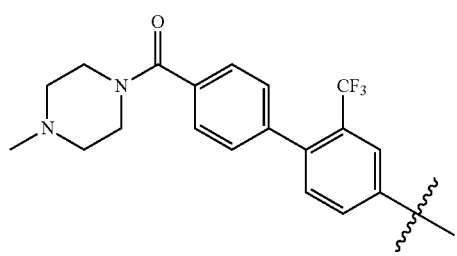 [SMILES: *c1ccc(-c2ccc(C(=O)N3CCN(C)CC3)cc2)c(C(F)(F)F)c1] q2
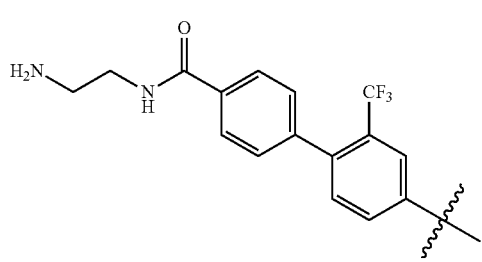 [SMILES: *c1ccc(-c2ccc(C(=O)NCCN)cc2)c(C(F)(F)F)c1] r2
TABLE 1-continued
Exemplary R¹ groups
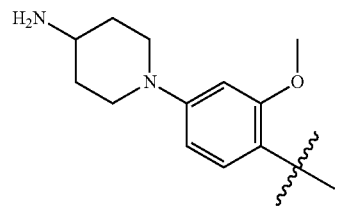 [SMILES: *c1ccc(N2CCC(N)CC2)cc1OC] s2
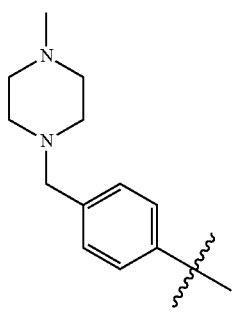 [SMILES: *c1ccc(CN2CCN(C)CC2)cc1] t2
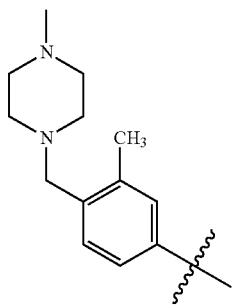 [SMILES: *c1ccc(CN2CCN(C)CC2)c(C)c1] u2
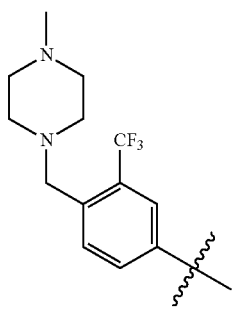 [SMILES: *c1ccc(CN2CCN(C)CC2)c(C(F)(F)F)c1] v2
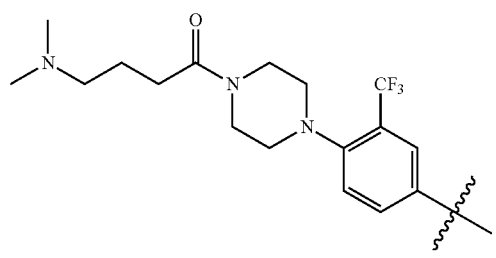 [SMILES: *c1ccc(N2CCN(C(=O)CCCN(C)C)CC2)c(C(F)(F)F)c1] w2

TABLE 1-continued
Exemplary R¹ groups
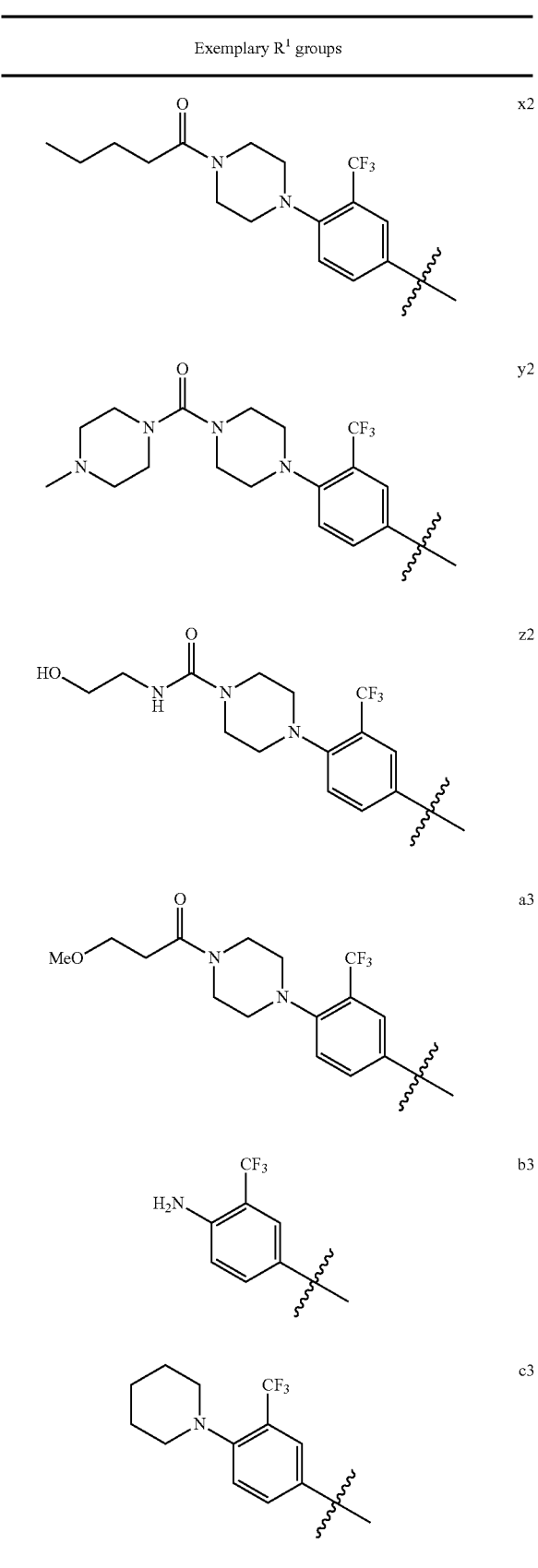
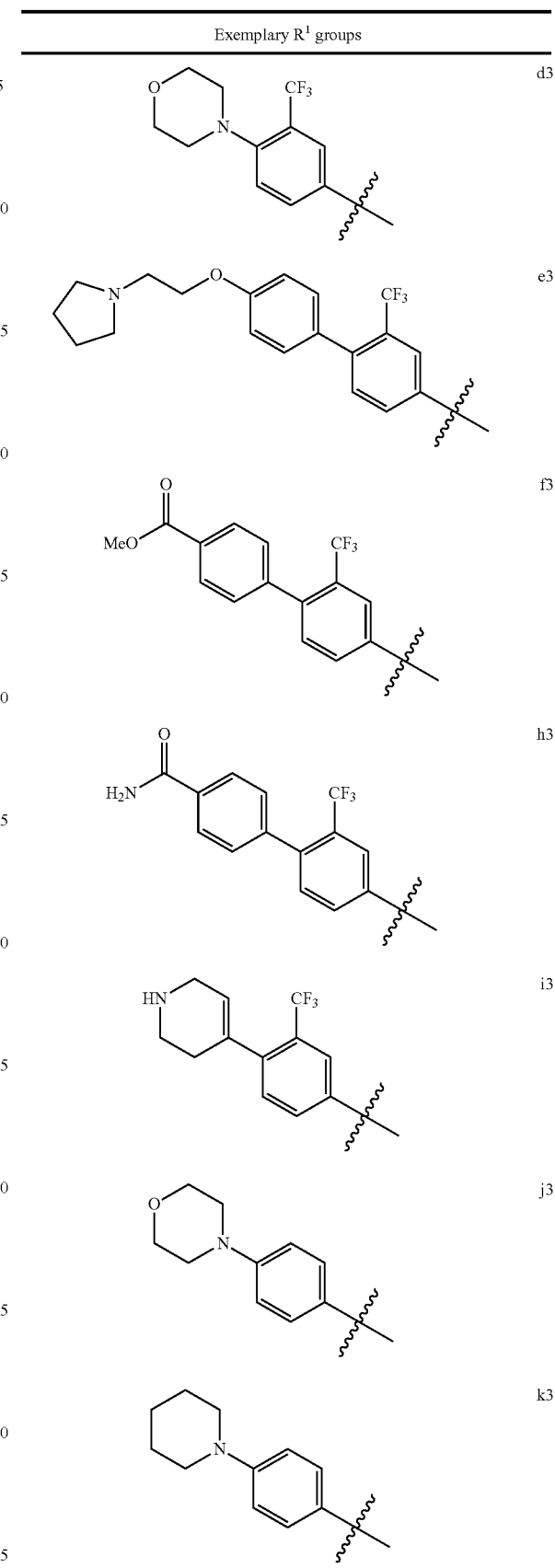

TABLE 1-continued
Exemplary R¹ groups
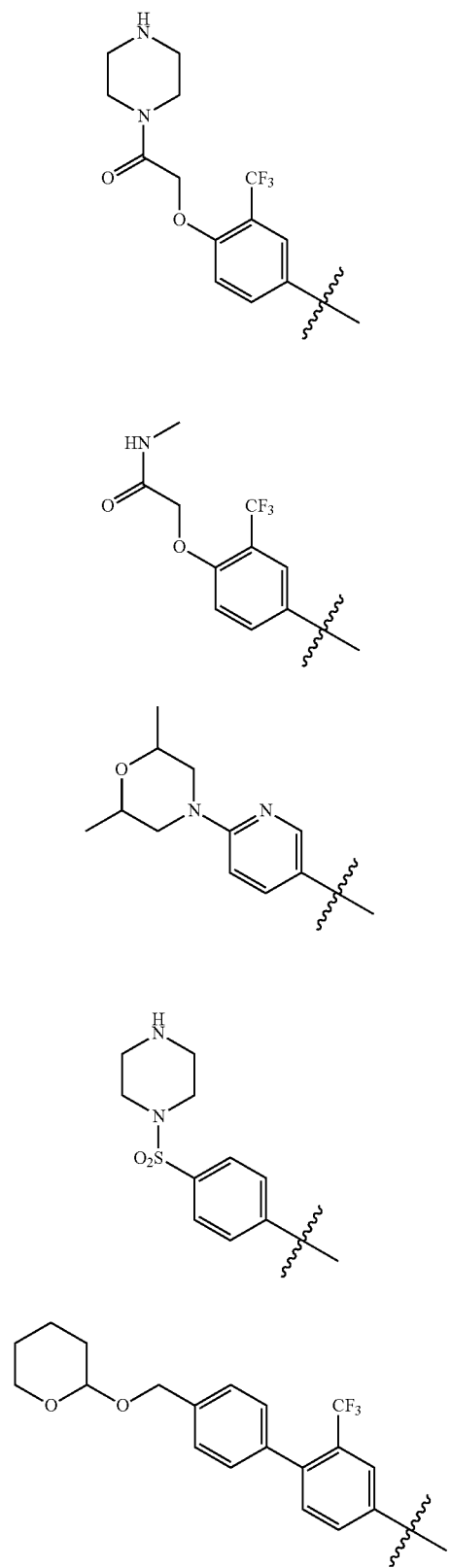
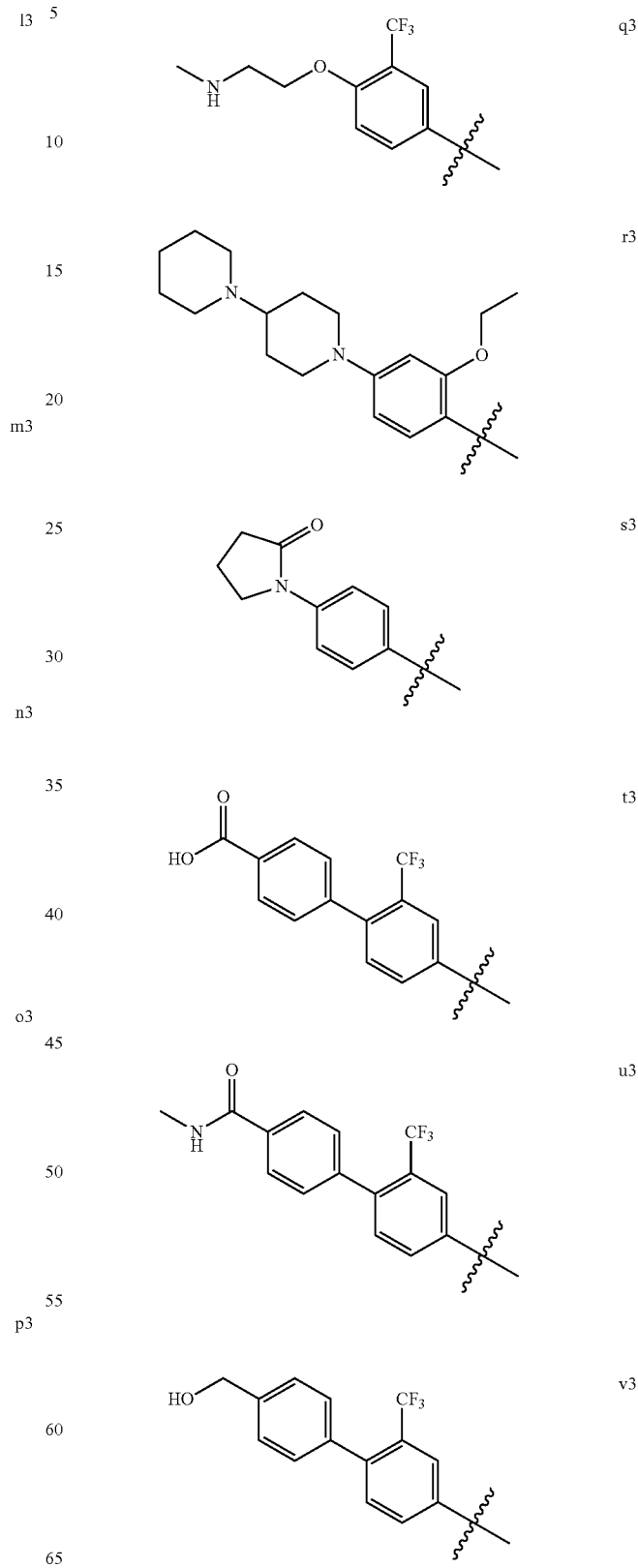

TABLE 1-continued

Exemplary R¹ groups

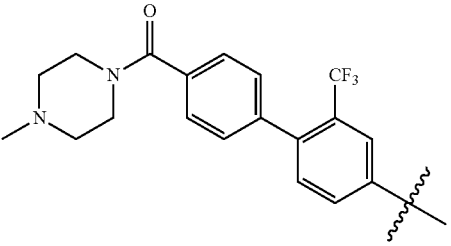 [SMILES: *c1ccc(-c2ccc(C(=O)N3CCN(C)CC3)cc2)c(C(F)(F)F)c1] w3

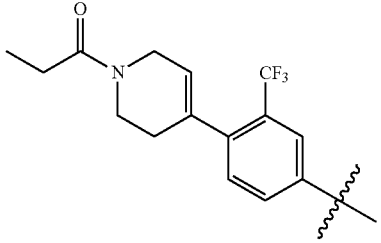 [SMILES: *c1ccc(C2=CCN(C(=O)CC)CC2)c(C(F)(F)F)c1] x3

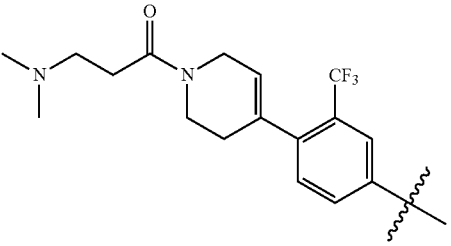 [SMILES: *c1ccc(C2=CCN(C(=O)CCN(C)C)CC2)c(C(F)(F)F)c1] y3

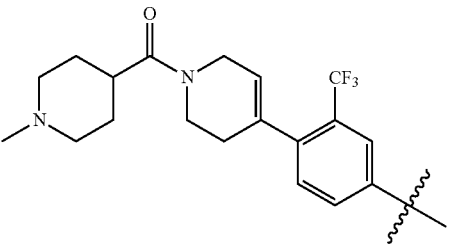 [SMILES: *c1ccc(C2=CCN(C(=O)C3CCN(C)CC3)CC2)c(C(F)(F)F)c1] z3

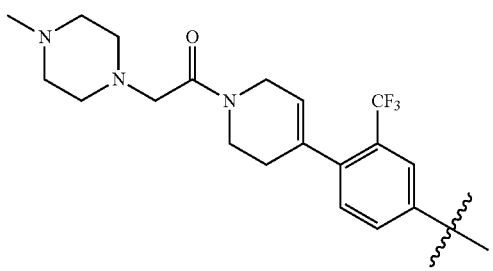 [SMILES: *c1ccc(C2=CCN(C(=O)CN3CCN(C)CC3)CC2)c(C(F)(F)F)c1] a4

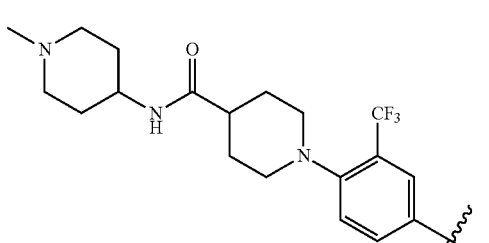 b4

TABLE 1-continued

Exemplary R¹ groups

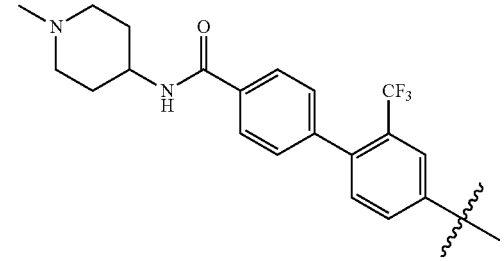 [SMILES: *c1ccc(-c2ccc(C(=O)NC3CCN(C)CC3)cc2)c(C(F)(F)F)c1] c4

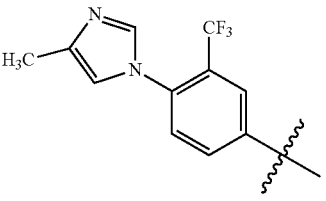 [SMILES: *c1ccc(-n2cnc(C)c2)c(C(F)(F)F)c1] d4

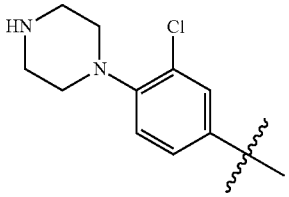 [SMILES: *c1ccc(N2CCNCC2)c(Cl)c1] e4

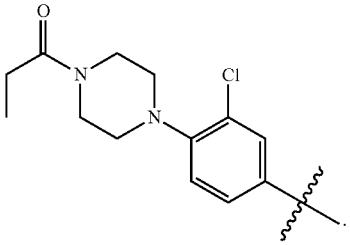 [SMILES: *c1ccc(N2CCN(C(=O)CC)CC2)c(Cl)c1] f4

In some embodiments, $R^2$ is halogen. In some embodiments, $R^2$ is —$NR_2$. In some embodiments, $R^2$ is —OR. In some embodiments, $R^2$ is —SR. In certain embodiments, $R^2$ is an optionally substituted $C_{1-12}$ acyl group. In certain embodiments, $R^2$ is an optionally substituted 6-10-membered aryl group. In certain embodiments, $R^2$ is an optionally substituted $C_{7-15}$ arylalkyl group. In certain embodiments, $R^2$ is an optionally substituted $C_{6-15}$ heteroarylalkyl group. In certain embodiments, $R^2$ is an optionally substituted $C_{1-12}$ aliphatic group. In certain embodiments, $R^2$ is an optionally substituted $C_{1-12}$ heteroaliphatic group. In certain embodiments, $R^2$ is an optionally substituted 5-10-membered heteroaryl group having 1-4 heteroatoms independently selected from the group consisting of nitrogen, oxygen, and sulfur. In certain embodiments, $R^2$ is an optionally substituted 4-7-membered heterocyclic group having 1-2 heteroatoms independently selected from the group consisting of nitrogen, oxygen, and sulfur.

In certain embodiments, $R^2$ is —$NR_2$ or an optionally substituted group selected from 6-10-membered aryl or 5-10-membered heteroaryl having 1-4 heteroatoms independently selected from the group consisting of nitrogen, oxygen, and sulfur. In certain embodiments, $R^2$ is —NHR, wherein R is an optionally substituted group selected from 6-10-membered aryl or 5-10-membered heteroaryl having 1-4 heteroatoms independently selected from the group consisting of nitrogen, oxygen, and sulfur. In some embodiments, $R^2$ is an optionally substituted monocyclic heteroaryl group. In some embodiments, $R^2$ is an optionally substituted bicyclic heteroaryl group.
Exemplary $R^2$ groups are set forth in Table 2, below.
TABLE 2
| Exemplary $R^2$ groups | |
|---|---|
| 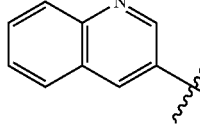 | aa |
| 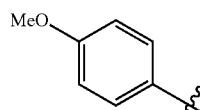 | bb |
| 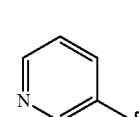 | cc |
| 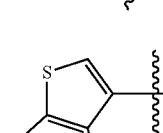 | dd |
| 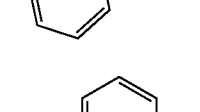 | ee |
| 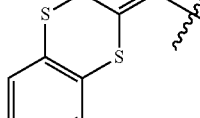 | ff |
| 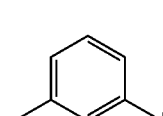 | gg |
| 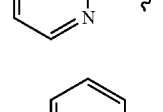 | hh |
TABLE 2-continued
| Exemplary $R^2$ groups | |
|---|---|
| 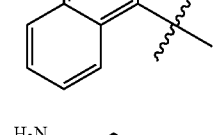 | jj |
|  | kk |
| 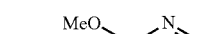 | ll |
|  | mm |
|  | nn |
|  | oo |
|  | pp |
| 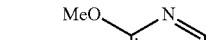 | qq |
|  | rr |
|  | ss |

TABLE 2-continued

Exemplary R² groups

| | |
|---|---|
| (thiophen-3-yl) | tt |
| (4-(piperazin-1-yl)pyridin-2-yl) | uu |
| (3,5-dimethoxyphenyl) | vv |
| (4-hydroxyphenyl) | ww |
| (4-cyanophenyl) | xx |
| (1H-pyrazol-4-yl) | yy |
| (6-methoxypyridin-3-yl) | zz |
| (6-methylpyridin-3-ylamino) | aaa |
| (4-aminopyridin-2-yl) | bbb |
| (thiazol-4-yl) | ccc |
| (5-hydroxy-1H-indol-2-yl) | ddd |
| (6-methoxypyridazin-3-yl) | eee |
| (5-(dimethylamino)pyrazin-2-yl) | fff |
| (1H-indol-6-yl) | ggg |
| (3-methyl-1H-indazol-5-yl) | hhh |
| (thiophen-2-yl) | iii |
| (6-cyanopyridin-3-yl) | jjj |
| (6-(trifluoromethyl)pyridin-3-yl) | kkk |
| (5-methoxypyridin-3-yl) | lll |
| (1-methyl-1H-pyrazol-3-yl) | mmm |

TABLE 2-continued

Exemplary R² groups

| | |
|---|---|
| nnn | (phenyl with attachment) |
| ooo | HO-pyridyl |
| ppp | O=pyridinone (NH) |
| qqq | 7-azaindole |
| rrr | N-methylpyrazole |
| sss | methylimidazole |
| ttt | indazole | or

In certain embodiments, j is 1. In certain embodiments, j is 2. In certain embodiments, j is 3. In certain embodiments, j is 4. In certain embodiments, j is 1 or 2.

In some embodiments, $R^3$ is hydrogen. In some embodiments, $R^3$ is halogen. In some embodiments, $R^3$ is optionally substituted $C_{1-6}$ aliphatic. In some embodiments, $R^3$ is methyl. In some embodiments, $R^3$ is ethyl. In some embodiments, $R^3$ is propyl. In some embodiments, $R^3$ is butyl.

In some embodiments, $R^4$ is hydrogen. In some embodiments, $R^4$ is halogen. In some embodiments, $R^4$ is optionally substituted $C_{1-6}$ aliphatic. In some embodiments, $R^4$ is methyl. In some embodiments, $R^4$ is ethyl. In some embodiments, $R^4$ is propyl. In some embodiments, $R^4$ is butyl. In some embodiments, $R^4$ is hydroxy.

In certain embodiments, $R^3$ and $R^4$ are both hydrogen. In certain embodiments, one of $R^3$ and $R^4$ is hydrogen. In certain embodiments, one of $R^3$ and $R^4$ is hydrogen and the other is methyl. In certain embodiments, $R^3$ is hydrogen and $R^4$ is methyl.

As defined above, in certain embodiments, $R^1$ is optionally substituted phenyl, providing a compound of formula II-a:

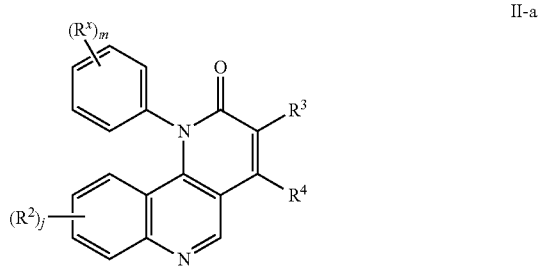

II-a wherein each of j, $R^2$, $R^3$, and $R^4$ is as defined above and described in classes and subclasses herein;

each occurrence of $R^x$ is independently halogen, —$NR_2$—OR, —SR, —$SO_2NR_2$, or an optionally substituted group selected from the group consisting of 6-10-membered aryl; $C_{7-15}$ arylalkyl; $C_{6-15}$ heteroarylalkyl; $C_{1-12}$ aliphatic; 5-10-membered heteroaryl having 1-4 heteroatoms independently selected from the group consisting of nitrogen, oxygen, and sulfur; and 4-7-membered heterocyclic having 1-2 heteroatoms independently selected from the group consisting of nitrogen, oxygen, and sulfur; and m is an integer from 1 to 4, inclusive; and when m is 2, 3, or 4, two $R^x$ substituents may join together to form a 5-7-membered cyclic group or a 5-7-membered heterocyclic group having 1-2 heteroatoms independently selected from the group consisting of nitrogen, oxygen, and sulfur; and wherein the 5-7-membered cyclic group or 5-7-membered heterocyclic group formed from two $R^x$ substituents is optionally substituted by one group selected from the group consisting of 6-10-membered aryl; 5-10-membered heteroaryl; $C_{7-15}$ arylalkyl; $C_{6-15}$ heteroarylalkyl; or $C_{1-12}$ aliphatic.

As defined above, in certain embodiments, $R^1$ is optionally substituted pyridyl, providing a compound of formula II-b, II-c, or II-d:

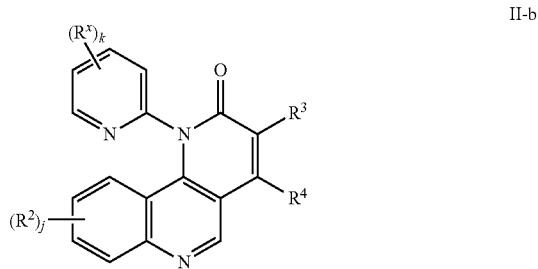

II-b

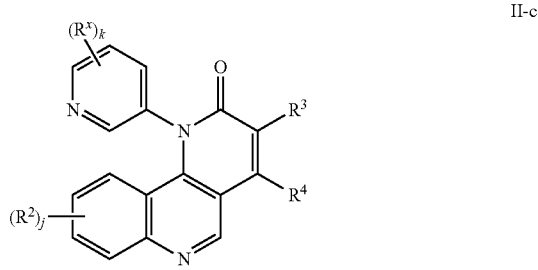

II-c

-continued

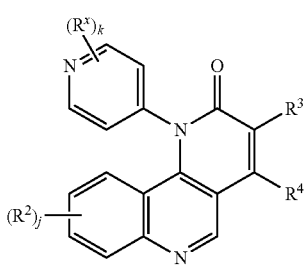

II-d wherein each of j, $R^x$, $R^2$, $R^3$, and $R^4$ is as defined above and described in classes and subclasses herein; and k is an integer from 1 to 5, inclusive; and when k is 2, 3, or 4, two $R^x$ substituents may join together to form a 5-7-membered cyclic group or a 5-7-membered heterocyclic group having 1-2 heteroatoms independently selected from the group consisting of nitrogen, oxygen, and sulfur; and wherein the 5-7-membered cyclic group or 5-7-membered heterocyclic group formed from two $R^x$ substituents is optionally substituted by one group selected from the group consisting of 6-10-membered aryl; 5-10-membered heteroaryl; $C_{7-15}$ arylalkyl; $C_{6-15}$ heteroarylalkyl; or $C_{1-12}$ aliphatic.

In some embodiments of compounds of formula II-a, II-b, II-c, or II-d, each occurrence of $R^x$ is independently —$NR_2$, —OR, —$SO_2NR_2$, or an optionally substituted group selected from the group consisting of 6-10-membered aryl; $C_{1-6}$ aliphatic; 5-10-membered heteroaryl having 1-4 heteroatoms independently selected from the group consisting of nitrogen, oxygen, and sulfur; and 4-7-membered heterocyclic having 1-2 heteroatoms independently selected from the group consisting of nitrogen, oxygen, and sulfur. In some embodiments, $R^x$ is —$NR_2$. In some embodiments, $R^x$ is —OR. In some embodiments, $R^x$ is —$SO_2NR_2$. In some embodiments, $R^x$ is optionally substituted 6-10-membered aryl. In some embodiments, $R^x$ is optionally substituted $C_{1-6}$ aliphatic. In some embodiments, $R^x$ is optionally substituted 5-10-membered heteroaryl having 1-4 heteroatoms independently selected from the group consisting of nitrogen, oxygen, and sulfur. In some embodiments, $R^x$ is optionally substituted 6-10-membered aryl. In some embodiments, $R^x$ is optionally substituted 4-7-membered heterocyclic having 1-2 heteroatoms independently selected from the group consisting of nitrogen, oxygen, and sulfur.

In some embodiments, at least one occurrence of $R^x$ is —$NR_2$, wherein two R on the same nitrogen atom are taken with the nitrogen to form a 5-6-membered heterocyclic ring having 1-2 heteroatoms independently selected from the group consisting of nitrogen, oxygen, and sulfur. In some embodiments, at least one occurrence of $R^x$ is 4-7-membered heterocyclic having 1-2 heteroatoms independently selected from the group consisting of nitrogen, oxygen, and sulfur. In some embodiments, each occurrence of $R^x$ is independently —$NH_2$, —OR, —$SO_2NR_2$, or an optionally substituted group selected from the group consisting of 6-membered aryl; $C_{1-4}$ aliphatic; and 5-6-membered heterocyclic having 1-2 heteroatoms independently selected from the group consisting of nitrogen, oxygen, and sulfur. In certain embodiments, at least one $R^x$ is:

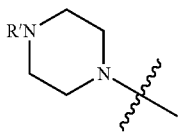

wherein $R^1$ is selected from the group consisting of hydrogen, acyl, sulphonyl, aliphatic, and heteroaliphatic.

In some embodiments, k is 1. In some embodiments, k is 2. In some embodiments, k is 3. In some embodiments, k is 4. In some embodiments, k is 1 or 2.

In some embodiments, m is 1. In some embodiments, m is 2. In some embodiments, m is 3. In some embodiments, m is 4. In some embodiments, m is 5. In some embodiments, m is 1 or 2.

Exemplary $R^x$ groups of inventive compounds are set forth in Table 3, below.

TABLE 3

Exemplary $R^x$ groups

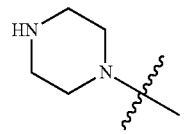 i

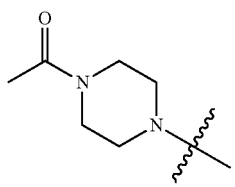 [SMILES: *N1CCN(C(C)=O)CC1] ii

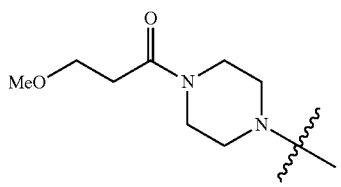 [SMILES: *N1CCN(C(=O)CCOC)CC1] iii

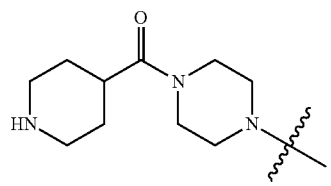 [SMILES: *N1CCN(C(=O)C2CCNCC2)CC1] iv

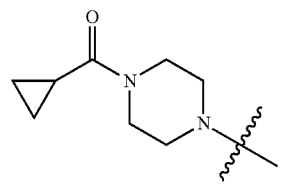 [SMILES: *N1CCN(C(=O)C2CC2)CC1] v

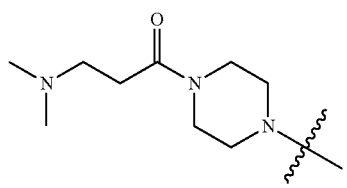 [SMILES: *N1CCN(C(=O)CCN(C)C)CC1] vi

TABLE 3-continued
Exemplary R^x groups
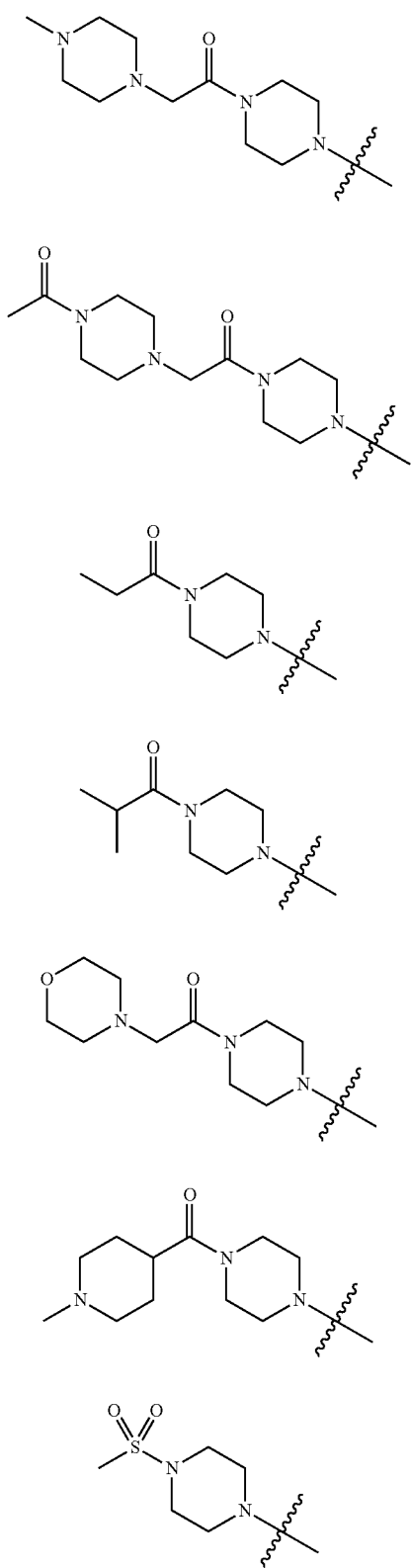
vii
viii
ix
x
xi
xii
xiii
TABLE 3-continued
Exemplary R^x groups
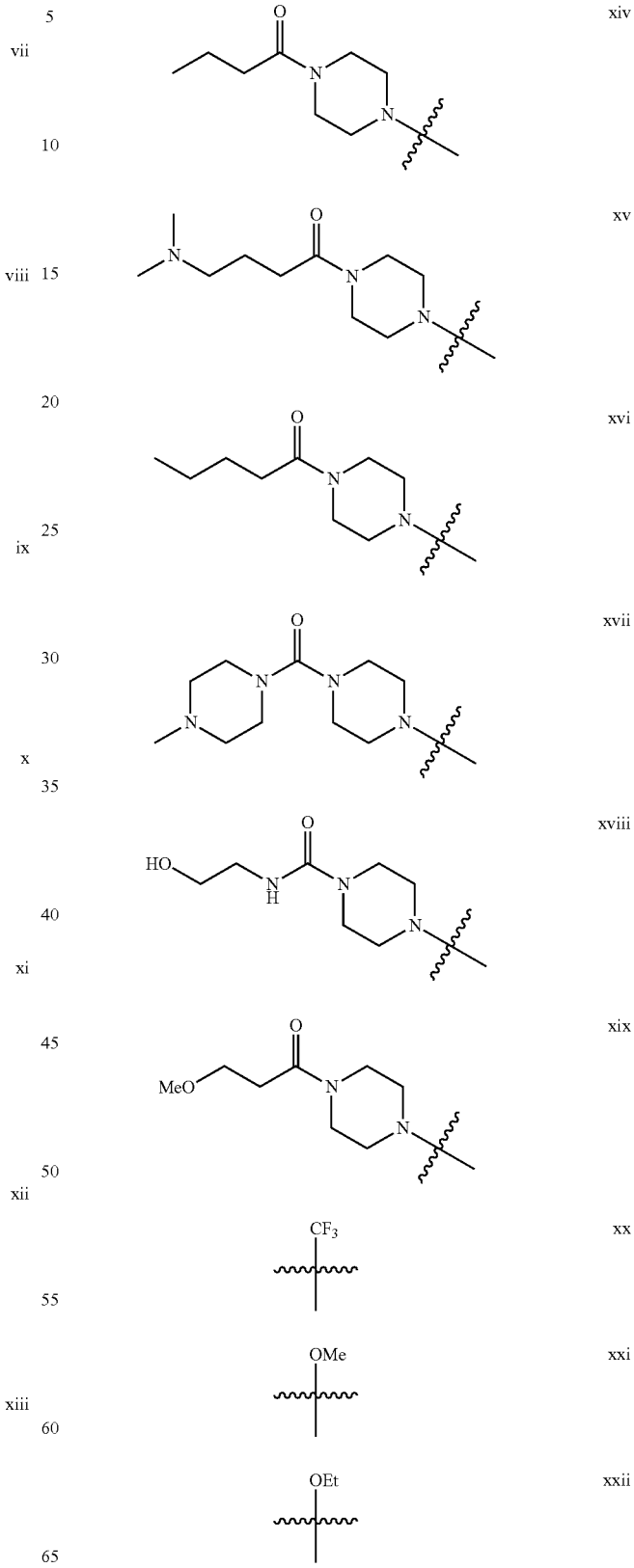
xiv
xv
xvi
xvii
xviii
xix
xx
xxi
xxii TABLE 3-continued Exemplary R^x groups

| | |
|---|---|
| xxiii | xxxiii |
| xxiv | xxxiv |
| xxv | xxxv |
| xxvi | xxxvi |
| xxvii | xxxvii |
| xxviii | xxxviii |
| xxix | xxxix |
| xxx | |
| xxxi | |
| xxxii | xl |

TABLE 3-continued
Exemplary R<sup>x</sup> groups
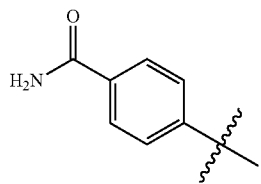 [SMILES: *c1ccc(C(N)=O)cc1] xli
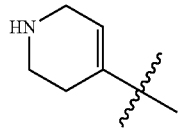 xlii
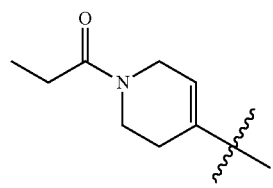 [SMILES: *C1=CCN(C(=O)CC)CC1] xliii
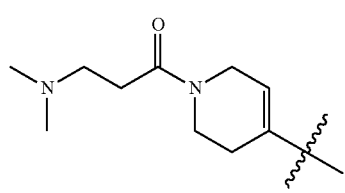 xliv
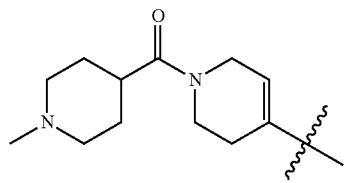 [SMILES: *C1=CCN(C(=O)C2CCN(C)CC2)CC1] xlv
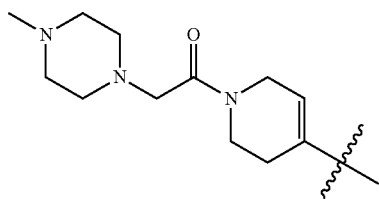 [SMILES: *C1=CCN(C(=O)CN2CCN(C)CC2)CC1] xlvi
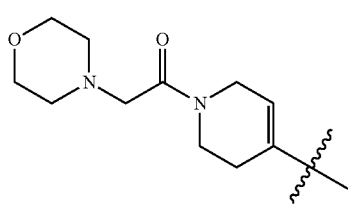 [SMILES: *C1=CCN(C(=O)CN2CCOCC2)CC1] xlvii
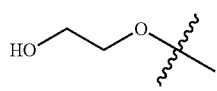 [SMILES: *OCCO] xlviii
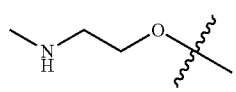 [SMILES: *OCCNC] xlix
TABLE 3-continued
Exemplary R<sup>x</sup> groups
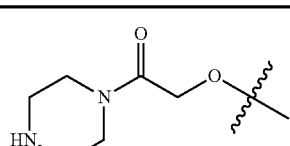 l
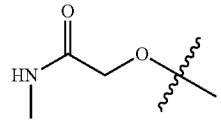 li
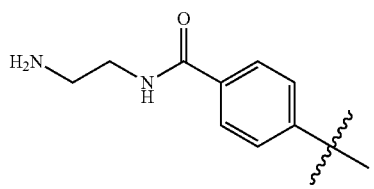 [SMILES: *c1ccc(C(=O)NCCN)cc1] lii
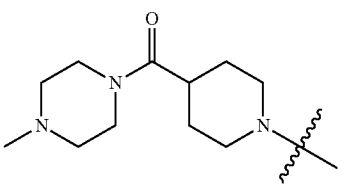 liii
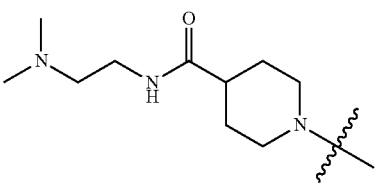 [SMILES: *N1CCC(C(=O)NCCN(C)C)CC1] liv
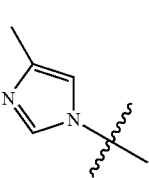 [SMILES: *n1cnc(C)c1] lv
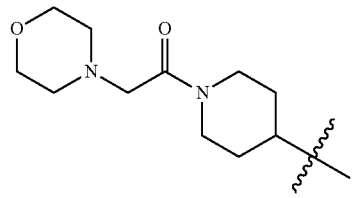 [SMILES: *C1CCN(C(=O)CN2CCOCC2)CC1] lvi
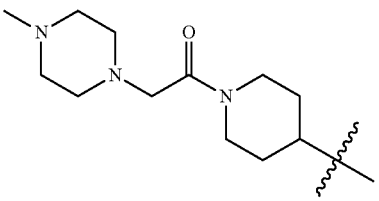 [SMILES: *C1CCN(C(=O)CN2CCN(C)CC2)CC1] lvii

TABLE 3-continued

Exemplary R$^x$ groups

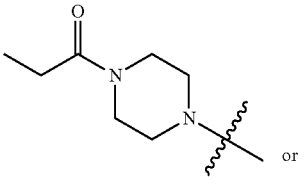 [SMILES: *N1CCN(C(=O)CC)CC1]

lviii or

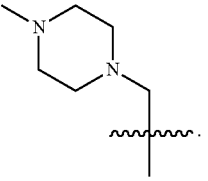 [SMILES: *CN1CCN(C)CC1]

liv

The invention further provides compounds of formula III:

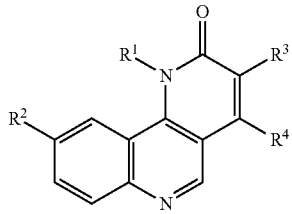

III wherein each of R$^1$, R$^2$, R$^3$, and R$^4$ is as defined above and described in classes and subclasses herein.

The invention further provides compounds of formula III-a:

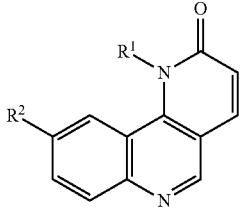

III-a wherein each of R$^1$ and R$^2$ is as defined above and described in classes and subclasses herein.

The invention further provides compounds of formula III-b:

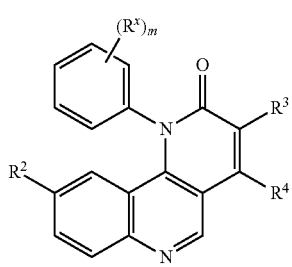

III-b wherein each of m, R$^x$, R$^2$, R$^3$, and R$^4$ is defined above and described in classes and subclasses herein.

The invention further provides compounds of formula IV:

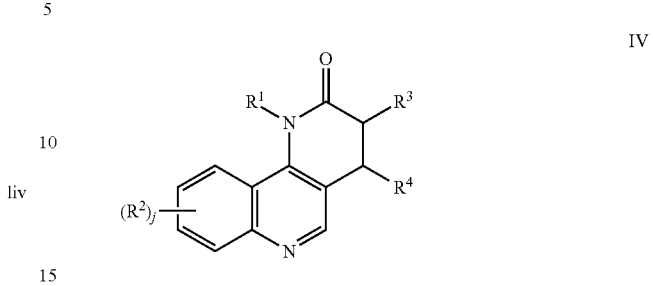

IV wherein each of j, R$^1$, R$^2$, R$^3$, and R$^4$ is as defined above and described in classes and subclasses herein.

The invention further provides compounds of formula V:

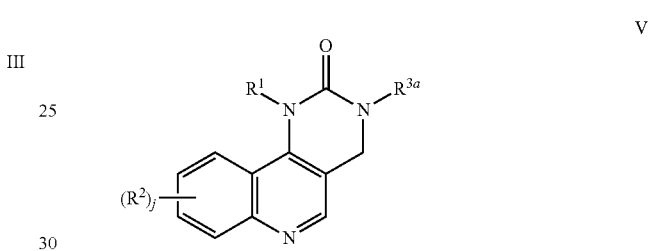

V wherein each of j, R$^1$, and R$^2$ is as defined above and described in classes and subclasses herein, and R$^{3a}$ is hydrogen, methyl, ethyl, or C$_{1-6}$ aliphatic.

The invention further provides compound of formula VI:

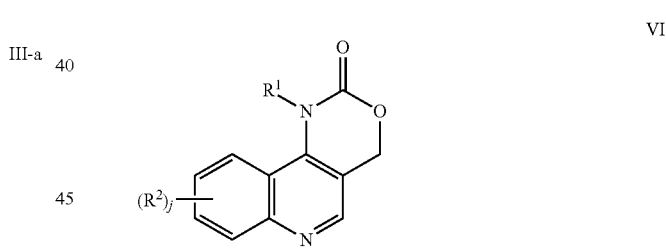

VI wherein each of j, R$^1$, and R$^2$ is as defined above and described in classes and subclasses herein.

In one aspect, the invention provides compound of formula VII:

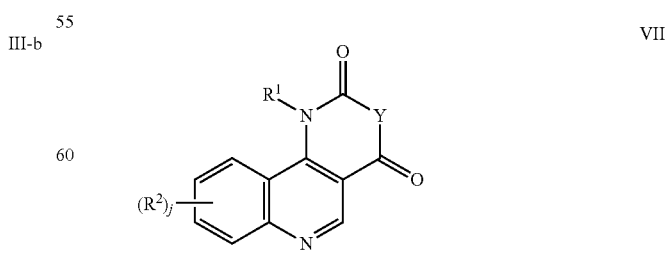

VII wherein each of j, Y, R$^x$, R$^1$, and R$^2$ are as defined above and described in classes and subclasses herein.

In some embodiments, R¹ is

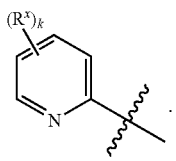

In some embodiments, R¹ is

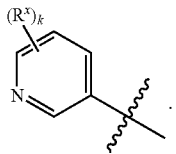

In some embodiments, R¹ is

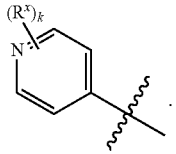

In certain embodiments j is 1, R² is

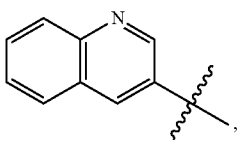 [SMILES: *c1cnc2ccccc2c1],

Y is O, and R¹ is

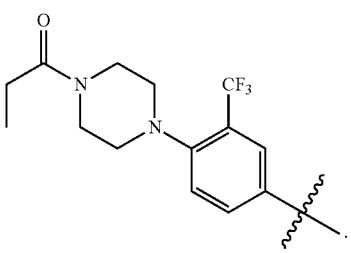 [SMILES: *c1ccc(N2CCN(C(=O)CC)CC2)c(C(F)(F)F)c1].

In certain embodiments j is 1, R² is

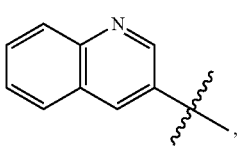 [SMILES: *c1cnc2ccccc2c1],

Y is NMe, and R¹ is

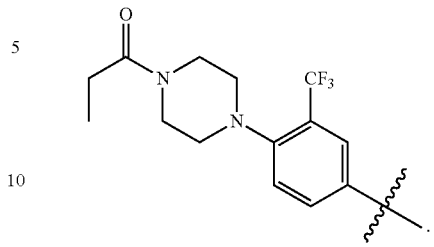.

In one aspect, the invention provides compound of formula VIII:

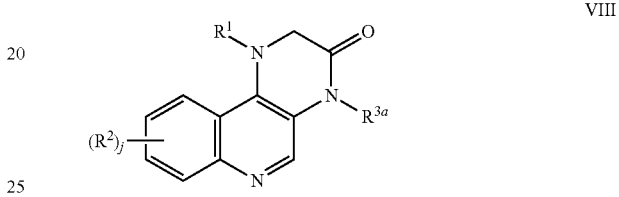

VIII wherein each of j, $R^x$, $R^1$, $R^2$, and $R^{3a}$ are as defined above and described in classes and subclasses herein.

In certain embodiments j is 1, R² is

, $R^{3a}$ is H, and R¹ is

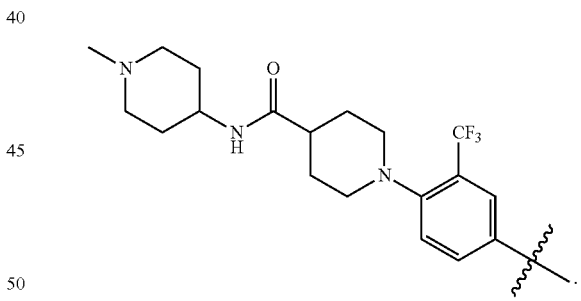.

In one aspect, the invention provides compound of formula IX:

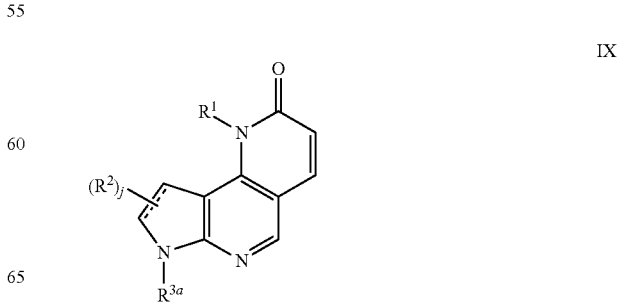

IX wherein each of $R^x$, $R^1$, $R^2$ and $R^{3a}$ are as defined above and described in classes and subclasses herein.

In some embodiments, ⸗ is ═

In certain embodiments, j is 0 or 1. In certain embodiments, j is 0. In certain embodiments, j is 1. In certain embodiments, j is 2.

ferent reaction conditions (e.g., temperature, solvent, concentration, etc.)

In one aspect, the present invention provides methods for the synthesis of compounds of formula I and intermediates thereto. In some embodiments, such methods are as shown in Scheme 1, below.

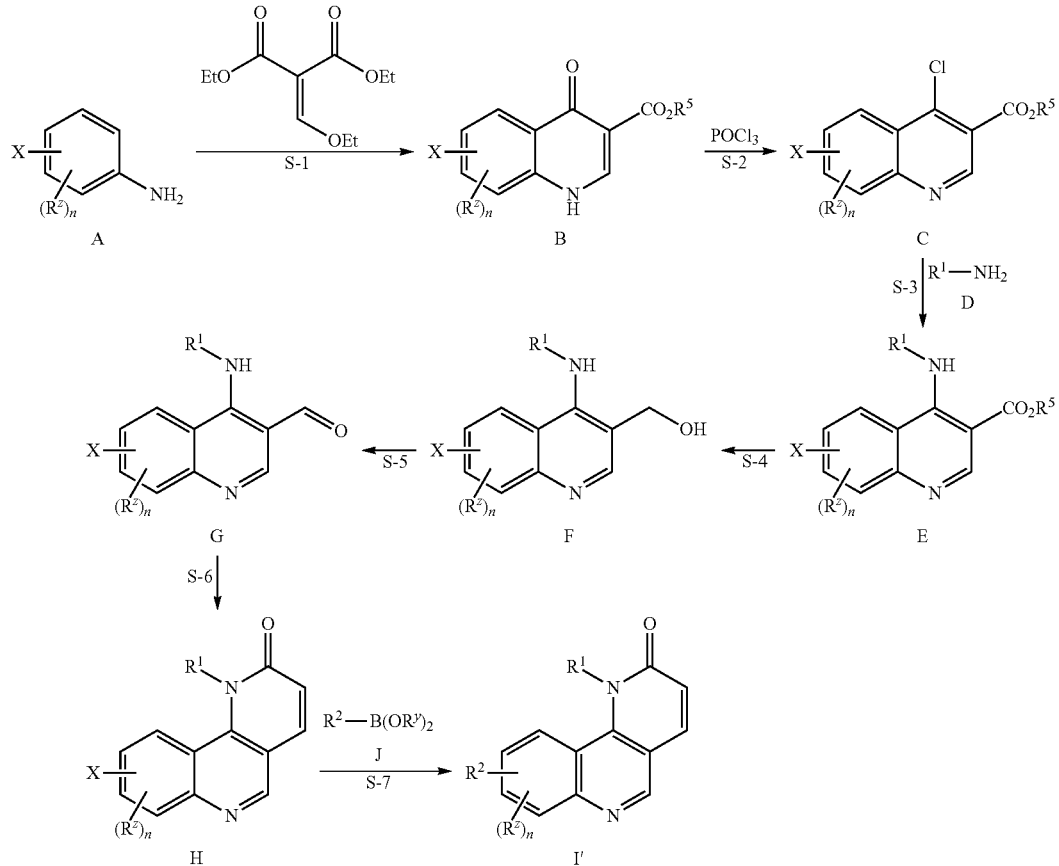

In some embodiments, ⸗ is ═, j is 0, and $R^{3a}$ is H. In some embodiments, ⸗ is ═, j is 0, $R^{3a}$ is H, and R1 is

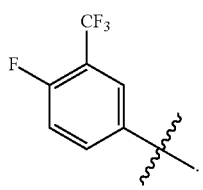

Synthesis of Compounds

Compounds of the invention may be synthesized according to the schemes described below. The reagents and conditions described are intended to be exemplary and not limiting. As one of skill in the art would appreciate, various analogs may be prepared by modifying the synthetic reactions such as using different starting materials, different reagents, and difwherein:
each of $R^1$ and $R^2$ is as defined above and described in classes and subclasses herein; n is an integer from 0 to 4, inclusive;
each occurrence of $R^z$ is independently halogen, —$NR_2$— OR, —SR, or an optionally substituted group selected from the group consisting of $C_{1-12}$ acyl; 6-10-membered aryl; $C_{7-15}$ arylalkyl; $C_{6-15}$ heteroarylalkyl; $C_{1-12}$ heteroaliphatic; $C_{1-12}$ aliphatic; 5-10-membered heteroaryl having 1-4 heteroatoms independently selected from the group consisting of nitrogen, oxygen, and sulfur; and 4-7-membered heterocyclic having 1-2 heteroatoms independently selected from the group consisting of nitrogen, oxygen, and sulfur;
each R is independently hydrogen, an optionally substituted group selected from the group consisting of $C_{1-12}$ acyl; 6-10-membered aryl; $C_{7-15}$ arylalkyl; $C_{6-15}$ heteroarylalkyl; $C_{1-12}$ aliphatic; 5-10-membered heteroaryl having 1-4 heteroatoms independently selected from nitrogen, oxygen, or sulfur; 4-7-membered heterocyclic having 1-2 heteroatoms independently selected from the group consisting of nitrogen, oxygen, and sulfur; and $C_{1-12}$ heteroaliphatic having 1-2 heteroatoms independently selected from the group consisting of nitrogen, oxygen, and sulfur; or two R on the same nitrogen atom are taken with the nitrogen to form a 4-7-membered heterocyclic ring having 1-2 heteroatoms independently selected from the group consisting of nitrogen, oxygen, and sulfur.

X is selected from the group consisting of chloro, iodo, bromo, fluoro, methanesulfonyl (mesyl), tosyl, and triflate;

$R^5$ is optionally substituted $C_{1-6}$ aliphatic; and $R^y$ is hydrogen or optionally substituted, straight or branched, $C_{1-12}$ aliphatic; or two $R^y$ attached to the same oxygen are taken together with their intervening atoms to form a monocyclic or bicyclic 5-8-membered ring.

In step S-1, an aniline of formula A is reacted with ethyl ethoxymethylenemalonate to form a compound of formula B. In step S-2, a compound of formula B is chlorinated to form quinoline C. Suitable reagents for effecting the chlorination are known in the art and include $POCl_3$. In step S-3, quinoline C is substituted with an amine of formula D to form ester E. In step S-4, ester E is reduced under suitable conditions to form a (quinoline-3-yl)methanol of formula F. In step S-5, a (quinoline-3-yl)methanol of formula F is oxidized under suitable conditions to provide aldehyde G. In step S-6, aldehyde G is cyclized to form a tricyclic compound of formula H. Suitable reagents for effecting the cyclization are known in the art and include triethyl phosphonoacetate. In step S-7, a tricyclic compound of formula H is coupled with boronate J under suitable coupling conditions in the presence of a suitable metal complex to form a compound of formula I'. In certain embodiments, the coupling is a Suzuki coupling. Suitable reduction conditions, oxidation conditions, coupling conditions, metals, and ligands are known in the art and include those described in March (supra).

In certain embodiments, the present invention provides a method for preparing a compound of formula I':

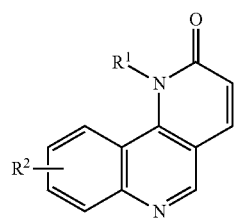

I' wherein:
$R^1$ is an optionally substituted group selected from the group consisting of 6-10-membered aryl; $C_{7-15}$ arylalkyl; $C_{6-15}$ heteroarylalkyl; $C_{1-12}$ heteroaliphatic; $C_{1-12}$ aliphatic; 5-10-membered heteroaryl having 1-4 heteroatoms independently selected from the group consisting of nitrogen, oxygen, and sulfur; and 4-7-membered heterocyclic having 1-2 heteroatoms independently selected from the group consisting of nitrogen, oxygen, and sulfur;

each occurrence of $R^2$ is independently halogen, —$NR_2$—OR, —SR, or an optionally substituted group selected from the group consisting of $C_{1-12}$ acyl; 6-10-membered aryl; $C_{7-15}$ arylalkyl; $C_{6-15}$ heteroarylalkyl; $C_{1-12}$ heteroaliphatic; $C_{1-12}$ aliphatic; 5-10-membered heteroaryl having 1-4 heteroatoms independently selected from the group consisting of nitrogen, oxygen, and sulfur; and 4-7-membered heterocyclic having 1-2 heteroatoms independently selected from the group consisting of nitrogen, oxygen, and sulfur; and each R is independently hydrogen, an optionally substituted group selected from the group consisting of $C_{1-12}$ acyl; 6-10-membered aryl; $C_{7-15}$ arylalkyl; $C_{6-15}$ heteroarylalkyl; $C_{1-12}$ aliphatic; 5-10-membered heteroaryl having 1-4 heteroatoms independently selected from the group consisting of nitrogen, oxygen, and sulfur; 4-7-membered heterocyclic having 1-2 heteroatoms independently selected from the group consisting of nitrogen, oxygen, and sulfur; and $C_{1-12}$ heteroaliphatic having 1-2 heteroatoms independently selected from the group consisting of nitrogen, oxygen, and sulfur; or:

two R on the same nitrogen atom are taken with the nitrogen to form a 4-7-membered heterocyclic ring having 1-2 heteroatoms independently selected from the group consisting of nitrogen, oxygen, and sulfur;

the method comprising the steps of:
(a) providing an aniline of formula A:

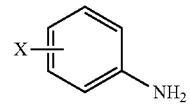

A wherein X is halogen, -Otf, or -OTs; and
(b) reacting the aniline of formula A with ethyl ethoxymethylenemalonate to form a compound of formula B:

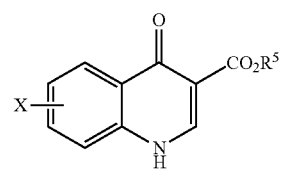

B wherein
X is halogen, -Otf, or -OTs;
$R^5$ is $C_{1-6}$ aliphatic; and
(c) chlorinating the compound of formula B to form a quinoline C:

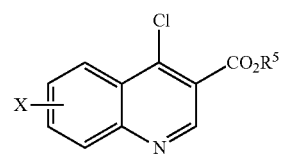

C wherein X is halogen, -Otf, or -OTs;
$R^5$ is $C_{1-6}$ aliphatic; and
(d) substituting the quinoline C with an amine of formula D:

$R^1$—$NH_2$  D wherein $R^1$ is an optionally substituted group selected from the group consisting of 6-10-membered aryl; $C_{7-15}$ arylalkyl; $C_{6-15}$ heteroarylalkyl; $C_{1-12}$ heteroaliphatic; $C_{1-12}$ aliphatic; 5-10-membered heteroaryl having 1-4 heteroatoms independently selected from the group consisting of nitrogen, oxygen, and sulfur; and 4-7-membered heterocyclic having 1-2 heteroatoms independently selected from the group consisting of nitrogen, oxygen, and sulfur;

to form an ester E:

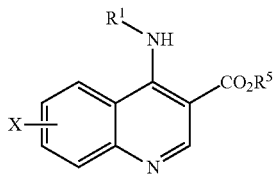

wherein:
X is halogen, -Otf, or -OTs;
R¹ is an optionally substituted group selected from the group consisting of 6-10-membered aryl; $C_{7-15}$ arylalkyl; $C_{6-15}$ heteroarylalkyl; $C_{1-12}$ heteroaliphatic; $C_{1-12}$ aliphatic; 5-10-membered heteroaryl having 1-4 heteroatoms independently selected from the group consisting of nitrogen, oxygen, and sulfur; and 4-7-membered heterocyclic having 1-2 heteroatoms independently selected from the group consisting of nitrogen, oxygen, and sulfur;
R⁵ is $C_{1-6}$ aliphatic; and
(e) reducing the ester E under suitable conditions to provide a (quinoline-3-yl)methanol of formula F:

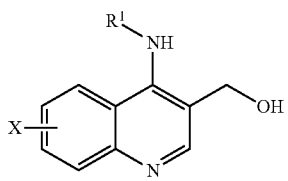

wherein:
X is halogen, -Otf, or -OTs;
R¹ is an optionally substituted group selected from the group consisting of 6-10-membered aryl; $C_{7-15}$ arylalkyl; $C_{6-15}$ heteroarylalkyl; $C_{1-12}$ heteroaliphatic; $C_{1-12}$ aliphatic; 5-10-membered heteroaryl having 1-4 heteroatoms independently selected from the group consisting of nitrogen, oxygen, and sulfur; and 4-7-membered heterocyclic having 1-2 heteroatoms independently selected from the group consisting of nitrogen, oxygen, and sulfur; and
(f) oxidizing the (quinoline-3-yl)methanol of formula F under suitable conditions to provide a quinoline-3-carbaldehyde of formula G:

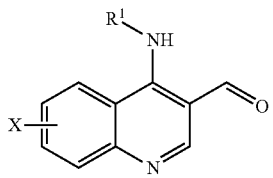

wherein:
X is halogen, -Otf, or -OTs;
R¹ is an optionally substituted group selected from the group consisting of 6-10-membered aryl; $C_{7-15}$ arylalkyl; $C_{6-15}$ heteroarylalkyl; $C_{1-12}$ heteroaliphatic; $C_{1-12}$ aliphatic; 5-10-membered heteroaryl having 1-4 heteroatoms independently selected from the group consisting of nitrogen, oxygen, and sulfur; and 4-7-membered heterocyclic having 1-2 heteroatoms independently selected from the group consisting of nitrogen, oxygen, and sulfur; and (g) cyclizing the quinoline-3-carbaldehyde of formula G with triethyl phosphonoacetate to form a tricyclic compound of formula H:

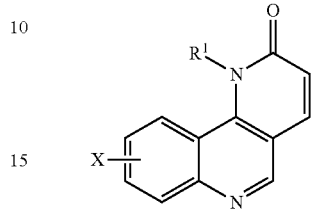

wherein:
X is halogen, -Otf, or -OTs;
R¹ is an optionally substituted group selected from the group consisting of 6-10-membered aryl; $C_{7-15}$ arylalkyl; $C_{6-15}$ heteroarylalkyl; $C_{1-12}$ heteroaliphatic; $C_{1-12}$ aliphatic; 5-10-membered heteroaryl having 1-4 heteroatoms independently selected from the group consisting of nitrogen, oxygen, and sulfur; and 4-7-membered heterocyclic having 1-2 heteroatoms independently selected from the group consisting of nitrogen, oxygen, and sulfur; and
(h) conjugating the tricyclic compound of formula H with a boronate of formula J:

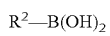

$$R^2—B(OH)_2 \qquad J$$

wherein R² is an optionally substituted group selected from the group consisting of $C_{1-12}$ acyl; 6-10-membered aryl; $C_{7-15}$ arylalkyl; $C_{6-15}$ heteroarylalkyl; $C_{1-12}$ heteroaliphatic; $C_{1-12}$ aliphatic; 5-10-membered heteroaryl having 1-4 heteroatoms independently selected from the group consisting of nitrogen, oxygen, and sulfur; and 4-7-membered heterocyclic having 1-2 heteroatoms independently selected from the group consisting of nitrogen, oxygen, and sulfur;
in the presence of a suitable metal complex to form a compound of formula I'.

In certain embodiments, each of the aforementioned synthetic steps may be performed sequentially with isolation of each intermediate performed after each step. Alternatively, each of steps S-1, S-2, S-3, S-4, S-5, S-6, and S-7 as depicted in Scheme I above, may be performed in a manner whereby no isolation of one or more intermediates B, C, E, F, G, or H is performed.

In certain embodiments, all the steps of the aforementioned synthesis may be performed to prepare the desired final product. In other embodiments, two, three, four, five, or more sequential steps may be performed to prepare an intermediate or the desired final product.

In certain embodiments, all the steps of the aforementioned synthesis may be performed using solution phase or solid phase synthetic techniques, or a combination thereof. In some embodiments, robotic techniques may be employed. In certain embodiments, automatic liquid handling reaction stations may be used. In some embodiments, parallel synthesis may be used. In some embodiments, high-throughput synthesis may be used. In some embodiments, one-by-one synthesis may be used.

Uses

Compounds of the present invention may be used in vitro or in vivo. The inventive compounds may be particularly useful in the treatment of neoplasms or other proliferative diseases in vivo. The inventive compounds may also be useful in the treatment of metabolic diseases in vivo. However, inventive compounds described above may also be used in vitro for research or clinical purposes (e.g., determining the susceptibility of a patient's disease to an inventive compound, researching the mechanism of action, elucidating a cellular pathway or process). In certain embodiments, compounds of the present invention are provided for use in medicine.

In some embodiments, the present invention provides a method of treating a proliferative disease in a subject suffering therefrom, the method comprising administering to the subject a therapeutically effective amount of an inventive compound. In certain embodiments, the proliferative disease is a benign neoplasm. In certain embodiments, the proliferative disease is cancer. In certain embodiments, the proliferative disease is an inflammatory disease. In certain embodiments, the proliferative disease is an autoimmune disease. In certain embodiments, the proliferative disease is diabetic retinopathy.

Compounds of the present invention may be used in the treatment of neoplasms. In certain embodiments, the neoplasm is a benign neoplasm. In other embodiments, the neoplasm is a malignant neoplasm.

In certain embodiments, the cancer is a solid tumor. Exemplary cancers that may be treated using compounds of the present invention include colon cancer, lung cancer, bone cancer, pancreatic cancer, stomach cancer, esophageal cancer, skin cancer, brain cancer, liver cancer, ovarian cancer, cervical cancer, uterine cancer, testicular cancer, prostate cancer, bladder cancer, kidney cancer, neuroendocrine cancer, breast cancer, gastric cancer, eye cancer, gallbladder cancer, laryngeal cancer, oral cancer, penile cancer, glandular tumors, rectal cancer, small intestine cancer, sarcoma, carcinoma, melanoma, urethral cancer, vaginal cancer, to name but a few. In some embodiments, tumors do not have mutations in the ras pathway.

In some embodiments, the cancer is a hematological malignancy. In some embodiments, the hematological malignancy is a lymphoma. In some embodiments, the hematological malignancy is a leukemia. Examples of hematological malignancies that may be treated using an inventive compound include, but are not limited to, acute lymphoblastic leukemia (ALL), acute myelogenous leukemia (AML), chronic myelogenous leukemia (CML), chronic lymphocytic leukemia (CLL), hairy cell leukemia, Hodgkin's lymphoma, non-Hodgkin's lymphoma, cutaneous T-cell lymphoma (CTCL), peripheral T-cell lymphoma (PTCL), Mantle cell lymphoma, B-cell lymphoma, acute lymphoblastic T cell leukemia (T-ALL), acute promyelocytic leukemia, and multiple myeloma.

In certain embodiments, an inventive compound is used to treat mantle cell lymphoma. In certain embodiments, an inventive compound is used to treat neurofibromatosis I. In certain embodiments, an inventive compound is used to treat endometrial cancer. In certain embodiments, an inventive compound is used to treat renal cell carcinoma. In certain embodiments, an inventive compound is used to treat hamartoma syndrome (e.g., tuberous sclerosis complex). In certain embodiments, an inventive compound is used to treat neurofibromas.

It has been found that the deletion of S6K1 protects against diet-induced insulin resistance, and it has been proposed that a connection exists between the S6K1 pathway, type II diabetes, and obesity. It has also been established that the deletion of Akt2 causes severe diabetes. Without wishing to be bound by any particular theory, it is believed that the inhibition of mTORC1/2 can serve to mimic S6K inhibition. Thus, in certain embodiments, the present invention provides a method for the suppression of acquired insulin resistance. In some embodiments, the suppression is from inhibition of mTORC1. In some embodiments, the suppression is from inhibition of mTORC2.

In some embodiments, the invention provides methods of treating a metabolic disease in a subject suffering therefrom comprising administering to the subject a therapeutically effective amount of a compound of formula I. In certain embodiments, the metabolic disease is type II diabetes. In some embodiments, the metabolic disease is metabolic syndrome. In some embodiments, the metabolic disease is insulin resistance. In some embodiments, the metabolic disease is obesity.

In certain embodiments, the invention provides methods of treating a disease associated with pathologic neovascularization in a subject suffering therefrom comprising administering to the subject a therapeutically effective amount of a compound of formula I.

In certain embodiments, the invention provides methods of treating a disease associated with angiogenesis in a subject suffering therefrom comprising administering to the subject a therapeutically effective amount of a compound of formula I.

In some embodiments, compounds of the present invention are useful for inhibiting smooth muscle cell proliferation. In some embodiments, compounds of the present invention are useful for inhibiting restenosis. In certain embodiments, such effects are achieved by using a drug-eluting stent coated with a composition comprising a compound of formula I.

In certain embodiments, the present invention provides a method for the inhibition of one or both of mTORC1 and mTORC2, the method comprising contacting said mTORC1 and mTORC2 with an effective amount of an inventive compound. In some embodiments, the inhibition of one or both of mTORC1 and/or mTORC2 occurs in a cell. In certain embodiments, both mTORC1 and mTORC2 are inhibited by an inventive compound. In certain embodiments, mTORC1 is selectively inhibited. In certain embodiments, mTORC2 is selectively inhibited. In certain embodiments, the relative inhibition of mTORC1 to mTORC2 is 1:10. In certain embodiments, the relative inhibition of mTORC1 to mTORC2 is 1:50. In certain embodiments, the relative inhibition of mTORC1 to mTORC2 is 1:100. In certain embodiments, the relative inhibition of mTORC1 to mTORC2 is 1:1,000. In certain embodiments, the relative inhibition of mTORC1 to mTORC2 is 1:10,000. In certain embodiments, the relative inhibition of mTORC1 to mTORC2 is 10:1. In certain embodiments, the relative inhibition of mTORC1 to mTORC2 is 50:1. In certain embodiments, the relative inhibition of mTORC1 to mTORC2 is 100:1. In certain embodiments, the relative inhibition of mTORC1 to mTORC2 is 1,000:1. In certain embodiments, the relative inhibition of mTORC1 to mTORC2 is 10,000:1. In some embodiments, the inhibition occurs via an ATP-competitive mechanism.

In some embodiments, the present invention provides a method for the inhibition of one or more protein kinases, wherein said protein kinase comprises a kinase domain with similarity to Pi3K. In some embodiments, the protein kinase is a member of the PIKK family of kinases. Exemplary protein kinases included but are not limited to, class I Pi3ks (alpha, beta, delta, gamma); class II Pi3ks (Pi3KC2alpha, beta, gamma); class II Pi3ks (Vps34); Pi4KIII alpha, beta; ATR; ATM; Smg1, TRAPP, and DNA-PK. In some embodiments, class I Pi3ks are inhibited. In some embodiments, class II Pi3ks are inhibited. In some embodiments, Vps34 is inhibited. In some embodiments, Pi4KIII is inhibited. In some embodiments, ATR is inhibited. In some embodiments, ATM is inhibited. In some embodiments, DNA-PK is inhibited.

In some embodiments, an inventive compound inhibits a protein kinase, wherein the kinase domain has a sequence identity greater than or equal to about 70% with respect to a Pi3K kinase domain. In some embodiments, the kinase domain has a sequence identity greater than or equal to about 75% with respect to a Pi3K kinase domain. In some embodiments, the kinase domain has a sequence identity greater than or equal to about 80% with respect to a Pi3K kinase domain. In some embodiments, the kinase domain has a sequence identity greater than or equal to about 85% with respect to a Pi3K kinase domain. In some embodiments, the kinase domain has a sequence identity greater than or equal to about 90% with respect to a Pi3K kinase domain. In some embodiments, the kinase domain has a sequence identity greater than or equal to about 95% with respect to a Pi3K kinase domain.

Purified Soluble mTORC1 and mTORC2 Kinase Complexes

While cell-based assays have been used to screen for mTOR inhibitors (Huang et al., Proc. Natl. Acad. Sci., 2004, 16594-16599), the complexity of the mTOR network can create difficulty in determining whether a putative inhibitor is binding an mTOR complex or some other component. The present disclosure describes preparations of purified, soluble mTORC1 and mTORC2 complexes. These complexes may be used for in vitro screening of modulators of each mTORC1/2 complex. Without wishing to be bound by any particular theory, it is believed that soluble mTORC1/2 complexes are more amenable to reagent aliquoting and other techniques used in high-throughput screening.

As described above, mTOR is the catalytic domain for the mTORC1 and mTORC2 complexes. Although it is possible to screen for modulators of mTOR kinase activity by using only the mTOR kinase domain, it is believed that the use of a full mTOR complex, as described herein, provides for the identification of molecules that modulate kinase activity directly as well as molecules acting as allosteric modulators. In certain embodiments, purified soluble mTOR complexes of the present invention comprise a full mTORC1 complex (mTOR, mLST8/GβL, PRAS40 and raptor). In certain embodiments, purified soluble mTOR complexes of the present invention comprise a full mTORC2 complex (mTOR, mLST8/GβL, rictor, and mSin1). In certain embodiments, purified soluble mTOR complexes of the present invention comprise a mixture of the full mTORC1 and mTORC2 complexes. In some embodiments, the complex comprises full length mTOR protein. In some embodiments, the complex comprises the mTOR kinase domain. In certain embodiments, the present invention provides a method for preparing purified soluble mTORC1 and mTORC2 kinase complexes. Complexes purified by this method can efficiently phosphorylate the native substrates S6K and Akt and are sensitive to the same inhibitors known to act in vivo. In some embodiments, the soluble complexes can be frozen and stored for extended periods of time, providing a means for maintaining consistency and reducing labor and cost across many experiments.

In one aspect, the present invention provides cell lines engineered to stably express a tagged component of an mTORC1/2 complex. In certain embodiments, HEK 293T cell lines stably express an N-terminally FLAG-tagged version of GbetaL, a component of both mTORC1 and mTORC2; an N-terminally FLAG-tagged version of Protor, a component of only mTORC2; or an N-terminally FLAG-tagged version of Raptor, a component of only mTORC1. In certain embodiments, the tagged component is a member of either mTORC1 or mTORC2. In some embodiments, the tagged component is a member of both mTORC1 and mTORC2. In certain embodiments, the tag is FLAG. In some embodiments, one or more components is non-recombinant. In some embodiments, all non-tagged components are non-recombinant.

In some embodiments, a mammalian cell line is used. In some embodiments, the mammalian cell line provides sufficient endogenous levels of non-tagged mTOR complex proteins so as to allow the formation of a full mTORC1 or mTORC2 complex upon expression of the tagged component. It will be appreciated that the stoichiometry of the expressed tagged component in relation to the endogenous components may affect the formation of a full mTORC1/2 complex. In certain embodiments, the stoichiometric ratio of the tagged component to other endogenous components of the complex is approximately 1:2. In certain embodiments, the stoichiometric ratio of the tagged component to other endogenous components of the complex is approximately 1:1. In certain embodiments, the stoichiometric ratio of the tagged component to other endogenous components of the complex is approximately 2:1. In certain embodiments, the stoichiometric ratio of the tagged component to other endogenous components of the complex is approximately 5:1. In certain embodiments, the stoichiometric ratio of the tagged component to other endogenous components of the complex is approximately 10:1. In certain embodiments, the stoichiometric ratio of the tagged component to other endogenous components of the complex is approximately 50:1.

In certain embodiments, the expression of the tagged component in a mammalian cell line is achieved by transfection or infection with a virus. In some embodiments, the virus is Murine Stem Cell Virus (MSCV). In some embodiments, expression of the tagged component in a mammalian cell line is achieved by transfection with a plasmid. Any suitable method of introducing a vector into mammalian cells for expression of the tagged component can be used. In certain embodiments, a suitable promoter may be used to direct expression. In some embodiments, the promotor is an MSCV promoter. Upon formation of a tagged mTOR complex, the complex may be purified. In some embodiments, a tag-specific antibody is used. In some embodiments, FLAG specific antibody is used to immunoprecipitate mTORC1/2 complexes from cells. Soluble complex is provided by dissociating the antibody from the mTORC1/2 complex. In certain embodiments, a gel fractionation or affinity chromatography column is used. In certain embodiments, FLAG peptide is used for elution. In certain embodiments, transfection of the tagged component is stable. In some embodiments, transfection of the tagged component is transient. One of ordinary skill will recognize that a variety of other affinity tags may be used. Suitable affinity tags include, but are not limited to, 6×His, HA tag, and Myc tag.

Purified, soluble complexes described herein may be kept active and stored for extended periods. In some embodiments, the complex may be stored in a lysis buffer as described herein (see Example 2).

In some embodiments, a provided soluble complex has a purity greater than 90%. In some embodiments, a provided soluble complex has a purity greater than 95%. In some embodiments, a provided soluble complex has a purity greater than 97%. In some embodiments, a provided soluble complex has a purity greater than 98%. In some embodiments, a provided soluble complex has a purity greater than 99%.

There is increasing evidence that defects in mTOR signaling are involved in many diseases, including cancer and diabetes. In particular, mTORC2 is known to regulate the protein Akt, an oncogene that is activated in many types of cancer. The present invention encompasses the recognition that it is useful to identify small molecules that inhibit or activate either complex as candidates for drug development or research tools. A soluble and storable preparation of an mTOR complex, such as one of the ones described herein, is a useful component of any high throughput screen of small molecule libraries.

mTOR Inhibition as an Anti-Cancer Therapy

The placement of mTOR in a pathway with a well-established role in cancer has generated substantial interest in the development and therapeutic use of mTOR inhibitors. Unfortunately, rapamycin has had limited clinical success as an anticancer therapy. Although some cancers respond well, including mantle cell lymphoma, endometrial cancer, and renal cell carcinoma, the lack of convenient, widely available, and validated biomarkers that correlate with efficacy make it difficult to understand what determines sensitivity to this drug. Another complicating feature of rapamycin treatment is that prolonged selective inhibition of mTORC1 can paradoxically activate oncogenic pathways in some cancer cell lines. S6K regulates a potent negative feedback loop that normally promotes degradation of the protein IRS1, which normally connects insulin receptor signaling to PI3K. Selective inhibition of mTORC1 relieves this suppression of insulin signaling and may have the counter-productive effect of hyperactivating the cell proliferation and survival pathways that lay downstream of PI3K.

There is evidence that rapamycin treatment inhibits mTORC2 as well as mTORC1 in at least some cell types, and that this effect may account for some of the successes of rapamycin as an anti-cancer drug. This inhibition appears to occur in two different ways. The first is that prolonged rapamycin treatment of some cancer cell lines interferes with mTORC2 assembly, presumably by physically disrupting the mTOR-Rictor interaction. The second is that high but clinically-relevant concentrations of rapamycin can inhibit mTOR directly even in the absence of FKBP12. Although it has not yet been shown that mTORC2 inhibition can account for rapamycin's uneven anti-cancer effects, it is possible that pathways downstream of mTORC2 are much more strongly associated with tumorigenesis than those that are downstream of mTORC1. In certain embodiments, compounds of the present invention are useful as general mTOR, mTORC1-specific, or mTORC2-specific inhibitors to modulate of these pathways.

It appears that mTORC1 may possess rapamycin-insensitive functions. In certain embodiments, ATP-competitive mTOR inhibition suppresses these functions. In some embodiments, the ATP-competitive mTOR inhibition is more strongly anti-proliferative than rapamycin alone. In certain embodiments, the present invention provides a method of inhibiting rapamycin-insentive features of mTORC1.

Development of mTOR Modulators

Because of the functionally distinct roles of mTORC1 and mTORC2, an in vitro method for identifying mTORC1/2-specific or general mTOR modulators was developed. Accomplishing this involves measuring the activity of each complex individually by using purified intact mTORC1 or mTORC2 kinase, and full-length S6K or Akt/PKB substrate. mTOR that lacks mTORC1- or mTORC2-specific binding partners shows deranged substrate specificity and loss of normal regulatory mechanisms. For instance, mTOR alone phosphorylates S6K but cannot phosphorylate Akt/PKB, precluding the identification of compounds that specifically inhibit mTORC2. Additionally, intact mTORC1/2 complex, but not mTOR alone, maintains regulation in vitro when purified from serum-starved or stimulated cells, indicating the existence of important regulatory mechanisms. Assays that fail to use intact mTORC1/2 are therefore unable to identify compounds that engage or interfere with Raptor- or Rictor-dependent regulatory mechanisms. Similarly, rheb can only activate intact mTORC1. Assays that fail to use mTORC1 cannot identify compounds that specifically interfere with this activating event.

The substrate used in mTORC1/2 assays also plays an important role in measuring mTORC1/2-specific activity. Akt/PKB and S6K are both members of the AGC family of kinases and share many structural features. An important difference is that Akt/PKB has an additional N-terminal pleckstrin-homology domain, and S6K has an additional C-termain domain that is often referred to as the auto-inhibitory domain. Normally, mTORC1 can only phosphorylate S6K and mTORC2 can only phosphorylate Akt/PKB. However, both complexes are able to phosphorylate a C-terminal truncation of S6K, indicating that interactions between each mTOR complex and domains in their respective substrates are involved in normal regulatory mechanisms. Therefore, assays that use truncated protein or peptide substrates may be limited in the ability to identify compounds that interfere with these mechanisms. Assays and methods provided by the present invention may be used to identify compounds that modulate mTORC1 and/or mTORC2 activity.

Assays

The present invention further provides methods for screening test compounds to identify those that exert an effect on mTORC1 or mTORC2. In certain embodiments, the methods are carried out in high-throughput fashion in multi-well plates, including, but not limited to, 24-well, 48-well, 96-well, 384-well, and 1536-well plate formats. In certain embodiments, the screen is used to identify compounds that specifically exert an effect on mTORC1. In certain embodiments, the screen is used to identify compounds that specifically exert an effect on mTORC2.

In some embodiments, the present invention provides a method for screening one or more test compounds to identify those that exert an effect on mTORC1, the method comprising the steps of:

a) introducing into each of a plurality of reaction vessels: purified mTORC1; mTORC1 substrate; ATP; and one or more test compounds whose effect on mTORC1 is to be evaluated;

b) incubating the vessels under suitable conditions and for a time sufficient to allow phosphorylation of the mTORC1 substrate; and c) assaying for the presence or amount of the phosphorylated mTORC1 substrate, thereby revealing the effect of the test compound on mTORC1.

In some embodiments, a mTORC1 substrate is any substrate that is phosphorylated by mTORC1. In certain embodiments, a purified mTORC1 substrate is S6K. In certain embodiments, a phosphorylated substrate is phospho-S6K. In some embodiments, a purified mTORC1 substrate comprises a fragment of mTORC1, wherein the fragment has at least 20 amino acids and has greater than 80% sequence homology with S6K. In some embodiments, the fragment has greater than 90% sequence homology with S6K. In some embodiments, the fragment has greater than 95% sequence homology with S6K. In some embodiments, the fragment has greater than 98% sequence homology with S6K. In some embodiments, the fragment has greater than 99% sequence homology with S6K. In some embodiments, the fragment comprises at least the phosphorylation site of S6K.

In some embodiments, a mTORC1 substrate is a variant of S6K having greater than 80% sequence homology with S6K. In some embodiments, a mTORC1 substrate is a variant of S6K having greater than 90% sequence homology with S6K. In some embodiments, a mTORC1 substrate is a variant of S6K having greater than 95% sequence homology with S6K. In some embodiments, a mTORC1 substrate is a variant of S6K having greater than 98% sequence homology with S6K. In some embodiments, a mTORC1 substrate is a variant of S6K having greater than 99% sequence homology with S6K. In some embodiments, a purified mTORC1 substrate is p70 S6K. In some embodiments, a purified mTORC1 substrate is p85 S6K. In some embodiments, a purified mTORC1 substrate is S6K2. In some embodiments, a purified mTORC1 substrate is 4E-BP1. In some embodiments, an mTORC1 substrate is labeled with a fluorophore (e.g., fluorescein, GFP, etc.).

In some embodiments, the mTORC1 complex is soluble. In some embodiments, the mTORC1 complex has been isolated.

In some embodiments, the present invention provides a method for screening one or more test compounds to identify those that exert an effect on mTORC2, the method comprising the steps of:

a) introducing into each of a plurality of reaction vessels: purified mTORC2; mTORC2 substrate; ATP; and one or more test compounds whose effect on mTORC2 is to be evaluated;

b) incubating the vessels under suitable conditions and for a time sufficient to allow phosphorylation of the mTORC2 substrate; and c) assaying for the presence or amount of the phosphorylated mTORC2 substrate, thereby revealing the effect of the test compound on mTORC2.

In some embodiments, a mTORC2 substrate is any substrate that is phosphorylated by mTORC2. In certain embodiments, a purified mTORC2 substrate is Akt/PKB. In certain embodiments, a phosphorylated substrate is phospho-Akt/PKB. In some embodiments, a purified mTORC2 substrate comprises a fragment of mTORC2, wherein the fragment has at least 20 amino acids and has greater than 80% sequence homology with Akt/PKB. In some embodiments, the fragment has greater than 90% sequence homology with Akt/PKB. In some embodiments, the fragment has greater than 95% sequence homology with Akt/PKB. In some embodiments, the fragment has greater than 98% sequence homology with Akt/PKB. In some embodiments, the fragment has greater than 99% sequence homology with Akt/PKB. In some embodiments, the fragment comprises at least the phosphorylation site of Akt/PKB.

In some embodiments, a mTORC2 substrate is a variant of Akt/PKB having greater than 80% sequence homology with Akt/PKB. In some embodiments, a mTORC2 substrate is a variant of Akt/PKB having greater than 90% sequence homology with Akt/PKB. In some embodiments, a mTORC2 substrate is a variant of Akt/PKB having greater than 95% sequence homology with Akt/PKB. In some embodiments, a mTORC2 substrate is a variant of Akt/PKB having greater than 98% sequence homology with Akt/PKB. In some embodiments, a mTORC2 substrate is a variant of Akt/PKB having greater than 99% sequence homology with Akt/PKB. In some embodiments, a purified mTORC2 substrate is Akt1. In some embodiments, a purified mTORC2 substrate is Akt2. In some embodiments, a purified mTORC2 substrate is Akt3. Other non-limiting examples of mTORC2 substrates are SGK1, SGK2, and SGK3. In some embodiments, an mTORC2 substrate is labeled with a fluorophore (e.g., fluorescein, GFP, etc.).

In some embodiments, the mTORC2 complex is soluble. In some embodiments, the mTORC2 complex has been isolated.

In certain embodiments, the methods described above further comprise a step of immobilizing proteins from the reaction vessels. In some embodiments, the step of immobilizing proteins comprises transferring the contents of the reaction vessels to a plate comprising a plurality of vessels. One of ordinary skill will appreciate that the transfer can be performed in a variety of ways, including both manual or robotic pipeting or pin tip transferring, to name but a few. In some embodiments, multi-well plates may be used, including, but not limited to, 24-well, 48-well, 96-well, 384-well, and 1536-well plates.

It will be appreciated that a variety of protein-immobilizing materials may be used in the aforementioned methods. In certain embodiments, the protein-immobilizing material is part of the plate. In some embodiments, the plate is a high-protein binding plate. In certain embodiments, the high-protein binding plate is constructed of a material comprising polystyrene. The protein binding may be through specific or non-specific interactions. In some embodiments, the protein-immobilizing material comprises antibodies. In some embodiments, the protein-immobilizing material comprises antibody fragments. In some embodiments, the antibodies or antibody fragments are specific for a phosphorylated mTORC1/2 substrate as described above.

In certain embodiments, the step of immobilizing proteins comprises the introduction of a protein-immobilizing surface into the reaction vessels. In some embodiments, the protein-immobilizing surface is a synthetic organic polymer. In some embodiments, the synthetic organic polymer comprises polystyrene.

In certain embodiments, for the methods described above, the step of assaying utilizes a detection technique selected from the group consisting of chemiluminescence, fluorescence, phosphorescence, radioactivity, colorimetry, ultraviolet spectroscopy, and infra-red spectroscopy. In some embodiments, the step of assaying utilizes chemiluminescence. In some embodiments, the step of assaying utilizes a fluorescent marker. In some embodiments, the step of assaying utilizes a radioisotope.

In some embodiments, each of the methods described above may employ one or more antibodies or antibody fragments. In certain embodiments, the antibody or antibody fragment is characterized in that is associates with a phosphorylated mTORC1/2 substrate whose presence or amount reveals the effect of a given test compound on mTORC1/2 kinase activity. In some embodiments, the step of assaying for the presence or amount of the phosphorylated mTORC1/2 substrate comprises assaying for association between an antibody and a phosphorylated mTORC1/2 substrate in the vessels. In certain embodiments, an antibody is contacted with soluble proteins. In some embodiments, an antibody is contacted with immobilized proteins. In some embodiments, an antibody is conjugated to an enzyme.

In certain embodiments, each of the methods described above may further comprise a step of introducing a secondary ligand that binds specifically to the antibody specific for phosphorylated mTORC1 or mTORC2 substrate, and wherein the step of assaying comprises assaying for bound secondary ligand. In some embodiments, the secondary ligand is an antibody. In some embodiments, the secondary ligand is an antibody fragment. In certain embodiments, the secondary ligand is conjugated to an enzyme. In some embodiments, the enzyme conjugated to either a primary or secondary antibody is horse radish peroxidase. In some embodiments, the enzyme conjugated to either a primary or secondary antibody is alkaline phosphatase. In some embodiments, the enzyme conjugated to either a primary or secondary antibody is glucose oxidase. In some embodiments, the secondary ligand is biotinylated. In some embodiments, the secondary ligand is conjugated to a fluorescent marker (e.g., fluorescein, phycoerythrin, Texas Red, AMCA, etc.). In some embodiments, the secondary ligand is conjugated to a radioisotope (e.g., $^{125}$I, $^{111}$In, etc.).

In certain embodiments, each of the methods described above may further comprise the introduction of Rheb into the reaction vessels in step (a). One of ordinary skill of the art will appreciate that Rheb functions as an activator of mTOR. The addition of Rheb can serve to identify test compounds that interfere with Rheb activation of mTOR.

In certain embodiments, each of the described above may further comprise a step of removing unassociated primary and/or secondary antibody from each reaction vessel. In some embodiments, a metal chelator may be added in step (b) or (c) of the methods described above. In some embodiments, the metal chelator quenches kinase activity. In some embodiments, the chelator is EDTA.

In some embodiments, a primary or secondary antibody used in the methods described above is labeled with a lanthanide. In some embodiments, the lanthanide is turbium. One of ordinary skill in the art will recognize that in cases wherein the substrate is labeled with a fluorophore, association with a lanthanide labeled antibody will allow for FRET-based detection of phosphorylation. While not wishing to be bound by any particular theory, it is believed that a lanthanide labeled detection system allows background signal to dissipate due to the delayed fluorescence property of lanthanides.

In some embodiments, the present invention provides a method for screening one or more test compounds to identify those that exert an effect on mTORC1, the method comprising the steps of:

a) introducing into each of a plurality of reaction vessels: purified mTORC1; mTORC1 substrate; ATP; and one or more test compounds whose effect on mTORC1 is to be evaluated;
 b) incubating the vessels under suitable conditions and for a time sufficient to allow phosphorylation of the mTORC1 substrate;
 c) immobilizing proteins from the reaction vessels;
 d) contacting said immobilized proteins with an antibody characterized in that it associates with a phosphorylated mTORC1 substrate whose presence or amount reveals the effect of a given test compound on mTORC1 kinase activity; and
 e) assaying for association between the antibody and the phosphorylated mTORC1 substrate in the vessels to assess the presence or amount of the phosphorylated mTORC1 substrate, thereby revealing the effect of the test compound on mTORC1.

In some embodiments, the present invention provides a method for screening one or more test compounds to identify those that exert an effect on mTORC2, the method comprising the steps of:

a) introducing into each of a plurality of reaction vessels: purified mTORC2; mTORC2 substrate; ATP; and one or more test compounds whose effect on mTORC2 is to be evaluated;
 b) incubating the vessels under suitable conditions and for a time sufficient to allow phosphorylation of the mTORC2 substrate;
 c) immobilizing proteins from the reaction vessels;
 d) contacting said immobilized proteins with an antibody characterized in that it associates with a phosphorylated mTORC2 substrate whose presence or amount reveals the effect of a given test compound on mTORC2 kinase activity; and
 e) assaying for association between the antibody and the phosphorylated mTORC2 substrate in the vessels to assess the presence or amount of the phosphorylated mTORC2 substrate, thereby revealing the effect of the test compound on mTORC2.

In some embodiments, the methods described above may be done in high-throughput fashion.

Other techniques, ligands, antibodies, and enzymes are known in the art and may be used in accordance with the present invention, including those described by Hornbeck, P., Curr Protoc Immunol., *Enzyme-Linked Immunosorbent Assays*, 2001 May; Chapter 2, Unit 2.1; Ausubel et al. *Current Protocols in Molecular Biology* (John Wiley & Sons, Inc., New York, 1999); *Molecular Cloning: A Laboratory Manual*, 2nd Ed., ed. by Sambrook, Fritsch, and Maniatis (Cold Spring Harbor Laboratory Press: 1989); *Antibodies: A Laboratory Manual*, E. Harlow and D. Lane, ed., Cold Spring Harbor Laboratory (Cold Spring Harbor, N.Y., 1988), each of which is herein incorporated by reference.

Definitions

Definitions of specific functional groups and chemical terms are described in more detail below. For purposes of this invention, the chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito: 1999, the entire contents of which are incorporated herein by reference.

Certain compounds of the present invention may exist in particular geometric or stereoisomeric forms. The present invention contemplates all such compounds, including cis- and trans-isomers, E- and Z-isomers, R- and S-enantiomers, diastereomers, (D)-isomers, (L)-isomers, (−)- and (+)-isomers, racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, chiral chromatography, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present invention. Those of ordinary skill in the art will readily appreciate that analogous ratios are contemplated for more complex isomer mixtures.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in inhibiting mTORC1/2. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

The term acyl as used herein refers to a moiety that includes a carbonyl group oro a group having the general formula —C(=O)R, where R is alkyl, alkenyl, alkynyl, aryl, carbocylic, heterocyclic, or aromatic heterocyclic. An example of an acyl group is acetyl.

The term aliphatic, as used herein, includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl", and the like. Furthermore, as used herein, the terms "alkyl", "alkenyl", "alkynyl", and the like encompass both substituted and unsubstituted groups. In certain embodiments, as used herein, "lower alkyl" is used to indicate those alkyl groups (cyclic, acyclic, substituted, unsubstituted, branched or unbranched) having 1-6 carbon atoms.

The term alkyl as used herein refers to saturated, straight- or branched-chain hydrocarbon radicals derived from a hydrocarbon moiety containing between one and twenty carbon atoms by removal of a single hydrogen atom. In some embodiments, the alkyl group employed in the invention contains 1-12 carbon atoms. In another embodiment, the alkyl group employed contains 1-8 carbon atoms. In still other embodiments, the alkyl group contains 1-6 carbon atoms. In yet another embodiment, the alkyl group contains 1-4 carbons. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like, which may bear one or more substituents.

In general, the terms aryl and heteroaryl, as used herein, refer to stable mono- or polycyclic, heterocyclic, polycyclic, and polyheterocyclic unsaturated moieties having preferably 3-14 carbon atoms, each of which may be substituted or unsubstituted. Substituents include, but are not limited to, any of the previously mentioned substituents, i.e., the substituents recited for aliphatic moieties, or for other moieties as disclosed herein, resulting in the formation of a stable compound. In certain embodiments of the present invention, aryl refers to a mono- or bicyclic carbocyclic ring system having one or two aromatic rings including, but not limited to, phenyl, naphthyl, tetrahydronaphthyl, indanyl, indenyl, and the like. In certain embodiments of the present invention, the term heteroaryl, as used herein, refers to a cyclic aromatic radical having from five to ten ring atoms of which one ring atom is selected from the group consisting of S, O, and N; zero, one, or two ring atoms are additional heteroatoms independently selected from the group consisting of S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups can be unsubstituted or substituted, wherein substitution includes replacement of one, two, three, or more of the hydrogen atoms thereon independently with any one or more of the following moieties including, but not limited to: aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term carboxylic acid as used herein refers to a group of formula —CO$_2$H.

The terms halo and halogen as used herein refer to an atom selected from the group consisting of fluorine, chlorine, bromine, and iodine.

The term heteroaliphatic, as used herein, refers to aliphatic moieties that contain one or more oxygen, sulfur, nitrogen, phosphorus, or silicon atoms, e.g., in place of carbon atoms. Heteroaliphatic moieties may be branched, unbranched, cyclic or acyclic and include saturated and unsaturated heterocycles such as morpholino, pyrrolidinyl, etc. In certain embodiments, heteroaliphatic moieties are substituted by independent replacement of one or more of the hydrogen atoms thereon with one or more moieties including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted.

The term heterocyclic, as used herein, refers to an aromatic or non-aromatic, partially unsaturated or fully saturated, 3- to 10-membered ring system, which includes single rings of 3 to 8 atoms in size and bi- and tri-cyclic ring systems which may include aromatic five- or six-membered aryl or aromatic heterocyclic groups fused to a non-aromatic ring. These heterocyclic rings include those having from one to three heteroatoms independently selected from the group consisting of oxygen, sulfur, and nitrogen, in which the nitrogen and sulfur heteroatoms may optionally be oxidized and the nitrogen heteroatom may optionally be quaternized. In certain embodiments, the term heterocyclic refers to a non-aromatic 5-, 6-, or 7-membered ring or a polycyclic group wherein at least one ring atom is a heteroatom selected from the group consisting of O, S, and N (wherein the nitrogen and sulfur heteroatoms may be optionally oxidized), including, but not limited to, a bi- or tri-cyclic group, comprising fused six-membered rings having between one and three heteroatoms independently selected from the group consisting of the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring.

The term aromatic heterocyclic, as used herein, refers to a cyclic aromatic radical having from five to ten ring atoms of which one ring atom is selected from the group consisting of sulfur, oxygen, and nitrogen; zero, one, or two ring atoms are additional heteroatoms independently selected from the group consisting of sulfur, oxygen, and nitrogen; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like. Aromatic heterocyclic groups can be unsubstituted or substituted with substituents selected from the group consisting of branched and unbranched alkyl, alkenyl, alkynyl, haloalkyl, alkoxy, thioalkoxy, amino, alkylamino, dialkylamino, trialkylamino, acylamino, cyano, hydroxy, halo, mercapto, nitro, carboxyaldehyde, carboxy, alkoxycarbonyl, and carboxamide.

Specific heterocyclic and aromatic heterocyclic groups that may be included in the compounds of the invention include: 3-methyl-4-(3-methylphenyl)piperazine, 3 methylpiperidine, 4-(bis-(4-fluorophenyl)methyl)piperazine, 4-(diphenylmethyl)piperazine, 4-(ethoxycarbonyl)piperazine, 4-(ethoxycarbonylmethyl)piperazine, 4-(phenylmethyl)piperazine, 4-(1-phenylethyl)piperazine, 4-(1,1-dimethylethoxycarbonyl)piperazine, 4-(2-(bis-(2-propenyl)amino)ethyl)piperazine, 4-(2-(diethylamino)ethyl)piperazine, 4-(2-chlorophenyl)piperazine, 4-(2-cyanophenyl)piperazine, 4-(2-ethoxyphenyl)piperazine, 4-(2-ethylphenyl)piperazine, 4-(2-fluorophenyl)piperazine, 4-(2-hydroxyethyl)piperazine, 4-(2-methoxyethyl)piperazine, 4-(2-methoxyphenyl)piperazine, 4-(2-methylphenyl)piperazine, 4-(2-methylthiophenyl)piperazine, 4-(2-nitrophenyl)piperazine, 4-(2-nitrophenyl)piperazine, 4-(2-phenylethyl)piperazine, 4-(2-pyridyl)piperazine, 4-(2-pyrimidinyl)piperazine, 4-(2,3-dimethylphenyl)piperazine, 4-(2,4-difluorophenyl)piperazine, 4-(2,4-dimethoxyphenyl)piperazine, 4-(2,4-dimethylphenyl)piperazine, 4-(2,5-dimethylphenyl)piperazine, 4-(2,6-dimethylphenyl)piperazine, 4-(3-chlorophenyl)piperazine, 4-(3-methylphenyl)piperazine, 4-(3-trifluoromethylphenyl)piperazine, 4-(3,4-dichlorophenyl)piperazine, 4-3,4-dimethoxyphenyl)piperazine, 4-(3,4-dimethylphenyl)piperazine, 4-(3,4-methylenedioxyphenyl)piperazine, 4-(3,4,5-trimethoxyphenyl)piperazine, 4-(3,5-dichlorophenyl)piperazine, 4-(3,5-dimethoxyphenyl)piperazine, 4-(4-(phenylmethoxy)phenyl)piperazine, 4-(4-(3,1-dimethylethyl)phenylmethyl)piperazine, 4-(4-chloro-3-trifluoromethylphenyl)piperazine, 4-(4-chlorophenyl)-3-methylpiperazine, 4-(4-chlorophenyl)piperazine, 4-(4-chlorophenyl)piperazine, 4-(4-chlorophenylmethyl)piperazine, 4-(4-fluorophenyl)piperazine, 4-(4-methoxyphenyl)piperazine, 4-(4-methylphenyl)piperazine, 4-(4-nitrophenyl)piperazine, 4-(4-trifluoromethylphenyl)piperazine, 4-cyclohexylpiperazine, 4-ethylpiperazine, 4-hydroxy-4-(4-chlorophenyl)methylpiperidine, 4-hydroxy-4-phenylpiperidine, 4-hydroxypyrrolidine, 4-methylpiperazine, 4-phenylpiperazine, 4-piperidinylpiperazine, 4-(2-furanyl)carbonyl)piperazine, 4-((1,3-dioxolan-5-yl)methyl)piperazine, 6-fluoro-1,2,3,4-tetrahydro-2-methylquinoline, 1,4-diazacylcloheptane, 2,3-dihydroindolyl, 3,3-dimethylpiperidine, 4,4-ethylenedioxypiperidine, 1,2,3,4-tetrahydroisoquinoline, 1,2,3,4-tetrahydroquinoline, azacyclooctane, decahydroquinoline, piperazine, piperidine, pyrrolidine, thiomorpholine, and triazole.

The terms substituted, whether preceded by the term "optionally" or not, and substituent, as used herein, refer to the ability, as appreciated by one skilled in this art, to change one functional group for another functional group provided that the valency of all atoms is maintained. When more than one position in any given structure may be substituted with more than one substituent selected from a specified group, the substituent may be either the same or different at every position. The substituents may also be further substituted (e.g., an aryl group substituent may have another substituent off it, such as another aryl group, which is further substituted with fluorine at one or more positions).

The term arylalkyl refers to alkyl groups in which a hydrogen atom has been replaced with an aryl group. Such groups include, without limitation, benzyl, cinnamyl, and dihyrocinnamyl.

The term heteroatom means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term unsaturated, as used herein, means that a moiety has one or more units of unsaturation.

As used herein, the term partially unsaturated refers to a ring moiety that includes at least one double or triple bond. The term "partially unsaturated" is intended to encompass rings having multiple sites of unsaturation, but is not intended to include aryl or heteroaryl moieties, as herein defined.

Additionally, unless otherwise stated, structures depicted herein are also meant to include compounds that differ only in the presence of one or more isotopically enriched positions of the compound. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention.

One of ordinary skill in the art will appreciate that the synthetic methods, as described herein, utilize a variety of protecting groups. By the term "protecting group," as used herein, it is meant that a particular functional moiety, e.g., O, S, or N, is masked or blocked, permitting, if desired, a reaction to be carried out selectively at another reactive site in a multifunctional compound. Suitable protecting groups are well known in the art and include those described in detail in *Protecting Groups in Organic Synthesis*, T. W. Greene and P. G. M. Wuts, $3^{rd}$ edition, John Wiley & Sons, 1999, the entirety of which is incorporated herein by reference. In certain embodiments, a protecting group reacts selectively in good yield to give a protected substrate that is stable to the projected reactions; the protecting group is preferably selectively removable by readily available, preferably non-toxic reagents that do not attack the other functional groups; the protecting group forms a separable derivative (more preferably without the generation of new stereogenic centers); and the protecting group will preferably have a minimum of additional functionality to avoid further sites of reaction. As detailed herein, oxygen, sulfur, nitrogen, and carbon protecting groups may be utilized. By way of non-limiting example, hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N, N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate. Amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide. Exemplary protecting groups are detailed herein, however, it will be appreciated that the present invention is not intended to be limited to these protecting groups; rather, a variety of additional equivalent protecting groups can be readily identified using the above criteria and utilized in the method of the present invention. Additionally, a variety of protecting groups are described by Greene and Wuts (supra).

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases.

Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

In other cases, the compounds of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary, tertiary, or quaternary amine. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate. Representative organic amines useful for the formation of base addition salts include ethylamine, diethylamine, ethylenediamine, ethanolamine, diethanolamine, piperazine and the like. See, for example, Berge et al., supra.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The term "soluble complex", as used herein, refers to a protein complex that is not bound to another protein or biological macromolecule which is non-essential for proper functioning of the protein complex. In certain embodiments, the protein complex is not bound to an antibody. In certain embodiments, the protein complex is not bound to an antibody fragment. In certain embodiments, the protein complex is not bound to a membrane.

The term "allosteric mTOR inhibitor", as used herein, refers to a molecule having an inhibitory effect on mTOR kinase activity without directly perturbing the kinase active site. In some embodiments, the allosteric mTOR inhibitor binds to mTOR. In some embodiments, the allosteric mTOR inhibitor binds to a component of mTORC1/2 other than mTOR.

The term "mTORC1/2", as used herein, refers to the mTORC1 complex, the mTORC2 complex, or both.

The term "full mTORC1 complex", as used herein, refers to an mTOR complex comprising at least mTOR, mLST8, and Raptor. A full mTORC1 complex may contain other proteins as well, as described herein.

The term "full mTORC2 complex", as used herein, refers to an mTOR complex comprising at least mTOR, mLST8, and Rictor. A full mTORC2 complex may contain other proteins as well, as described herein.

The term "rapalog", as used herein, refers to analogs, homologs, derivatives and other compounds related structurally to rapamycin.

As used herein, a substance and/or entity is "pure" if it is substantially free of other components. Such relative assessments of components can be determined by molar ratio, dry weight, volume, various analytical techniques (e.g., photometry, spectrometry, spectrophotometry, spectroscopy), etc. In some embodiments, a preparation that contains more than about 75% of a particular substance and/or entity is considered to be a pure preparation. In some embodiments, a substance and/or entity is at least 80%, 85%, 90%, 91%, 92%, 93%, 94%, 95%, 96%, 97%, 98%, or 99% pure.

As used herein, the term "isolated" refers to a substance or entity that has been separated from at least some of the components with which it was associated when initially produced (whether in nature or in an experimental setting). Isolated substances and/or entities may be separated from at least about 10%, about 20%, about 30%, about 40%, about 50%, about 60%, about 70%, about 80%, about 90%, or more of the other components with which they were initially associated. In some embodiments, isolated agents are more than about 80%, about 85%, about 90%, about 91%, about 92%, about 93%, about 94%, about 95%, about 96%, about 97%, about 98%, about 99%, or more than about 99% pure.

As used herein and in the claims, the singular forms "a", "an", and "the" include the plural reference unless the context clearly indicates otherwise. Thus, for example, a reference to "a compound" includes a plurality of such compounds.

Pharmaceutical Compositions

Inventive compounds may be combined with a pharmaceutically acceptable excipient to form a pharmaceutical composition. In certain embodiments, the pharmaceutical composition includes a pharmaceutically acceptable amount of an inventive compound. The amount of active ingredient which is combined with a carrier material to produce a single dosage form will vary depending upon the subject being treated, and the particular mode of administration. The amount of active ingredient that is combined with a carrier material to produce a single dosage form will generally be that amount of the compound which produces a therapeutic effect. Generally, this amount will range from about 1% to about 99% of the composition, from about 5% to about 70%, or from about 10% to about 30%.

In one aspect, the present invention provides "pharmaceutically acceptable" compositions, which comprise a therapeutically effective amount of one or more of the compounds described herein, formulated together with one or more pharmaceutically acceptable carriers (additives) and/or diluents. As described in detail, the pharmaceutical compositions of the present invention may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream or foam; sublingually; ocularly; transdermally; or nasally, pulmonary and to other mucosal surfaces.

In certain embodiments, a pharmaceutical composition may further comprise an allosteric mTOR inhibitor. In some embodiments, the allosteric mTOR inhibitor is a rapalog. Non-limiting examples of rapalogs that may be used in accordance with the present invention include rapamycin, norrapamycin, deoxorapamycin, desmethylrapamycins, desmethoxyrapamycins, AP 22594, 28-epi-rapamycin, 24,30-tetrahydro-rapamycin, AP 23573, trans-3-aza-bicyclo[3.1.0]hexane-2-carboxylic acid rapamycin, ABT-578, SDZ RAD, CCI-779, AP 20840, AP 23464, AP23675, AP23841, TAFA93, 40-0-(2-hydroxyethyl)-rapamycin, 32-deoxorapamycin, 16-pent-2-ynyloxy-32-deoxorapamycin, 16-pent-2-ynyloxy-32(S or R)-dihydro-rapamycin, 16-pent-2-ynyloxy-32(S or R)-dihydro-40-O-(2-hydroxyethyl)-rapamycin, 40-[3-hydroxy-2-(hydroxy-methyl)-2-methylpropanoate]-rapamycin (also called CC1779), 40-epi-(tetrazolyl)-rapamycin (also called ABT578), TAFA-93, biolimus-7, biolimus-9, and combinations thereof.

In certain embodiments, compounds and pharmaceutical compositions of the present invention can be employed in combination therapies, that is, the compounds and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anticancer agent), or they may achieve different effects (e.g., control of any adverse effects).

For example, other therapies or anticancer agents that may be used in combination with the inventive anticancer agents of the present invention include surgery, radiotherapy (γ-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), to name a few. Additionally, the present invention also encompasses the use of certain cytotoxic or anticancer agents currently in clinical trials and which may ultimately be approved by the FDA (including, but not limited to, epothilones and analogues thereof and geldanamycins and analogues thereof). For a more comprehensive discussion of updated cancer therapies see, www.nci.nih.gov, a list of the FDA approved oncology drugs at www.fda.gov/cder/cancer/druglistframe.htm, and The Merck Manual, Seventeenth Ed. 1999, the entire contents of which are hereby incorporated by reference.

In some embodiments, other agents that may be used in combination with the inventive anticancer agents of the present invention include MEK (mitogen-activated protein kinase-kinase) inhibitors and farnesyl transferase inhibitors (for example, Zarnestra, lonafarnib, SCH44342, or Tipifarnab).

In certain embodiments, inventive compounds are useful in treating a subject in clinical remission. In some embodiments, the subject has been treated by surgery and may have limited unresected disease.

Wetting agents, emulsifiers, and lubricants, as well as coloring agents, release agents, coating agents, sweetening, flavoring and perfuming agents, preservatives and antioxidants, can also be present in the compositions.

Examples of pharmaceutically acceptable antioxidants include water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal, and/or parenteral administration. The formulations may conveniently be presented in unit dosage form and may be prepared by any methods well known in the art of pharmacy. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary, or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol, glycerol monostearate, and non-ionic surfactants; absorbents, such as kaolin and bentonite clay; lubricants, such as talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made in a suitable machine in which a mixture of the powdered compound is moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Dissolving or dispersing the compound in the proper medium can make such dosage forms. Absorption enhancers can also be used to increase the flux of the compound across the skin. Either providing a rate controlling membrane or dispersing the compound in a polymer matrix or gel can control the rate of such flux.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions, which are compatible with body tissue.

In certain embodiments, a compound or pharmaceutical preparation is administered orally. In other embodiments, the compound or pharmaceutical preparation is administered intravenously. Alternative routes of administration include sublingual, intramuscular, and transdermal administrations.

When the compounds of the present invention are administered as pharmaceuticals, to humans and animals, they can be given per se or as a pharmaceutical composition containing, for example, 0.1% to 99.5%, or 0.5% to 90%, of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required to achieve the desired therapeutic effect and then gradually increasing the dosage until the desired effect is achieved.

In some embodiments, a compound or pharmaceutical composition of the invention is provided to a subject chronically. Chronic treatments include any form of repeated administration for an extended period of time, such as repeated administrations for one or more months, between a month and a year, one or more years, or longer. In many embodiments, a chronic treatment involves administering a compound or pharmaceutical composition of the invention repeatedly over the life of the subject. Preferred chronic treatments involve regular administrations, for example one or more times a day, one or more times a week, or one or more times a month. In general, a suitable dose such as a daily dose of a compound of the invention will be that amount of the compound that is the lowest dose effective to produce a therapeutic effect. Such an effective dose will generally depend upon the factors described above. Generally doses of the compounds of this invention for a patient, when used for the indicated effects, will range from about 0.0001 to about 100 mg per kg of body weight per day. Preferably the daily dosage will range from 0.001 to 50 mg of compound per kg of body weight, and even more preferably from 0.01 to 10 mg of compound per kg of body weight. However, lower or higher doses can be used. In some embodiments, the dose administered to a subject may be modified as the physiology of the subject changes due to age, disease progression, weight, or other factors.

If desired, the effective daily dose of the active compound may be administered as two, three, four, five, six, or more sub-doses administered separately at appropriate intervals throughout the day, optionally, in unit dosage forms.

While it is possible for a compound of the present invention to be administered alone, it is preferable to administer the compound as a pharmaceutical formulation (composition) as described above.

The compounds according to the invention may be formulated for administration in any convenient way for use in human or veterinary medicine, by analogy with other pharmaceuticals.

The invention provides kits comprising pharmaceutical compositions of an inventive compound. In certain embodiments, such kits including the combination of an inventive compound and another chemotherapeutic agent. The agents may be packaged separately or together. The kit optionally includes instructions for prescribing the medication. In certain embodiments, the kit includes multiple doses of each agent. The kit may include sufficient quantities of each component to treat a subject for a week, two weeks, three weeks, four weeks, or multiple months. The kit may include a full cycle of chemotherapy. In certain embodiments, the kit includes multiple cycles of chemotherapy.

The entire contents of all references cited above and herein are hereby incorporated by reference.

EXAMPLES

Synthesis of Common Starting Materials

Ethyl-6-chloro-4-oxo-1,4-dihydroquinoline-3-carboxylate

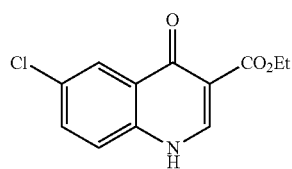 [SMILES: CCOC(=O)c1c[nH]c2ccc(Cl)cc2c1=O]

A mixture of 4-chloroaniline (156.7 mmol) and ethyl ethoxymethylenemalonate (156.7 mmol) was stirred at room temperature until homogeneous. The homogeneous solution was heated in an oil bath at 165° C. for 6 hours. The reaction mixture was cooled to room temperature and 1 N HCl (3 mL) was added. The reaction mixture was stirred and heated to 115° C. for 3 hours. The mixture was cooled to room temperature and then treated with 20 mL of water. The resulting suspension treated with 10 N NaOH solutions to reach the pH about 8. It was partitioned between ethyl acetate and water. The organic layer was separated and the aqueous layer was extracted with ethyl acetate. The combined organic extracts were washed with brine, dried over MgSO$_4$, filtered and concentrated. The crude product was purified by flash column chromatography using a 9:1 v/v hexane:ethyl acetate as solvent to afford title compound (28 g, 71% yield) as a yellow solid.

H NMR 600 MHz (DMSO-d$_6$) δ 10.58 (br, 1H), 8.28 (s, 1H), 7.52 (m, 2H), 7.32 (d, J=2.4 Hz, 1H), 4.16 (q, 2H), 1.21 (t, 3H), MS m/z: 251.90 (M+1).

Ethyl-4,6-dichloroquinoline-3-carboxylate

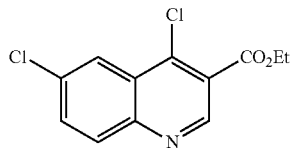 [SMILES: CCOC(=O)c1cnc2ccc(Cl)cc2c1Cl]

Ethyl-6-chloro-4-oxo-1,4-dihydroquinoline-3-carboxylate (19.8 mmol) and phosphorus (V) oxychloride (99.3 mmol) was stirred and heated to 125° C. for 12 hours. The mixture was cooled to ambient temperature and the phosphorus (V) oxychloride was evaporated. The crude product was used without further purification. MS m/z 271.80 (M+1).

Example 1

Scheme 1—Synthesis of 1-(4-benzylphenyl)-9-(4-hydroxyphenyl)benzo[h][1,6]naphthyridin-2(1H)one

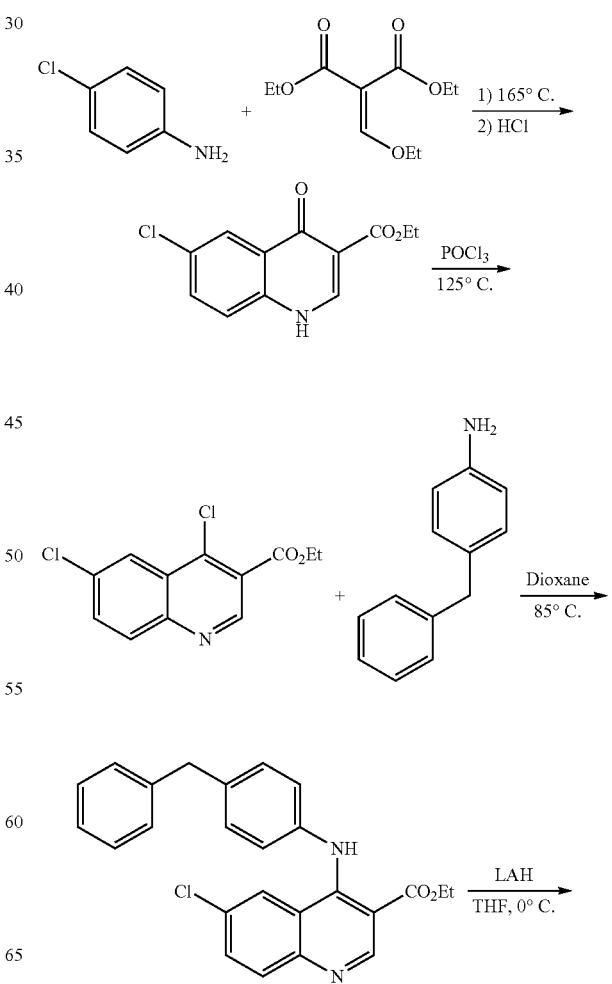

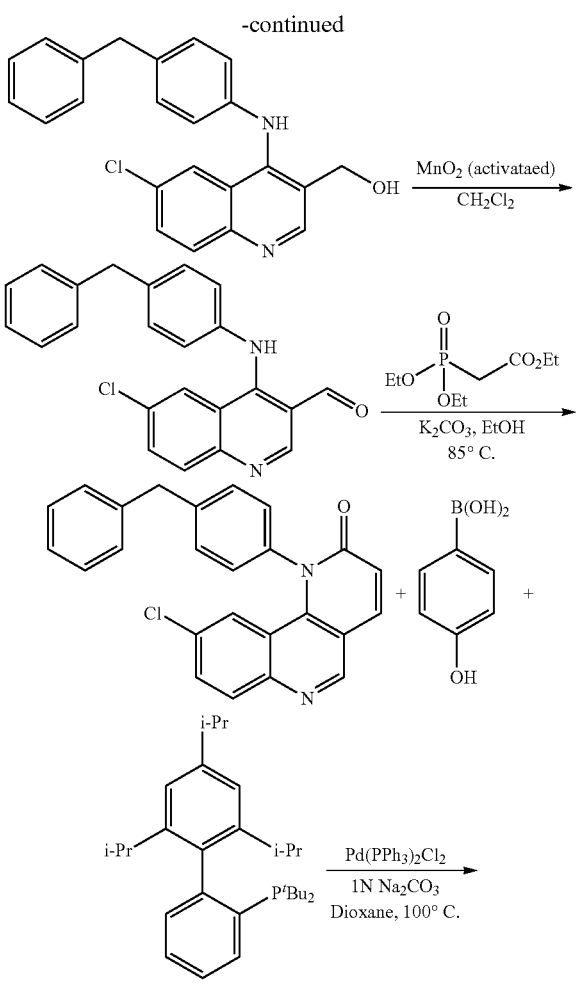

temperature until homogeneous. The homogeneous solution was heated in an oil bath at 165° C. for 6 hours. The reaction mixture was cooled to room temperature and 1 N HCl (3 mL) was added. The reaction mixture was stirred and heated to 115° C. for 3 hours. The mixture was cooled to room temperature and then treated with 20 mL of water. The resulting suspension treated with 10 N NaOH solutions to reach the pH about 8. It was partitioned between ethyl acetate and water. The organic layer was separated and the aqueous layer was extracted with ethyl acetate. The combined organic extracts were washed with brine, dried over $MgSO_4$, filtered and concentrated. The crude product was purified by flash column chromatography using a 9:1 v/v hexane:ethyl acetate as solvent to afford title compound (28 g, 71% yield) as a yellow solid.

$^1$H NMR 600 MHz (DMSO-$d_6$) δ 10.58 (br, 1H), 8.28 (s, 1H), 7.52 (m, 2H), 7.32 (d, J=2.4 Hz, 1H), 4.16 (q, 2H), 1.21 (t, 3H), MS m/z: 251.90 (M+1).

Ethyl-4,6-dichloroquinoline-3-carboxylate

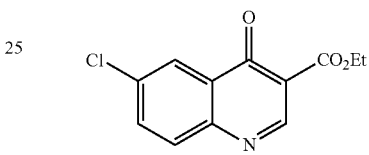

Ethyl-6-chloro-4-oxo-1,4-dihydroquinoline-3-carboxylate (19.8 mmol) and phosphorus (V) oxychloride (99.3 mmol) was stirred and heated to 125° C. for 12 hours. The mixture was cooled to ambient temperature and the phosphorus (V) oxychloride was evaporated. The crude product was used without further purification. MS m/z: 271.80 (M+1).

Ethyl 4-(4-benzylphenylamino)-6-chloroquinoline-3-carboxylate

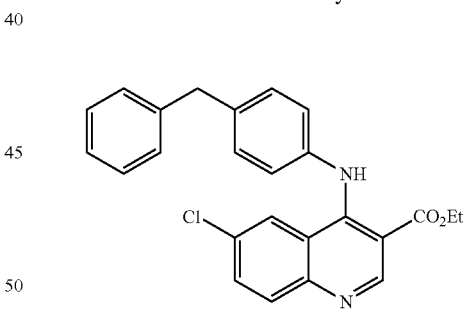

Ethyl-6-chloro-4-oxo-1,4-dihydroquinoline-3-carboxylate

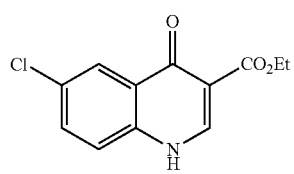 [SMILES: CCOC(=O)c1c[nH]c2ccc(Cl)cc2c1=O]

A mixture of 4-chloroaniline (156.7 mmol) and ethyl ethoxymethylenemalonate (156.7 mmol) was stirred at room To a solution of Ethyl-4,6-dichloroquinoline-3-carboxylate (1.0 g, 3.7 mmol) in 1,4-dioxane (10 mL) was added a solution of 4-benzylbenzenamine (733 mg, 4.0 mmol) in 1,4-dioxane (10 mL) at room temperature. After stirred at 85° C. 1 hour, the reaction mixture was then cooled down to room temperature and then treated with 20 mL of water. The resulting suspension treated with 10 N NaOH solutions to reach the pH about 9. It was partitioned between ethyl acetate and water. The organic layer was separated and the aqueous layer was extracted with ethyl acetate. The combined organic extracts were washed with brine, dried over $MgSO_4$, filtered and concentrated. The crude product was purified by flash column chromatography using a 9:1 v/v hexane:ethyl acetate as solvent to afford title compound (1.1 g, 65% yield) as a yellow solid.

$^1$H NMR 600 MHz (DMSO-d$_6$) δ 9.69 (s, 1H), 8.12 (d, J=2.1 Hz, 1H), 7.91 (d, J=8.8 Hz, 1H), 7.74 (dd, J=2.1, 6.7 Hz, 1H), 7.46 (m, 1H), 7.24 (m, 3H), 7.16 (m, 3H), 7.00 (d, J=8.2 Hz, 2H), 3.90 (s, 2H), 3.86 (s, 1H), 3.84 (q, J=7.0 Hz, 2H), 1.03 (t, J=7.3 Hz, 3H), MS m/z 417.36 (M+1).

(4-(4-benzylphenylamino)-6-chloroquinolin-3-yl)methanol

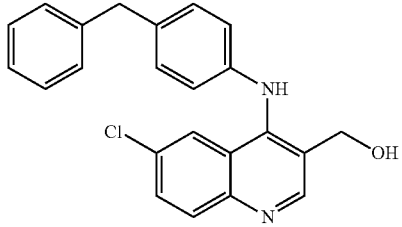 [SMILES: OCc1cnc2ccc(Cl)cc2c1Nc1ccc(Cc2ccccc2)cc1]

To a solution of Ethyl 4-(4-benzylphenylamino)-6-chloroquinoline-3-carboxylate (1.1 g, 2.6 mmol) in THF (13 mL) was added lithium aluminum hydride 2 M solution in THF (4.0 mL, 8.0 mmol) in portions over 10 min at 0° C. The dark brown reaction mixture was stirred at room temperature for 30 min and then treated with 3 mL of water. The resulting solution was dried over MgSO$_4$, filtered and concentrated. The crude product was purified by flash column chromatography using a 95:5 v/v CH$_2$Cl$_2$: EtOH as solvent to afford title compound (880 mg, 88% yield) as a yellow solid.

$^1$H NMR 600 MHz (DMSO-d$_6$) δ 8.91 (s, 1H), 8.39 (s, 1H), 8.03 (d, J=2.3 Hz, 1H), 7.97 (d, J=8.8 Hz, 1H), 7.66 (dd, J=2.3, 6.7 Hz, 1H), 7.25 (m, 2H), 7.15 (m, 2H), 7.04 (d, J=8.2 Hz, 2H), 6.64 (d, J=8.5 Hz, 2H), 4.42 (d, J=4.7 Hz, 2H), 3.83 (s, 2H), MS m/z: 375.26 (M+1).

4-(4-benzylphenylamino)-6-chloroquinoline-3-carbaldehyde

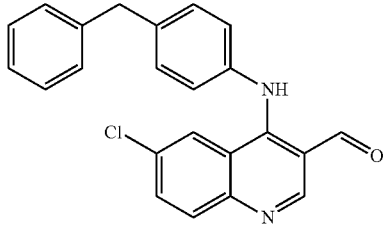 [SMILES: O=Cc1cnc2ccc(Cl)cc2c1Nc1ccc(Cc2ccccc2)cc1]

To a solution of (4-(4-benzylphenylamino)-6-chloroquinolin-3-yl)methanol (800 mg, 2.1 mmol) in CH$_2$Cl$_2$ (9 mL) was added 4-Methylmorpholine N-oxide (377 mg, 3.2 mmol) and tetrapropylammonium perruthenate at room temperature and stirred for overnight. The reaction mixture was filtered and concentrated. The crude product was used without further purification. MS m/z: 373.28 (M+1).

1-(4-benzylphenyl)-9-chlorobenzo[h][1,6]naphthyridin-2(1H)-one

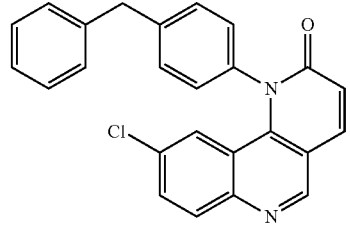 [SMILES: O=c1ccc2cnc3ccc(Cl)cc3c2n1-c1ccc(Cc2ccccc2)cc1]

To a solution of 4-(4-benzylphenylamino)-6-chloroquinoline-3-carbaldehyde (750 mg, 2.0 mmol) in EtOH (18 mL) was added triethyl phosphonoacetate (1.1 mL, 5.6 mmol) and K$_2$CO$_3$ (1.3 g, 9.3 mmol). The reaction mixture was stirred at 85° C. for 8 hours and then removed solvent. The reaction mixture was treated with 10 mL of water. It was partitioned between ethyl acetate and water. The organic layer was separated and the aqueous layer was extracted with ethyl acetate. The combined organic extracts were washed with brine, dried over MgSO$_4$, filtered and concentrated. The crude product was purified by flash column chromatography using a 97:3 v/v CH$_2$Cl$_2$: EtOH as solvent to afford title compound (510 mg, 64% yield) as a yellow solid.

$^1$H NMR 600 MHz (CDCl$_3$) δ 9.11 (s, 1H), 8.36 (s, 1H), 8.00 (d, J=2.1 Hz, 1H), 7.91 (d, J=8.4 Hz, 1H), 7.68 (dd, J=2.4, 6.7 Hz, 1H), 7.23 (m, 2H), 7.14 (m, 2H), 7.03 (m, 3H), 6.72 (d, J=8.6 Hz, 2H), 6.54 (dd, J=2.3, 6.2 Hz, 1H), 3.80 (s, 2H), MS m/z: 397.23 (M+1).

1-(4-benzylphenyl)-9-(4-hydroxyphenyl)benzo[h][1,6]naphthyridin-2(1H)one

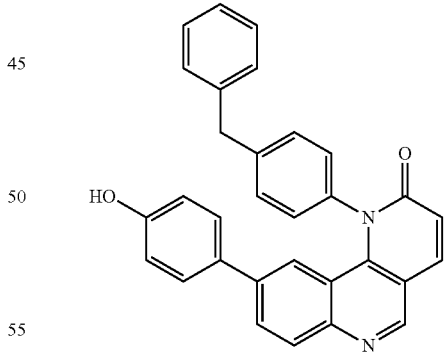

To a solution of 1-(4-benzylphenyl)-9-chlorobenzo[h][1,6]naphthyridin-2(1H)-one (100 mg, 0.22 mmol) in 1,4-dioxane (0.6 mL) was added 4-hydroxyphenylboronic acid (45 mg, 0.33 mmol) and 1 N Na$_2$CO$_3$ (0.66 mL, 0.66 mmol). The reaction mixture was degassed using Argon gas for 10 min and added Pd(PPh$_3$)$_2$Cl$_2$ (15 mg, 0.02 mmol) and di-tert-butyl (2',4',6'-triisopropylbiphenyl-2-yl)phosphine (15 mg, 0.04 mmol). The reaction flask was put into the preheated oil-bath at 100° C. The reaction mixture was further stirred at 100° C. a period of 8 hours after which, it was filtered and partitioned between ethyl acetate and water. The organic layer was separated and the aqueous layer was extracted with ethyl acetate. The combined organic extracts were washed with brine, dried over MgSO₄, filtered and concentrated. The crude product was purified by flash column chromatography using a 97:3 v/v CH₂Cl₂: EtOH as solvent to afford title compound (64 mg, 64% yield) as a yellow solid. ¹H NMR 600 MHz (CDCl₃) δ 9.08 (s, 1H), 8.42 (s, 1H), 8.04 (d, J=2.4 Hz, 1H), 7.95 (d, J=8.2 Hz, 1H), 7.61 (dd, J=2.1, 6.6 Hz, 1H), 7.25 (m, 2H), 7.12 (m, 4H), 7.00 (m, 5H), 6.75 (d, J=8.4 Hz, 2H), 6.48 (dd, J=2.4, 6.2 Hz, 1H), 3.88 (s, 2H), MS m/z: 455.27 (M+1).

Example 2

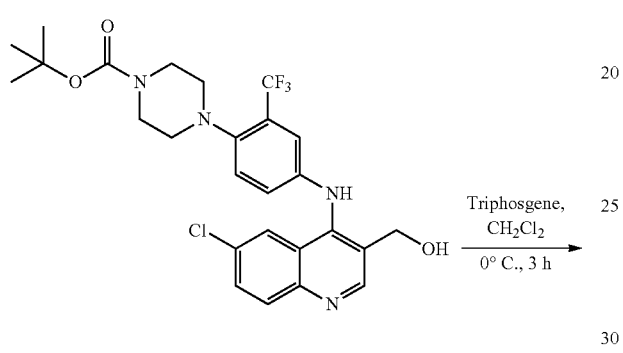

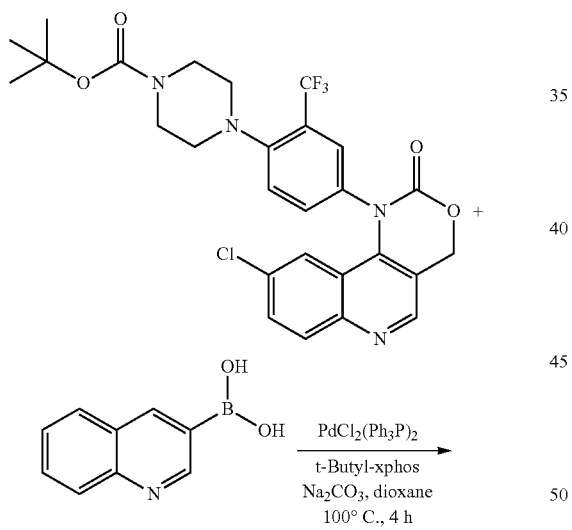

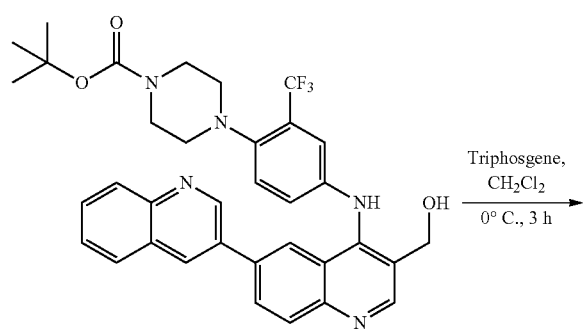

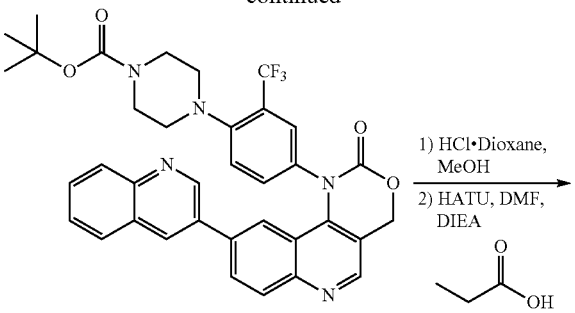

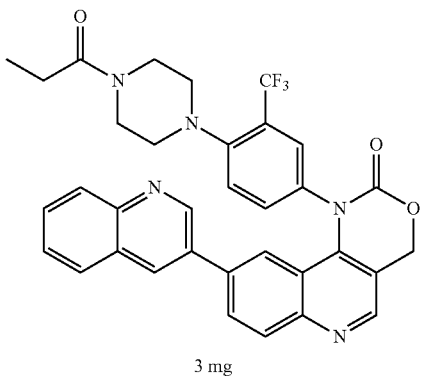

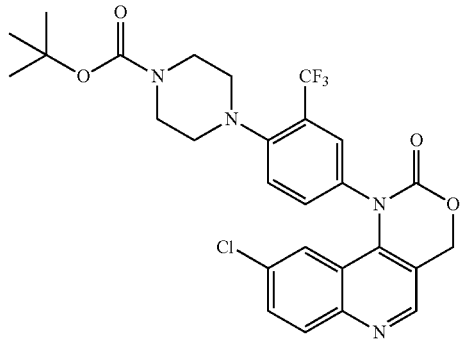

3 mg

Tert-butyl 4-(4-(9-chloro-2-oxo-2H-[1,3]oxazino[5,4-c]quinolin-1(4H)-yl)-2-(trifluoromethyl)phenyl)piperazine-1-carboxylate. To a solution of tert-butyl 4-(4-(6-chloro-3-(hydroxymethyl)quinolin-4-ylamino)-2-(trifluoromethyl)phenyl)piperazine-1-carboxylate (407 mg, 0.75 mmol) in dichloromethane (10 mL) at 0° C. was added triphosgene (225 mg, 0.75 mmol) and Et₃N (125 μL, 0.9 mmol). The resultant solution was allowed to warm up to room temperature and continued to stir for 4 h before being quenched with a satd. aqueous sodium bicarbonate (10 mL), extracted with EtOAc (3×20 mL), and dried over Na₂SO₄. After removal of the solvent in vacuo, the residue was purified by flash column chromatography to afford the title product (57%) as colorless oil. LC-MS: (M+H)=563.26

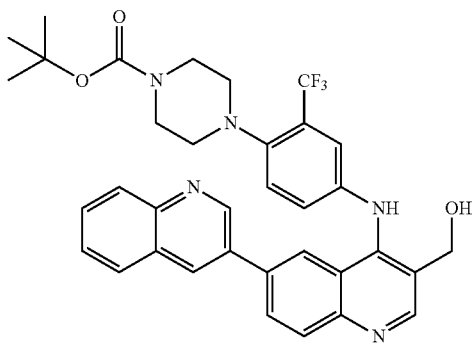 [SMILES: CC(C)(C)OC(=O)N1CCN(c2ccc(Nc3c(CO)cnc4ccc(-c5cnc6ccccc6c5)cc34)cc2C(F)(F)F)CC1]

Tert-butyl-4-(4-(3'-(hydroxymethyl)-3,6'-biquinolin-4'-ylamino)-2-(trifluoromethyl)phenyl)piperazine-1-carboxylate. To a solution of tert-butyl 4-(4-(9-chloro-2-oxo-2H-[1,3]oxazino[5,4-c]quinolin-1(4H)-yl)-2-(trifluoromethyl)phenyl)piperazine-1-carboxylate (56 mg, 0.1 mmol) and quinolin-3-ylboronic acid (25 mg, 0.15 mmol) in 1,4-dioxane (1 mL) at room temperature was added bischlorotriphenyl phosphine palladium (4 mg, 0.005 mmol), tert-butyl Xphos (4 mg, 0.01 mmol), and Na$_2$CO$_3$ (0.3 mL, 0.3 mmol). The resultant solution was heated to 100° C. for 4 h and then allowed to cool to room temperature, filtered through celite, and washed with EtOAc (3×10 mL). After removal of solvent in vacuo, the residue was purified by flash column chromatography to afford the title compound (35 mg, 55%). LC-MS: (M+H)=630.30

1-(4-(4-propionylpiperazin-1-yl)-3-(trifluoromethyl)phenyl)-9-(quinolin-3-yl)-1H-[1,3]oxazino[5,4-c]quinolin-2(4H)-one. To a solution of tert-butyl 4-(4-(2-oxo-9-(quinolin-3-yl)-2H-[1,3]oxazino[5,4-c]quinolin-1(4H)-yl)-2-(trifluoromethyl)phenyl)piperazine-1-carboxylate obtained from above reaction in EtOH (0.5 mL) at room temperature was added HCl in dioxane (4.0 M, 1 mL). After 4 h, the solvent was removed and the residue was redissolved in DMF (2 mL). Propionic acid (8 μL, 0.1 mmol), HATU (38 mg, 0.1 mmol) and DIEA (26 μL, 0.15 mmol) was added and the resultant solution was stirred at room temperature for 4 h. After filtration, the reaction mixture was subjected to LC-MS-HPLC purification and afforded pure product (2.0 mg). LC-MS: (M+H)=612.22

Example 3

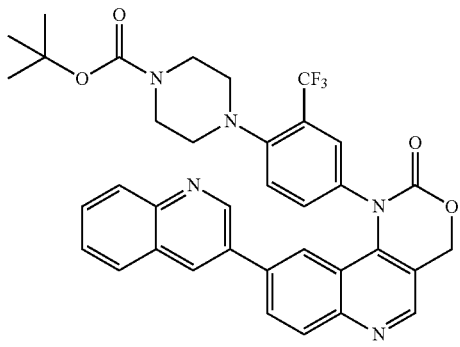 [SMILES: CC(C)(C)OC(=O)N1CCN(c2ccc(N3C(=O)OCc4cnc5ccc(-c6cnc7ccccc7c6)cc5c43)cc2C(F)(F)F)CC1]

Tert-butyl 4-(4-(2-oxo-9-(quinolin-3-yl)-2H-[1,3]oxazino[5,4-c]quinolin-1(4H)-yl)-2-(trifluoromethyl)phenyl)piperazine-1-carboxylate. To a solution of tert-butyl 4-(4-(3'-(hydroxymethyl)-3,6'-biquinolin-4'-ylamino)-2-(trifluoromethyl)phenyl)piperazine-1-carboxylate (35 mg, 0.05 mmol) in dichloromethane (5 mL) at 0° C. was added triphosgene (16 mg, 0.05 mmol), and the resultant solution was allowed to warm up to room temperature. The reaction was allowed to proceed for 4 h before quenching with a satd. aqueous sodium carbonate solution (3 mL). The reaction mixture was extracted with EtOAc (3×10 mL) and dried over Na$_2$SO$_4$. The crude product was taken onto the next step without further purification. LC-MS: (M+1)=656.30

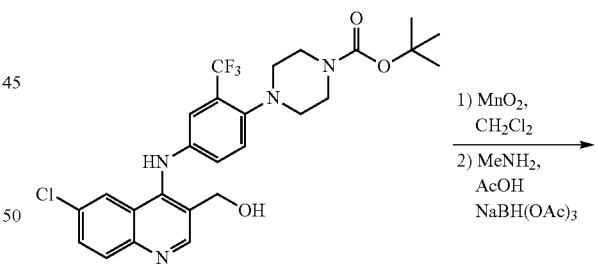

-continued

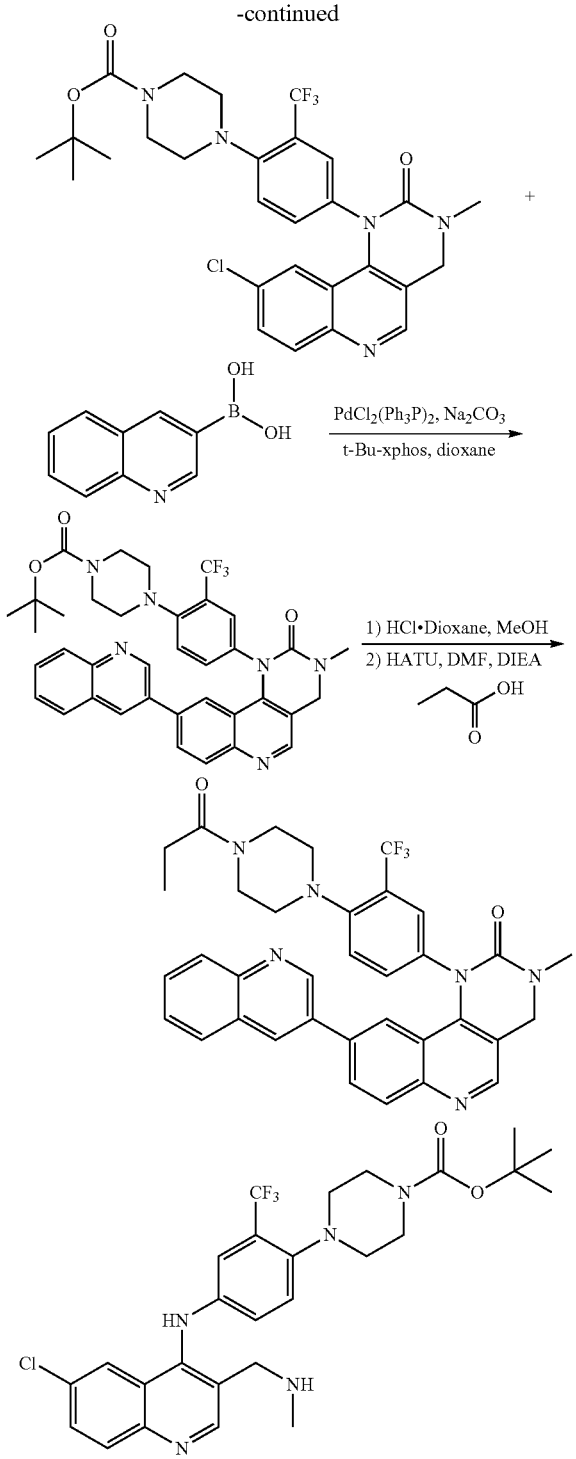

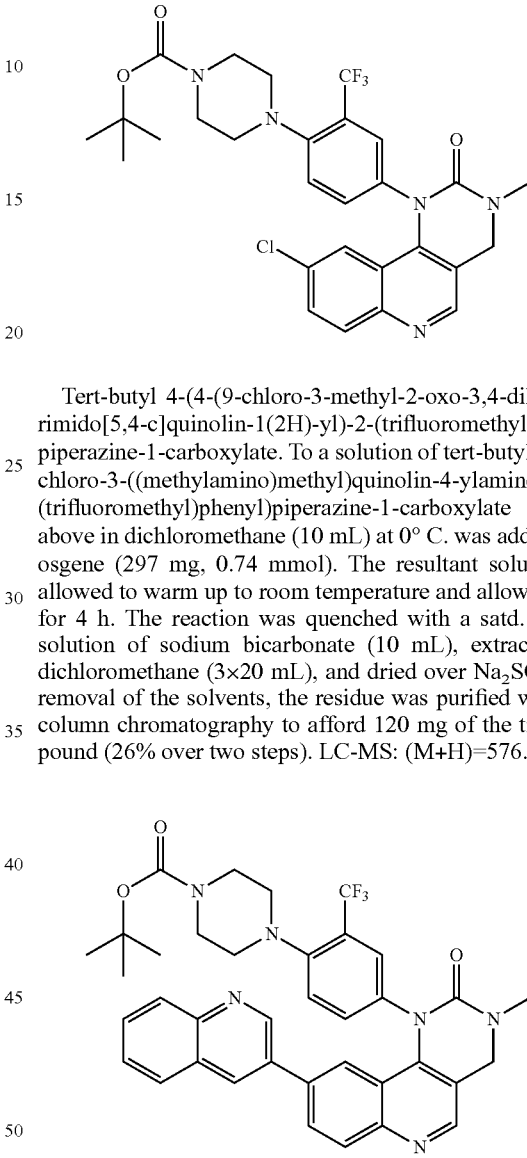

The solution was stirred at room temperature overnight, quenched with NaHCO$_3$ (sat. 10 mL), extracted with EtOAc (20 mL×3), and dried over Na$_2$SO$_4$. After removal of solvent in vacuo, the crude product was taken to next step without further purification. LC-MS: (M+H)=550.32

Tert-butyl 4-(4-(9-chloro-3-methyl-2-oxo-3,4-dihydropyrimido[5,4-c]quinolin-1(2H)-yl)-2-(trifluoromethyl)phenyl)piperazine-1-carboxylate. To a solution of tert-butyl 4-(4-(6-chloro-3-((methylamino)methyl)quinolin-4-ylamino)-2-(trifluoromethyl)phenyl)piperazine-1-carboxylate obtained above in dichloromethane (10 mL) at 0° C. was added triphosgene (297 mg, 0.74 mmol). The resultant solution was allowed to warm up to room temperature and allowed to stir for 4 h. The reaction was quenched with a satd. aqueous solution of sodium bicarbonate (10 mL), extracted with dichloromethane (3×20 mL), and dried over Na$_2$SO$_4$. After removal of the solvents, the residue was purified with flash column chromatography to afford 120 mg of the title compound (26% over two steps). LC-MS: (M+H)=576.19

Tert-butyl 4-(4-(3-methyl-2-oxo-9-(quinolin-3-yl)-3,4-dihydropyrimido[5,4-c]quinolin-1(2H)-yl)-2-(trifluoromethyl)phenyl)piperazine-1-carboxylate. To a solution of tert-butyl 4-(4-(9-chloro-3-methyl-2-oxo-3,4-dihydropyrimido[5,4-c]quinolin-1(2H)-yl)-2-(trifluoromethyl)phenyl)piperazine-1-carboxylate (57 mg, 0.1 mmol) and quinolin-3-ylboronic acid (26 mg, 0.15 mmol) in 1,4-dioxane (2 mL) at room temperature was added bischlorotriphenylphosphine (4 mg, 0.005 mmol), tert-butyl xphos (4 mg, 0.01 mmol), and Na$_2$CO$_3$ (0.3 mL, 0.3 mmol). The resultant solution was heated to 100° C. for 12 h before cooling to room temperature. The reaction mixture was filtered through celite. The solvent was removed in vacuo and the resulting crude residue was purified by flash column chromatography to afford the title product 32 mg (47%). LC-MS: (M+H)=668.38

Tert-butyl 4-(4-(6-chloro-3-((methylamino)methyl)quinolin-4-ylamino)-2-(trifluoromethyl)phenyl)piperazine-1-carboxylate. To a solution of tert-butyl 4-(4-(6-chloro-3-(hydroxymethyl)quinolin-4-ylamino)-2-(trifluoromethyl)phenyl)piperazine-1-carboxylate (400 mg, 0.74 mmol) in dichloromethane (10 mL) at room temperature was added MnO$_2$ (2 g). The resultant solution was stirred for 3 h before filtering through celite and washing with dichloromethane (20 mL). After removal solvent in vacuo, the residue was redisolved in THF (5 mL), to which NaBH(OAc)$_3$ (443 mg, 2.1 mmol) and CH$_3$NH$_2$HCl (140 mg, 2.1 mmol) were added.

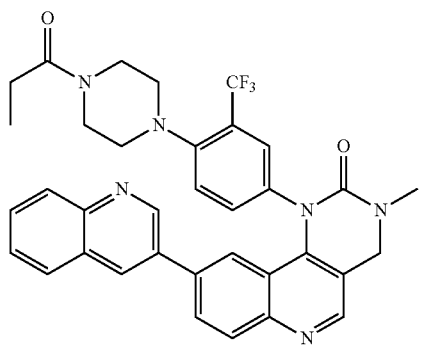

3-Methyl-1-(4-(4-propionylpiperazin-1-yl)-3-(trifluoromethyl)phenyl)-9-(quinolin-3-yl)-3,4-dihydropyrimido[5,4-c]quinolin-2(1H)-one. To a solution of tert-butyl 4-(4-(3-methyl-2-oxo-9-(quinolin-3-yl)-3,4-dihydropyrimido[5,4-c]quinolin-1(2H)-yl)-2-(trifluoromethyl)phenyl)piperazine-1-carboxylate (32 mg, 0.047 mmol) in EtOH (1 mL) at room temperature was added a solution of hydrochloric acid in dioxane (4M, 2 mL). The resulting solution was allowed to stir for 4 h. After removal of solvents in vacuo, the residue was redissolved in DMF (2 mL), to which HATU (53 mg, 0.14 mmol), propionic acid (8 μL, 0.094 mmol), and DIEA (24 μL, 0.14 mmol) were added. The resultant solution was stirred for 4 h before filtration. The crude product was subjected to LC-MS-HPLC purification to afford 5 mg of product. LC-MS: (M+H)=9025.22.

Example 4

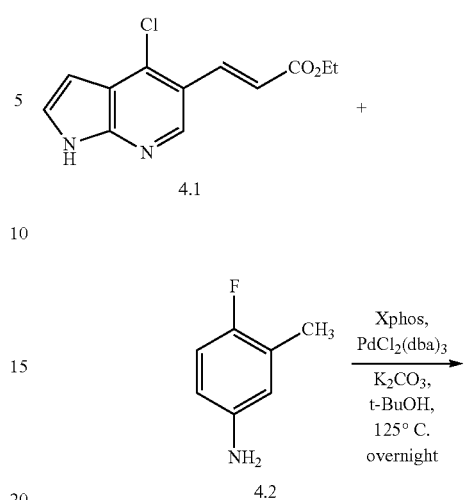

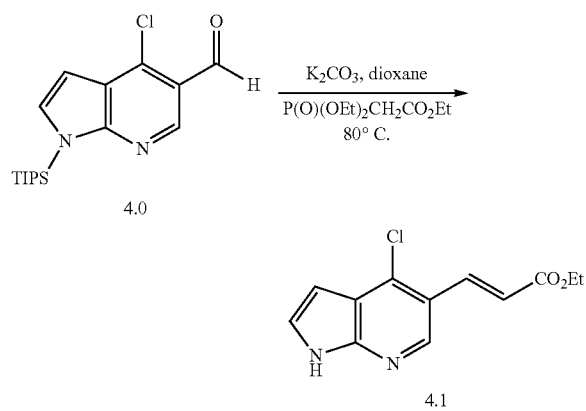

To a solution of compound 4.0 4-chloro-1-(triisopropylsilyl)-1H-pyrrolo[2,3-b]pyridine-5-carbaldehyde (1.7 g, 5 mmol, 1 equiv.) in dioxane (20 mL) at room temperature was added triethyl phosphonoacetate (3 mL, 15 mmol, 3 equiv.) and $K_2CO_3$ (3.45 g, 25 mmol, 5 equiv.). The resulting mixture was heated overnight at 80° C. under argon. Upon cooling to room temperature, the mixture was diluted with EtOAc (50 mL) and washed with water (50 mL) and brine (50 mL). The organic phase was dried over $Na_2SO_4$, after removal of solvent under vacuum. The resulting residue was purified with flash chromatography (Hexanes: EtOAc=6:1) to afford the desired product 4.1 (E)-ethyl 3-(4-chloro-1H-pyrrolo[2,3-b]pyridin-5-yl)acrylate (0.63 g; 50%). LC-MS: (M+H) 251.29

To a solution of 4.1 (E)-ethyl 3-(4-chloro-1H-pyrrolo[2,3-b]pyridin-5-yl)acrylate (510 mg, 2 mmol, 1 equiv.) in t-BuOH (30 mL) in a sealed tube at room temperature was added 4.2 4-fluoro-3-methylbenzenamine (510 mg, 4 mmol, 2 equiv.), Xphos (95 mg, 0.2 mmol, 0.1 equiv.), $PdCl_2(dba)_3$ (92 mg, 0.1 mmol, 0.05 equiv.) and $K_2CO_3$ (607 mg, 4.4 mmol, 2.2 equiv.). The resulting mixture was degassed, sealed, and heated overnight at 125° C. Upon cooling to room temperature, the reaction mixture was filtered through celite, washed with EtOAc (50 mL×3), concentrated, and the resulting residue was purified via flash chromatography (Hexanes: EtOAc 1:1) to afford the desired product 4.3 (E)-ethyl 3-(4-(3-fluoro-4-methylphenylamino)-1H-pyrrolo[2,3-b]pyridin-5-yl)acrylate (540 mg; 78%). LC-MS: (M+H) 340.24

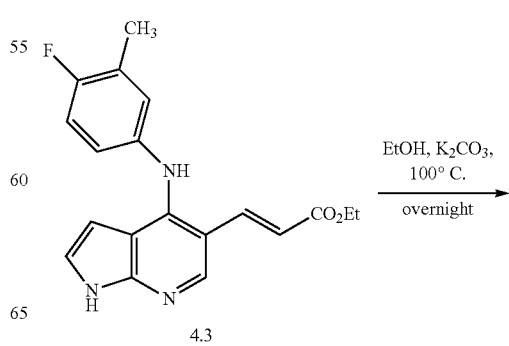

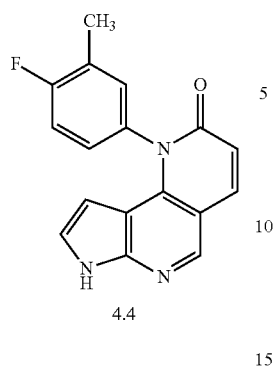

4.4

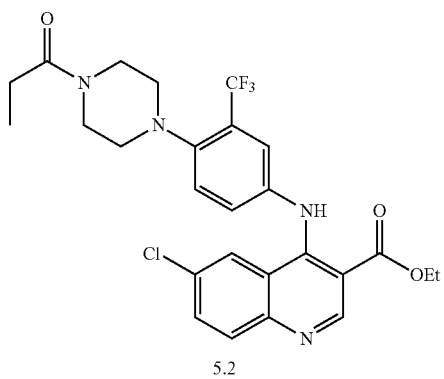

5.2

To a solution of 4.3 (E)-ethyl 3-(4-(3-fluoro-4-methylphenylamino)-1H-pyrrolo[2,3-b]pyridin-5-yl)acrylate (540 mg, 1.59 mmol, 1 equiv.) in EtOH (10 mL) in a sealed tube at room temperature was added $K_2CO_3$ (1.1 g, 7.96 mmol, 5 equiv.). The reaction mixture was sealed, stirred, and heated overnight to 100° C. Upon cooling to room temperature, the resulting mixture was diluted with EtOAc (50 mL) and washed with $H_2O$ (30 mL×3) and brine (30 mL). The organic phase was dried over $Na_2SO_4$. After removal of solvent, the residue was purified with flash chromatography to afford the desired product 4.4 1-(4-fluoro-3-methylphenyl)-1H-pyrrolo[2,3-h][1,6]naphthyridin-2(7H)-one (370 mg; 80%). LC-MS: (M+H) 294.37

Example 5

To a solution of 5.0 ethyl 4,6-dichloroquinoline-3-carboxylate (1.08 g, 4 mmol, 1 equiv.) in 1,4-dioxane (10 mL) at room temperature was added compound 5.1 1-(4-(4-amino-2-(trifluoromethyl)phenyl)piperazin-1-yl)propan-1-one (1.2 g, 4 mmol, 1 equiv.). The resulting solution was heated to 80° C. and stirred 4 h before cooling to room temperature. NaOH ON aqueous solution, 3 mL) was added. The solution was diluted with EtOAc (30 mL) and washed with water (30 mL×2) and brine (30 mL). The organic phase was dried over $Na_2SO_4$. After removal of solvents, the residue was purified via flash chromatography ($CH_2Cl_2$: MeOH=20:1) to afford the desired product 5.2 ethyl 6-chloro-4-(4-(4-propionylpiperazin-1-yl)-3-(trifluoromethyl)phenylamino)quinoline-3-carboxylate (2 g; 93%). LC-MS: (M+H): 622.20

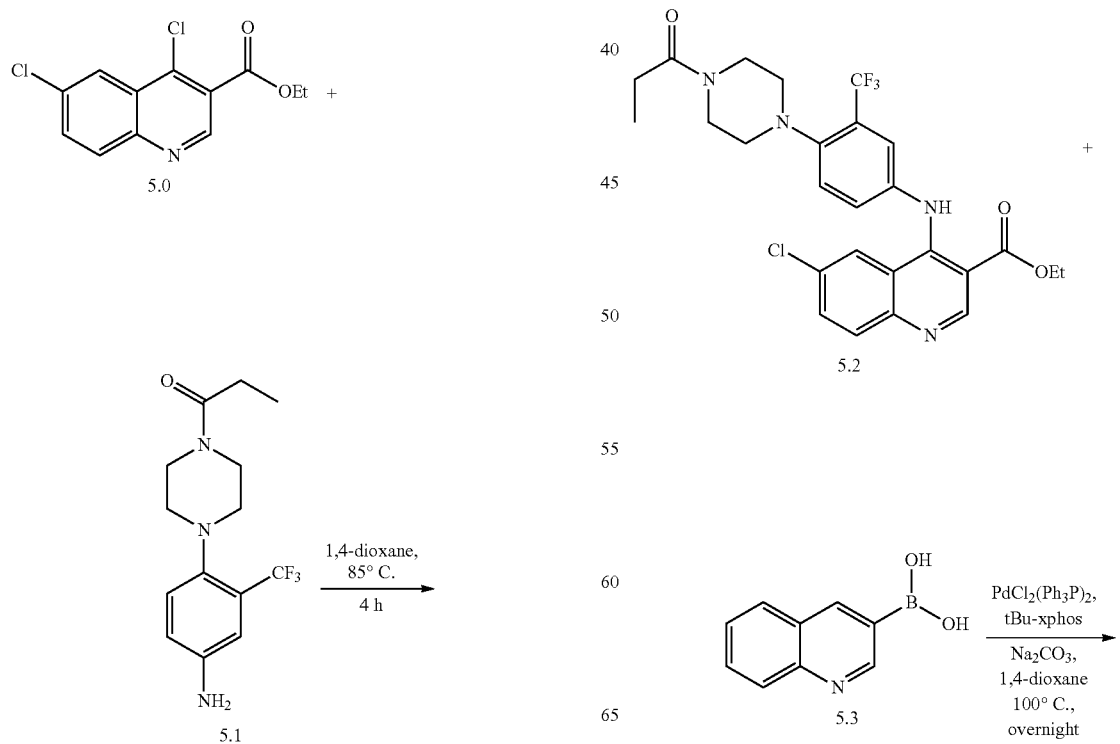

-continued

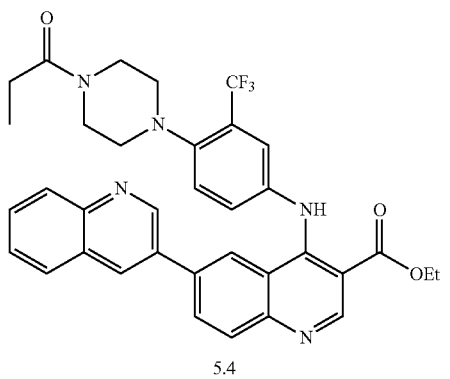

5.4

To a solution of compound 5.2 ethyl 6-chloro-4-(4-(4-propionylpiperazin-1-yl)-3-(trifluoromethyl)phenylamino)quinoline-3-carboxylate (1 g, 1.6 mmol, 1 equiv.) in dioxane (5 mL) at room temperature was sequentially added 3-qunionline boronic acid 5.3 (350 mg, 2 mmol, 1.1 equiv.), PdCl$_2$(Ph$_3$P)$_2$ (130 mg, 0.19 mmol, 0.1 equiv.), t-Bu-Xphos (78 mg, 0.19 mmol, 0.1 equiv.) and Na$_2$CO$_3$ (1N, 5.5 mL, 5.5 mmol, 3 equiv.). The mixture was degassed, sealed under argon, and heated overnight at 100° C. Upon cooling to room temperature, the mixture was diluted with EtOAc (20 mL), filtered through celite, and washed with EtOAc (20 mL×2). The resulting solution was concentrated and the residue was purified via flash chromagraphy (CH$_2$Cl$_2$: MeOH=30:1) to afford the desired product 5.4 ethyl 4'-(4-(4-propionylpiperazin-1-yl)-3-(trifluoromethyl)phenylamino)-3,6'-biquinoline-3'-carboxylate (360 mg; 31%). LC-MS: (M+H): 535.20

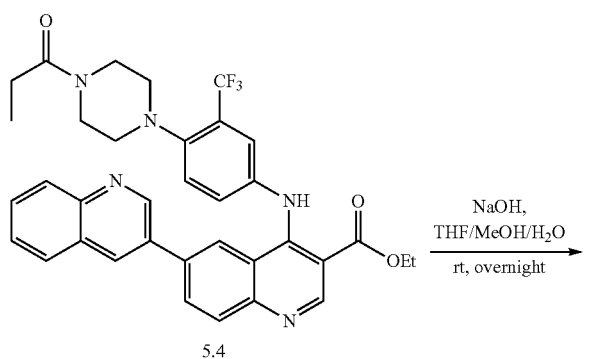

-continued

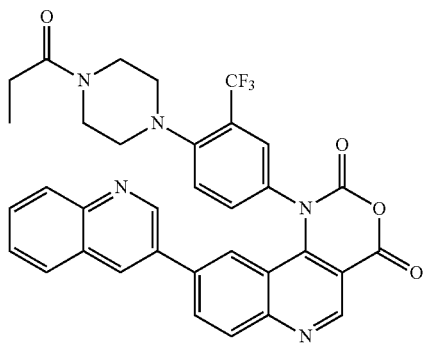

5.6

To a solution of compound 5.4 ethyl 4'-(4-(4-propionylpiperazin-1-yl)-3-(trifluoromethyl)phenylamino)-3,6'-biquinoline-3'-carboxylate in THF/MeOH/H$_2$O (1:1:1, 6 mL) at room temperature was added NaOH (76 mg, 1.9 mmol, 5 equiv.). The resulting solution was stirred overnight. To the mixture was added HCl (1N) to adjust the pH to 4, and EtOAC (20 mL) to extract the product. The organic layer was concentrated to afford the desired product 5.5 4'-(4-(4-propionylpiperazin-1-yl)-3-(trifluoromethyl)phenylamino)-3,6'-biquinoline-3'-carboxylic acid. LC-MS (M+H): 622.21

The crude compound 5.5 4'-(4-(4-propionylpiperazin-1-yl)-3(trifluoromethyl)phenylamino)-3,6'-biquinoline-3'-carboxylic acid (20 mg, 0.033 mmol, 1 equiv.) in CH$_2$Cl$_2$ (3 mL) at 0° C. was added triphosgene (10 mg, 0.033 mmol, 1 equiv.) and DIEA (17 µL, 0.1 mmol, 3 equiv.). The resulting solution was warmed to room temperature in 3 hours and further stirred for 1 hour before being quenched with NaHCO$_3$ (sat. 1 mL) and extracted with CH$_2$Cl$_2$ (5 mL×2). The organic phase was dried over Na$_2$SO$_4$ and the residue was purified via preparative LC-MS (CH$_3$CN: H$_2$O) to afford the desired product 5.6 1-(4-(4-propionylpiperazin-1-yl)-3-(trifluoromethyl)phenyl)-9-(quinolin-3-yl)-1H-[1,3]oxazino[5,4-c]quinoline-2,4-dione (1.3 mg). LC-MS (M+H): 626.20

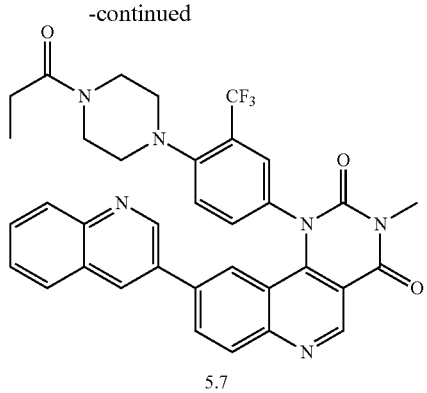

5.7

To a solution of compound 5.6 1-(4-(4-propionylpiperazin-1-yl)-3-(trifluoromethyl)phenyl)-9-(quinolin-3-yl)-1H-[1,3]oxazino[5,4-c]quinoline-2,4-dione (20 mg, 0.032 mmol, 1 equiv.) in THF/CH$_2$Cl$_2$ (5 mL, 1:1) at room temperature was added MeNH$_2$ (5 mg, 0.16 mmol, 5 equiv.). The resulting solution was heated to 40° C. and stirred for 2 h. Upon concentration, the mixture was purified via preparative LC-MS (CH$_3$CN:H$_2$O) to furnish the desired compound 5.7 3-methyl-1-(4-(4-propionylpiperazin-1-yl)-3-(trifluoromethyl)phenyl)-9-(quinolin-3-yl)pyrimido[5,4-c]quinoline-2,4(1H,3H)-dione (3 mg). LC-MS (M+H): 639.49

Example 6

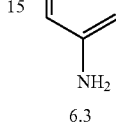
6.0

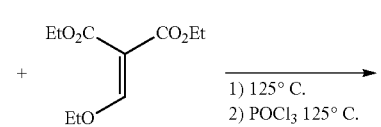
6.1

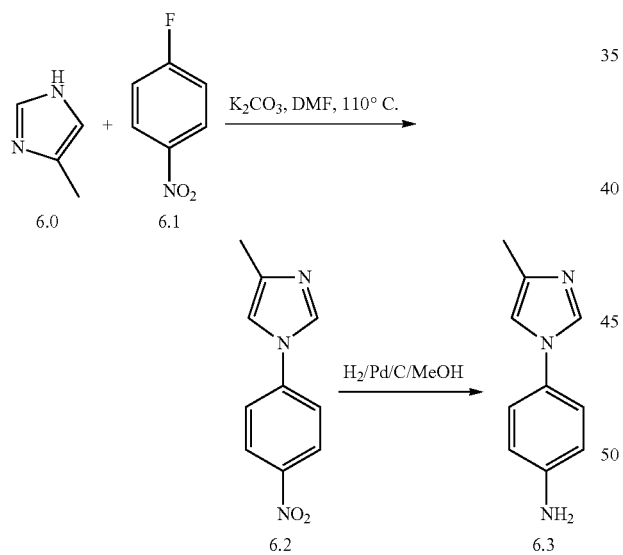
6.2        6.3

To a solution of compound 6.0 4-methyl imidazole (1 mL, 10 mmol, 1 equiv.) in DMF at room temperature was added 1-fluoro-4-nitrobenzene 6.1 (820 mg, 10 mmol, 1 equiv.) and K$_2$CO$_3$ (1.38 g, 10 mmol, 1 equiv.). The resulting mixture was heated to 110° C. for 4 h before being cooled to room temperature, filtered through celite, and washed with EtOAc (20 mL×4). The collected filtrate was further washed with brine (50 mL×3) and dried over Na$_2$SO$_4$. After removal of solvent, the residue was diluted with MeOH (20 mL). Pd/C (50 mg, 5% mass equiv.) was added and the reaction flask was charged with a H$_2$ balloon and stirred overnight at room temperature. The mixture was filtered through celite and washed with EtOAc (20 mL×3). The collected filtrate was concentrated and the residue was purified via flash chromatography (hexanes: EtOAc=1:1) to afford the desired product 6.3 4-(4-methyl-1H-imidazol-1-yl)benzenamine (1.0 g; 60%). LC-MS (M+H):174.15

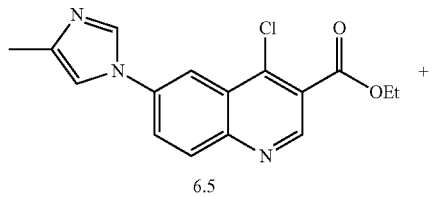
6.4

6.5

6.6

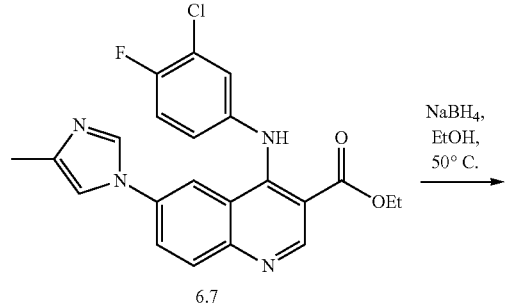
6.7

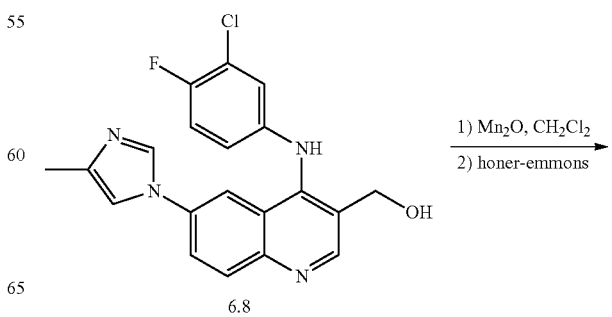
6.8

103
-continued

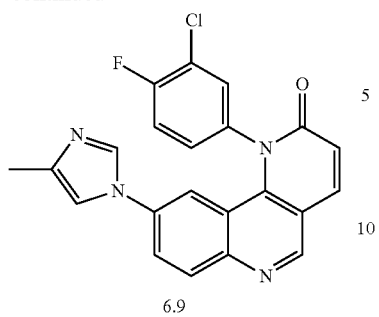
6.9

Compound 6.9 was similarly prepared from compound 6.3 according to the above described procedures.

Example 7

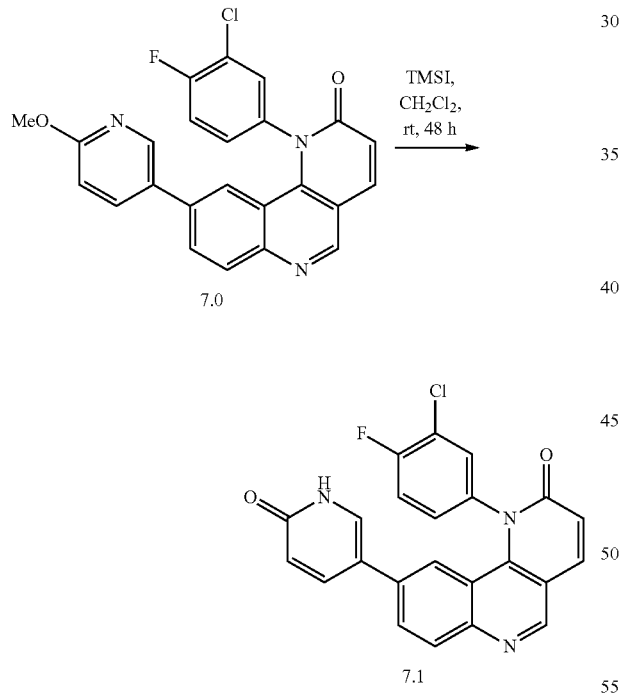

To a solution of compound 7.0 1-(3-chloro-4-fluorophenyl)-9-(6-methoxypyridin-3-yl)benzo[h][1,6]naphthyridin-2(1H)-one (21 mg, 0.05 mmol, 1 equiv.) in CH₂Cl₂ (2 mL) at room temperature was added TMSI (70 µL, 0.5 mmol, 10 equiv.). The resulting solution was stirred at 50° C. for 48 h before being cooled to room temperature and quenched with Na₂CO₃ (sat. 2 mL). After separation, the organic phase was dried over Na₂SO₄ and evaporated under vacuum. The residue was diluted with DMF (2 mL) and purified via preparative LC-MS (CH₃CN: H₂O) to afford the desired product 7.1

104

1-(3-chloro-4-fluorophenyl)-9-(6-oxo-1,6-dihydropyridin-3-yl)benzo[h][1,6]naphthyridin-2(1H)-one (3 mg). LC-MS (M+H): 417.07

Example 8

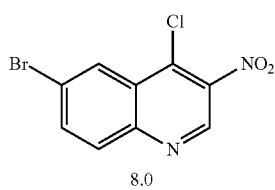
8.0

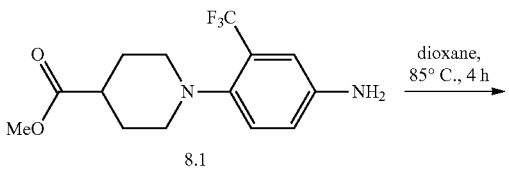
8.1

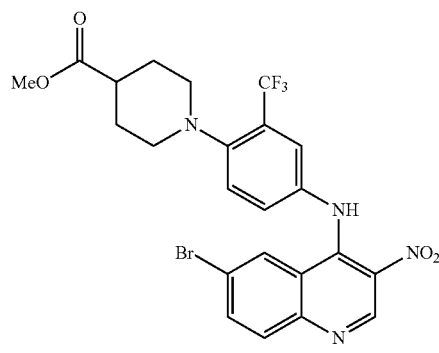
8.2

To a solution of compound 8.0 6-bromo-4-chloro-3-nitroquinoline (0.29 g, 1.0 mmol, 1 equiv.) in dioxane (5 mL) at room temperature was added 8.1 methyl 1-(4-amino-2-(trifluoromethyl)phenyl)piperidine-4-carboxylate (0.3 g, 1.0 mmol, 1 equiv.). The resulting mixture was heated overnight to 85° C. under argon. Upon cooling to room temperature, the mixture was neutralized with aqueous NaHCO₃, diluted with EtOAc (50 mL), and washed with water (50 mL) and brine (50 mL). The organic phase was dried over Na₂SO₄. After removal of solvent under vacuum, the resulting residue was purified via flash chromatography (Hexanes: EtOAc=4:1) to afford desired product 8.2 methyl 1-(4-(6-bromo-3-nitroquinolin-4-ylamino)-2-(trifluoromethyl)phenyl)piperidine-4-carboxylate (0.50 g; 90%). LC-MS (M+H): 555.10

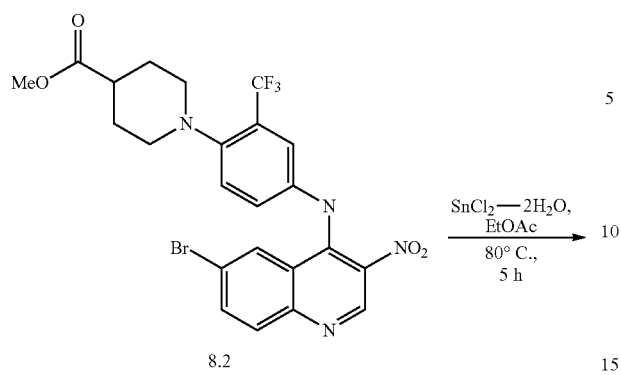

8.2

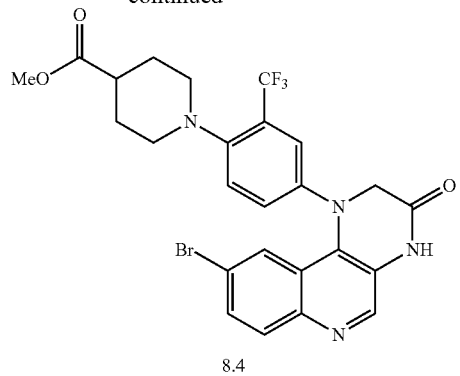

8.4

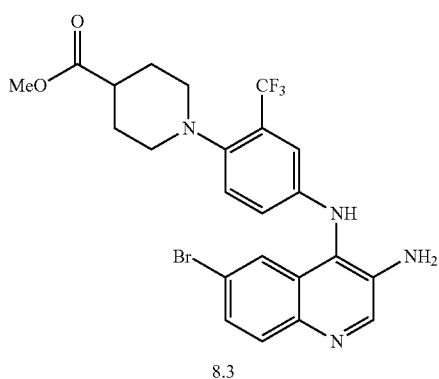

8.3

To a solution of compound 8.2 methyl 1-(4-(6-bromo-3-nitroquinolin-4-ylamino)-2-(trifluoromethyl)phenyl)piperidine-4-carboxylate (0.26 g, 0.47 mmol, 1 equiv.) in dioxane (3 mL) at room temperature was added Tin(II) chloride dihydrate (0.53 g, 2.35 mmol, 5 equiv.). The resulting mixture was heated to 80° C. under argon for 5 hours. Upon cooling to room temperature, the mixture was neutralized with aqueous NaHCO$_3$ and filtered. The filtrate was extracted with EtOAc (30 mL×2) and the combined organic layer was washed with water (50 mL) and brine (50 mL). The organic phase was dried over Na$_2$SO$_4$. After removal of solvent under vacuum, the resulting residue was purified via flash chromatography (hexanes:EtOAc 1:1) to afford desired product 8.3 methyl 1-(4-(3-amino-6-bromoquinolin-4-ylamino)-2-(trifluoromethyl)phenyl)piperidine-4-carboxylate (0.18 g; 73%). LC-MS (M+H): 523.10

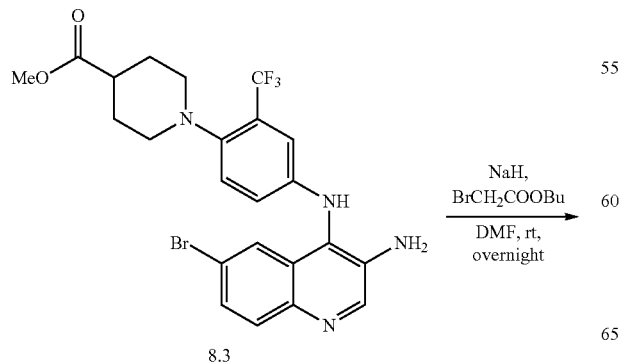

8.3

To a solution of compound 8.3 methyl 1-(4-(3-amino-6-bromoquinolin-4-ylamino)-2-(trifluoromethyl)phenyl)piperidine-4-carboxylate (60 mg, 0.115 mmol, 1 equiv.) in anhydrous DMF (3 mL) at 0° C. was added sodium hydride (60%, 5.0 mg, 0.126 mmol, 1.1 equiv.). After the mixture solution was stirred for 15 minutes, tert-Butyl bromoacetate (19 [L, 0.126 mmol, 1.1 equiv.) was added. The resulting mixture was stirred overnight at room temperature under argon. Upon quenching with water, the mixture was concentrated under vacuum, diluted with EtOAc (20 mL), and washed with water (20 mL) and brine (20 mL). The organic phase was dried over Na$_2$SO$_4$. After removal of solvent under vacuum, the resulting residue was purified via flash chromatography (CH$_2$Cl$_2$:MeOH=35:1) to afford the desired product 8.4 methyl 1-(4-(9-bromo-3-oxo-3,4-dihydropyrazino[2,3-c]quinolin-1(2H)-yl)-2-(trifluoromethyl)phenyl)piperidine-4-carboxylate (61 mg; 94%). LC-MS (M+H): 563.15

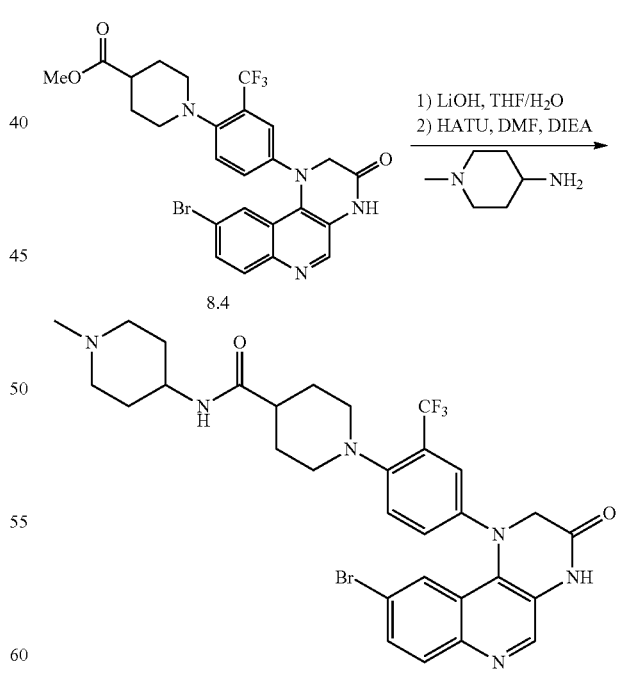

8.4

8.5

To a solution of compound 8.4 methyl 1-(4-(9-bromo-3-oxo-3,4-dihydropyrazino[2,3-c]quinolin-1(2H)-yl)-2-(trifluoromethyl)phenyl)piperidine-4-carboxylate (55 mg, 0.10 mmol, 1 equiv.) in THF/H$_2$O (1.0 mL/1.5 mL) was added lithium hydroxide monohydrate (13 mg, 0.30 mmol, 1 equiv.). The resulting mixture was stirred overnight at room temperature. Upon completion, the reaction was diluted with CH$_2$Cl, (5 mL) and water (5 mL). The aqueous layer was adjusted with 1 N HCl to about pH3 and extracted with CH$_2$Cl$_2$ (5 mL×3). The combined organic layer was washed with brine (20 mL) and dried over Na$_2$SO$_4$. After removal of solvent under vacuum, the resulting residue was used for the next step without further purification. To a solution of the above acid in DMF (2 mL) was added 1-methylpiperidin-4-amine (25 µL, 0.20 mmol, 2 equiv.), O-(7-Azabenzotriazol-1-yl)-N,N,N',N'-tetramethyluronium hexafluorophosphate (HATU) (95 mg, 0.25 mmol, 2.5 equiv.) and DIEA (52 µL, 0.30 mmol, 3 equiv.). The reaction mixture was stirred at room temperature for overnight. After removal of the solvent, the residue was diluted with EtOAc (20 mL) and washed with water (20 mL) and brine (20 mL). The organic phase was dried over Na$_2$SO$_4$. Removal of solvent under vacuum afforded crude product 8.5 1-(4-(9-bromo-3-oxo-3,4-dihydropyrazino[2,3-c]quinolin-1(2H)-yl)-2-(trifluoromethyl)phenyl)-N-(1-methylpiperidin-4-yl)piperidine-4-carboxamide 46 mg. It was used for next step without further purification. LC-MS (M+H): 645.22

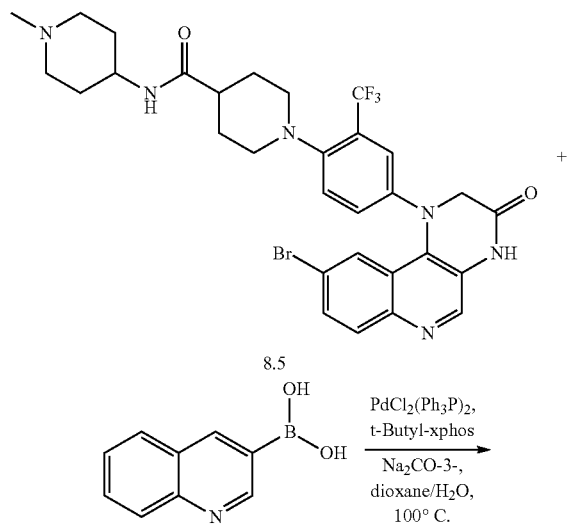

8.5

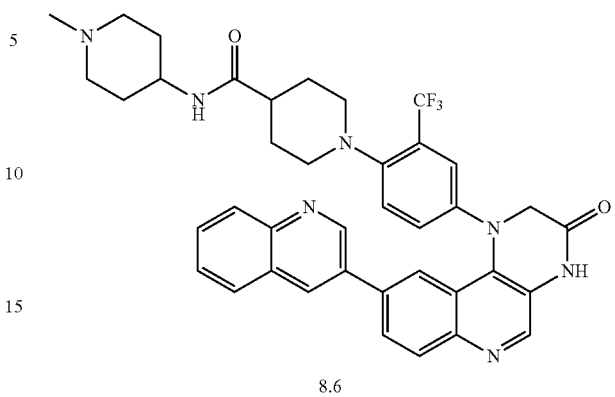

8.6

To a solution of 8.5 1-(4-(9-bromo-3-oxo-3,4-dihydropyrazino[2,3-c]quinolin-1(2H)-yl)-2-(trifluoromethyl)phenyl)-N-(1-methylpiperidin-4-yl)piperidine-4-carboxamide (46 mg, 0.07 mmol, 1 equiv.) in dioxane (2 mL) and 1N sodium carbonate solution (0.6 mL) in a sealed tube at room temperature was added 7 quinolin-3-yl-boronic acid (24 mg, 0.14 mmol, 2 equiv.), t-butyl-Xphos (3 mg, 0.007 mmol, 0.1 equiv.), and PdCl$_2$(Ph$_3$P)$_2$ (4.9 mg, 0.007 mmol, 0.1 equiv.). The resulting mixture was degassed, sealed and heated overnight to 100° C. Upon cooling to room temperature, the reaction mixture was filtered through celite and washed with EtOAc (2 mL). The collected solution was evaporated and the residue was purified via HPLC to afford the desired product 8.6 N-(1-methylpiperidin-4-yl)-1-(4-(3-oxo-9-(quinolin-3-yl)-3,4-dihydropyrazino[2,3-c]quinolin-1(2H)-yl)-2-(trifluoromethyl)phenyl)piperidine-4-carboxamide 1.5 mg. LC-MS: (M+H) 694.40

By repeating the procedures described in the above examples, additional compounds were made from their respective anilines, as set forth in Table 4, below.

TABLE 4

| Compound Number | Structure | Physical Data $^1$H NMR 600 MHz and/or MS (m/z) |
|---|---|---|
| 1 | 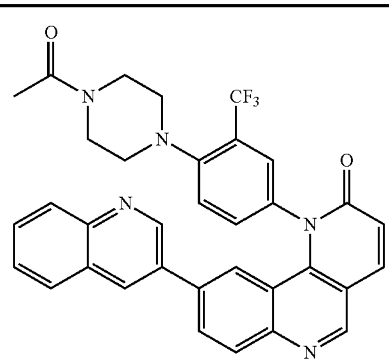 | MS m/z: 594.84 (M + 1). |

TABLE 4-continued

| Compound Number | Structure | Physical Data<br>¹H NMR 600 MHz and/or MS (m/z) |
|---|---|---|
| 2 | 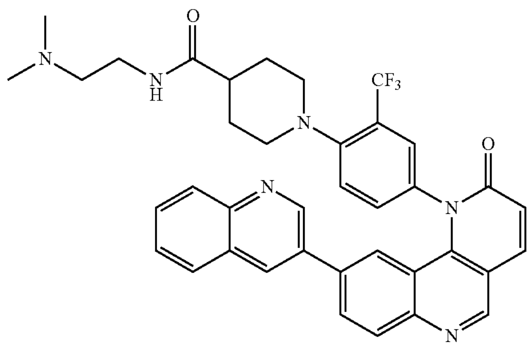 [SMILES: CN(C)CCNC(=O)C1CCN(c2ccc(-n3c(=O)ccc4cnc5ccc(-c6cnc7ccccc7c6)cc5c43)cc2C(F)(F)F)CC1] | LC-MS: 665.48 |
| 3 | 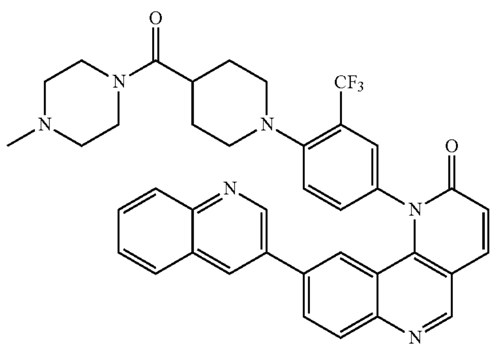 [SMILES: CN1CCN(C(=O)C2CCN(c3ccc(-n4c(=O)ccc5cnc6ccc(-c7cnc8ccccc8c7)cc6c54)cc3C(F)(F)F)CC2)CC1] | LC-MS: 677.39 |
| 4 | 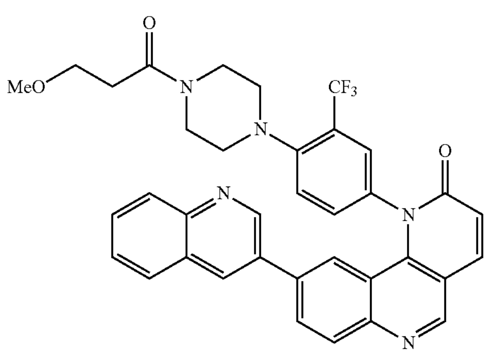 [SMILES: COCCC(=O)N1CCN(c2ccc(-n3c(=O)ccc4cnc5ccc(-c6cnc7ccccc7c6)cc5c43)cc2C(F)(F)F)CC1] | ¹H NMR 600 MHz (DMSO-d₆) δ 9.15 (s, 1H), 8.57 (d, J = 2.3 Hz, 1H), 8.32 (d, J = 9.3 Hz, 1H), 8.25 (d, J = 2.4 Hz, 1H), 8.18 (d, J = 8.5 Hz, 1H), 8.13 (dd, J = 1.7, 6.8 Hz, 1H), 8.03 (d, J = 8.2 Hz, 1H), 7.96 (m, 2H), 7.79 (m, 2H), 7.70 (d, J = 8.4 Hz, 1H), 7.66 (t, J = 7.1 Hz, 1H), 7.10 (d, J = 1.8 Hz, 1H), 6.94 (d, J = 9.4 Hz, 1H), 3.66 (m, 2H), 3.58 (m, 4H), 3.22 (s, 3H), 2.95 (m, 2H), 2.89 (m, 2H), 2.65 (t, J = 6.7 Hz, 2H), MS m/z: 638.00 (M + 1). |
| 5 | 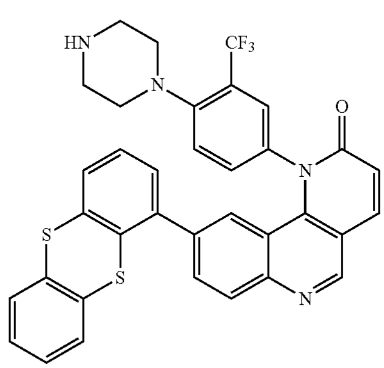 [SMILES: O=c1ccc2cnc3ccc(-c4cccc5c4Sc4ccccc4S5)cc3c2n1-c1ccc(N2CCNCC2)c(C(F)(F)F)c1] | MS m/z: 639.68 (M + 1). |

TABLE 4-continued

| Compound Number | Structure | Physical Data<br>¹H NMR 600 MHz and/or MS (m/z) |
|---|---|---|
| 6 | 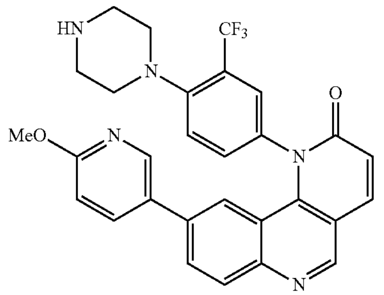 [SMILES: COc1ccc(-c2ccc3ncc4ccc(=O)n(-c5ccc(N6CCNCC6)c(C(F)(F)F)c5)c4c3c2)cn1] | |
| 7 | 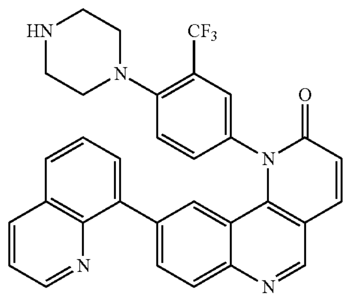 [SMILES: O=c1ccc2cnc3ccc(-c4cccc5cccnc45)cc3c2n1-c1ccc(N2CCNCC2)c(C(F)(F)F)c1] | ¹H NMR 600 MHz (DMSO-d₆) δ 9.24 (s, 1H), 8.38 (d, J = 9.2 Hz, 1H), 8.06 (d, J = 8.2 Hz, 1H), 7.81 (m, 4H), 7.70 (m, 4H), 7.46 (d, J = 6.0 Hz, 1H), 7.04 (s, 1H), 6.86 (d, J = 8.4 Hz, 1H), 6.79 (d, J = 7.8 Hz, 1H), 3.36 (m, 4H), 2.98 (m, 4H), MS m/z: 552.42 (M + 1). |
| 8 | 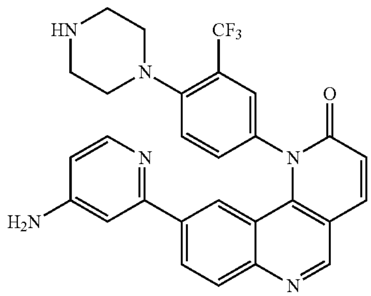 [SMILES: Nc1ccnc(-c2ccc3ncc4ccc(=O)n(-c5ccc(N6CCNCC6)c(C(F)(F)F)c5)c4c3c2)c1] | |
| 9 | 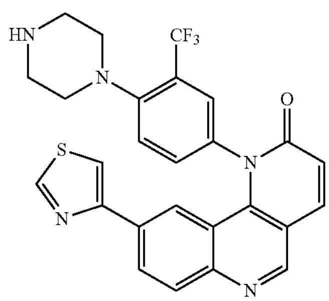 [SMILES: O=c1ccc2cnc3ccc(-c4cscn4)cc3c2n1-c1ccc(N2CCNCC2)c(C(F)(F)F)c1] | |
| 10 | 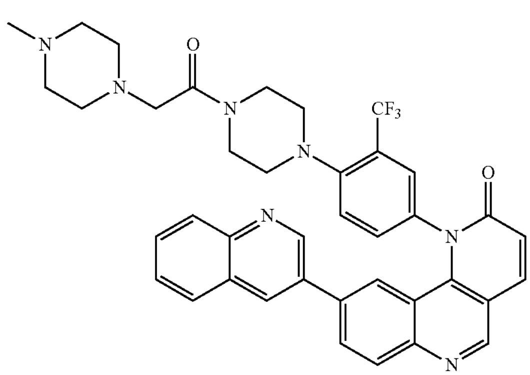 [SMILES: CN1CCN(CC(=O)N2CCN(c3ccc(-n4c(=O)ccc5cnc6ccc(-c7cnc8ccccc8c7)cc6c54)cc3C(F)(F)F)CC2)CC1] | MS m/z: 692.26 (M + 1). |

TABLE 4-continued

| Compound Number | Structure | Physical Data<br>¹H NMR 600 MHz and/or MS (m/z) |
|---|---|---|
| 11 | 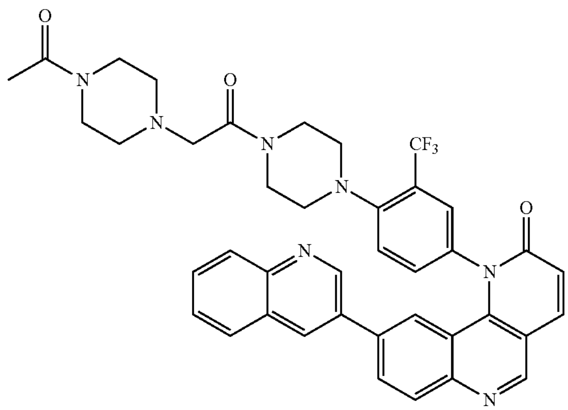 [SMILES: CC(=O)N1CCN(CC(=O)N2CCN(c3ccc(-n4c(=O)ccc5cnc6ccc(-c7cnc8ccccc8c7)cc6c54)cc3C(F)(F)F)CC2)CC1] | MS m/z: 720.31 (M + 1). |
| 12 | 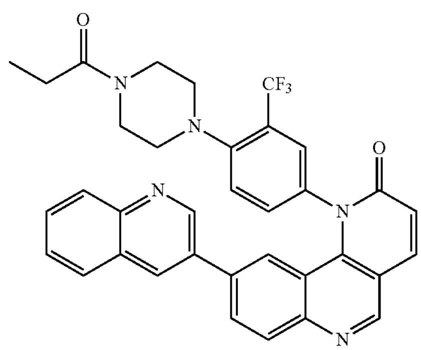 | MS m/z: 608.23 (M + 1). |
| 13 | 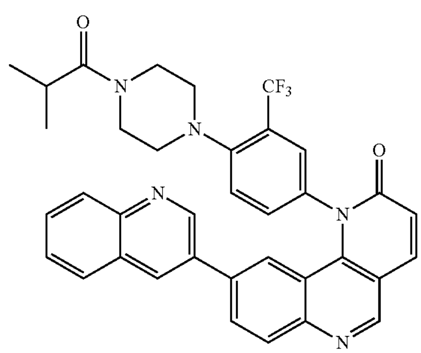 | ¹H NMR 600 MHz (DMSO-d₆) δ 9.28 (s, 1H), 8.67 (d, J = 2.3 Hz, 1H), 8.42 (d, J = 9.4 Hz, 1H), 8.35 (d, J = 2.1 Hz, 1H), 8.28 (d, J = 8.8 Hz, 1H), 8.23 (dd, J = 2.1, 6.7 Hz, 1H), 8.11 (d, J = 8.5 Hz, 1H), 8.05 (m, 2H), 7.85 (m, 2H), 7.77 (m, 2H), 7.17 (d, J = 1.8 Hz, 1H), 7.03 (d, J = 9.7 Hz, 1H), 3.56 (m, 4H), 2.77 (m, 1H), 2.67 (m, 4H), 1.07 (d, J = 2.3 Hz, 6H), MS m/z: 622.29 (M + 1). |
| 14 | 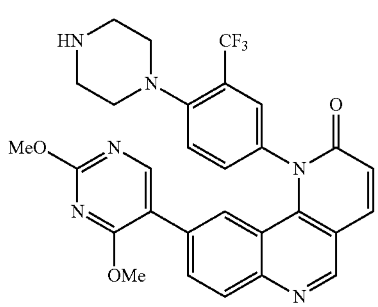 [SMILES: COc1ncc(-c2ccc3ncc4ccc(=O)n(-c5ccc(N6CCNCC6)c(C(F)(F)F)c5)c4c3c2)c(OC)n1] | ¹H NMR 600 MHz (DMSO-d₆) δ 9.14 (s, 1H), 8.31 (d, J = 9.4 Hz, 1H), 8.06 (d, J = 8.5 Hz, 1H), 7.82 (m, 2H), 7.75 (dd, J = 2.3, 6.2 Hz, 1H), 7.71 (s, 1H), 7.68 (d, J = 8.5 Hz, 1H), 6.91 (d, J = 9.4 Hz, 1H), 6.68 (d, J = 1.8 Hz, 1H), 3.89 (s, 3H), 3.85 (s, 3H), 2.96 (m, 4H), 2.80 (m, 4H), MS m/z: 563.95 (M + 1). |

TABLE 4-continued

| Compound Number | Structure | Physical Data<br>¹H NMR 600 MHz and/or MS (m/z) |
|---|---|---|
| 15 | 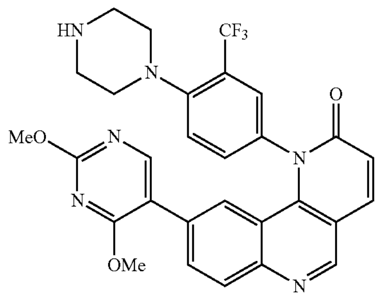 [SMILES: COc1ncc(-c2ccc3ncc4ccc(=O)n(-c5ccc(N6CCNCC6)c(C(F)(F)F)c5)c4c3c2)c(OC)n1] | ¹H NMR 600 MHz (DMSO-d₆) δ 9.11 (s, 1H), 8.30 (d, J = 9.7 Hz, 1H), 8.01 (d, J = 8.5 Hz, 1H), 7.84 (d, J = 2.6 Hz, 1H), 7.78 (dd, J = 1.8, 6.7 Hz, 1H), 7.69 (dd, J = 2.3, 6.2 Hz, 1H), 7.61 (d, J = 8.5 Hz, 1H), 7.14 (d, J = 8.2 Hz, 1H), 6.90 (d, J = 9.4 Hz, 1H), 6.66 (d, J = 1.5 Hz, 1H), 6.32 (d, J = 7.9 Hz, 1H), 3.86 (s, 3H), 3.80 (s, 3H), 2.93 (m, 6H), 2.77 (m, 2H), MS m/z: 562.10 (M + 1). |
| 16 | 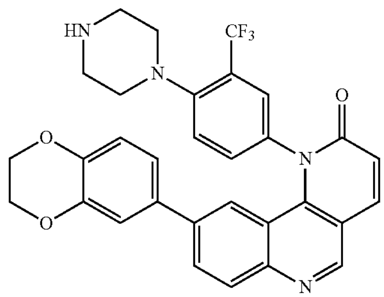 [SMILES: O=c1ccc2cnc3ccc(-c4ccc5c(c4)OCCO5)cc3c2n1-c1ccc(N2CCNCC2)c(C(F)(F)F)c1] | ¹H NMR 600 MHz (DMSO-d₆) δ 9.10 (s, 1H), 8.29 (d, J = 9.4 Hz, 1H), 8.04 (d, J = 8.5 Hz, 1H), 7.93 (d, J = 2.3, 1H), 7.89 (dd, J = 2.0, 6.4 Hz, 1H), 7.70 (dd, J = 2.3, 5.9 hz, 1H), 7.66 (d, J = 8.5 Hz, 1H), 7.02 (d, J = 1.8 Hz, 1H), 6.89 (d, J = 9.4 Hz, 1H), 6.77 (d J = 8.2 Hz, 1H), 6.67 (d, J = 2.1 Hz, 1H), 6.55 (dd, J = 2.3, 6.2 Hz, 1H), 4.23 (m, 4H), 3.02 (m, 4H), 2.96 (m, 2H), 2.88 (m, 2H), MS m/z: 559.07 (M + 1). |
| 17 | 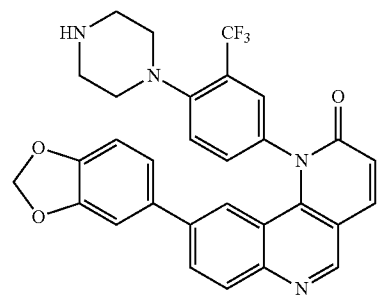 [SMILES: O=c1ccc2cnc3ccc(-c4ccc5c(c4)OCO5)cc3c2n1-c1ccc(N2CCNCC2)c(C(F)(F)F)c1] | ¹H NMR 600 MHz (DMSO-d₆) δ 9.11 (s, 1H), 8.30 (d, J = 9.4 Hz, 1H), 8.05 (d, J = 8.5 Hz, 1H), 7.97 (d, J = 2.3, 1H), 7.90 (dd, J = 2.1, 6.7 Hz, 1H), 7.72 (m, 2H), 6.99 (s, 1H), 6.90 (d, J = 9.4 Hz, 1H), 6.87 (d, J = 8.2 Hz, 1H), 6.66 (dd, J = 1.8, 6.2 Hz, 1H), 6.62 (s, 1H), 6.04 (d, J = 0.9 Hz, 1H), 6.02 (d, J = 1.2 Hz, 1H), 3.22 (m, 4H), 3.02 (m, 2H), 2.90 (m, 2H), MS m/z: 545.01 (M + 1). |
| 18 | 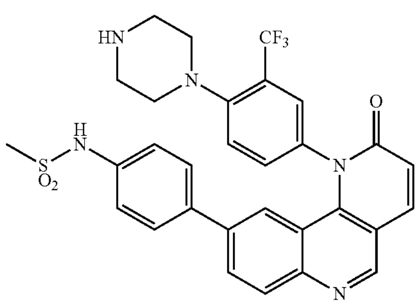 [SMILES: CS(=O)(=O)Nc1ccc(-c2ccc3ncc4ccc(=O)n(-c5ccc(N6CCNCC6)c(C(F)(F)F)c5)c4c3c2)cc1] | ¹H NMR 600 MHz (DMSO-d₆) δ 9.11 (s, 1H), 8.30 (d, J = 9.4 Hz, 1H), 8.08 (d, J = 8.5 Hz, 1H), 8.00 (s, 1H), 7.95 (dd, J = 1.8, 6.7 Hz, 1H), 7.68 (m, 2H), 7.31 (t, J = 7.3 Hz, 1H), 7.18 (m, 2H), 7.09 (m, 2H), 6.91 (d, J = 9.4 Hz, 1H), 3.02 (m, 6H), 2.95 (s, 3H), 2.85 (m, 2H), MS m/z: 594.84 (M + 1). |
| 19 | 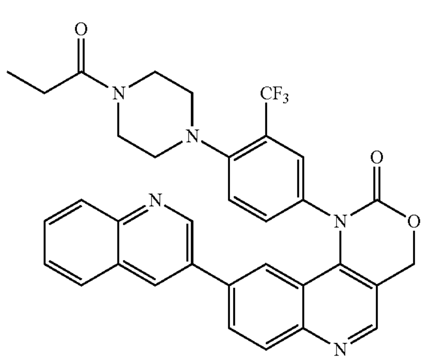 [SMILES: CCC(=O)N1CCN(c2ccc(N3C(=O)OCc4cnc5ccc(-c6cnc7ccccc7c6)cc5c43)cc2C(F)(F)F)CC1] | LC-MS: 612.22 |

TABLE 4-continued

| Compound Number | Structure | Physical Data<br>¹H NMR 600 MHz and/or MS (m/z) |
|---|---|---|
| 20 | 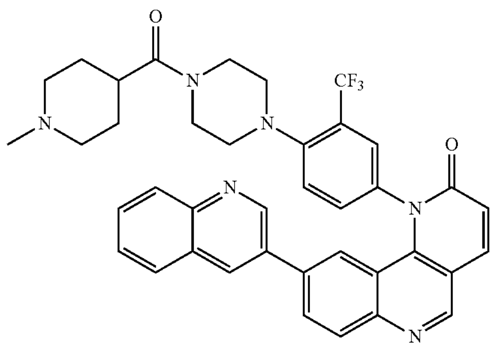 | MS m/z: 677.34 (M + 1). |
| 21 | 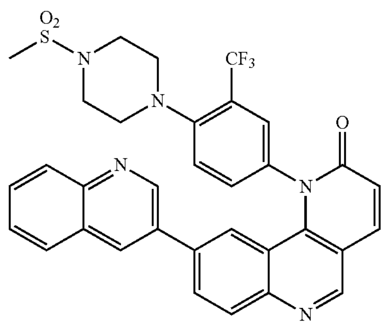 [SMILES: CS(=O)(=O)N1CCN(c2ccc(-n3c(=O)ccc4cnc5ccc(-c6cnc7ccccc7c6)cc5c43)cc2C(F)(F)F)CC1] | MS m/z: 630.48 (M + 1). |
| 22 | 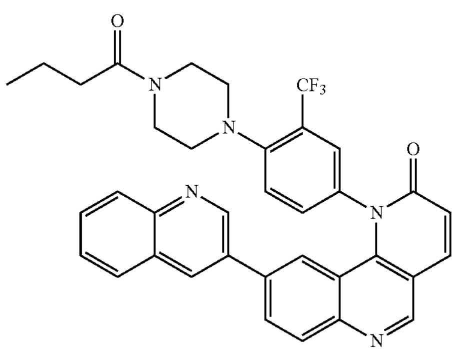 [SMILES: CCCC(=O)N1CCN(c2ccc(-n3c(=O)ccc4cnc5ccc(-c6cnc7ccccc7c6)cc5c43)cc2C(F)(F)F)CC1] | MS m/z: 622.29 (M + 1). |
| 23 | 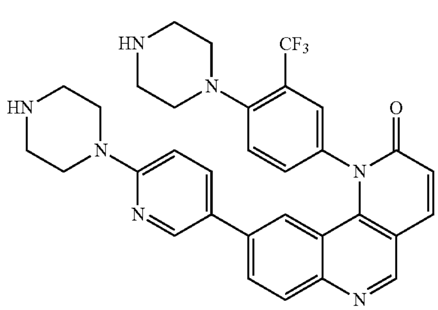 [SMILES: O=c1ccc2cnc3ccc(-c4ccc(N5CCNCC5)nc4)cc3c2n1-c1ccc(N2CCNCC2)c(C(F)(F)F)c1] | MS m/z: 586.85 (M + 1). |

TABLE 4-continued

| Compound Number | Structure | Physical Data ¹H NMR 600 MHz and/or MS (m/z) |
|---|---|---|
| 24 | 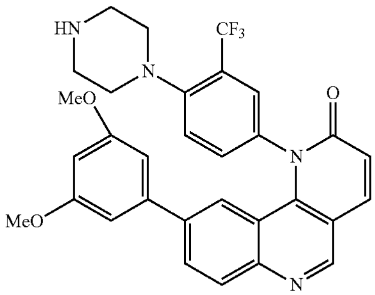 [SMILES: COc1cc(OC)cc(-c2ccc3ncc4ccc(=O)n(-c5ccc(N6CCNCC6)c(C(F)(F)F)c5)c4c3c2)c1] | ¹H NMR 600 MHz (DMSO-d$_6$) δ 9.12 (s, 1H), 8.29 (d, J = 9.4 Hz, 1H), 8.07 (d, J = 8.5 Hz, 1H), 7.92 (dd, J = 1.8, 6.7 Hz, 1H), 7.85 (d, J = 2.3 Hz, 1H), 7.71 (dd, J = 2.3, 6.2 Hz, 1H), 7.63 (d, J = 8.5 Hz, 1H), 7.03 (d, J = 1.8 Hz, 1H), 6.90 (d, J = 9.4 Hz, 1H), 6.47 (t, J = 2.1 Hz, 1H), 6.27 (m, 2H), 3.74 (s, 6H), 2.91 (m, 4H), 2.77 (m, 4H), MS m/z: 561.84 (M + 1). |
| 25 | 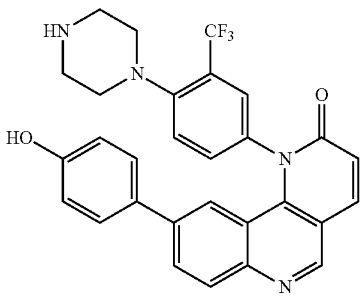 [SMILES: N#Cc1ccc(-c2ccc3ncc4ccc(=O)n(-c5ccc(N6CCNCC6)c(C(F)(F)F)c5)c4c3c2)cc1] | ¹H NMR 600 MHz (DMSO-d$_6$) δ 9.08 (s, 1H), 8.28 (d, J = 9.4 Hz, 1H), 8.03 (d, J = 8.5 Hz, 1H), 7.97 (s, 1H), 7.89 (dd, J = 2.1, 6.8 Hz, 1H), 7.64 (m, 2H), 7.03 (d, J = 1.8 Hz, 1H), 6.96 (m, 2H), 6.89 (d, J = 9.4 Hz, 1H), 6.72 (m, 2H), 2.94 (m, 6H), 2.79 (m, 2H), MS m/z: 517.83 (M + 1). |
| 26 | 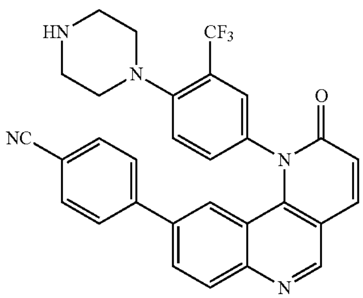 | ¹H NMR 600 MHz (DMSO-d$_6$) δ 9.17 (s, 1H), 8.32 (d, J = 9.7 Hz, 1H), 8.13 (d, J = 8.5 Hz, 1H), 7.97 (m, 3H), 7.79 (m, 2H), 7.67 (dd, J = 2.0, 6.2 Hz, 1H), 7.60 (t, J = 8.5 Hz, 1H), 7.36 (d, J = 8.2 Hz, 1H), 6.97 (s, 1H), 6.88 (d, J = 8.5 Hz, 1H) 3.31 (m, 4H), 2.89 (m, 4H), 2.84 (m, 2H), 2.59 (m, 2H), MS m/z: 526.87 (M + 1). |
| 27 | 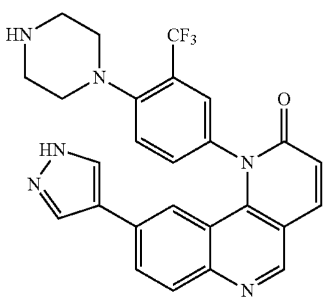 | ¹H NMR 600 MHz (DMSO-d$_6$) δ 13.03 (bs, 1H), 9.05 (s, 1H), 8.27 (d, J = 9.4 Hz, 1H), 8.00 (d, J = 8.5 Hz, 1H), 7.93 (m, 2H), 7.75 (m, 3H), 7.03 (d, J = 1.8 Hz, 1H), 6.89 (m, 2H), 3.00 (m, 6H), 2.81 (m, 2H), MS m/z: 491.83 (M + 1). |
| 28 | 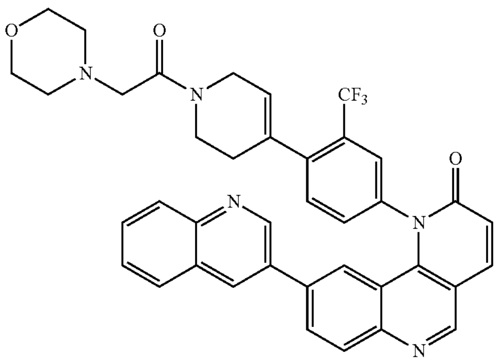 [SMILES: O=C(CN1CCOCC1)N1CC=C(c2ccc(-n3c(=O)ccc4cnc5ccc(-c6cnc7ccccc7c6)cc5c43)cc2C(F)(F)F)CC1] | MS m/z: 676.41 (M + 1). |

TABLE 4-continued

| Compound Number | Structure | Physical Data ¹H NMR 600 MHz and/or MS (m/z) |
|---|---|---|
| 29 | 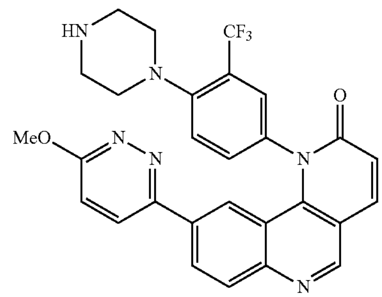 [SMILES: COc1ccc(-c2ccc3ncc4ccc(=O)n(-c5ccc(N6CCNCC6)c(C(F)(F)F)c5)c4c3c2)nn1] | |
| 30 | 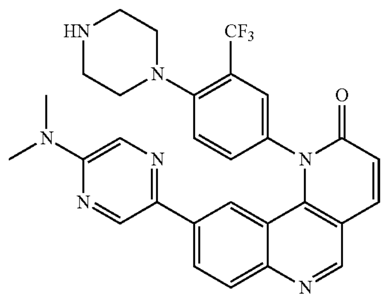 [SMILES: CN(C)c1cnc(-c2ccc3ncc4ccc(=O)n(-c5ccc(N6CCNCC6)c(C(F)(F)F)c5)c4c3c2)cn1] | |
| 31 | 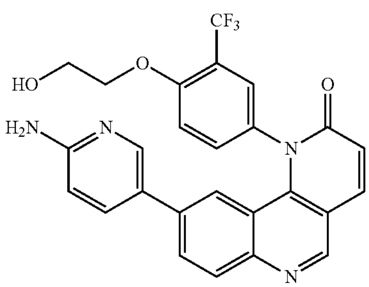 [SMILES: Nc1ccc(-c2ccc3ncc4ccc(=O)n(-c5ccc(OCCO)c(C(F)(F)F)c5)c4c3c2)cn1] | |
| 32 | 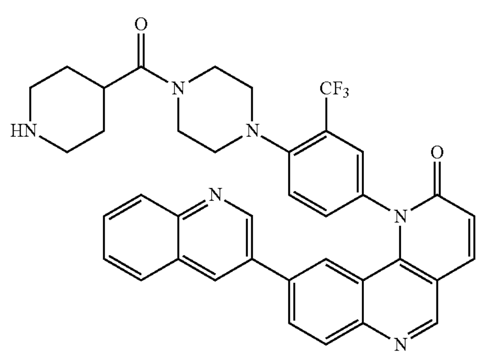 [SMILES: O=C(C1CCNCC1)N1CCN(c2ccc(-n3c(=O)ccc4cnc5ccc(-c6cnc7ccccc7c6)cc5c43)cc2C(F)(F)F)CC1] | ¹H NMR 600 MHz (DMSO-d₆) δ 9.19 (s, 1H), 8.57 (d, J = 2.3 Hz, 1H), 8.34 (d, J = 9.4 Hz, 1H), 8.28 (d, J = 2.1 Hz, 1H), 8.20 (d, J = 8.5 Hz, 1H), 8.16 (dd, J = 1.8, 6.7 Hz, 1H), 8.03 (d, J = 8.5 Hz, 1H), 7.98 (m, 2H), 7.81 (m, 2H), 7.70 (m, 2H), 7.12 (d, J = 1.8 Hz, 1H), 6.95 (d, J = 9.4 Hz, 1H), 2.86 (m, 4H), 2.71 (m, 4H), 2.59 (m, 1H), 1.67 (m, 4H), 1.21 (m, 4H), MS m/z: 663.28 (M + 1). |
| 33 | 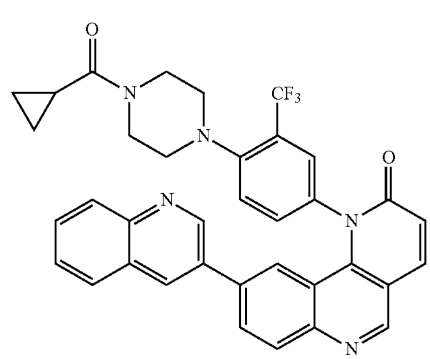 [SMILES: O=C(C1CC1)N1CCN(c2ccc(-n3c(=O)ccc4cnc5ccc(-c6cnc7ccccc7c6)cc5c43)cc2C(F)(F)F)CC1] | ¹H NMR 600 MHz (DMSO-d₆) δ 9.18 (s, 1H), 8.57 (d, J = 2.3 Hz, 1H), 8.34 (d, J = 9.4 Hz, 1H), 8.26 (d, J = 2.3 Hz, 1H), 8.19 (d, J = 8.5 Hz, 1H), 8.15 (dd, J = 1.8, 6.7 Hz, 1H), 8.03 (d, J = 8.2 Hz, 1H), 7.97 (m, 2H), 7.79 (m, 2H), 7.72 (d, J = 8.5 Hz, 1H), 7.67 (t, J = 7.0 Hz, 1H), 7.10 (d, J = 1.8 Hz, 1H), 6.95 (d, J = 9.4 Hz, 1H), 3.68 (m, 2H), 3.52 (m, 4H), 3.38 (m, 2H), 1.90 (m, 1H), 1.21 (m, 2H), 0.83 (m, 2H), MS m/z: 620.18 (M + 1). |

TABLE 4-continued
| Compound Number | Structure | Physical Data<br>¹H NMR 600 MHz and/or MS (m/z) |
|---|---|---|
| 34 | 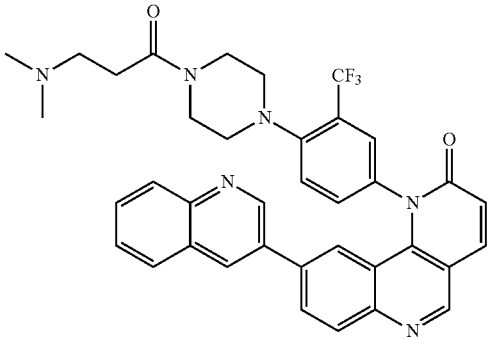 [SMILES: CN(C)CCC(=O)N1CCN(c2ccc(-n3c(=O)ccc4cnc5ccc(-c6cnc7ccccc7c6)cc5c43)cc2C(F)(F)F)CC1] | MS m/z: 651.20 (M + 1). |
| 35 | 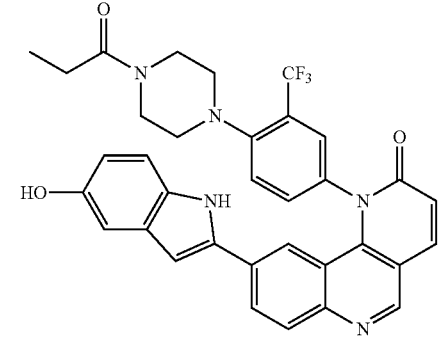 [SMILES: CCC(=O)N1CCN(c2ccc(-n3c(=O)ccc4cnc5ccc(-c6cc7cc(O)ccc7[nH]6)cc5c43)cc2C(F)(F)F)CC1] | LC-MS: 613.21 |
| 36 | 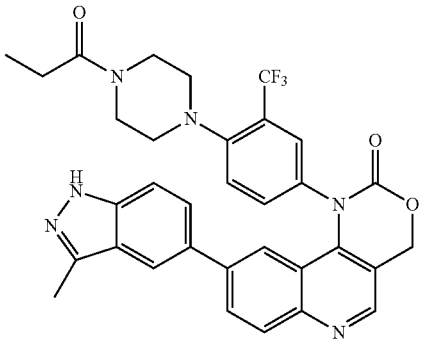 [SMILES: CCC(=O)N1CCN(c2ccc(N3C(=O)OCc4cnc5ccc(-c6ccc7[nH]nc(C)c7c6)cc5c43)cc2C(F)(F)F)CC1] | LC-MS: 615.19 |
| 37 | 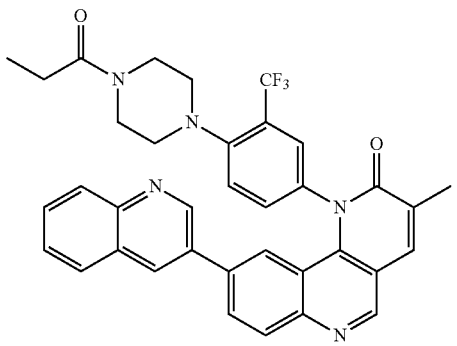 [SMILES: CCC(=O)N1CCN(c2ccc(-n3c(=O)c(C)cc4cnc5ccc(-c6cnc7ccccc7c6)cc5c43)cc2C(F)(F)F)CC1] | LC-MS: 622.38 |

TABLE 4-continued

| Compound Number | Structure | Physical Data ¹H NMR 600 MHz and/or MS (m/z) |
|---|---|---|
| 38 | 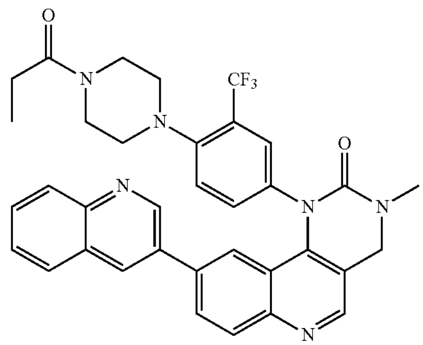 [SMILES: CCC(=O)N1CCN(c2ccc(N3C(=O)N(C)Cc4cnc5ccc(-c6cnc7ccccc7c6)cc5c43)cc2C(F)(F)F)CC1] | LC-MS: 625.22 (M + 1) |
| 39 | 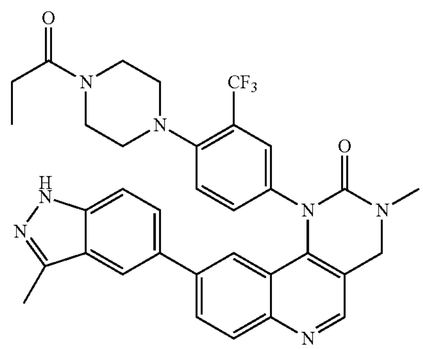 [SMILES: CCC(=O)N1CCN(c2ccc(N3C(=O)N(C)Cc4cnc5ccc(-c6ccc7[nH]nc(C)c7c6)cc5c43)cc2C(F)(F)F)CC1] | LC-MS: 628.19 (M + 1) |
| 40 | 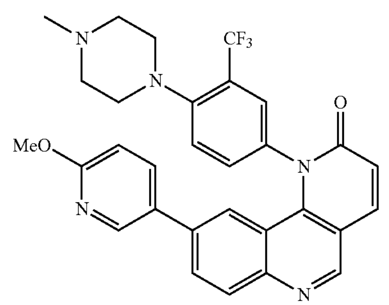 [SMILES: COc1ccc(-c2ccc3ncc4ccc(=O)n(-c5ccc(N6CCN(C)CC6)c(C(F)(F)F)c5)c4c3c2)cn1] | MS m/z: 546.39 (M + 1). |
| 41 | 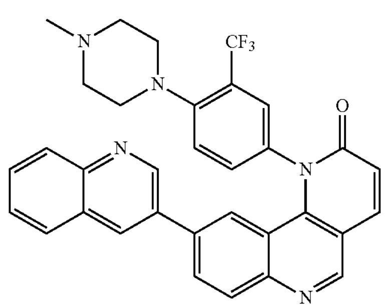 [SMILES: CN1CCN(c2ccc(-n3c(=O)ccc4cnc5ccc(-c6cnc7ccccc7c6)cc5c43)cc2C(F)(F)F)CC1] | MS m/z: 566.18 (M + 1). |
| 42 | 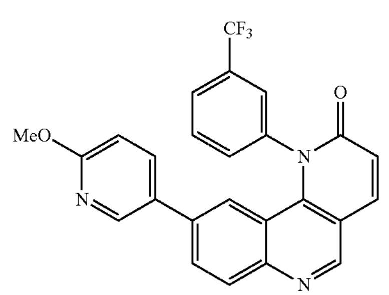 [SMILES: COc1ccc(-c2ccc3ncc4ccc(=O)n(-c5cccc(C(F)(F)F)c5)c4c3c2)cn1] | ¹H NMR 600 MHz (DMSO-d₆) δ 9.37 (s, 1H), 9.10 (s, 1H), 8.52 (d, J = 7.8 Hz, 1H), 8.30 (d, J = 7.0 Hz, 1H), 8.02 (m, 2H), 7.86 (m, 3H), 7.54 (d, J = 6.8 Hz, 1H), 7.14 (s, 1H), 7.01 (d, J = 8.2 Hz, 1H), 6.88 (d, J = 7.8 Hz, 1H), 3.88 (s, 3H), MS m/z: 448.27 (M + 1). |

TABLE 4-continued

| Compound Number | Structure | Physical Data $^1$H NMR 600 MHz and/or MS (m/z) |
|---|---|---|
| 43 | 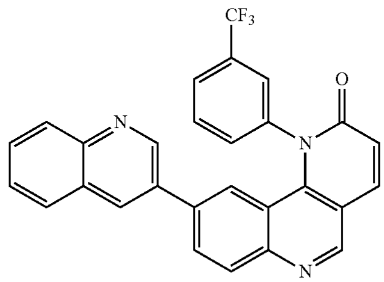 [SMILES: O=c1ccc2cnc3ccc(-c4cnc5ccccc5c4)cc3c2n1-c1cccc(C(F)(F)F)c1] | $^1$H NMR 600 MHz (DMSO-d$_6$) δ 9.18 (m, 2H), 8.98 (s, 1H), 8.28 (d, J = 8.0 Hz, 1H), 8.00 (d, J = 7.6 Hz, 1H), 7.85 (m, 3H), 7.59 (m, 3H), 7.48 (d, J = 6.4 Hz, 1H), 7.00 (m, 2H), 6.88 (d, J = 8.0 Hz, 1H), 6.75 (d, J = 7.1 Hz, 1H), MS m/z: 468.38 (M + 1). |
| 44 | 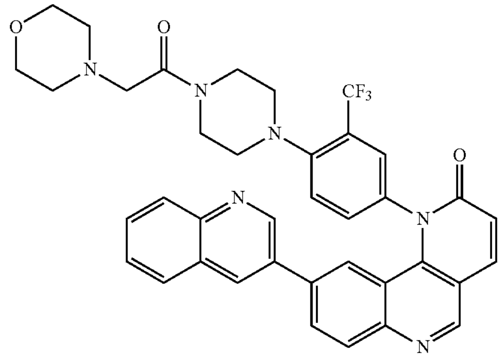 | $^1$H NMR 600 MHz (DMSO-d$_6$) δ 9.19 (s, 1H), 8.34 (d, J = 9.4 Hz, 1H), 8.20 (d, J = 8.5 Hz, 1H), 8.16 (dd, J = 1.8, 6.7 Hz, 1H), 8.10 (dd, J = 2.1, 6.2 Hz, 1H), 7.99 (m, 3H), 7.81 (m, 2H), 7.69 (m, 3H), 7.12 (m, 1H), 6.95 (d, J = 9.7 Hz, 1H), 3.55 (m, 2H), 3.43 (m, 6H), 3.22 (s, 2H), 3.13 (m, 2H), 2.61 (m, 2H), 2.57 (m, 2H), 2.36 (m, 2H), MS m/z: 679.32 (M + 1). |
| 45 | 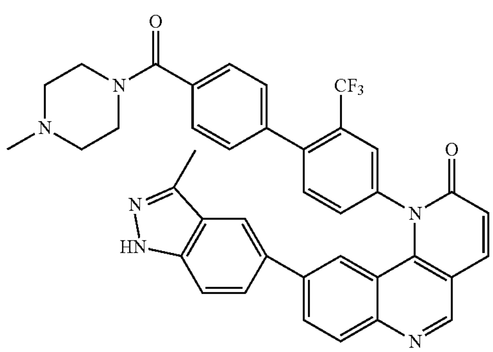 [SMILES: Cc1n[nH]c2ccc(-c3ccc4ncc5ccc(=O)n(-c6ccc(-c7ccc(C(=O)N8CCN(C)CC8)cc7)c(C(F)(F)F)c6)c5c4c3)cc12] | LC-MS: 673.40 |
| 46 | 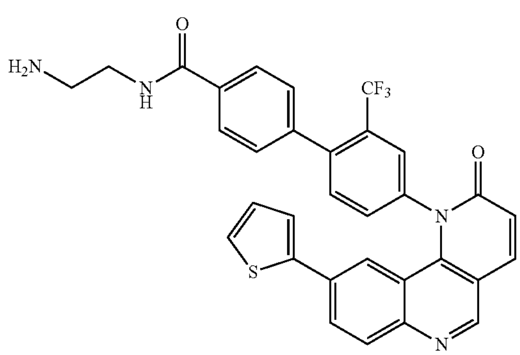 [SMILES: NCCNC(=O)c1ccc(-c2ccc(-n3c(=O)ccc4cnc5ccc(-c6cccs6)cc5c43)cc2C(F)(F)F)cc1] | LC-MS: 585.23 |

TABLE 4-continued

| Compound Number | Structure | Physical Data $^1$H NMR 600 MHz and/or MS (m/z) |
|---|---|---|
| 47 | 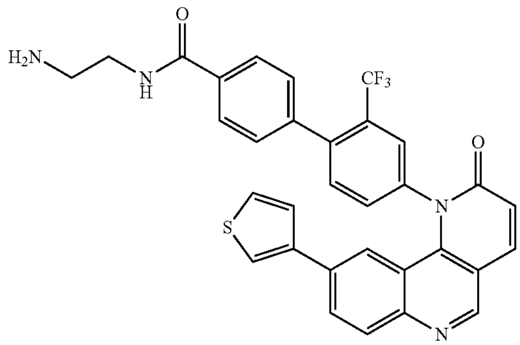 [SMILES: NCCNC(=O)c1ccc(-c2ccc(-n3c(=O)ccc4cnc5ccc(-c6ccsc6)cc5c43)cc2C(F)(F)F)cc1] | LC-MS: 585.23 |
| 48 | 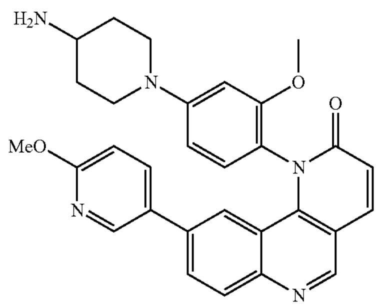 [SMILES: COc1ccc(-c2ccc3ncc4ccc(=O)n(-c5ccc(N6CCC(N)CC6)cc5OC)c4c3c2)cn1] | MS m/z: 508.06 (M + 1). |
| 49 | 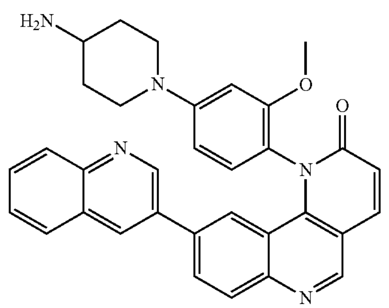 [SMILES: COc1cc(N2CCC(N)CC2)ccc1-n1c(=O)ccc2cnc3ccc(-c4cnc5ccccc5c4)cc3c21] | MS m/z: 528.12 (M + 1). |
| 50 | 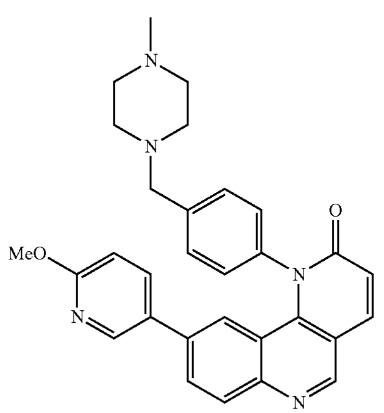 [SMILES: COc1ccc(-c2ccc3ncc4ccc(=O)n(-c5ccc(CN6CCN(C)CC6)cc5)c4c3c2)cn1] | MS m/z: 492.09 (M + 1). |

TABLE 4-continued

| Compound Number | Structure | Physical Data<br>¹H NMR 600 MHz and/or MS (m/z) |
|---|---|---|
| 51 | 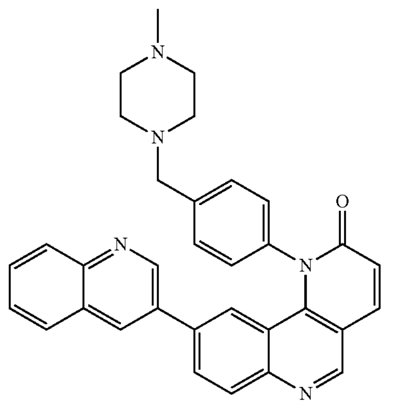 [SMILES: CN1CCN(Cc2ccc(-n3c(=O)ccc4cnc5ccc(-c6cnc7ccccc7c6)cc5c43)cc2)CC1] | MS m/z: 512.02 (M + 1). |
| 52 | 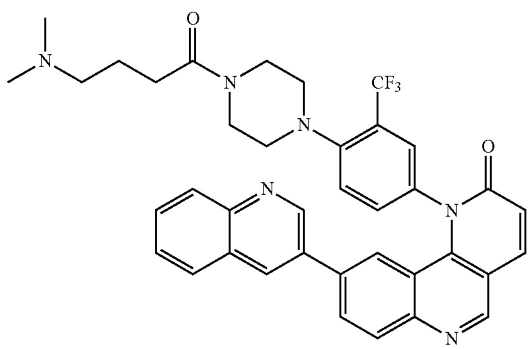 [SMILES: CN(C)CCCC(=O)N1CCN(c2ccc(-n3c(=O)ccc4cnc5ccc(-c6cnc7ccccc7c6)cc5c43)cc2C(F)(F)F)CC1] | MS m/z: 665.39 (M + 1). |
| 53 | 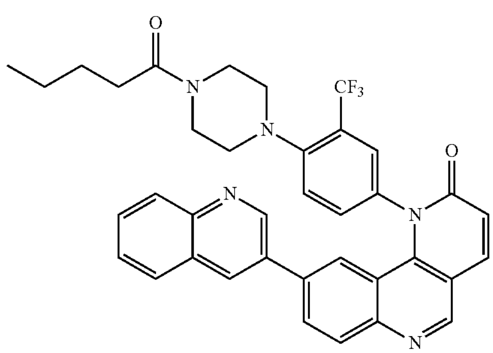 [SMILES: CCCCC(=O)N1CCN(c2ccc(-n3c(=O)ccc4cnc5ccc(-c6cnc7ccccc7c6)cc5c43)cc2C(F)(F)F)CC1] | MS m/z: 636.35 (M + 1). |
| 54 | 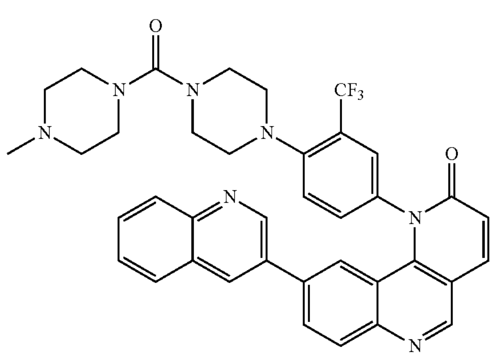 [SMILES: CN1CCN(C(=O)N2CCN(c3ccc(-n4c(=O)ccc5cnc6ccc(-c7cnc8ccccc8c7)cc6c54)cc3C(F)(F)F)CC2)CC1] | MS m/z: 678.46 (M + 1). |

TABLE 4-continued

| Compound Number | Structure | Physical Data<br>¹H NMR 600 MHz and/or MS (m/z) |
|---|---|---|
| 55 | 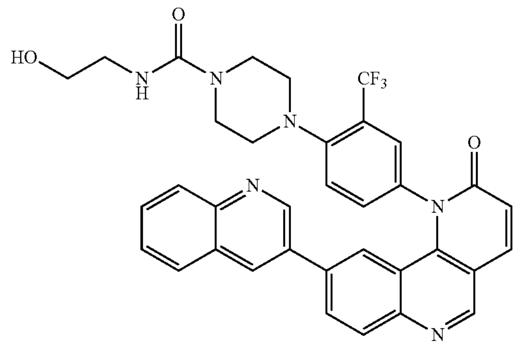 [SMILES: O=C(NCCO)N1CCN(c2ccc(-n3c(=O)ccc4cnc5ccc(-c6cnc7ccccc7c6)cc5c43)cc2C(F)(F)F)CC1] | MS m/z: 639.32 (M + 1). |
| 56 | 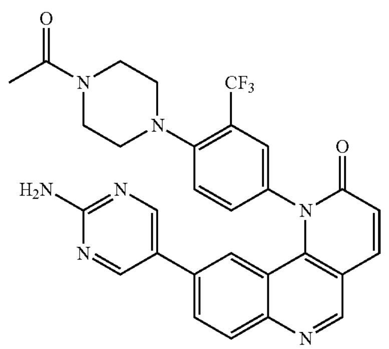 [SMILES: CC(=O)N1CCN(c2ccc(-n3c(=O)ccc4cnc5ccc(-c6cnc(N)nc6)cc5c43)cc2C(F)(F)F)CC1] | ¹H NMR 600 MHz (DMSO-d₆) δ 9.10 (s, 1H), 8.30 (d, J = 9.4 Hz, 1H), 8.06 (d, J = 8.8 Hz, 1H), 8.02 (m, 2H), 7.94 (dd, J = 2.1, 6.7 Hz, 1H), 7.90 (s, 1H), 7.77 (m, 2H), 6.87 (m, 2H), 3.59 (m, 4H), 2.89 (m, 4H), 2.06 (s, 3H), MS m/z: 560.26 (M + 1). |
| 57 | 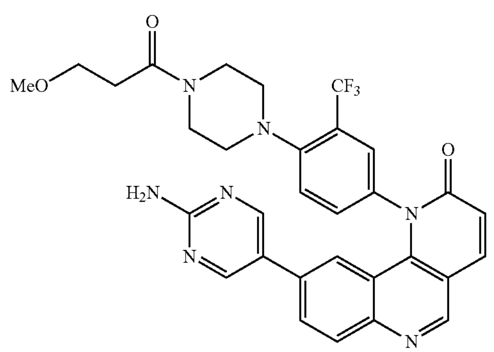 [SMILES: COCCC(=O)N1CCN(c2ccc(-n3c(=O)ccc4cnc5ccc(-c6cnc(N)nc6)cc5c43)cc2C(F)(F)F)CC1] | ¹H NMR 600 MHz (DMSO-d₆) δ 9.10 (s, 1H), 8.29 (d, J = 9.4 Hz, 1H), 8.06 (d, J = 8.5 Hz, 1H), 8.02 (m, 2H), 7.94 (dd, J = 1.8, 6.7 Hz, 1H), 7.91 (s, 1H), 7.76 (m, 2H), 6.88 (m, 2H), 3.66 (m, 2H), 3.58 (m, 4H), 3.23 (s, 3H), 2.94 (m, 2H), 2.89 (m, 2H), 2.63 (t, J = 6.7 Hz, 2H), MS m/z: 604.28 (M + 1). |
| 58 | 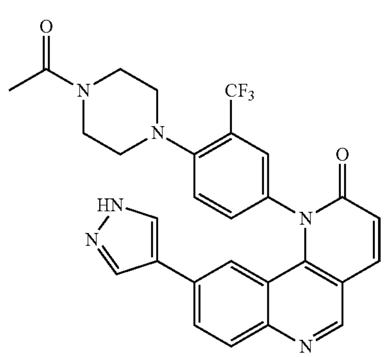 [SMILES: CC(=O)N1CCN(c2ccc(-n3c(=O)ccc4cnc5ccc(-c6cn[nH]c6)cc5c43)cc2C(F)(F)F)CC1] | ¹H NMR 600 MHz (DMSO-d₆) δ 13.06 (bs, 1H), 9.05 (s, 1H), 8.27 (d, J = 9.4 Hz, 1H), 8.00 (d, J = 8.5 Hz, 1H), 7.94 (m, 3H), 7.83 (d, J = 8.5 Hz, 1H), 7.76 (m, 2H), 7.02 (d, J = 1.8 Hz, 1H), 6.89 (d, J = 9.4 Hz, 1H), 3.62 (m, 4H), 2.94 (m, 4H), 2.06 (s, 3H), MS m/z: 533.40 (M + 1). |

TABLE 4-continued

| Compound Number | Structure | Physical Data ¹H NMR 600 MHz and/or MS (m/z) |
|---|---|---|
| 59 | 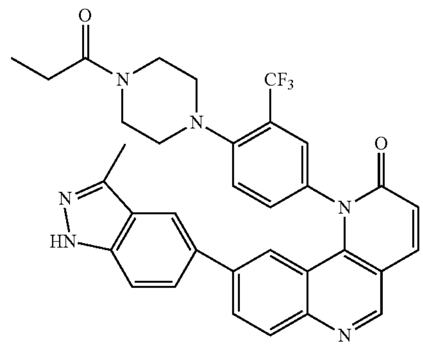 [SMILES: CCC(=O)N1CCN(c2ccc(-n3c(=O)ccc4cnc5ccc(-c6ccc7[nH]nc(C)c7c6)cc5c43)cc2C(F)(F)F)CC1] | LC-MS: 611.33 |
| 60 | 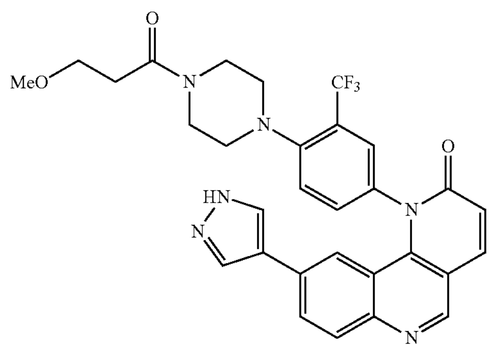 [SMILES: COCCC(=O)N1CCN(c2ccc(-n3c(=O)ccc4cnc5ccc(-c6cn[nH]c6)cc5c43)cc2C(F)(F)F)CC1] | ¹H NMR 600 MHz (DMSO-d$_6$) δ 13.06 (bs, 1H), 9.05 (s, 1H), 8.27 (d, J = 9.4 Hz, 1H), 8.00 (d, J = 8.5 Hz, 1H), 7.94 (m, 2H), 7.82 (d, J = 8.5 Hz, 1H), 7.74 (m, 2H), 7.28 (s, 1H), 7.02 (d, J = 1.8 Hz, 1H), 6.89 (d, J = 9.4 Hz, 1H), 3.61 (m, 2H), 3.48 (s, 3H), 3.20 (m, 4H), 3.00 (m, 2H), 2.94 (m, 2H), 2.63 (m, 2H), MS m/z: 577.28 (M + 1). |
| 61 | 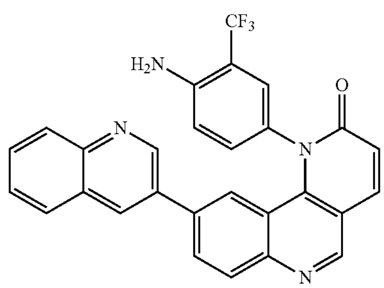 [SMILES: Nc1ccc(-n2c(=O)ccc3cnc4ccc(-c5cnc6ccccc6c5)cc4c32)cc1C(F)(F)F] | MS m/z: 483.25 (M + 1). |
| 62 | 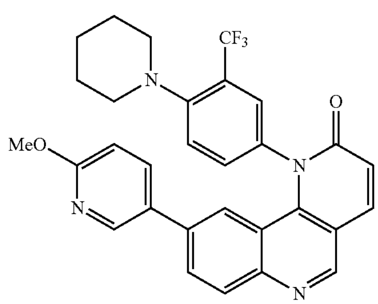 [SMILES: COc1ccc(-c2ccc3ncc4ccc(=O)n(-c5ccc(N6CCCCC6)c(C(F)(F)F)c5)c4c3c2)cn1] | ¹H NMR 600 MHz (DMSO-d$_6$) δ 9.08 (s, 1H), 8.34 (d, J = 9.1 Hz, 1H), 8.13 (d, J = 8.6 Hz, 1H), 7.90 (m, 2H), 7.76 (m, 3H), 7.56 (d, J = 6.1 Hz, 1H), 7.10 (s, 1H), 6.95 (d, J = 9.0 Hz, 1H), 6.80 (d, J = 8.1 Hz, 1H), 3.80 (s, 3H), 2.84 (m, 4H), 1.72 (m, 6H), MS m/z: 531.32 (M + 1). |
| 63 | 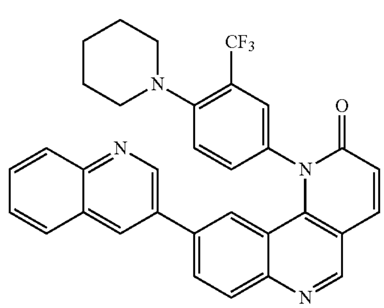 [SMILES: O=c1ccc2cnc3ccc(-c4cnc5ccccc5c4)cc3c2n1-c1ccc(N2CCCCC2)c(C(F)(F)F)c1] | ¹H NMR 600 MHz (DMSO-d$_6$) δ 9.14 (s, 1H), 8.41 (d, J = 7.6 Hz, 1H), 8.08 (d, J = 6.8 Hz, 1H), 7.80 (m, 3H), 7.68 (m, 4H), 7.40 (d, J = 6.8 Hz, 1H), 7.10 (m, 2H), 6.90 (d, J = 8.0 Hz, 1H), 6.78 (d, J = 7.4 Hz, 1H), 2.76 (m, 4H), 1.69 (m, 6H), MS m/z: 551.27 (M + 1). |

TABLE 4-continued

| Compound Number | Structure | Physical Data ¹H NMR 600 MHz and/or MS (m/z) |
|---|---|---|
| 64 | 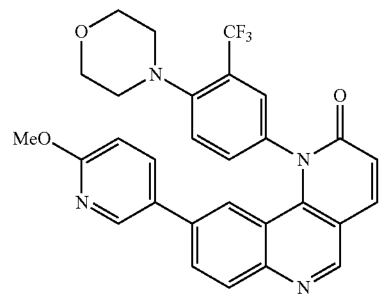 [SMILES: COc1ccc(-c2ccc3ncc4ccc(=O)n(-c5ccc(N6CCOCC6)c(C(F)(F)F)c5)c4c3c2)cn1] | ¹H NMR 600 MHz (DMSO-d₆) δ 9.26 (s, 1H), 8.42 (d, J = 8.8 Hz, 1H), 8.10 (d, J = 6.8 Hz, 1H), 7.88 (m, 2H), 7.70 (m, 3H), 7.58 (d, J = 6.7 Hz, 1H), 7.00 (s, 1H), 6.90 (d, J = 9.1 Hz, 1H), 6.74 (d, J = 8.2 Hz, 1H), 3.94 (s, 3H), 3.86 (m, 4H), 2.84 (m, 4H), MS m/z: 533.24 (M + 1). |
| 65 | 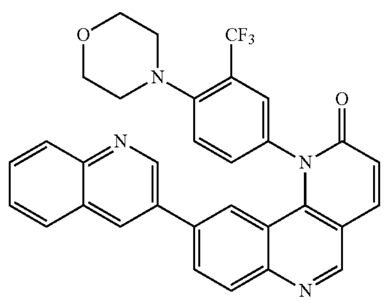 [SMILES: O=c1ccc2cnc3ccc(-c4cnc5ccccc5c4)cc3c2n1-c1ccc(N2CCOCC2)c(C(F)(F)F)c1] | ¹H NMR 600 MHz (DMSO-d₆) δ 9.08 (s, 1H), 8.45 (d, J = 9.0 Hz, 1H), 8.08 (d, J = 8.1 Hz, 1H), 7.99 (m, 3H), 7.64 (m, 4H), 7.58 (d, J = 5.8 Hz, 1H), 7.12 (m, 2H), 6.84 (d, J = 7.5 Hz, 1H), 6.62 (d, J = 6.8 Hz, 1H), 3.82 (m, 4H), 3.02 (m, 4H), MS m/z: 553.17 (M + 1). |
| 66 | 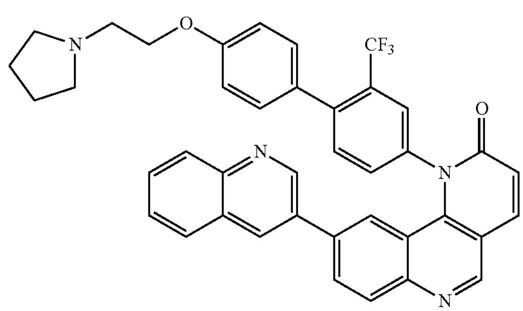 [SMILES: O=c1ccc2cnc3ccc(-c4cnc5ccccc5c4)cc3c2n1-c1ccc(-c2ccc(OCCN3CCCC3)cc2)c(C(F)(F)F)c1] | ¹H NMR 600 MHz (CDCl₃) δ 9.02 (s, 1H), 8.90 (d, J = 1.8 Hz, 1H), 8.28 (d, J = 8.4 Hz, 1H), 8.12 (d, J = 8.4 Hz, 1H), 8.02 (m, 2H), 7.89 (d, J = 7.2 Hz, 1H), 7.75 (m, 1H), 7.70 (d, J = 1.8 Hz, 1H), 7.61 (m, 3H), 7.24 (d, J = 9 Hz, 1H), 6.98 (d, J = 9 Hz, 1H), 4.29 (m, 1H), 4.19 (m, 1H), 2.99 (bs, 2H), 2.65 (bs, 4H), 1.82 (bs, 4H), MS m/z: 581.28 (M + 1). |
| 67 | 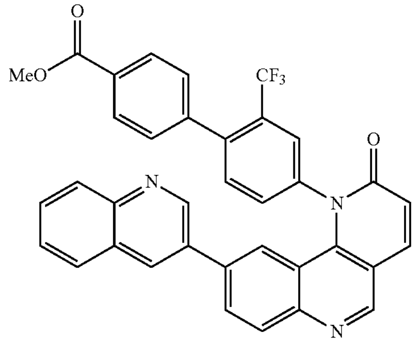 [SMILES: COC(=O)c1ccc(-c2ccc(-n3c(=O)ccc4cnc5ccc(-c6cnc7ccccc7c6)cc5c43)cc2C(F)(F)F)cc1] | ¹H NMR 600 MHz (CDCl₃) δ 9.07 (s, 1H), 8.72 (d, J = 2.4 Hz, 1H), 8.30 (d, J = 8.4 Hz, 1H), 8.21 (d, J = 8.4 Hz, 1H), 8.08 (d, J = 9 Hz, 1H), 8.02 (dd, J = 8.4, 1.8 Hz, 1H), 7.99 (d, J = 1.8 Hz, 1H), 7.91 (d, J = 8.4 Hz, 2H), 7.81 (m, 2H), 7.77 (d, J = 7.8 Hz, 1H), 7.71 (d, J = 8.4 Hz, 2H), 7.58 (m, 2H), 7.24 (m, 2H), 7.02 (d, J = 9.6 Hz, 1H), 3.96 (s, 3H), MS m/z: 602.23 (M + 1). |

TABLE 4-continued

| Compound Number | Structure | Physical Data<br>¹H NMR 600 MHz and/or MS (m/z) |
|---|---|---|
| 68 | 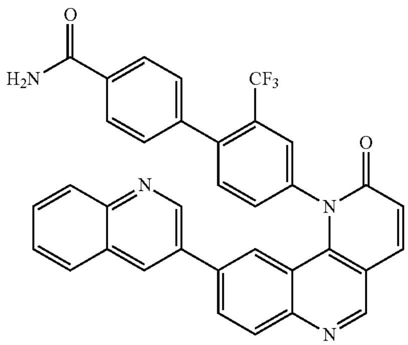 [SMILES: NC(=O)c1ccc(-c2ccc(-n3c(=O)ccc4cnc5ccc(-c6cnc7ccccc7c6)cc5c43)cc2C(F)(F)F)cc1] | MS m/z: 587.25 (M + 1). |
| 69 | 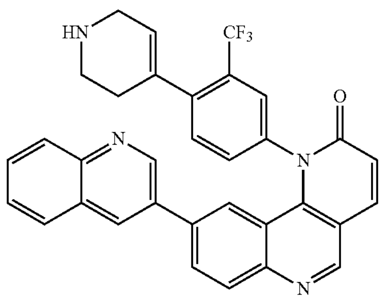 [SMILES: O=c1ccc2cnc3ccc(-c4cnc5ccccc5c4)cc3c2n1-c1ccc(C2=CCNCC2)c(C(F)(F)F)c1] | MS m/z: 549.30 (M + 1). |
| 70 | 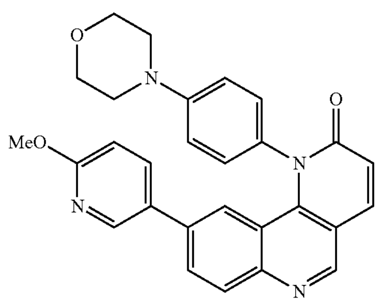 [SMILES: COc1ccc(-c2ccc3ncc4ccc(=O)n(-c5ccc(N6CCOCC6)cc5)c4c3c2)cn1] | ¹H NMR 600 MHz (DMSO-d₆) δ 9.04 (s, 1H), 8.52 (d, J = 8.2 Hz, 1H), 8.34 (d, J = 7.8 Hz, 1H), 7.72 (m, 2H), 7.38 (m, 3H), 7.05 (s, 1H), 6.82 (m, 3H), 6.69 (d, J = 8.0 Hz, 1H), 3.92 (s, 3H), 3.88 (m, 4H), 2.97 (m, 4H), MS m/z: 465.67 (M + 1). |
| 71 | 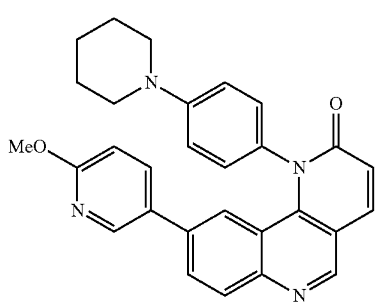 [SMILES: COc1ccc(-c2ccc3ncc4ccc(=O)n(-c5ccc(N6CCCCC6)cc5)c4c3c2)cn1] | ¹H NMR 600 MHz (DMSO-d₆) δ 9.11 (s, 1H), 8.48 (d, J = 8.8 Hz, 1H), 8.28 (d, J = 8.0 Hz, 1H), 7.68 (m, 3H), 7.48 (m, 2H), 7.11 (s, 1H), 6.77 (m, 3H), 6.70 (d, J = 7.4 Hz, 1H), 3.78 (s, 3H), 2.77 (m, 4H), 1.88 (m, 5H), MS m/z: 463.68 (M + 1). |

TABLE 4-continued

| Compound Number | Structure | Physical Data $^1$H NMR 600 MHz and/or MS (m/z) |
|---|---|---|
| 72 | 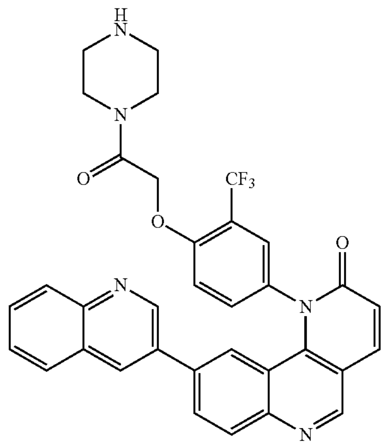 [SMILES: O=C(COc1ccc(-n2c(=O)ccc3cnc4ccc(-c5cnc6ccccc6c5)cc4c32)cc1C(F)(F)F)N1CCNCC1] | |
| 73 | 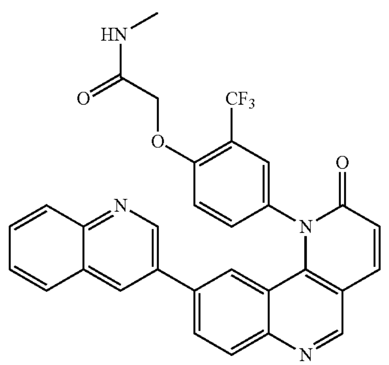 [SMILES: CNC(=O)COc1ccc(-n2c(=O)ccc3cnc4ccc(-c5cnc6ccccc6c5)cc4c32)cc1C(F)(F)F] | |
| 74 | 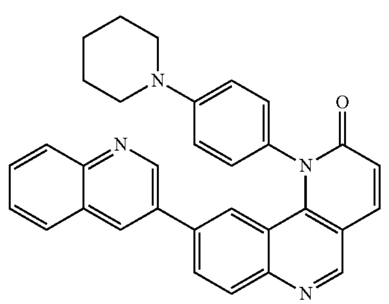 [SMILES: O=c1ccc2cnc3ccc(-c4cnc5ccccc5c4)cc3c2n1-c1ccc(N2CCCCC2)cc1] | MS m/z: 483.59 (M + 1). |
| 75 | 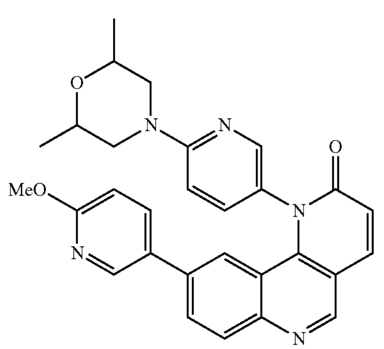 [SMILES: COc1ccc(-c2ccc3ncc4ccc(=O)n(-c5ccc(N6CC(C)OC(C)C6)nc5)c4c3c2)cn1] | MS m/z: 494.07 (M + 1). |

TABLE 4-continued

| Compound Number | Structure | Physical Data<br>¹H NMR 600 MHz and/or MS (m/z) |
|---|---|---|
| 76 | 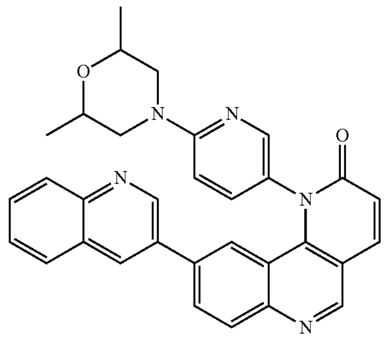 [SMILES: CC1CN(c2ccc(-n3c(=O)ccc4cnc5ccc(-c6cnc7ccccc7c6)cc5c43)cn2)CC(C)O1] | MS m/z: 514.06 (M + 1). |
| 77 | 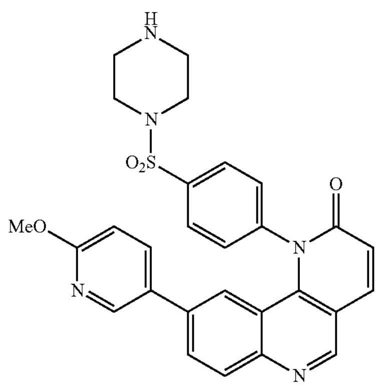 [SMILES: COc1ccc(-c2ccc3ncc4ccc(=O)n(-c5ccc(S(=O)(=O)N6CCNCC6)cc5)c4c3c2)cn1] | MS m/z: 527.99 (M + 1). |
| 78 | 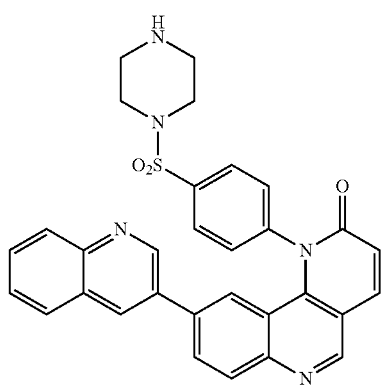 [SMILES: O=c1ccc2cnc3ccc(-c4cnc5ccccc5c4)cc3c2n1-c1ccc(S(=O)(=O)N2CCNCC2)cc1] | MS m/z: 547.99 (M + 1). |
| 79 | 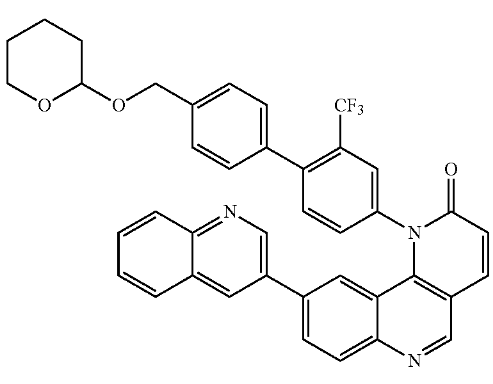 [SMILES: O=c1ccc2cnc3ccc(-c4cnc5ccccc5c4)cc3c2n1-c1ccc(-c2ccc(COC3CCCCO3)cc2)c(C(F)(F)F)c1] | ¹H NMR 600 MHz (CDCl₃) δ 9.06 (s, 1H), 8.78 (d, J = 2.4 Hz, 1H), 8.29 (d, J = 8.4 Hz, 1H), 8.18 (d, J = 8.4 Hz, 1H), 8.07 (d, J = 9 Hz, 1H), 8.01 (dd, J = 9, 1.8 Hz, 1H), 7.94 (d, J = 1.8 Hz, 1H), 7.79 (d, J = 1.8 Hz, 1H), 7.77 (m, 1H), 7.73 (d, J = 7.8 Hz, 1H), 7.66 (dd, J = 8.4, 2.4 Hz, 1H), 7.56 (m, 2H), 7.23 (d, J = 1.8 Hz, 1H), 7.22 (d, J = 7.8 Hz, 2H), 7.08 (d, J = 7.8 Hz, 2H), 7.02 (d, J = 9 Hz, 1H), 4.83 (d, J = 12 Hz, 1H), 4.75 (q, J = 3 Hz, 1H), 4.54 (dd, J = 12, 1.2 Hz, 1H), 3.95 (m, 1H), 3.61 (m, 1H), 1.93 (m, 1H), 1.79 (m, 1H), 1.71 (m, 1H), 1.60 (m, 4H), MS m/z: 658.30 (M + 1). |

TABLE 4-continued

| Compound Number | Structure | Physical Data $^1$H NMR 600 MHz and/or MS (m/z) |
|---|---|---|
| 80 | 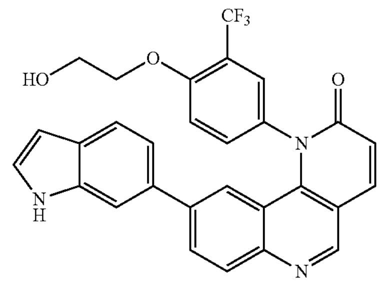 [SMILES: O=c1ccc2cnc3ccc(-c4ccc5cc[nH]c5c4)cc3c2n1-c1ccc(OCCO)c(C(F)(F)F)c1] | |
| 81 | 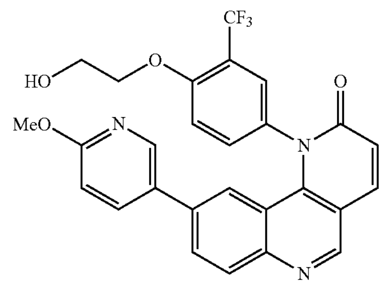 [SMILES: COc1ccc(-c2ccc3ncc4ccc(=O)n(-c5ccc(OCCO)c(C(F)(F)F)c5)c4c3c2)cn1] | |
| 82 | 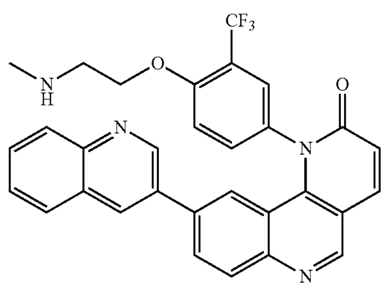 [SMILES: CNCCOc1ccc(-n2c(=O)ccc3cnc4ccc(-c5cnc6ccccc6c5)cc4c32)cc1C(F)(F)F] | |
| 83 | 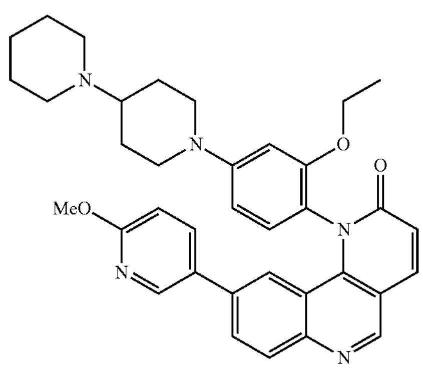 [SMILES: CCOc1cc(N2CCC(N3CCCCC3)CC2)ccc1-n1c(=O)ccc2cnc3ccc(-c4ccc(OC)nc4)cc3c21] | MS m/z: 590.35 (M + 1). |
| 84 | 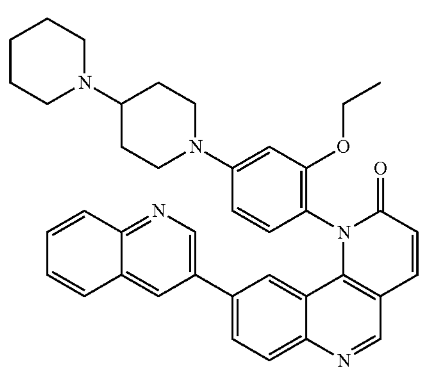 [SMILES: CCOc1cc(N2CCC(N3CCCCC3)CC2)ccc1-n1c(=O)ccc2cnc3ccc(-c4cnc5ccccc5c4)cc3c21] | MS m/z: 610.02 (M + 1). |

TABLE 4-continued

| Compound Number | Structure | Physical Data $^1$H NMR 600 MHz and/or MS (m/z) |
|---|---|---|
| 85 | 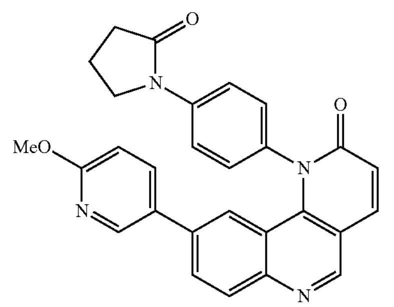 [SMILES: COc1ccc(-c2ccc3ncc4ccc(=O)n(-c5ccc(N6CCCC6=O)cc5)c4c3c2)cn1] | MS m/z: 462.86 (M + 1). |
| 86 | 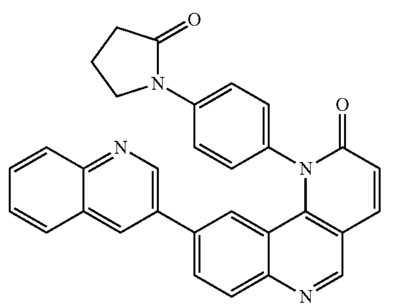 [SMILES: O=C1CCCN1c1ccc(-n2c(=O)ccc3cnc4ccc(-c5cnc6ccccc6c5)cc4c32)cc1] | MS m/z: 482.12 (M + 1). |
| 87 | 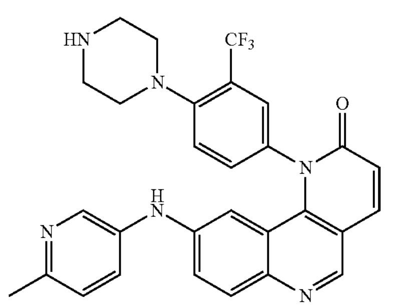 [SMILES: Cc1ccc(Nc2ccc3ncc4ccc(=O)n(-c5ccc(N6CCNCC6)c(C(F)(F)F)c5)c4c3c2)cn1] | $^1$H NMR 600 MHz (CDCl$_3$) δ 8.81 (s, 1H), 8.08 (d, J = 2.4 Hz, 1H), 8.01 (d, J = 8.4 Hz, 1H), 7.95 (d, J = 9 Hz, 1H), 7.48 (m, 2H), 7.36 (d, J = 9 Hz, 1H), 7.29 (dd, J = 9, 2.4 Hz, 1H), 7.10 (dd, J = 9, 2.4 Hz, 1H), 7.04 (d, J = 8.4 Hz, 1H), 6.90 (d, J = 9 Hz, 1H), 3.06 (m, 4H), 2.91 (m, 2H), 2.79 (m, 2H), 2.52 (s, 3H), MS m/z: 531.29 (M + 1). |
| 88 | 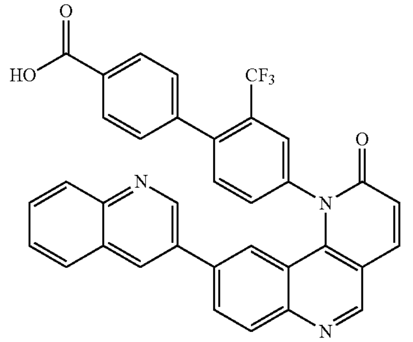 [SMILES: O=C(O)c1ccc(-c2ccc(-n3c(=O)ccc4cnc5ccc(-c6cnc7ccccc7c6)cc5c43)cc2C(F)(F)F)cc1] | MS m/z: 588.27 (M + 1). |

TABLE 4-continued

| Compound Number | Structure | Physical Data<br>¹H NMR 600 MHz and/or MS (m/z) |
|---|---|---|
| 89 | 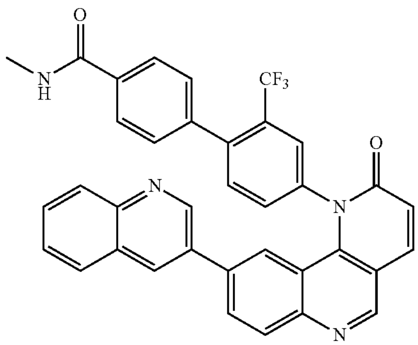 [SMILES: CNC(=O)c1ccc(-c2ccc(-n3c(=O)ccc4cnc5ccc(-c6cnc7ccccc7c6)cc5c43)cc2C(F)(F)F)cc1] | MS m/z: 601.29 (M + 1). |
| 90 | 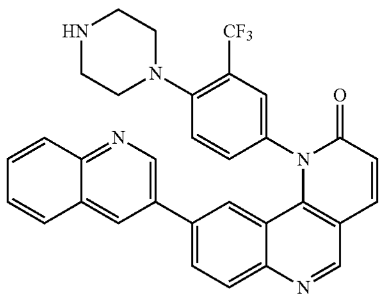 | ¹H NMR 600 MHz (DMSO-d₆) δ 9.18 (s, 1H), 8.45 (d, J = 9.0 Hz, 1H), 8.12 (d, J = 8.6 Hz, 1H), 7.88 (m, 3H), 7.74 (m, 4H), 7.60 (d, J = 6.4 Hz, 1H), 7.04 (m, 2H), 6.96 (d, J = 8.4 Hz, 1H), 6.82 (d, J = 8.0 Hz, 1H), 3.31 (m, 4H), 3.00 (m, 4H), MS m/z: 552.21 (M + 1). |
| 91 | 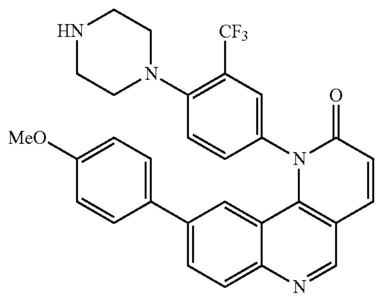 [SMILES: COc1ccc(-c2ccc3ncc4ccc(=O)n(-c5ccc(N6CCNCC6)c(C(F)(F)F)c5)c4c3c2)cc1] | ¹H NMR 600 MHz (DMSO-d₆) δ 8.92 (s, 1H), 8.32 (d, J = 9.2 Hz, 1H), 8.12 (d, J = 8.2 Hz, 1H), 7.80 (m, 2H), 7.71 (m, 3H), 7.54 (d, J = 6.3 Hz, 1H), 6.98 (m, 2H), 6.88 (d, J = 9.0 Hz, 1H), 6.78 (d, J = 8.1 Hz, 1H), 3.80 (s, 3H), 3.38 (m, 4H), 3.01 (m, 4H), MS m/z: 531.28 (M + 1). |
| 92 | 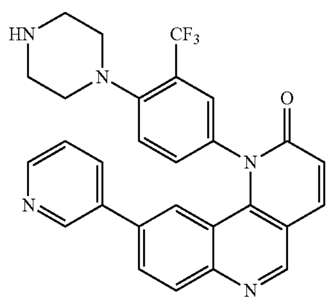 [SMILES: O=c1ccc2cnc3ccc(-c4cccnc4)cc3c2n1-c1ccc(N2CCNCC2)c(C(F)(F)F)c1] | ¹H NMR 600 MHz (DMSO-d₆) δ 9.25 (s, 1H), 9.12 (m, 2H), 8.40 (d, J = 9.1 Hz, 1H), 8.34 (d, J = 8.8 Hz, 1H), 7.84 (m, 2H), 7.68 (m, 2H), 7.48 (d, J = 6.1 Hz, 1H), 7.12 (s, 1H), 6.90 (d, J = 8.1 Hz, 1H), 6.78 (d, J = 7.6 Hz, 1H), 3.34 (m, 4H), 2.98 (m, 4H), MS m/z: 502.34 (M + 1). |
| 93 | 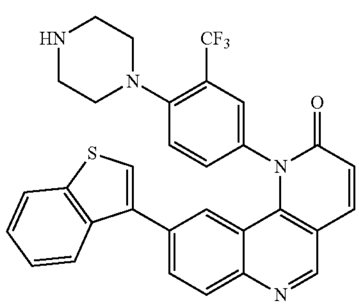 [SMILES: O=c1ccc2cnc3ccc(-c4csc5ccccc45)cc3c2n1-c1ccc(N2CCNCC2)c(C(F)(F)F)c1] | MS m/z: 577.47 (M + 1). |

TABLE 4-continued

| Compound Number | Structure | Physical Data<br>¹H NMR 600 MHz and/or MS (m/z) |
|---|---|---|
| 94 | 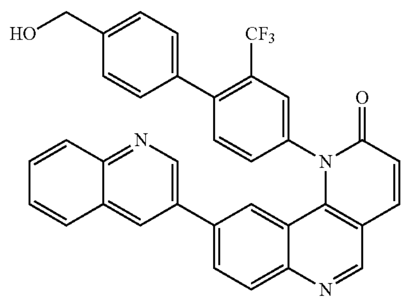 [SMILES: O=c1ccc2cnc3ccc(-c4cnc5ccccc5c4)cc3c2n1-c1ccc(-c2ccc(CO)cc2)c(C(F)(F)F)c1] | ¹H NMR 600 MHz (CDCl₃) δ 9.06 (s, 1H), 8.75 (bs, 1H), 8.30 (d, J = 8.4 Hz, 1H), 8.18 (d, J = 9 Hz, 1H), 8.07 (d, J = 9.6 Hz, 1H), 8.10 (dd, J = 8.4, 1.8 Hz, 1H), 7.96 (d, J = 2.4 Hz, 1H), 7.79-7.75 (m, 3H), 7.67 (dd, J = 7.8, 1.8 Hz, 1H), 7.57 (m, 2H), 7.24 (d, J = 9 Hz, 2H), 7.02 (d, J = 9 Hz, 1H), 4.73 (s, 2H), MS m/z: 574.35 (M + 1). |
| 95 | 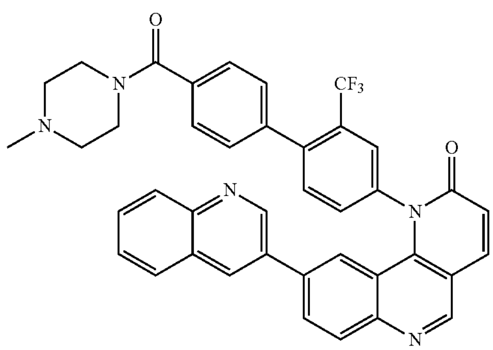 [SMILES: CN1CCN(C(=O)c2ccc(-c3ccc(-n4c(=O)ccc5cnc6ccc(-c7cnc8ccccc8c7)cc6c54)cc3C(F)(F)F)cc2)CC1] | ¹H NMR 600 MHz (CDCl₃) δ 9.07 (s, 1H), 8.73 (d, J = 1.8 Hz, 1H), 8.31 (d, J = 9 Hz, 1H), 8.17 (d, J = 8.4 Hz, 1H), 8.08 (d, J = 8.4 Hz, 1H), 9.02 (dd, J = 8.4, 1.8 Hz, 1H), 7.99 (d, J = 1.8 Hz, 1H), 7.80 (d, J = 1.8 Hz, 1H), 7.78 (m, 2H), 7.70 (dd, J = 7.8, 2.4 Hz, 1H), 7.58 (m, 2H), 7.27 (m, 2H), 7.22 (d, J = 1.8 Hz, 1H), 7.16 (d, J = 7.2 Hz, 2H), 7.03 (d, J = 9.6 Hz, 1H), 3.84 (m, 2H), 3.49 (m, 2H), 3.35 (s, 3H), 2.53 (m, 2H), 2.40 (m, 2H), MS m/z: 670.31 (M + 1). |
| 96 | 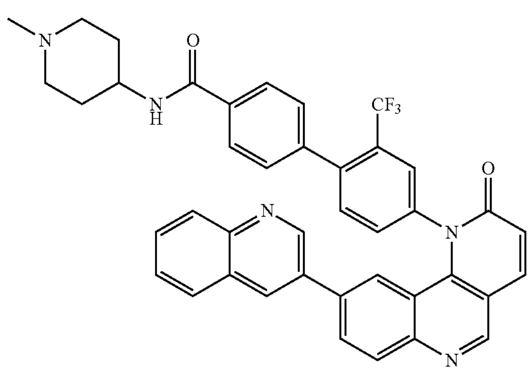 [SMILES: CN1CCC(NC(=O)c2ccc(-c3ccc(-n4c(=O)ccc5cnc6ccc(-c7cnc8ccccc8c7)cc6c54)cc3C(F)(F)F)cc2)CC1] | ¹H NMR 600 MHz (CDCl₃) δ 9.06 (s, 1H), 8.71 (d, J = 2.4 Hz, 1H), 8.30 (d, J = 3.0 Hz, 1H), 8.20 (d, J = 2.4 Hz, 1H), 8.08 (d, J = 9.6 Hz, 1H), 8.01 (dd, J = 8.4, 1.2 Hz, 1H), 7.99 (d, J = 1.8 Hz, 1H), 7.80 (t, J = 8.4 Hz, 2H), 7.76 (d, J = 7.8 Hz, 1H), 7.58 (d, J = 7.8 Hz, 3H), 7.55 (t, J = 8.4 Hz, 1H), 7.19 (d, J = 7.8 Hz, 3H), 7.02 (d, J = 9 Hz, 1H), 5.99 (d, J = 7.2 Hz, 1H), 4.04 (m, 1H), 2.91 (m, 2H), 2.36 (s, 3H), 2.2 (m, 2H), 3.11 (m, 2H), 1.66 (m, 2H), MS m/z: 684.37 (M + 1). |
| 97 | 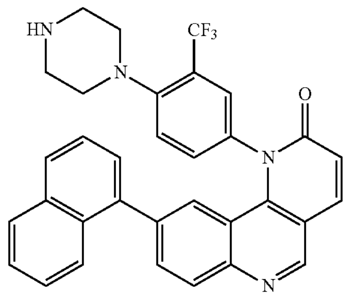 [SMILES: O=c1ccc2cnc3ccc(-c4cccc5ccccc45)cc3c2n1-c1ccc(N2CCNCC2)c(C(F)(F)F)c1] | ¹H NMR 600 MHz (DMSO-d₆) δ 9.04 (s, 1H), 8.24 (d, J = 7.4 Hz, 1H), 8.01 (d, J = 6.8 Hz, 1H), 7.80 (m, 3H), 7.67 (m, 5H), 7.32 (m, 2H), 7.14 (s, 1H), 6.94 (d, J = 8.0 Hz, 1H), 6.62 (d, J = 7.1 Hz, 1H), 3.31 (m, 4H), 3.02 (m, 4H), MS m/z: 551.13 (M + 1). |

TABLE 4-continued

| Compound Number | Structure | Physical Data ¹H NMR 600 MHz and/or MS (m/z) |
|---|---|---|
| 98 | 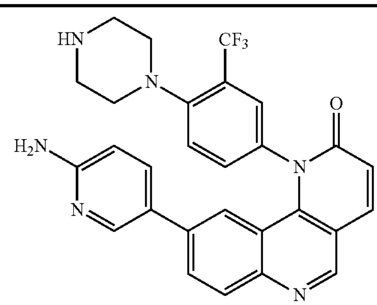 | ¹H NMR 600 MHz (DMSO-d₆) δ 9.07 (s, 1H), 8.28 (d, J = 9.7 Hz, 1H), 8.03 (d, J = 8.8 Hz, 1H), 7.93 (s, 1H), 7.89 (dd, J = 1.8, 6.7 Hz, 1H), 7.73 (d, J = 2.3 Hz, 1H), 7.53 (dd, J = 1.2, 7.3 Hz, 1H), 7.37 (t, J = 7.3 Hz, 1H), 7.11 (dd, J = 2.6, 6.2 Hz, 1H), 6.95 (d, J = 1.8 Hz, 1H), 6.89 (d, J = 9.4 Hz, 1H), 6.39 (d, J = 8.5 Hz, 1H), 2.95 (m, 8H), MS m/z: 517.23 (M + 1). |
| 99 | 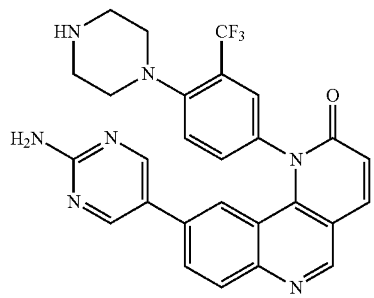 | ¹H NMR 600 MHz (DMSO-d₆) δ 9.11 (s, 1H), 8.54 (s, 1H), 8.30 (d, J = 9.7 Hz, 1H), 8.07 (d, J = 8.5 Hz, 1H), 7.93 (m, 2H), 7.76 (dd, J = 2.3, 6.2 Hz, 1H), 7.59 (dd, J = 1.2, 7.3 Hz, 1H), 7.41 (t, J = 7.9 Hz, 1H), 6.90 (m, 2H), 3.05 (m, 4H), 2.94 (m, 2H), 2.83 (m, 2H), MS m/z: 518.22 (M + 1). |
| 100 | 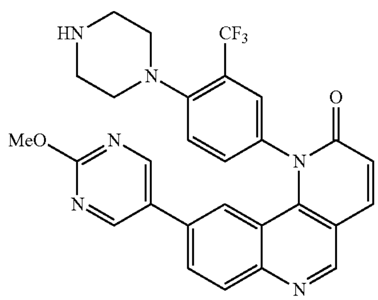 [SMILES: COc1ncc(-c2ccc3ncc4ccc(=O)n(-c5ccc(N6CCNCC6)c(C(F)(F)F)c5)c4c3c2)cn1] | ¹H NMR 600 MHz (DMSO-d₆) δ 9.16 (s, 1H), 8.37 (s, 1H), 8.31 (d, J = 9.4 Hz, 1H), 8.13 (d, J = 8.5 Hz, 1H), 8.03 (dd, J = 1.5, 7.0 Hz, 1H), 7.90 (d, J = 2.1 Hz, 1H), 7.78 (dd, J = 2.1, 6.5 Hz, 1H), 7.73 (d, J = 8.5 Hz, 1H), 7.00 (d, J = 1.5 Hz, 1H), 6.93 (d, J = 9.4 Hz, 1H), 6.50 (s, 1H), 3.91 (s, 3H), 2.95 (m, 6H), 2.81 (m, 2H), MS m/z: 533.93 (M + 1). |
| 101 | 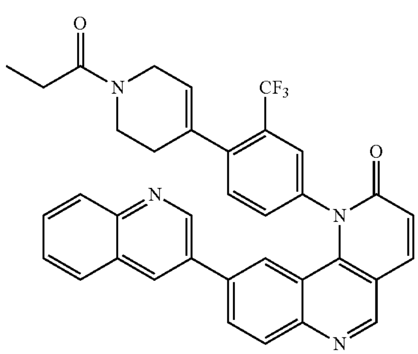 [SMILES: CCC(=O)N1CC=C(c2ccc(-n3c(=O)ccc4cnc5ccc(-c6cnc7ccccc7c6)cc5c43)cc2C(F)(F)F)CC1] | MS m/z: 605.33 (M + 1). |
| 102 | 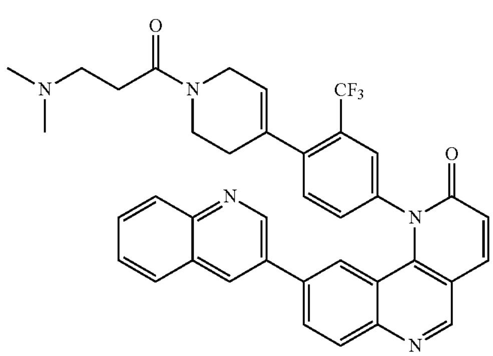 [SMILES: CN(C)CCC(=O)N1CC=C(c2ccc(-n3c(=O)ccc4cnc5ccc(-c6cnc7ccccc7c6)cc5c43)cc2C(F)(F)F)CC1] | MS m/z: 648.36 (M + 1). |

TABLE 4-continued

| Compound Number | Structure | Physical Data ¹H NMR 600 MHz and/or MS (m/z) |
|---|---|---|
| 103 | 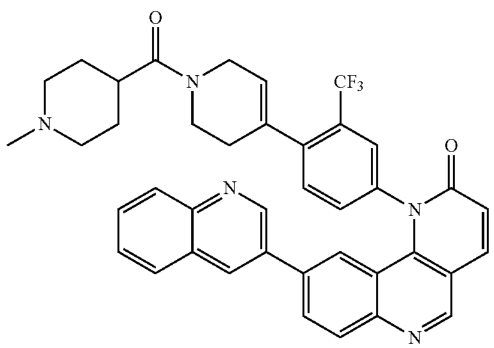 | MS m/z: 674.43 (M + 1). |
| 104 | 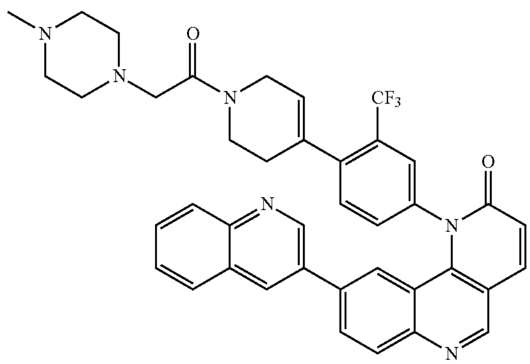 [SMILES: CN1CCN(CC(=O)N2CC=C(c3ccc(-n4c(=O)ccc5cnc6ccc(-c7cnc8ccccc8c7)cc6c54)cc3C(F)(F)F)CC2)CC1] | MS m/z: 689.55 (M + 1). |
| 105 | 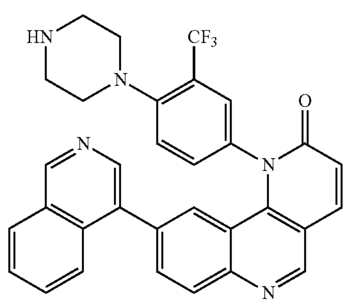 [SMILES: O=c1ccc2cnc3ccc(-c4cncc5ccccc45)cc3c2n1-c1ccc(N2CCNCC2)c(C(F)(F)F)c1] | MS m/z: 552.87 (M + 1). |
| 106 | 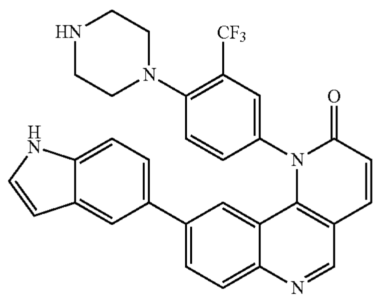 [SMILES: O=c1ccc2cnc3ccc(-c4ccc5[nH]ccc5c4)cc3c2n1-c1ccc(N2CCNCC2)c(C(F)(F)F)c1] | ¹H NMR 600 MHz (DMSO-d$_6$) δ 11.14 (s, 1H), 9.10 (s, 1H), 8.30 (d, J = 9.7 Hz, 1H), 8.09 (m, 2H), 7.98 (dd, J = 1.7, 6.7 Hz, 1H), 7.66 (m, 2H), 7.34 (m, 3H), 7.03 (d, J = 1.8 Hz, 1H), 6.90 (m, 2H), 6.40 (s, 1H), 3.10 (m, 2H), 2.94 (m, 4H), 2.67 (m, 2H), MS m/z: 540.92 (M + 1). |

TABLE 4-continued
| Compound Number | Structure | Physical Data $^1$H NMR 600 MHz and/or MS (m/z) |
|---|---|---|
| 107 | 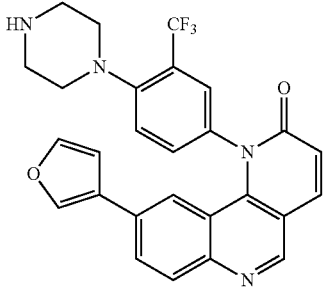 [SMILES: O=c1ccc2cnc3ccc(-c4ccoc4)cc3c2n1-c1ccc(N2CCNCC2)c(C(F)(F)F)c1] | $^1$H NMR 600 MHz (DMSO-d$_6$) δ 9.13 (s, 1H), 8.28 (d, J = 9.3 Hz, 1H), 8.04 (m, 2H), 7.99 (s, 1H), 7.80 (m, 2H), 7.53 (m, 1H), 7.42 (m, 1H), 7.20 (s, 1H), 6.77 (d, J = 9.1 Hz, 1H), 6.65 (dd, J = 1.4, 4.1 Hz, 1H), 3.00 (m, 6H), 2.81 (m, 2H), MS m/z: 491.04 (M + 1). |
| 108 | 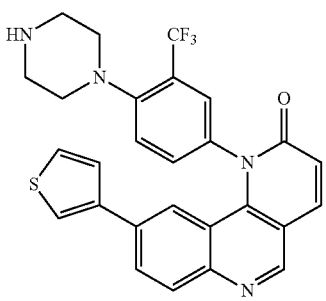 [SMILES: O=c1ccc2cnc3ccc(-c4ccsc4)cc3c2n1-c1ccc(N2CCNCC2)c(C(F)(F)F)c1] | $^1$H NMR 600 MHz (DMSO-d$_6$) δ 9.10 (s, 1H), 8.29 (d, J = 9.7 Hz, 1H), 8.05 (m, 2H), 7.98 (s, 1H), 7.74 (m, 2H), 7.57 (m, 1H), 7.50 (m, 1H), 7.18 (s, 1H), 6.90 (d, J = 9.4 Hz, 1H), 6.81 (dd, J = 1.2, 3.8 Hz, 1H), 3.03 (m, 6H), 2.84 (m, 2H), MS m/z: 507.66 (M + 1). |
| 109 | 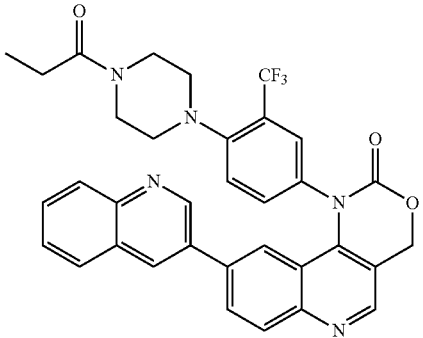 [SMILES: CCC(=O)N1CCN(c2ccc(N3C(=O)OCc4cnc5ccc(-c6cnc7ccccc7c6)cc5c43)cc2C(F)(F)F)CC1] | C34H28F3N5O3 LC-MS (M + H): 612.22 |
| 110 | 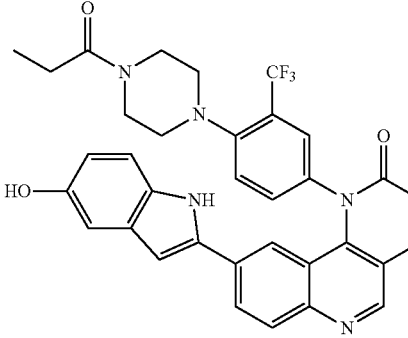 | C34H28F3N5O3 LC-MS (MH): 613.21 |

TABLE 4-continued

| Compound Number | Structure | Physical Data <br> ¹H NMR 600 MHz and/or MS (m/z) |
| --- | --- | --- |
| 111 | 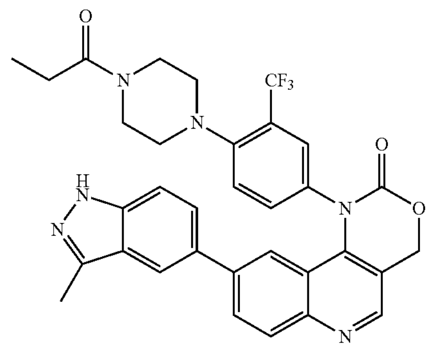 [SMILES: CCC(=O)N1CCN(c2ccc(N3C(=O)OCc4cnc5ccc(-c6ccc7[nH]nc(C)c7c6)cc5c43)cc2C(F)(F)F)CC1] | C33H29F3N6O3 <br> LC-MS (M + H): 615.19 |
| 112 | 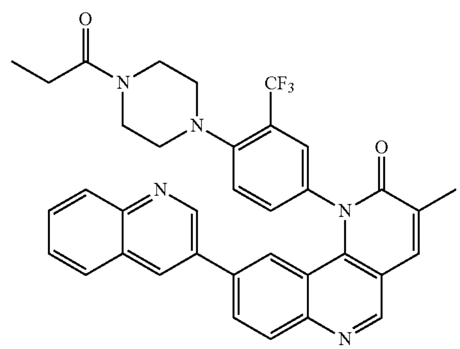 [SMILES: CCC(=O)N1CCN(c2ccc(-n3c(=O)c(C)cc4cnc5ccc(-c6cnc7ccccc7c6)cc5c43)cc2C(F)(F)F)CC1] | C36H30F3N5O2 <br> LC-MS (M + H): 622.38 |
| 113 | 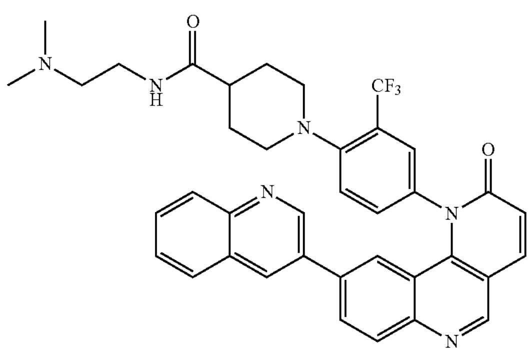 [SMILES: CN(C)CCNC(=O)C1CCN(c2ccc(-n3c(=O)ccc4cnc5ccc(-c6cnc7ccccc7c6)cc5c43)cc2C(F)(F)F)CC1] | C38H35F3N6O2 <br> LC-MS (M + H): 665.48 |
| 114 | 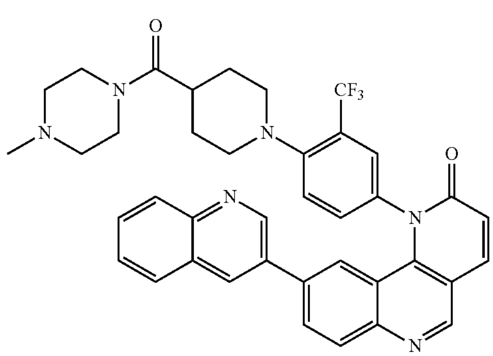 [SMILES: CN1CCN(C(=O)C2CCN(c3ccc(-n4c(=O)ccc5cnc6ccc(-c7cnc8ccccc8c7)cc6c54)cc3C(F)(F)F)CC2)CC1] | C39H35F3N6O2 <br> LC-MS (M + H): 677.39 |

TABLE 4-continued

| Compound Number | Structure | Physical Data<br>¹H NMR 600 MHz and/or MS (m/z) |
|---|---|---|
| 115 | 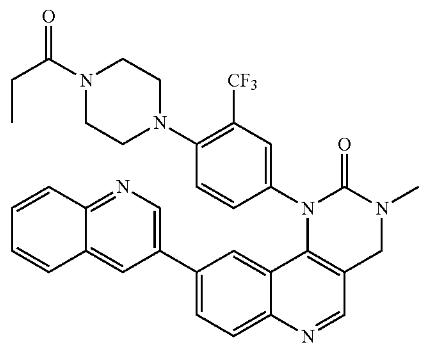 [SMILES: CCC(=O)N1CCN(c2ccc(N3C(=O)N(C)Cc4cnc5ccc(-c6cnc7ccccc7c6)cc5c43)cc2C(F)(F)F)CC1] | C35H31F3N6O2<br>LC-MS (M + H): 625.22 |
| 116 | 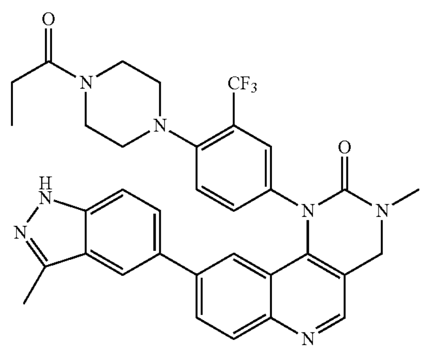 [SMILES: CCC(=O)N1CCN(c2ccc(N3C(=O)N(C)Cc4cnc5ccc(-c6ccc7[nH]nc(C)c7c6)cc5c43)cc2C(F)(F)F)CC1] | C34H32F3N7O2<br>LC-MS (M + H): 628.19 |
| 117 | 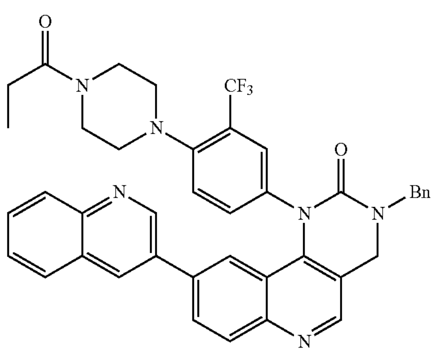 [SMILES: CCC(=O)N1CCN(c2ccc(N3C(=O)N(Cc4ccccc4)Cc4cnc5ccc(-c6cnc7ccccc7c6)cc5c43)cc2C(F)(F)F)CC1] | C41H35F3N6O2<br>LC-MS (M + H): 701.33 |
| 118 | 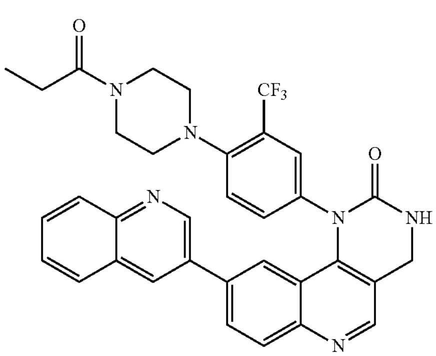 [SMILES: CCC(=O)N1CCN(c2ccc(N3C(=O)NCc4cnc5ccc(-c6cnc7ccccc7c6)cc5c43)cc2C(F)(F)F)CC1] | C34H29F3N6O2<br>LC-MS (M + H): 611.12 |

TABLE 4-continued

| Compound Number | Structure | Physical Data ¹H NMR 600 MHz and/or MS (m/z) |
|---|---|---|
| 119 | 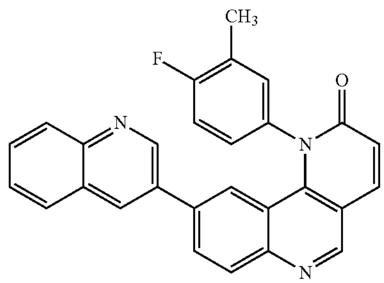 | C28H18FN3O<br>LC-MS (M + H): 432.08 |
| 120 | 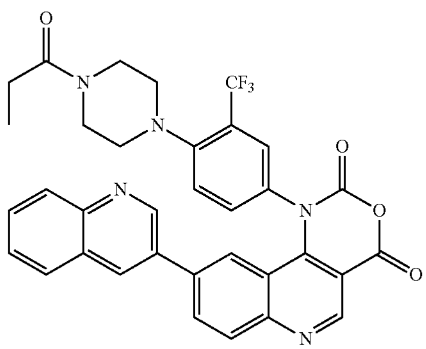 [SMILES: CCC(=O)N1CCN(c2ccc(-n3c(=O)oc(=O)c4cnc5ccc(-c6cnc7ccccc7c6)cc5c43)cc2C(F)(F)F)CC1] | C34H26F3N5O4<br>LC-MS (M + H): 626.20 |
| 121 | 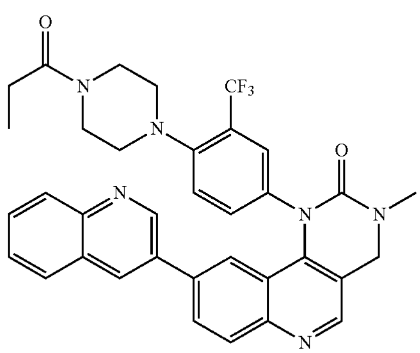 [SMILES: CCC(=O)N1CCN(c2ccc(N3C(=O)N(C)Cc4cnc5ccc(-c6cnc7ccccc7c6)cc5c43)cc2C(F)(F)F)CC1] | C35H31F3N6O2<br>LC-MS (M + H): 625.17 |
| 122 | 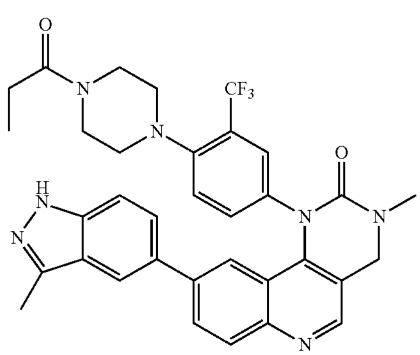 [SMILES: CCC(=O)N1CCN(c2ccc(N3C(=O)N(C)Cc4cnc5ccc(-c6ccc7[nH]nc(C)c7c6)cc5c43)cc2C(F)(F)F)CC1] | C34H32F3N7O2<br>LC-MS (M + H): 628.14 |

TABLE 4-continued

| Compound Number | Structure | Physical Data<br>¹H NMR 600 MHz and/or MS (m/z) |
|---|---|---|
| 123 | 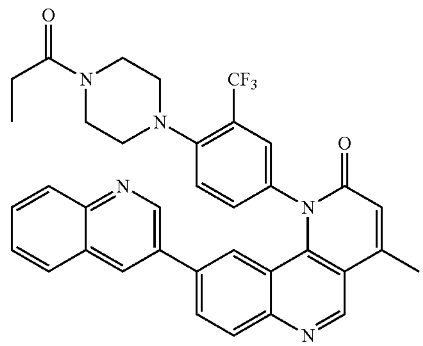 [SMILES: CCC(=O)N1CCN(c2ccc(-n3c(=O)cc(C)c4cnc5ccc(-c6cnc7ccccc7c6)cc5c43)cc2C(F)(F)F)CC1] | C36H30F3N5O2<br>LC-MS (M + H): 622.14 |
| 124 | 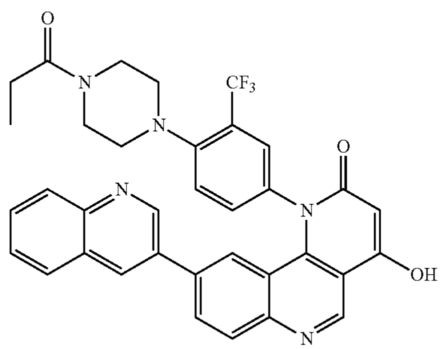 [SMILES: CCC(=O)N1CCN(c2ccc(-n3c(=O)cc(O)c4cnc5ccc(-c6cnc7ccccc7c6)cc5c43)cc2C(F)(F)F)CC1] | C35H28F3N5O3<br>LC-MS (M + H): 624.45 |
| 125 | 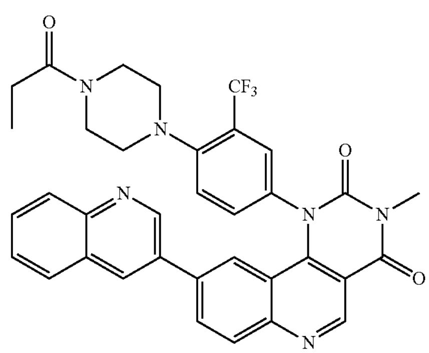 [SMILES: CCC(=O)N1CCN(c2ccc(-n3c(=O)n(C)c(=O)c4cnc5ccc(-c6cnc7ccccc7c6)cc5c43)cc2C(F)(F)F)CC1] | C35H29F3N6O3<br>LC-MS (M + H): 639.49 |
| 126 | 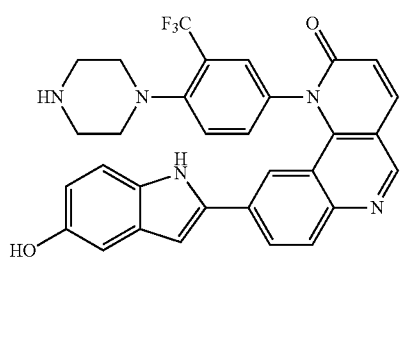 [SMILES: O=c1ccc2cnc3ccc(-c4cc5cc(O)ccc5[nH]4)cc3c2n1-c1ccc(N2CCNCC2)c(C(F)(F)F)c1] | C31H24F3N5O2<br>LC-MS (M + H): 556.09 |

TABLE 4-continued

| Compound Number | Structure | Physical Data<br>$^1$H NMR 600 MHz and/or MS (m/z) |
|---|---|---|
| 127 | 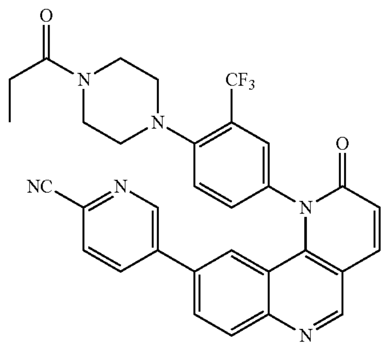 [SMILES: CCC(=O)N1CCN(c2ccc(-n3c(=O)ccc4cnc5ccc(-c6ccc(C#N)nc6)cc5c43)cc2C(F)(F)F)CC1] | C32H25F3N6O2<br>LC-MS (M + H): 583.37 |
| 128 | 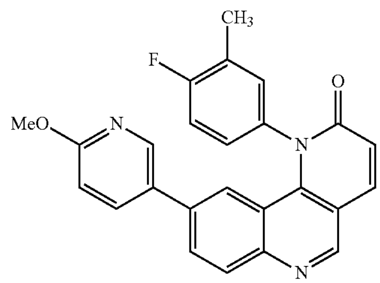 | C25H18FN3O2<br>LC-MS (M + H): 412.25 |
| 129 | 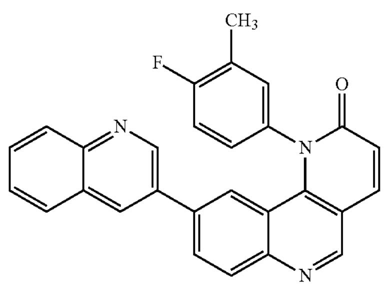 | C28H18FN3O<br>LC-MS (M + H): 432.20 |
| 130 | 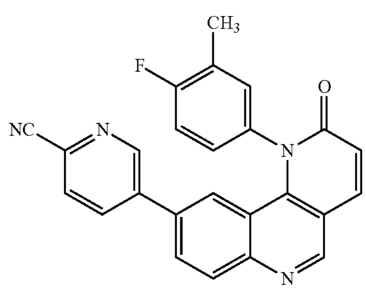 [SMILES: Cc1cc(-n2c(=O)ccc3cnc4ccc(-c5ccc(C#N)nc5)cc4c32)ccc1F] | C25H15FN4O<br>LC-MS (M + H): 407.26 |
| 131 | 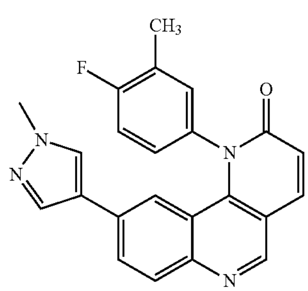 [SMILES: Cc1cc(-n2c(=O)ccc3cnc4ccc(-c5cnn(C)c5)cc4c32)ccc1F] | C23H17FN4O<br>LC-MS (M + H): 385.27 |

TABLE 4-continued

| Compound Number | Structure | Physical Data <br> ¹H NMR 600 MHz and/or MS (m/z) |
|---|---|---|
| 132 | 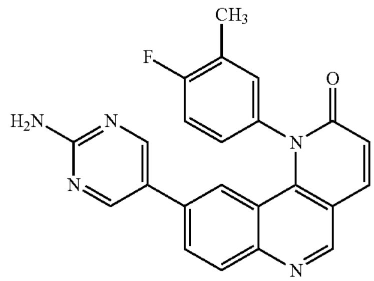 | C23H16FN5O <br> LC-MS (M + H): 398.25 <br> ¹H NMR 600 Hz (DMSO) δ 9.64 (s, 1H), 8.94 (s, 1H), 8.44 (d, J = 4.8 Hz, 2H), 8.23 (d, J = 9.6 Hz, 1H), 7.92 (d, J = 9 Hz, 1H), 7.79 (d, J = 1.8 Hz, 1H), 7.67 (dd, J = 8.4, 1.8 Hz, 1H), 7.27-7.21 (m, 3H), 6.87 (t, J = 4.8 Hz, 1H), 6.83 (d, J = 8.4 Hz, 1H), 2.14 (s, 3H) |
| 133 | 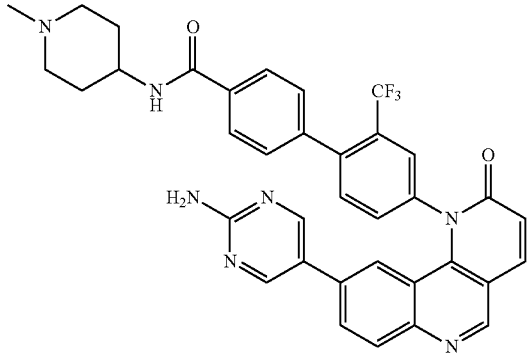 [SMILES: CN1CCC(NC(=O)c2ccc(-c3ccc(-n4c(=O)ccc5cnc6ccc(-c7cnc(N)nc7)cc6c54)cc3C(F)(F)F)cc2)CC1] | C36H30F3N7O2 <br> LC-MS (M + H): 650.34 |
| 134 | 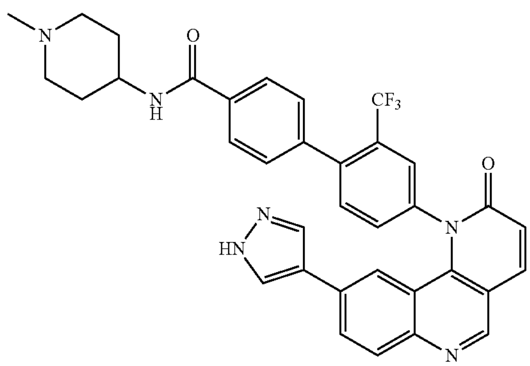 [SMILES: CN1CCC(NC(=O)c2ccc(-c3ccc(-n4c(=O)ccc5cnc6ccc(-c7cn[nH]c7)cc6c54)cc3C(F)(F)F)cc2)CC1] | C35H29F3N6O2 <br> LC-MS (M + H): 623.34 |
| 135 | 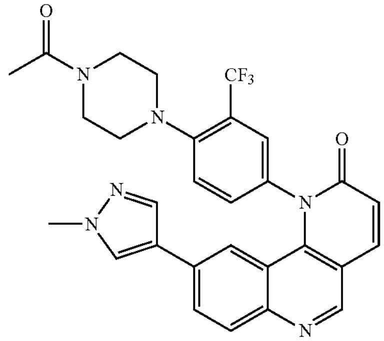 [SMILES: CC(=O)N1CCN(c2ccc(-n3c(=O)ccc4cnc5ccc(-c6cnn(C)c6)cc5c43)cc2C(F)(F)F)CC1] | C29H25F3N6O2 <br> LC-MS (M + H): 547.27 |

TABLE 4-continued

| Compound Number | Structure | Physical Data<br>¹H NMR 600 MHz and/or MS (m/z) |
|---|---|---|
| 136 | 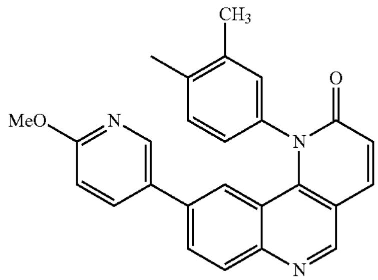 [SMILES: COc1ccc(-c2ccc3ncc4ccc(=O)n(-c5ccc(C)c(C)c5)c4c3c2)cn1] | C26H21N3O2<br>LC-MS (M + H): 408.24 |
| 137 | 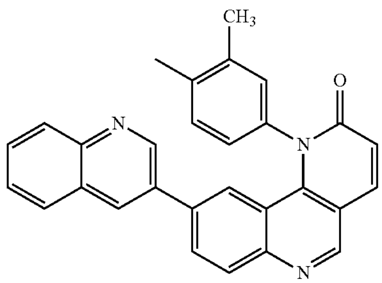 [SMILES: Cc1ccc(-n2c(=O)ccc3cnc4ccc(-c5cnc6ccccc6c5)cc4c32)cc1C] | C29H21N3O<br>LC-MS (M + H): 428.22 |
| 138 | 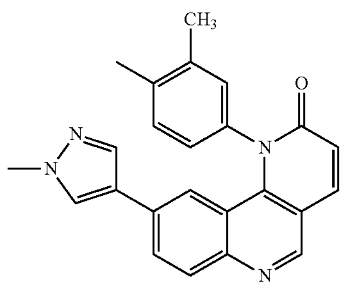 [SMILES: Cc1ccc(-n2c(=O)ccc3cnc4ccc(-c5cnn(C)c5)cc4c32)cc1C] | C24H20N4O<br>LC-MS (M + H): 381.27 |
| 139 | 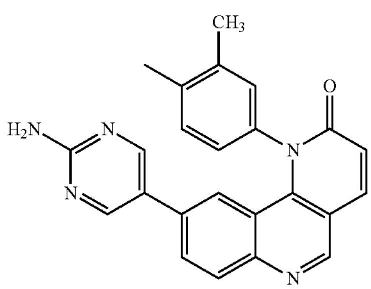 [SMILES: Cc1ccc(-n2c(=O)ccc3cnc4ccc(-c5cnc(N)nc5)cc4c32)cc1C] | C24H19N5O<br>LC-MS (M + H): 394.26 |
| 140 | 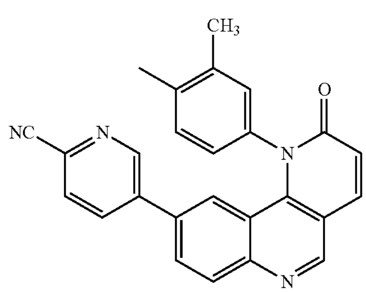 [SMILES: Cc1ccc(-n2c(=O)ccc3cnc4ccc(-c5ccc(C#N)nc5)cc4c32)cc1C] | C26H18N4O<br>LC-MS (M + H): 403.23 |

TABLE 4-continued

| Compound Number | Structure | Physical Data $^1$H NMR 600 MHz and/or MS (m/z) |
|---|---|---|
| 141 | 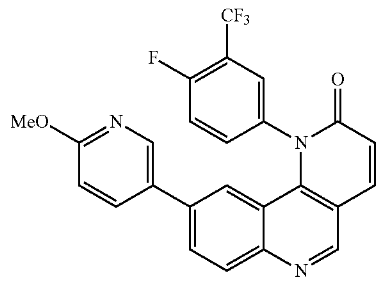 [SMILES: COc1ccc(-c2ccc3ncc4ccc(=O)n(-c5ccc(F)c(C(F)(F)F)c5)c4c3c2)cn1] | C25H15F4N3O2<br>LC-MS (M + H): 466.24 |
| 142 | 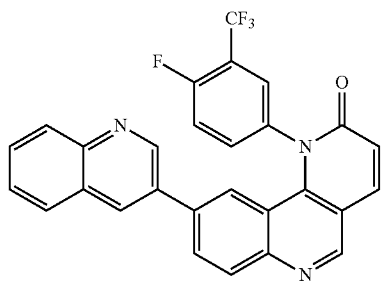 [SMILES: O=c1ccc2cnc3ccc(-c4cnc5ccccc5c4)cc3c2n1-c1ccc(F)c(C(F)(F)F)c1] | C28H15F4N3O<br>LC-MS (M + H): 486.22 |
| 143 | 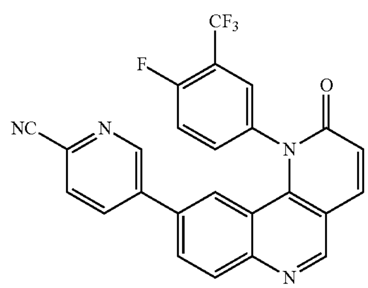 [SMILES: N#Cc1ccc(-c2ccc3ncc4ccc(=O)n(-c5ccc(F)c(C(F)(F)F)c5)c4c3c2)cn1] | C25H12F4N4O<br>LC-MS (M + H): 461.23 |
| 144 | 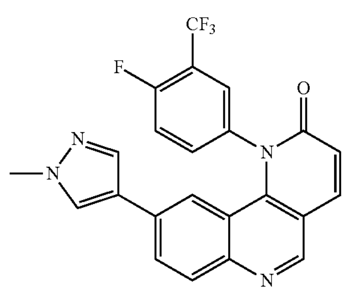 [SMILES: Cn1cc(-c2ccc3ncc4ccc(=O)n(-c5ccc(F)c(C(F)(F)F)c5)c4c3c2)cn1] | C23H14F4N4O<br>LC-MS (M + H): 439.26 |
| 145 | 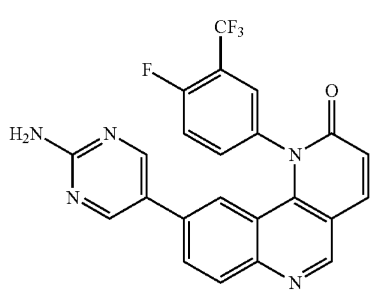 | C23H13F4N5O<br>LC-MS (M + H): 452.19 |

TABLE 4-continued

| Compound Number | Structure | Physical Data ¹H NMR 600 MHz and/or MS (m/z) |
|---|---|---|
| 146 | (structure) | C22H12F4N4O<br>LC-MS (M + H): 425.22 |
| 147 | (structure) | C22H15FN4O<br>LC-MS (M + H): 371.28<br>¹H NMR 600 Hz (DMSO) δ 13.04 (bs, 1H), 9.04 (s, 1H), 8.27 (d, J = 9.6 Hz, 1H), 7.99 (d, J = 9 Hz, 1H), 7.95 (dd, J = 9, 1.8 Hz, 1H), 7.80 (s, 1H), 7.50-7.49 (m, 1H), 7.48 (d, J = 9 Hz, 1H), 7.36-7.34 (m, 1H), 7.28 (s, 1H), 7.02 (d, J = 1.2 Hz), 6.89 (d, J = 9.6 Hz, 1H), 2.31 (s, 3H) |
| 148 | (structure) | C25H18FN3O3<br>LC-MS (M + H): 428.25 |
| 149 | (structure) | C28H18FN3O2<br>LC-MS (M + H): 448.30 |
| 150 | (structure) | C25H15FN4O2<br>LC-MS (M + H): 423.17 |

TABLE 4-continued

| Compound Number | Structure | Physical Data ¹H NMR 600 MHz and/or MS (m/z) |
|---|---|---|
| 151 | 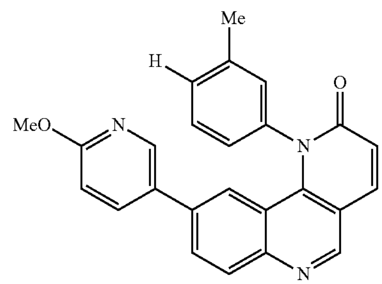 [SMILES: COc1ccc(-c2ccc3ncc4ccc(=O)n(-c5cccc(C)c5)c4c3c2)cn1] | C25H19N3O2<br>LC-MS (M + H): 394.29 |
| 152 | 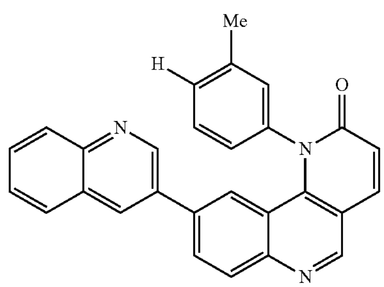 [SMILES: Cc1cccc(-n2c(=O)ccc3cnc4ccc(-c5cnc6ccccc6c5)cc4c32)c1] | C28H19N3O<br>LC-MS (M + H): 414.34 |
| 153 | 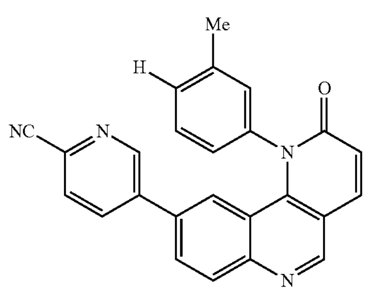 [SMILES: Cc1cccc(-n2c(=O)ccc3cnc4ccc(-c5ccc(C#N)nc5)cc4c32)c1] | C25H16N4O<br>LC-MS (M + H): 389.28 |
| 154 | 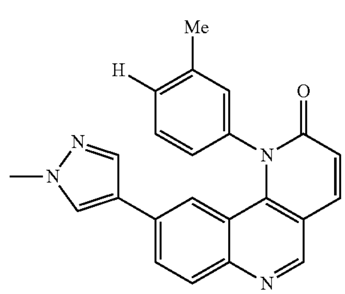 [SMILES: Cc1cccc(-n2c(=O)ccc3cnc4ccc(-c5cnn(C)c5)cc4c32)c1] | C23H18N4O<br>LC-MS (M + H): 367.33 |
| 155 | 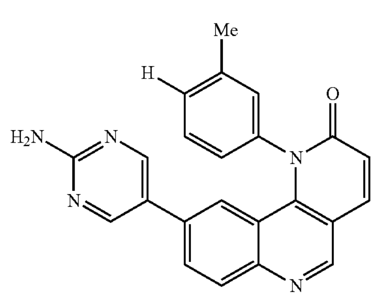 [SMILES: Cc1cccc(-n2c(=O)ccc3cnc4ccc(-c5cnc(N)nc5)cc4c32)c1] | C23H17N5O<br>LC-MS (M + H): 380.18<br>QL-V-120-2 NMR:<br>¹H NMR 600 Hz (DMSO) δ 9.53 (s, 1H), 8.93 (s, 1H), 8.42 (d, J = 4.8 Hz, 2H), 8.22 (d, J = 9 Hz, 1H), 7.91 (d, J = 9 Hz, 1H), 7.74 (d, J = 2.4 Hz, 1H), 7.64 (dd, J = 9, 2.4 Hz, 1H), 7.32 (t, J = 7.2 Hz, 1H), 7.13-7.07 (m, 3H), 6.84 (t, J = 4.8 Hz, 1H), 6.82 (d, J = 9 Hz, 1H), 2.22 (s, 3H). |

TABLE 4-continued

| Compound Number | Structure | Physical Data ¹H NMR 600 MHz and/or MS (m/z) |
|---|---|---|
| 156 | 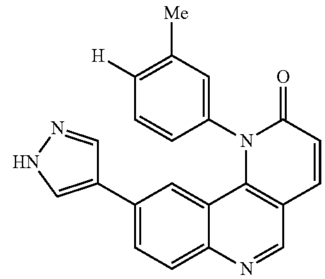 [SMILES: Cc1cccc(-n2c(=O)ccc3cnc4ccc(-c5cn[nH]c5)cc4c32)c1] | C22H16N4O<br>LC-MS (M + H): 353.29 |
| 157 | 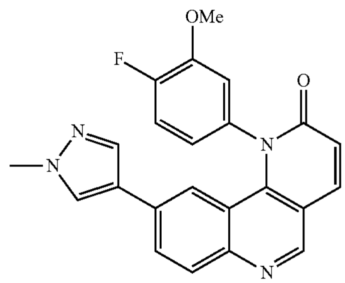 [SMILES: COc1cc(-n2c(=O)ccc3cnc4ccc(-c5cnn(C)c5)cc4c32)ccc1F] | C23H17FN4O2<br>LC-MS (M + H): 401.15 |
| 158 | 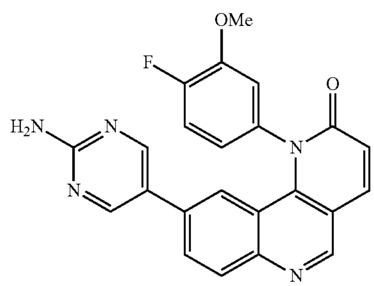 [SMILES: COc1cc(-n2c(=O)ccc3cnc4ccc(-c5cnc(N)nc5)cc4c32)ccc1F] | C23H16FN5O2<br>LC-MS (M + H): 414.14 |
| 159 | 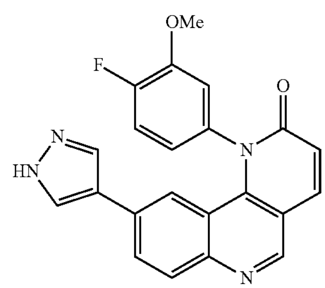 [SMILES: COc1cc(-n2c(=O)ccc3cnc4ccc(-c5cn[nH]c5)cc4c32)ccc1F] | C22H15FN4O2<br>LC-MS (M + H): 387.11 |
| 160 | 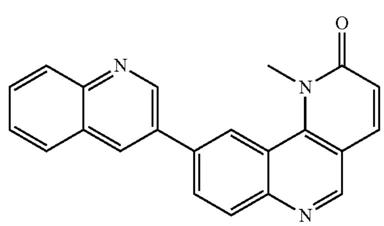 [SMILES: Cn1c(=O)ccc2cnc3ccc(-c4cnc5ccccc5c4)cc3c21] | C22H15N3O<br>LC-MS (M + H): 338.26 |
| 161 | 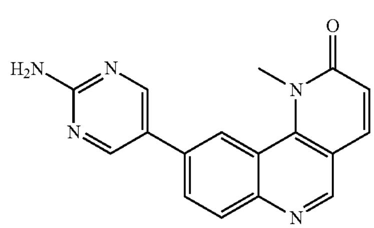 [SMILES: Cn1c(=O)ccc2cnc3ccc(-c4cnc(N)nc4)cc3c21] | C17H13N5O<br>LC-MS (M + H): 304.32 |

TABLE 4-continued

| Compound Number | Structure | Physical Data $^1$H NMR 600 MHz and/or MS (m/z) |
|---|---|---|
| 162 | 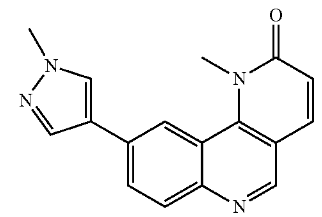 [SMILES: Cn1cc(-c2ccc3ncc4ccc(=O)n(C)c4c3c2)cn1] | C17H14N4O<br>LC-MS (M + H): 291.34 |
| 163 | 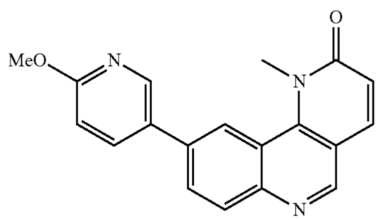 [SMILES: COc1ccc(-c2ccc3ncc4ccc(=O)n(C)c4c3c2)cn1] | C19H15N3O2<br>LC-MS (M + H): 318.29 |
| 164 | 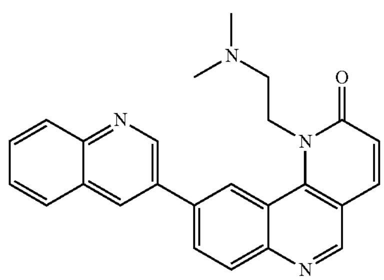 [SMILES: CN(C)CCn1c(=O)ccc2cnc3ccc(-c4cnc5ccccc5c4)cc3c21] | C25H22N4O<br>LC-MS (M + H): 395.28 |
| 165 | 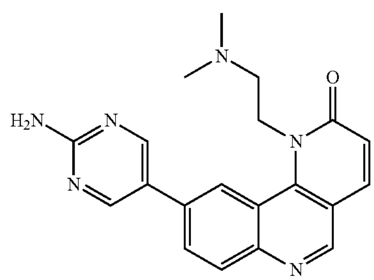 [SMILES: CN(C)CCn1c(=O)ccc2cnc3ccc(-c4cnc(N)nc4)cc3c21] | C20H20N6O<br>LC-MS (M + H): 361.26 |
| 166 | 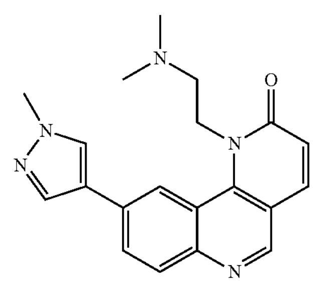 [SMILES: CN(C)CCn1c(=O)ccc2cnc3ccc(-c4cnn(C)c4)cc3c21] | C20H21N5O<br>LC-MS (M + H): 348.34 |
| 167 | 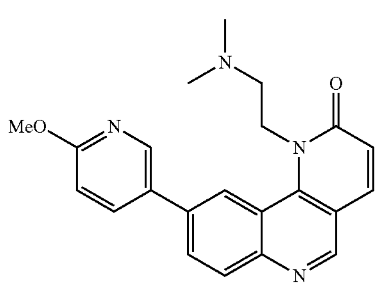 [SMILES: COc1ccc(-c2ccc3ncc4ccc(=O)n(CCN(C)C)c4c3c2)cn1] | C22H22N4O2<br>LC-MS (M + H): 375.30 |

| Compound Number | Structure | Physical Data $^1$H NMR 600 MHz and/or MS (m/z) |
|---|---|---|
| 168 | 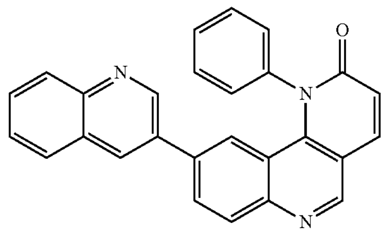 [SMILES: O=c1ccc2cnc3ccc(-c4cnc5ccccc5c4)cc3c2n1-c1ccccc1] | C27H17N3O<br>LC-MS (M + H): 400.29 |
| 169 | 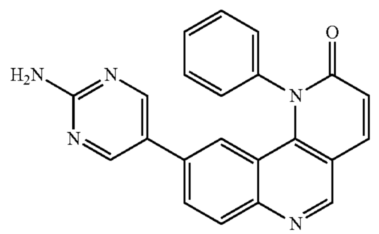 [SMILES: Nc1ncc(-c2ccc3ncc4ccc(=O)n(-c5ccccc5)c4c3c2)cn1] | C22H15N5O<br>LC-MS (M + H): 366.27<br>$^1$H NMR 600 Hz (DMSO) δ 9.56 (s, 1H), 8.93 (s, 1H), 8.45 (d, J = 4.8 Hz, 2H), 8.23 (d, J = 9 Hz, 1H), 7.90 (d, J = 9 Hz, 1H), 7.80 (d, J = 1.8 Hz, 1H), 7.64 (dd, J = 9.0, 2.4 Hz, 1H), 7.45 (t, J = 7.8 Hz, 2H), 7.32 (d, J = 7.8 Hz, 2H), 7.24 (t, J = 7.8 Hz, 1H), 6.84-6.81 (m, 2H). |
| 170 | 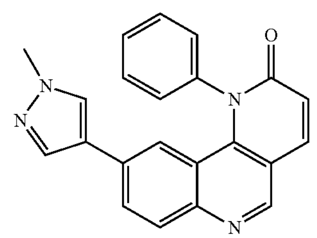 [SMILES: Cn1cc(-c2ccc3ncc4ccc(=O)n(-c5ccccc5)c4c3c2)cn1] | C22H16N4O<br>LC-MS (M + H): 353.29 |
| 171 | 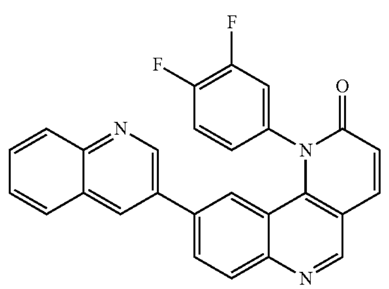 [SMILES: O=c1ccc2cnc3ccc(-c4cnc5ccccc5c4)cc3c2n1-c1ccc(F)c(F)c1] | C27H15F2M3O<br>LC-MS (M + H): 436.23 |
| 172 | 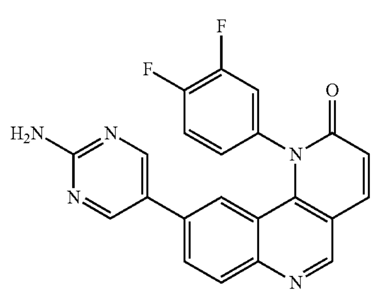 [SMILES: Nc1ncc(-c2ccc3ncc4ccc(=O)n(-c5ccc(F)c(F)c5)c4c3c2)cn1] | C22H13F2N5O<br>LC-MS (M + H): 402.27 |

TABLE 4-continued

| Compound Number | Structure | Physical Data $^1$H NMR 600 MHz and/or MS (m/z) |
|---|---|---|
| 173 | 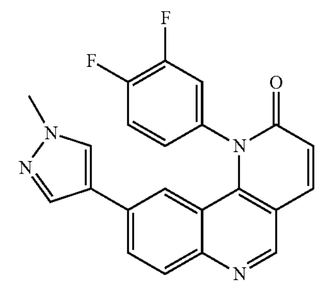 [SMILES: Cn1cc(-c2ccc3ncc4ccc(=O)n(-c5ccc(F)c(F)c5)c4c3c2)cn1] | C22H14F2N4O<br>LC-MS (M + H): 389.15 |
| 174 | 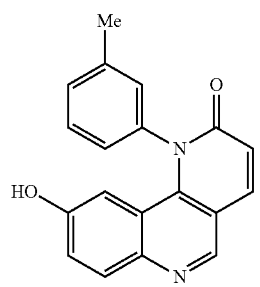 [SMILES: Cc1cccc(-n2c(=O)ccc3cnc4ccc(O)cc4c32)c1] | C19H14N2O2<br>LC-MS (M + H): 303.26 |
| 175 | 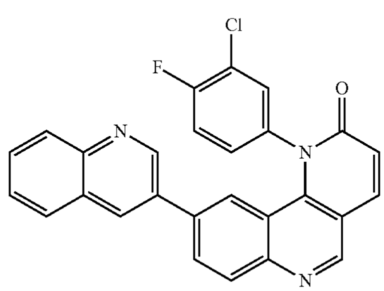 [SMILES: O=c1ccc2cnc3ccc(-c4cnc5ccccc5c4)cc3c2n1-c1ccc(F)c(Cl)c1] | C27H15ClFN3O<br>LC-MS (M + H): 452.19<br>$^1$H NMR 600 Hz (DMSO) δ 9.19 (s, 1H), 8.86 (d, J = 8.4 Hz, 1H), 8.35 (d, J = 9.6 Hz, 1H), 8.25 (dd, J = 8.4, 1.8 Hz, 1H), 8.21 (d, J = 8.4 Hz, 1H), 8.07 (m, 2H), 8.02 (d, J = 1.8 Hz, 1H), 7.98 (d, J = 8.4 Hz, 1H), 7.80 (m, 2H), 7.71 (t, J = 8.4 Hz, 1H), 7.63 (m, 1H), 7.29 (d, J = 1.8 Hz, 1H), 6.96 (d, J = 9 Hz, 1H) |
| 176 | 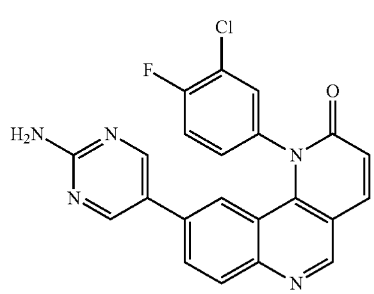 [SMILES: Nc1ncc(-c2ccc3ncc4ccc(=O)n(-c5ccc(F)c(Cl)c5)c4c3c2)cn1] | C22H13ClFN5O<br>LC-MS (M + H): 418.29<br>$^1$H NMR 600 Hz (DMSO) δ 9.11 (s, 1H), 8.31 (d, J = 9 Hz, 1H), 8.09 (s, 2H), 8.08 (d, J = 9 Hz, 1H), 7.99 (m, 2H), 7.73 (t, J = 9H, 1H), 7.57 (m, 1H), 7.0 (m, 3H), 6.92 (d, J = 9.6 Hz, 1H) |
| 177 | 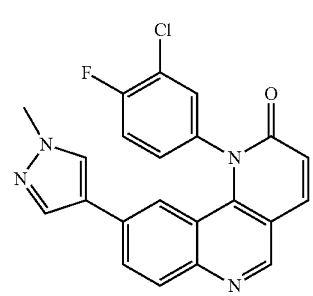 [SMILES: Cn1cc(-c2ccc3ncc4ccc(=O)n(-c5ccc(F)c(Cl)c5)c4c3c2)cn1] | C22H14ClFN4O<br>LC-MS (M + H): 405.17<br>$^1$H NMR 600 Hz (DMSO) δ 9.05 (s, 1H), 8.29 (d, J = 9.6 Hz, 1H), 8.0 (m, 2H), 7.89 (dd, J = 8.4, 1.8 Hz, 1H), 7.85 (s, 1H), 7.78 (t, J = 9 Hz, 1H), 7.58 (m, 1H), 7.14 (s, 1H), 6.95 (s, 1H), 6.91 (d, J = 9 Hz, 1H), 3.83 (s, 1H) |

TABLE 4-continued

| Compound Number | Structure | Physical Data<br>¹H NMR 600 MHz and/or MS (m/z) |
|---|---|---|
| 178 | 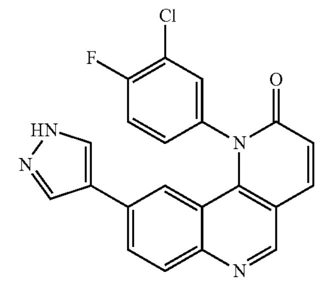 [SMILES: O=c1ccc2cnc3ccc(-c4cn[nH]c4)cc3c2n1-c1ccc(F)c(Cl)c1] | C21H12ClFN4O<br>LC-MS (M + H): 391.13<br>¹H NMR 600 Hz (DMSO) δ 13.09 (s, 1H), 9.05 (s, 1H), 8.29 (d, J = 9.6 Hz, 1H), 8.05 (m, 2H), 7.96 (d, J = 8.4 Hz, 1H), 7.85 (s, 1H), 7.78 (t, J = 9 Hz, 1H), 7.58 (m, 1H), 7.27 (s, 1H), 6.99 (s, 1H), 6.91 (d, J = 9 Hz, 1H) |
| 179 | 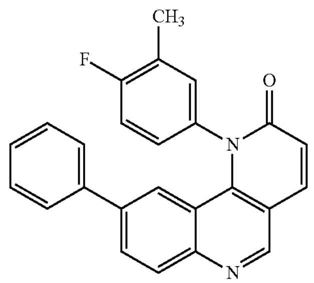 [SMILES: Cc1cc(-n2c(=O)ccc3cnc4ccc(-c5ccccc5)cc4c32)ccc1F] | C25H17FN2O<br>LC-MS (M + H): 381.24<br>¹H NMR 600 Hz (DMSO) δ 9.12 (s, 1H), 8.30 (d, J = 9.6 Hz, 1H), 8.10 (d, J = 8.4 Hz, 1H), 8.0 (dd, J = 8.4, 1.8 Hz, 1H), 7.54 (dd, J = 6.6, 2.4 Hz, 1H), 7.42-7.36 (m, 4H), 7.33-7.30 (m, 1H), 7.20 (d, J = 9 Hz, 2H), 7.17 (d, J = 1.8 Hz, 1H), 6.91 (d, J = 9 Hz, 1H), 2.31 (s, 3H) |
| 180 | 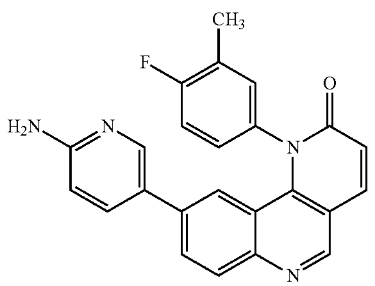 | C24H17FN4O<br>LC-MS (M + H): 397.19<br>¹H NMR 600 Hz (DMSO) δ 9.06 (s, 1H), 8.28 (d, J = 9 Hz, 1H), 8.02 (d, J = 8.4 Hz, 1H), 7.92 (dd, J = 9, 1.8 Hz, 1H), 7.82 (d, J = 2.4 Hz, 1H), 7.51 (dd, J = 6, 1.8 Hz, 1H), 7.42 (t, J = 9 Hz, 1H), 7.33 (m, 1H), 7.18 (dd, J = 9, 2.4 Hz, 1H), 7.06 (d, J = 1.2 Hz, 1H), 6.89 (d, J = 9.6 Hz, 1H), 6.44 (d, J = 9 Hz, 1H), 6.19 (s, 2H), 2.30 (s, 3H) |
| 181 | 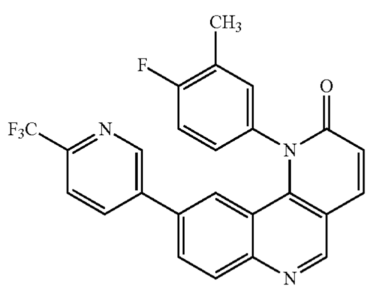 [SMILES: Cc1cc(-n2c(=O)ccc3cnc4ccc(-c5ccc(C(F)(F)F)nc5)cc4c32)ccc1F] | C25H15F4N3O<br>LC-MS (M + H): 450.08<br>¹H NMR 600 Hz (DMSO) δ 9.18 (s, 1H), 8.57 (d, J = 1.8 Hz, 1H), 8.33 (d, J = 9.6 Hz, 1H), 8.17 (d, J = 8.4 Hz, 1H), 8.13 (dd, J = 9, 2.4 Hz, 1H), 7.49 (d, J = 8.4 Hz, 1H), 7.88 (dd, J = 8.4, 1.8 Hz, 1H), 7.54 (dd, J = 9.6, 2.4 Hz, 1H), 7.42 (t, J = 9 Hz, 1H), 7.46 (m, 1H), 7.16 (d, J = 1.8 Hz, 1H), 6.94 (d, J = 9.6 Hz, 1H), 2.30 (s, 3H) |
| 182 | 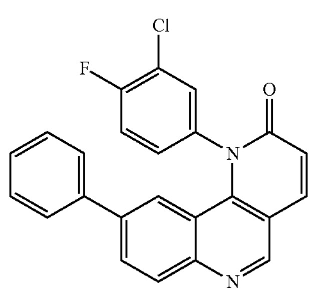 [SMILES: O=c1ccc2cnc3ccc(-c4ccccc4)cc3c2n1-c1ccc(F)c(Cl)c1] | C24H14ClFN2O<br>LC-MS (M + H): 401.15<br>¹H NMR 600 Hz (DMSO) δ 9.14 (s, 1H), 8.32 (d, J = 9.6 Hz, 1H), 8.12 (d, J = 8.4 Hz, 1H), 8.04-8.01 (m, 2H), 7.72 (t, J = 9 Hz, 1H), 7.58-7.55 (m, 1H), 7.41-7.37 (m, 3H), 7.22 (d, J = 6.8 Hz, 2H), 7.12 (d, J = 1.8 Hz, 1H), 6.93 (d, J = 9.6 Hz, 1H), |

TABLE 4-continued

| Compound Number | Structure | Physical Data<br>¹H NMR 600 MHz and/or MS (m/z) |
|---|---|---|
| 183 | 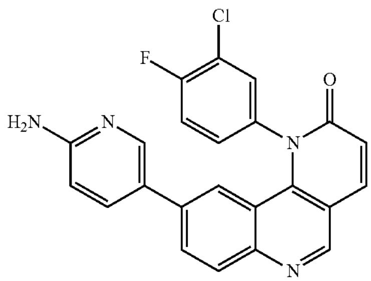 [SMILES: Nc1ccc(-c2ccc3ncc4ccc(=O)n(-c5ccc(F)c(Cl)c5)c4c3c2)cn1] | C23H14ClFN4O<br>LC-MS (M + H): 417.17<br>¹H NMR 600 Hz (DMSO) δ 9.07 (s, 1H), 8.30 (d, J = 9.6 Hz, 1H), 8.05 (d, J = 9 Hz, 1H), 8.0 (d, J = 4.8 Hz, 1H), 7.94 (d, J = 8.4 Hz, 1H), 7.81 (s, 1H), 7.73 (t, J = 9.6 Hz, 1H), 7.56 (m, 1H), 7.19 (d, J = 9 Hz, 1H), 7.01 (s, 1H), 6.91 (d, J = 9.6 Hz, 1H), 6.45 (d, J = 8.4 Hz, 1H), 6.23 (s, 2H), |
| 184 | 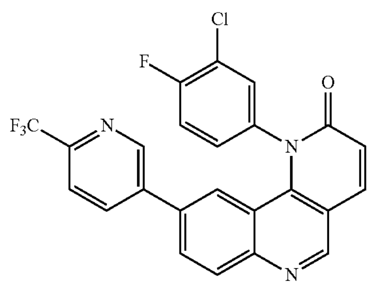 [SMILES: O=c1ccc2cnc3ccc(-c4ccc(C(F)(F)F)nc4)cc3c2n1-c1ccc(F)c(Cl)c1] | C24H12ClF4N3O<br>LC-MS (M + H): 470.13<br>¹H NMR 600 Hz (DMSO) δ 9.20 (s, 1H), 8.57 (s, 1H), 8.34 (d, J = 9 Hz, 1H), 8.20 (d, J = 9 Hz, 1H), 8.14 (dd, J = 8.4, 1.8 Hz, 1H), 8.0 (dd, J = 6.6, 2.4 Hz, 1H), 7.93 (s, 2H), 7.74 (t, J = 8.4 Hz, 1H), 7.62-7.59 (m, 1H), 7.15 (d, J = 1.2 Hz, 1H), 6.96 (d, 9 Hz, 1H), |
| 185 | 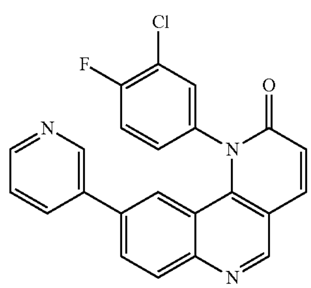 [SMILES: O=c1ccc2cnc3ccc(-c4cccnc4)cc3c2n1-c1ccc(F)c(Cl)c1] | C23H13ClFN3O<br>LC-MS (M + H): 402.20<br>¹H NMR 600 Hz (DMSO) δ 9.17 (s, 1H), 8.57 (d, J = 5.6 Hz, 1H), 8.41 (s, 1H), 8.33 (d, J = 9 Hz, 1H), 8.16 (d, J = 8.4 Hz, 1H), 8.08 (d, J = 8.4 Hz, 1H), 8.02 (dd, J = 6.6, 2.4 Hz, 1H), 7.73 (t, J = 9 Hz, 1H), 7.63 (d, J = 8.4 Hz, 1H), 7.59-7.57 (m, 1H), 7.44 (dd, J = 7.2, 4.2 Hz, 1H), 7.12 (s, 1H), 6.94 (d, J = 9.6 Hz, 1H) |
| 186 | 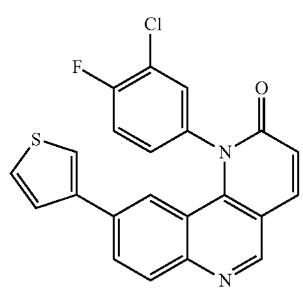 [SMILES: O=c1ccc2cnc3ccc(-c4ccsc4)cc3c2n1-c1ccc(F)c(Cl)c1] | C22H12ClFN2OS<br>LC-MS (M + H): 407.08<br>¹H NMR 600 Hz (DMSO) δ 9.10 (s, 1H), 8.30 (d, J = 9.6 Hz, 1H), 8.07 (m, 2H), 8.02 (dd, J = 6.6, 2.4 Hz, 1H), 7.76 (t, J = 8.4 Hz, 1H), 7.65 (q, J = 3 Hz, 1H), 7.59-7.56 (m, 2H), 7.16 (s, 1H), 6.92 (d, J = 9 Hz, 1H), 6.87 (d, J = 5.4 Hz, 1H), |
| 187 | 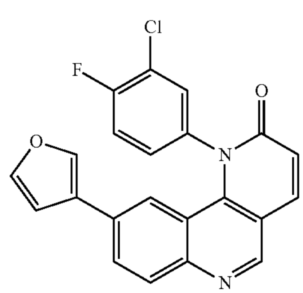 [SMILES: O=c1ccc2cnc3ccc(-c4ccoc4)cc3c2n1-c1ccc(F)c(Cl)c1] | C22H12ClFN2O2<br>LC-MS (M + H): 391.19<br>¹H NMR 600 Hz (DMSO) δ 9.09 (s, 1H), 8.30 (d, J = 9.6 Hz, 1H), 8.04 (d, J = 9 Hz, 1H), 8.0 (dd, J = 6.6, 2.4 Hz, 1H), 7.98 (dd, J = 9.0, 1.8 Hz, 1H), 7.95 (s, 1H), 7.78 (m, 2H), 7.60 (m, 1H), 6.97 (d, J = 1.2 Hz, 1H), 6.92 (d, J = 9 Hz, 1H), 6.17 (s, 1H), |

TABLE 4-continued

| Compound Number | Structure | Physical Data <sup>1</sup>H NMR 600 MHz and/or MS (m/z) |
|---|---|---|
| 188 | 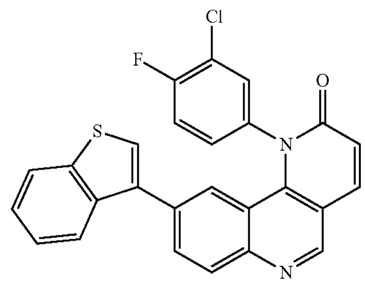 [SMILES: O=c1ccc2cnc3ccc(-c4csc5ccccc45)cc3c2n1-c1ccc(F)c(Cl)c1] | C26H14ClFN2OS<br>LC-MS (M + H): 457.14<br><sup>1</sup>H NMR 600 Hz (DMSO) δ 9.18 (s, 1H), 8.33 (d, J = 9.6 Hz, 1H), 8.19 (d, J = 8.4 Hz, 1H), 8.06 (dd, J = 9, 1.2 Hz, 2H), 7.56 (m, 2H), 7.46-7.42 (m, 4H), 7.21 (s, 1H), 6.93 (d, J = 9.6 Hz, 1H), |
| 189 | 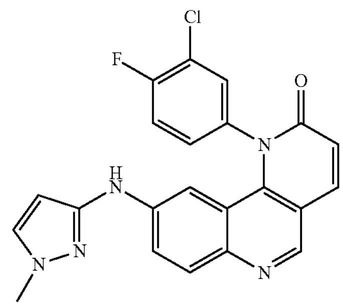 [SMILES: Cn1ccc(Nc2ccc3ncc4ccc(=O)n(-c5ccc(F)c(Cl)c5)c4c3c2)n1] | C22H15ClFN5O<br>LC-MS (M + H): 420.21<br><sup>1</sup>H NMR 600 Hz (DMSO) δ 8.79 (s, 1H), 8.34 (s, 1H), 8.18 (d, J = 9.6 Hz, 1H), 7.83 (d, J = 9.6 Hz, 1H), 7.65 (dd, J = 6.6, 2.4 Hz, 1H), 7.42 (m, 2H), 7.31 (m, 1H), 6.79 (d, J = 9.6 Hz, 1H), 6.57 (d, J = 2.4 Hz, 1H), 5.53 (d, J = 2.4 Hz, 1H) |
| 190 | 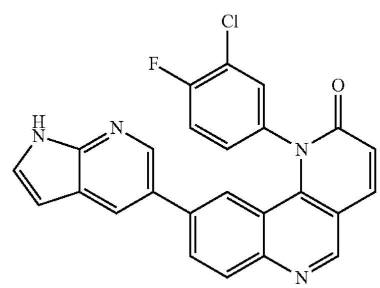 | C25H14ClFN4O<br>LC-MS (M + H): 441.18 |
| 191 | 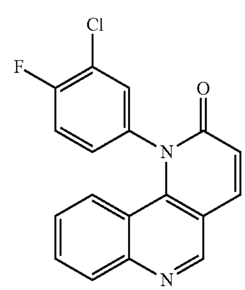 [SMILES: O=c1ccc2cnc3ccccc3c2n1-c1ccc(F)c(Cl)c1] | C18H10ClFN2O<br>LC-MS (M + H): 324.74 |
| 192 | 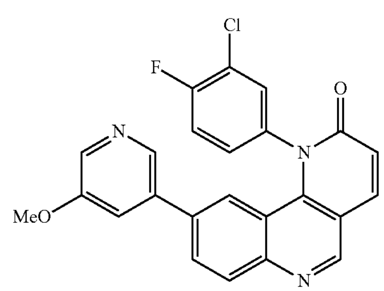 [SMILES: COc1cncc(-c2ccc3ncc4ccc(=O)n(-c5ccc(F)c(Cl)c5)c4c3c2)c1] | C24H15ClFN3O2<br>LC-MS (M + H): 431.85 |

TABLE 4-continued

| Compound Number | Structure | Physical Data <br> $^1$H NMR 600 MHz and/or MS (m/z) |
|---|---|---|
| 193 | 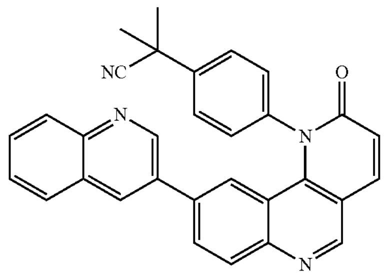 [SMILES: CC(C)(C#N)c1ccc(-n2c(=O)ccc3cnc4ccc(-c5cnc6ccccc6c5)cc4c32)cc1] | C31H22N4O <br> LC-MS (M + H): 467.29 |
| 194 | 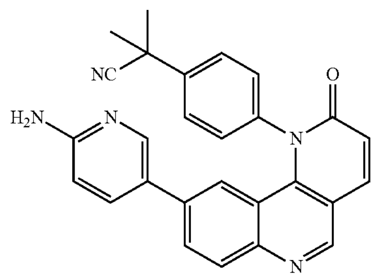 [SMILES: CC(C)(C#N)c1ccc(-n2c(=O)ccc3cnc4ccc(-c5ccc(N)nc5)cc4c32)cc1] | C27H21N5O <br> LC-MS (M + H): 432.37 |
| 195 | 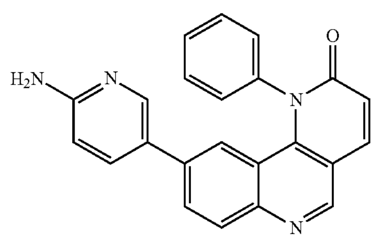 [SMILES: Nc1ccc(-c2ccc3ncc4ccc(=O)n(-c5ccccc5)c4c3c2)cn1] | C23H16N4O <br> LC-MS (M + H): 365.28 |
| 196 | 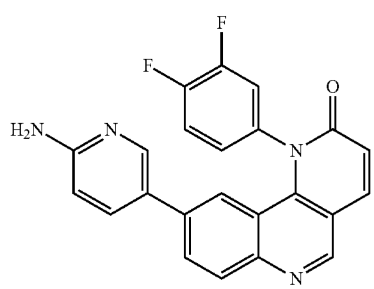 [SMILES: Nc1ccc(-c2ccc3ncc4ccc(=O)n(-c5ccc(F)c(F)c5)c4c3c2)cn1] | C23H14F2N4O <br> LC-MS (M + H): 401.28 |
| 197 | 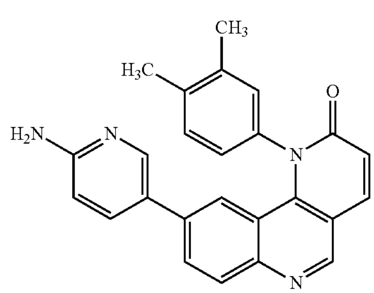 | C25H20N4O <br> LC-MS (M + H): 393.17 |

TABLE 4-continued

| Compound Number | Structure | Physical Data<br>¹H NMR 600 MHz and/or MS (m/z) |
|---|---|---|
| 198 | 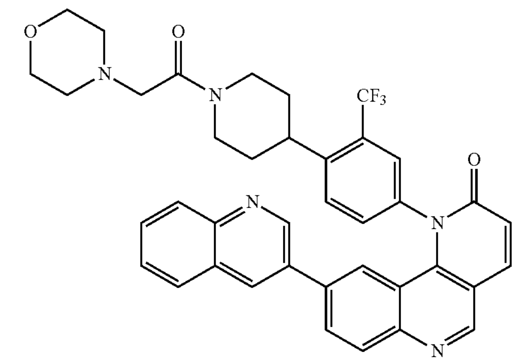 | C39H34F3N5O3<br>LC-MS (M + H): 678.36 |
| 199 | 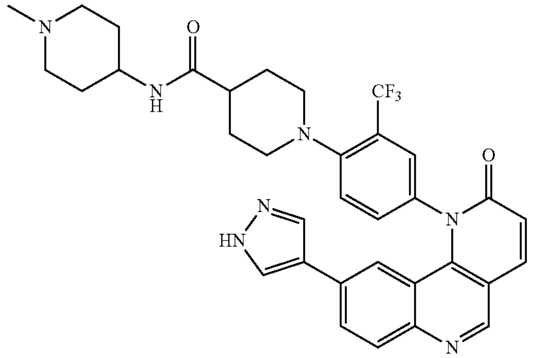 [SMILES: CN1CCC(NC(=O)C2CCN(c3ccc(-n4c(=O)ccc5cnc6ccc(-c7cn[nH]c7)cc6c54)cc3C(F)(F)F)CC2)CC1] | C34H34F3N7O2<br>LC-MS (M + H): 630.25 |
| 200 | 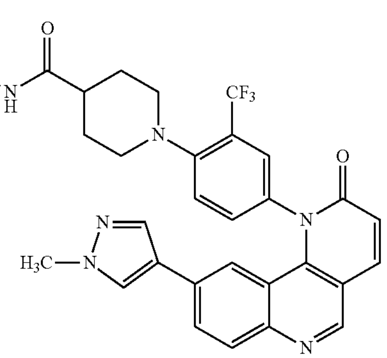 | C35H36F3N7O2<br>LC-MS (M + H): 644.31 |
| 201 | 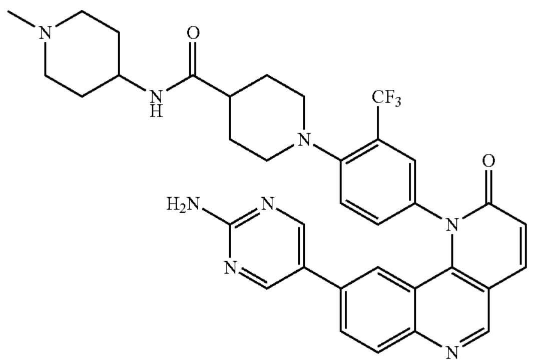 [SMILES: CN1CCC(NC(=O)C2CCN(c3ccc(-n4c(=O)ccc5cnc6ccc(-c7cnc(N)nc7)cc6c54)cc3C(F)(F)F)CC2)CC1] | C35H35F3N8O2<br>LC-MS (M + H): 657.38 |

TABLE 4-continued
| Compound Number | Structure | Physical Data $^1$H NMR 600 MHz and/or MS (m/z) |
|---|---|---|
| 202 | 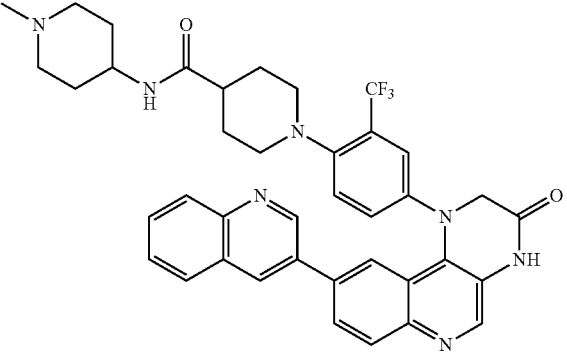 [SMILES: CN1CCC(NC(=O)C2CCN(c3ccc(N4CC(=O)Nc5cnc6ccc(-c7cnc8ccccc8c7)cc6c54)cc3C(F)(F)F)CC2)CC1] | C39H38F3N7O2<br>LC-MS (M + H): 694.40 |
| 203 | 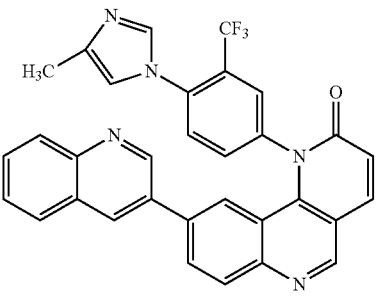 [SMILES: Cc1cn(-c2ccc(-n3c(=O)ccc4cnc5ccc(-c6cnc7ccccc7c6)cc5c43)cc2C(F)(F)F)cn1] | C32H20F3N5O<br>LC-MS (M + H): 548.24 |
| 204 | 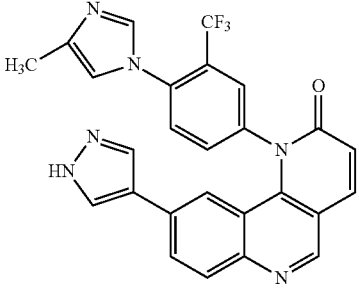 [SMILES: Cc1cn(-c2ccc(-n3c(=O)ccc4cnc5ccc(-c6cn[nH]c6)cc5c43)cc2C(F)(F)F)cn1] | JC26H17F3N6O<br>LC-MS (M + H): 487.15 |
| 205 | 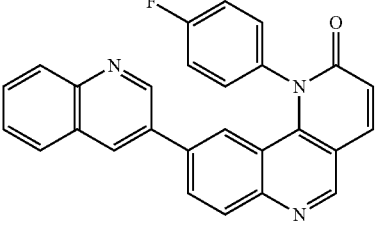 | C27H16FN3O<br>LC-MS (M + H): 418.13 |
| 206 | 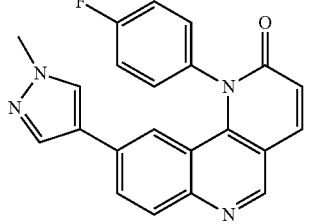 | C22H15FN4O<br>LC-MS (M + H): 371.12 |

TABLE 4-continued

| Compound Number | Structure | Physical Data <br> ¹H NMR 600 MHz and/or MS (m/z) |
|---|---|---|
| 207 | 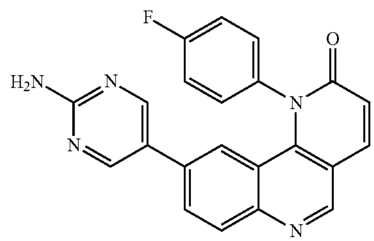 [SMILES: Nc1ncc(-c2ccc3ncc4ccc(=O)n(-c5ccc(F)cc5)c4c3c2)cn1] | C22H14FN5O <br> LC-MS (M + H): 384.17 |
| 208 | 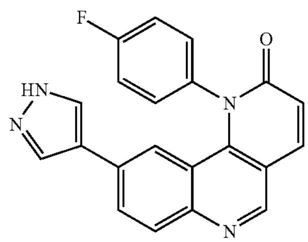 [SMILES: O=c1ccc2cnc3ccc(-c4cn[nH]c4)cc3c2n1-c1ccc(F)cc1] | C21H13FN4O <br> LC-MS (M + H): 357.21 |
| 209 | 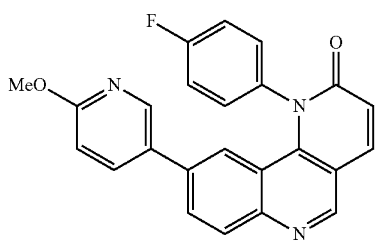 [SMILES: COc1ccc(-c2ccc3ncc4ccc(=O)n(-c5ccc(F)cc5)c4c3c2)cn1] | C24H16FN3O2 <br> LC-MS (M + H): 398.35 |
| 210 | 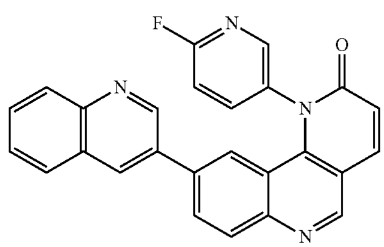 [SMILES: O=c1ccc2cnc3ccc(-c4cnc5ccccc5c4)cc3c2n1-c1ccc(F)nc1] | C26H15FN4O <br> LC-MS (M + H): 419.28 |
| 211 | 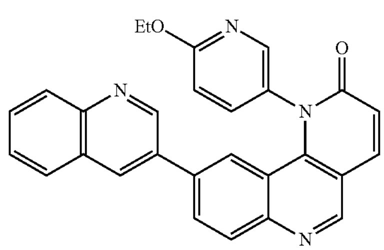 [SMILES: CCOc1ccc(-n2c(=O)ccc3cnc4ccc(-c5cnc6ccccc6c5)cc4c32)cn1] | C28H20N4O2 <br> LC-MS (M + H): 445.33 |
| 212 | 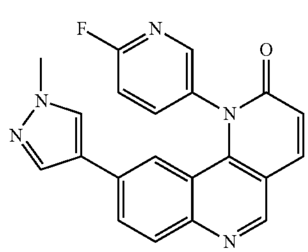 [SMILES: Cn1cc(-c2ccc3ncc4ccc(=O)n(-c5ccc(F)nc5)c4c3c2)cn1] | C21H14FN5O <br> LC-MS (M + H): 372.124 |

TABLE 4-continued

| Compound Number | Structure | Physical Data $^1$H NMR 600 MHz and/or MS (m/z) |
|---|---|---|
| 213 | 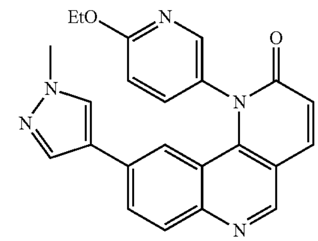 [SMILES: CCOc1ccc(-n2c(=O)ccc3cnc4ccc(-c5cnn(C)c5)cc4c32)cn1] | C23H19N5O2 LC-MS (M + H): 398.18 |
| 214 | 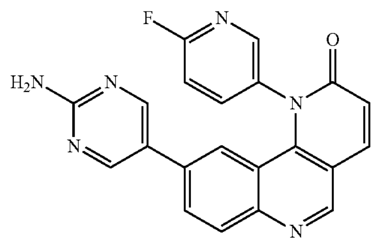 [SMILES: Nc1ncc(-c2ccc3ncc4ccc(=O)n(-c5ccc(F)nc5)c4c3c2)cn1] | C21H13FN6O LC-MS (M + H): 385.26 |
| 215 | 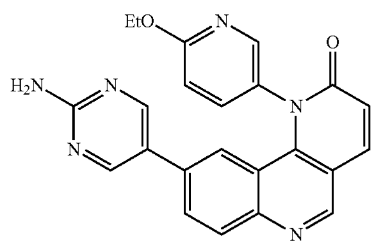 [SMILES: CCOc1ccc(-n2c(=O)ccc3cnc4ccc(-c5cnc(N)nc5)cc4c32)cn1] | C23H18N6O2 LC-MS (M + H): 411.24 |
| 216 | 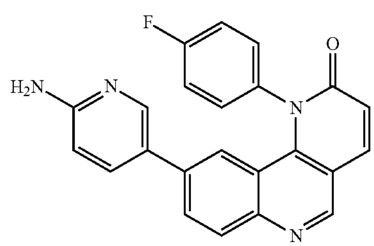 [SMILES: Nc1ccc(-c2ccc3ncc4ccc(=O)n(-c5ccc(F)cc5)c4c3c2)cn1] | C23H15FN4O LC-MS (M + H): 383.28 |
| 217 | 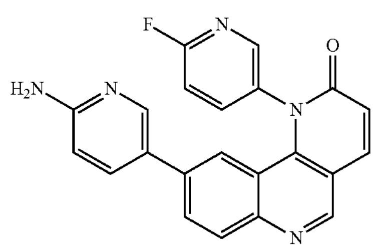 [SMILES: Nc1ccc(-c2ccc3ncc4ccc(=O)n(-c5ccc(F)nc5)c4c3c2)cn1] | C22H14FN5O LC-MS (M + H): 384.20 |
| 218 | 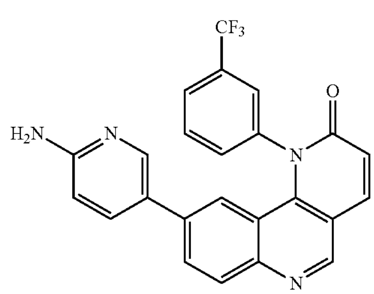 [SMILES: Nc1ccc(-c2ccc3ncc4ccc(=O)n(-c5cccc(C(F)(F)F)c5)c4c3c2)cn1] | C24H15F3N4O LC-MS (M + H): 433.20 |

TABLE 4-continued

| Compound Number | Structure | Physical Data $^1$H NMR 600 MHz and/or MS (m/z) |
|---|---|---|
| 219 | 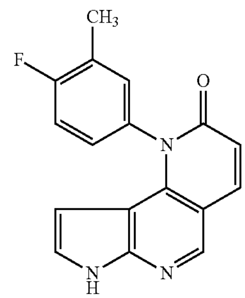 [SMILES: Cc1cc(-n2c(=O)ccc3cnc4[nH]ccc4c32)ccc1F] | C17H12FN3O<br>LC-MS (M + H): 294.37 |
| 220 | 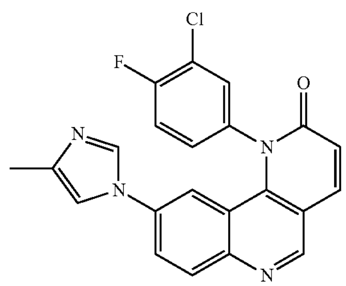 [SMILES: Cc1cn(-c2ccc3ncc4ccc(=O)n(-c5ccc(F)c(Cl)c5)c4c3c2)cn1] | C22H14ClFN4O<br>LC-MS (M + H): 404.08 |
| 221 | 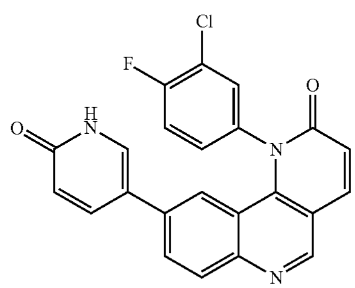 [SMILES: O=c1ccc(-c2ccc3ncc4ccc(=O)n(-c5ccc(F)c(Cl)c5)c4c3c2)c[nH]1] | C23H13ClFN3O2<br>LC-MS (M + H): 417.07 |
| 222 | 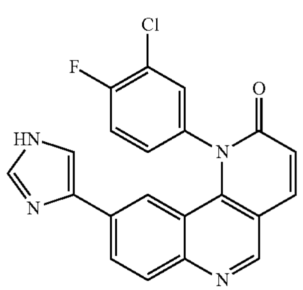 [SMILES: O=c1ccc2cnc3ccc(-c4c[nH]cn4)cc3c2n1-c1ccc(F)c(Cl)c1] | C21H12ClFN4O<br>LC-MS (M + H): 391.19 |
| 223 | 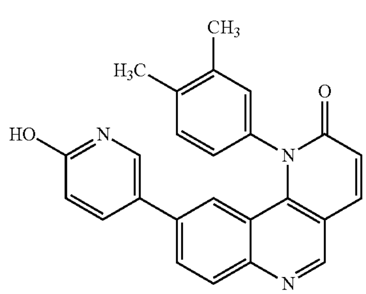 | C25H19N3O2<br>LC-MS (M + H): 394.09 |

TABLE 4-continued

| Compound Number | Structure | Physical Data $^1$H NMR 600 MHz and/or MS (m/z) |
|---|---|---|
| 224 | 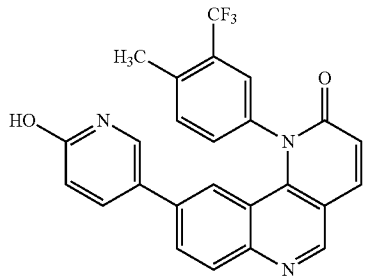 | C25H16F3N3O2<br>LC-MS (M + H): 448.04 |
| 225 | 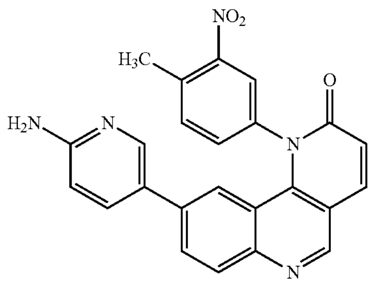 [SMILES: Cc1ccc(-n2c(=O)ccc3cnc4ccc(-c5ccc(N)nc5)cc4c32)cc1[N+](=O)[O-]] | C24H17N5O3<br>LC-MS (M + H): 424.16 |
| 226 | 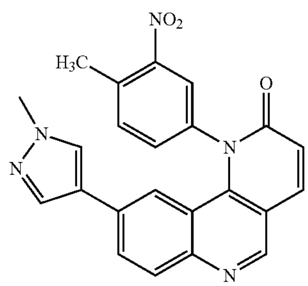 [SMILES: Cc1ccc(-n2c(=O)ccc3cnc4ccc(-c5cnn(C)c5)cc4c32)cc1[N+](=O)[O-]] | C23H17N5O3<br>LC-MS (M + H): 412.16 |
| 227 | 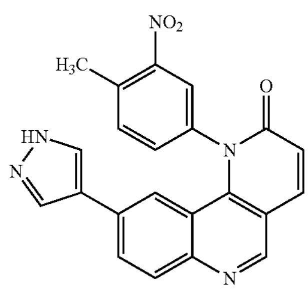 [SMILES: Cc1ccc(-n2c(=O)ccc3cnc4ccc(-c5cn[nH]c5)cc4c32)cc1[N+](=O)[O-]] | C22H15N5O3<br>LC-MS (M + H): 398.18 |
| 228 | 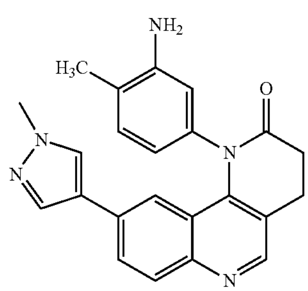 [SMILES: Cc1ccc(N2C(=O)CCc3cnc4ccc(-c5cnn(C)c5)cc4c32)cc1N] | C23H21N5O<br>LC-MS (M + H): 384.27 |

TABLE 4-continued

| Compound Number | Structure | Physical Data ¹H NMR 600 MHz and/or MS (m/z) |
|---|---|---|
| 229 | 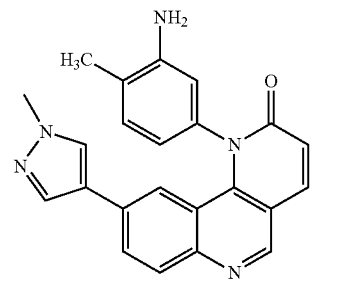 | C23H19N5O<br>LC-MS (M + H): 382.23 |
| 230 | 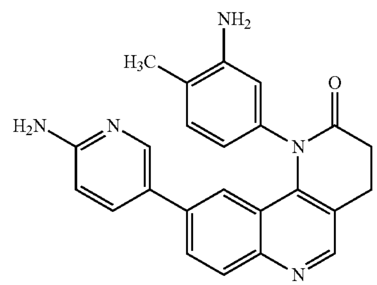 [SMILES: Cc1ccc(N2C(=O)CCc3cnc4ccc(-c5ccc(N)nc5)cc4c32)cc1N] | C24H21N5O<br>LC-MS (M + H): 396.20 |
| 231 | 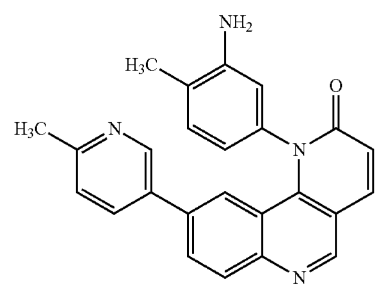 [SMILES: Cc1ccc(-c2ccc3ncc4ccc(=O)n(-c5ccc(C)c(N)c5)c4c3c2)cn1] | C24H19N5O<br>LC-MS (M + H): 394.16 |
| 232 | 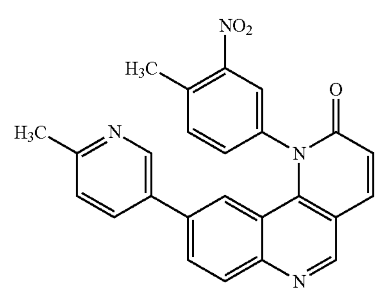 | C25H18N4O4<br>LC-MS (M + H): 439.07 |
| 233 | 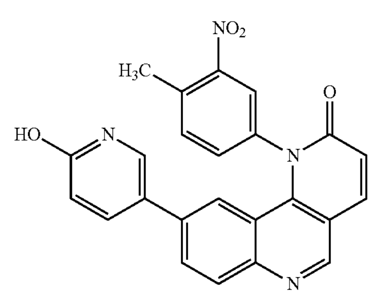 | C24H16N4O4<br>LC-MS (M + H): 425.15 |

TABLE 4-continued

| Compound Number | Structure | Physical Data $^1$H NMR 600 MHz and/or MS (m/z) |
|---|---|---|
| 234 | 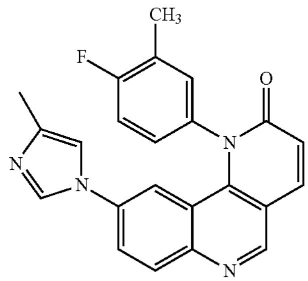 [SMILES: Cc1cn(-c2ccc3ncc4ccc(=O)n(-c5ccc(F)c(C)c5)c4c3c2)cn1] | C23H17FN4O<br>LC-MS (M + H): 385.19 |
| 235 | 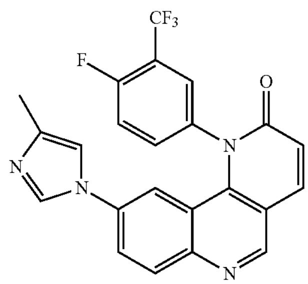 [SMILES: Cc1cn(-c2ccc3ncc4ccc(=O)n(-c5ccc(F)c(C(F)(F)F)c5)c4c3c2)cn1] | C23H14F4N4O<br>LC-MS (M + H): 439.07 |
| 236 | 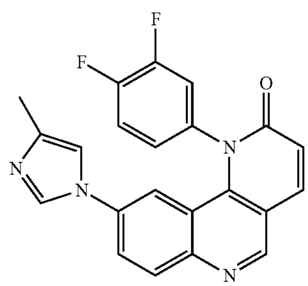 [SMILES: Cc1cn(-c2ccc3ncc4ccc(=O)n(-c5ccc(F)c(F)c5)c4c3c2)cn1] | C22H14F2N4O<br>LC-MS (M + H): 389.08 |
| 237 | 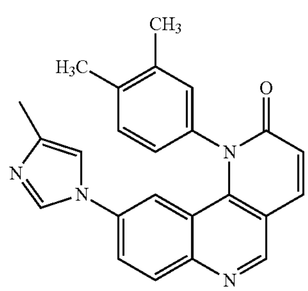 [SMILES: Cc1cn(-c2ccc3ncc4ccc(=O)n(-c5ccc(C)c(C)c5)c4c3c2)cn1] | C24H20N4O<br>LC-MS (M + H): 381.17 |
| 238 | 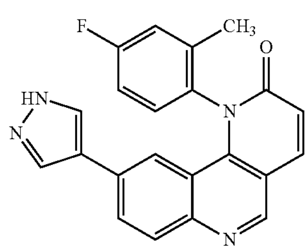 | C22H15FN4O<br>LC-MS (M + H): 371.15 |

TABLE 4-continued

| Compound Number | Structure | Physical Data<br>¹H NMR 600 MHz and/or MS (m/z) |
|---|---|---|
| 239 | 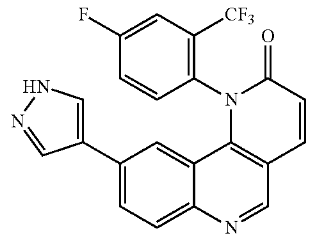 [SMILES: O=c1ccc2cnc3ccc(-c4cn[nH]c4)cc3c2n1-c1ccc(F)cc1C(F)(F)F] | C22H12F4N4O<br>LC-MS (M + H): 425.15 |
| 240 | 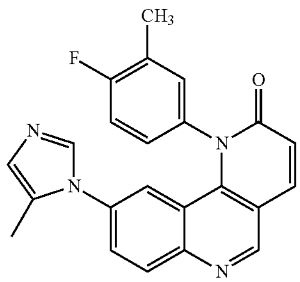 [SMILES: Cc1cc(-n2c(=O)ccc3cnc4ccc(-n5cncc5C)cc4c32)ccc1F] | C23H17FN4O<br>LC-MS (M + H): 385.19 |
| 241 | 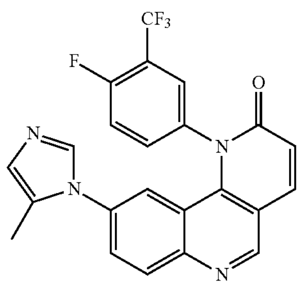 [SMILES: Cc1cncn1-c1ccc2ncc3ccc(=O)n(-c4ccc(F)c(C(F)(F)F)c4)c3c2c1] | C23H14F4N4O<br>LC-MS (M + H): 439.07 |
| 242 | 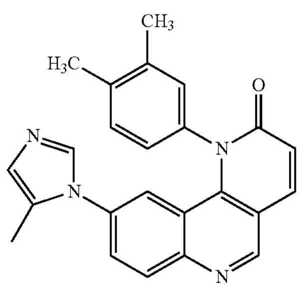 [SMILES: Cc1ccc(-n2c(=O)ccc3cnc4ccc(-n5cncc5C)cc4c32)cc1C] | C24H20N4O<br>LC-MS (M + H): 381.17<br>¹H NMR 600 Hz (DMSO) δ 9.17 (s, 1H), 8.31 (d, J = 9 Hz, 1H), 8.14 (d, J = 9 Hz, 1H), 7.76 (dd, J = 9, 2.4 Hz, 1H), 7.33 (d, J = 7.8 Hz, 1H), 7.22 (s, 1H), 7.14 (dd, J = 7.8, 2.4 Hz, 1H), 7.07 (s, 1H), 6.93 (d, J = 9.6 Hz, 1H), 6.73 (s, 1H), 6.54 (d, J = 2.4 Hz, 1H), 2.27 (s, 3H), 2.21 (s, 3H), 1.93 (s, 3H) |
| 243 | 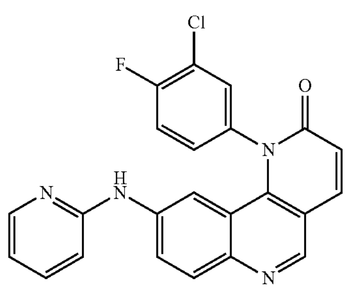 [SMILES: O=c1ccc2cnc3ccc(Nc4ccccn4)cc3c2n1-c1ccc(F)c(Cl)c1] | C23H14ClFN4O<br>LC-MS (M + H): 417.17 |

TABLE 4-continued

| Compound Number | Structure | Physical Data<br>¹H NMR 600 MHz and/or MS (m/z) |
|---|---|---|
| 244 | 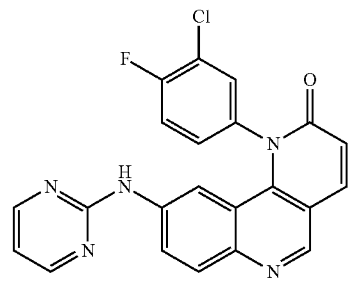 [SMILES: O=c1ccc2cnc3ccc(Nc4ncccn4)cc3c2n1-c1ccc(F)c(Cl)c1] | C22H13ClFN5O<br>LC-MS (M + H): 418.10 |
| 245 | 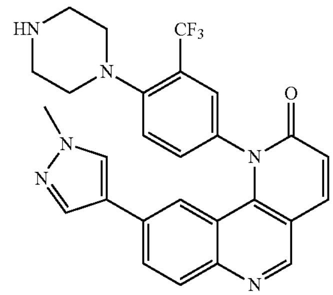 [SMILES: Cn1cc(-c2ccc3ncc4ccc(=O)n(-c5ccc(N6CCNCC6)c(C(F)(F)F)c5)c4c3c2)cn1] | C27H23F3N6O<br>LC-MS (M + H): 504.94 |
| 246 | 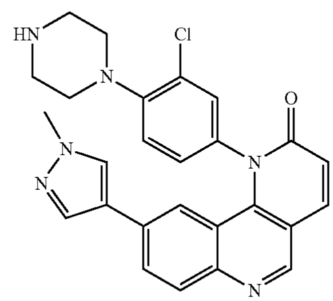 [SMILES: Cn1cc(-c2ccc3ncc4ccc(=O)n(-c5ccc(N6CCNCC6)c(Cl)c5)c4c3c2)cn1] | C26H23ClN6O<br>LC-MS (M + H): 470.98 |
| 247 | 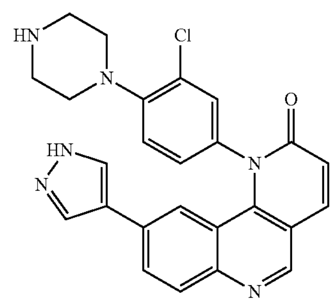 [SMILES: O=c1ccc2cnc3ccc(-c4cn[nH]c4)cc3c2n1-c1ccc(N2CCNCC2)c(Cl)c1] | C25H21ClN6O<br>LC-MS (M + H): 456.93 |
| 248 | 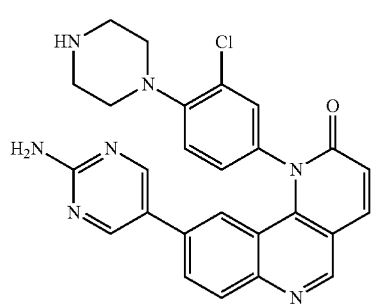 [SMILES: Nc1ncc(-c2ccc3ncc4ccc(=O)n(-c5ccc(N6CCNCC6)c(Cl)c5)c4c3c2)cn1] | C26H22ClN7O<br>LC-MS (M + H): 483.84 |

TABLE 4-continued

| Compound Number | Structure | Physical Data<br>¹H NMR 600 MHz and/or MS (m/z) |
| --- | --- | --- |
| 249 | 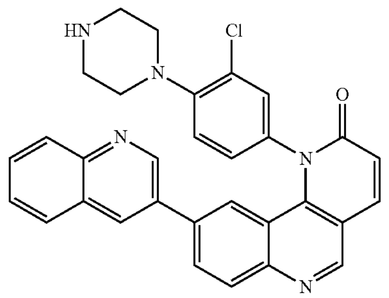 [SMILES: O=c1ccc2cnc3ccc(-c4cnc5ccccc5c4)cc3c2n1-c1ccc(N2CCNCC2)c(Cl)c1] | C31H24ClN5O<br>LC-MS (M + H): 517.94 |
| 250 | 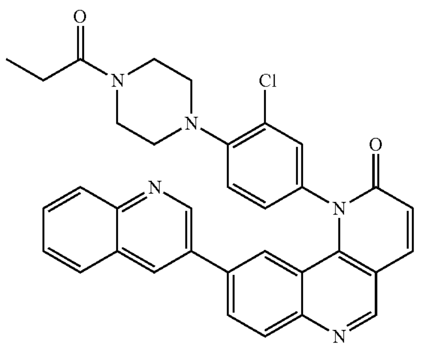 [SMILES: CCC(=O)N1CCN(c2ccc(-n3c(=O)ccc4cnc5ccc(-c6cnc7ccccc7c6)cc5c43)cc2Cl)CC1] | C34H28ClN5O2<br>LC-MS (M + H): 574.01 |
| 251 | 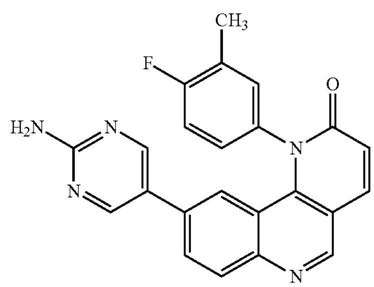 | C23H16FN5O<br>LC-MS (M + H): 397.99 |
| 252 | 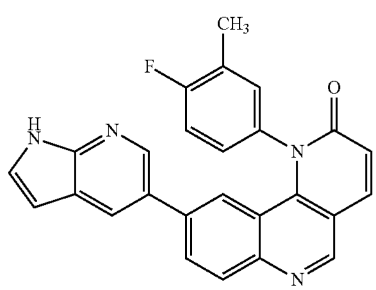 [SMILES: Cc1cc(-n2c(=O)ccc3cnc4ccc(-c5cnc6[nH]ccc6c5)cc4c32)ccc1F] | C26H17FN4O<br>LC-MS (M + H): 421.00 |
| 253 | 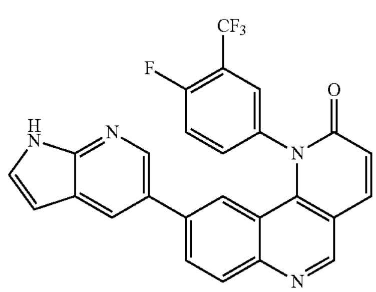 [SMILES: O=c1ccc2cnc3ccc(-c4cnc5[nH]ccc5c4)cc3c2n1-c1ccc(F)c(C(F)(F)F)c1] | C26H14F4N4O<br>LC-MS (M + H): 474.94 |

TABLE 4-continued

| Compound Number | Structure | Physical Data<br>¹H NMR 600 MHz and/or MS (m/z) |
|---|---|---|
| 254 | 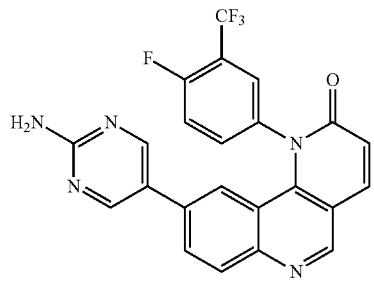 [SMILES: Nc1ncc(-c2ccc3ncc4ccc(=O)n(-c5ccc(F)c(C(F)(F)F)c5)c4c3c2)cn1] | C23H13F4N5O<br>LC-MS (M + H): 451.86 |
| 255 | 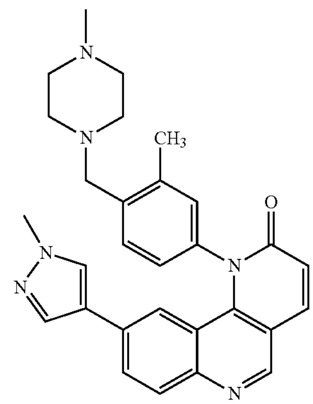 [SMILES: Cc1cc(-n2c(=O)ccc3cnc4ccc(-c5cnn(C)c5)cc4c32)ccc1CN1CCN(C)CC1] | C29H30N6O<br>LC-MS (M + H): 479.02 |
| 256 | 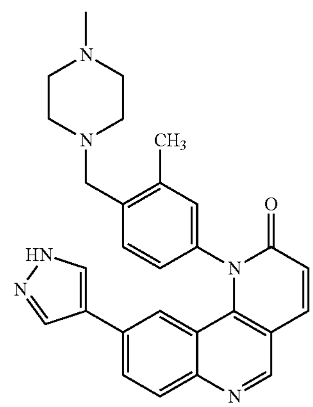 [SMILES: Cc1cc(-n2c(=O)ccc3cnc4ccc(-c5cn[nH]c5)cc4c32)ccc1CN1CCN(C)CC1] | C28H28N6O<br>LC-MS (M + H): 464.91 |
| 257 | 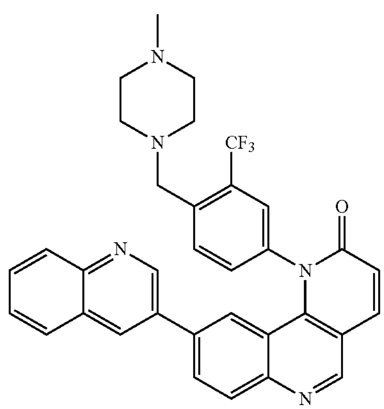 [SMILES: CN1CCN(Cc2ccc(-n3c(=O)ccc4cnc5ccc(-c6cnc7ccccc7c6)cc5c43)cc2C(F)(F)F)CC1] | C34H28F3N5O<br>LC-MS (M + H): 579.94 |

TABLE 4-continued

| Compound Number | Structure | Physical Data<br>$^1$H NMR 600 MHz and/or MS (m/z) |
|---|---|---|
| 258 | 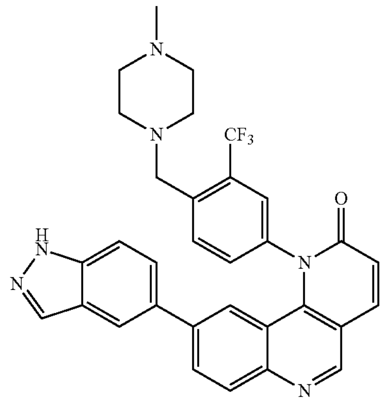 [SMILES: CN1CCN(Cc2ccc(-n3c(=O)ccc4cnc5ccc(-c6ccc7[nH]ncc7c6)cc5c43)cc2C(F)(F)F)CC1] | C32H27F3N6O<br>LC-MS (M + H): 568.79 |
| 259 | 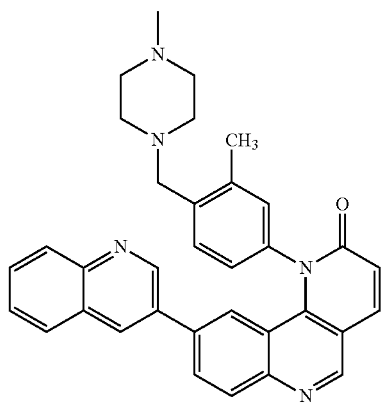 | C34H33N5O<br>LC-MS (M + H): 527.83 |
| 260 | 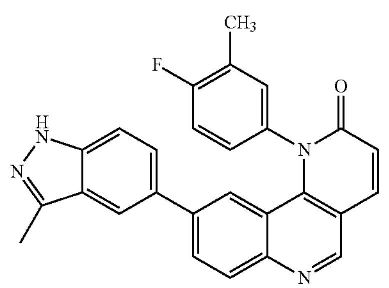 [SMILES: Cc1cc(-n2c(=O)ccc3cnc4ccc(-c5ccc6[nH]nc(C)c6c5)cc4c32)ccc1F] | C27H19FN4O<br>LC-MS (M + H): 434.78 |
| 261 | 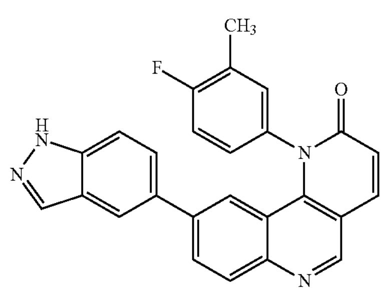 [SMILES: Cc1cc(-n2c(=O)ccc3cnc4ccc(-c5ccc6[nH]ncc6c5)cc4c32)ccc1F] | C26H17FN4O<br>LC-MS (M + H): 420.87 |

TABLE 4-continued

| Compound Number | Structure | Physical Data<br>¹H NMR 600 MHz and/or MS (m/z) |
|---|---|---|
| 262 | 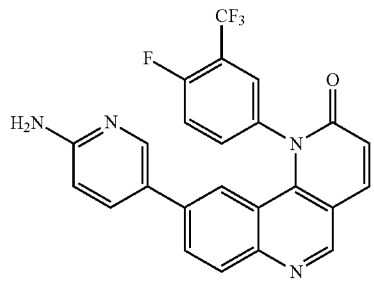 [SMILES: Nc1ccc(-c2ccc3ncc4ccc(=O)n(-c5ccc(F)c(C(F)(F)F)c5)c4c3c2)cn1] | C24H14F4N4O<br>LC-MS (M + H): 450.80 |
| 263 | 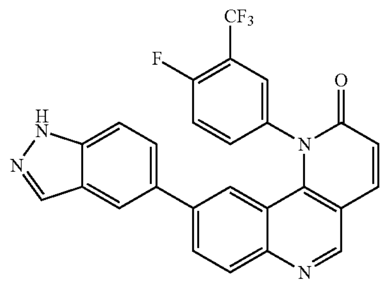 [SMILES: O=c1ccc2cnc3ccc(-c4ccc5[nH]ncc5c4)cc3c2n1-c1ccc(F)c(C(F)(F)F)c1] | C26H14F4N4O<br>LC-MS (M + H): 474.80 |
| 264 | 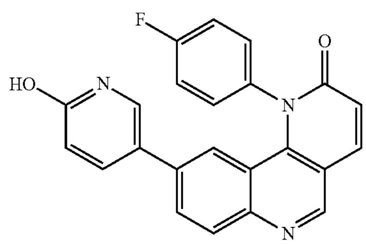 [SMILES: O=c1ccc2cnc3ccc(-c4ccc(O)nc4)cc3c2n1-c1ccc(F)cc1] | C23H14FN3O2<br>LC-MS (M + H): 384.20 |
| 265 | 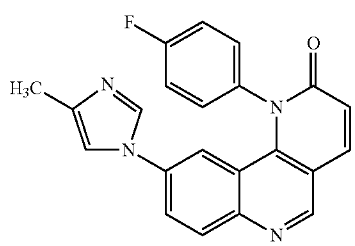 [SMILES: Cc1cn(-c2ccc3ncc4ccc(=O)n(-c5ccc(F)cc5)c4c3c2)cn1] | C22H15FN4O<br>LC-MS (M + H): 371.15 |
| 266 | 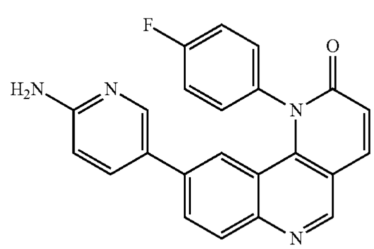 [SMILES: Nc1ccc(-c2ccc3ncc4ccc(=O)n(-c5ccc(F)cc5)c4c3c2)cn1] | C23H15FN4O<br>LC-MS (M + H): 383.15 |
| 267 | 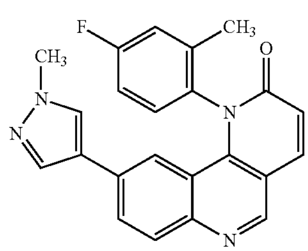 [SMILES: Cc1cc(F)ccc1-n1c(=O)ccc2cnc3ccc(-c4cnn(C)c4)cc3c21] | C23H17FN4O<br>LC-MS (M + H): 385.01 |

TABLE 4-continued

| Compound Number | Structure | Physical Data ¹H NMR 600 MHz and/or MS (m/z) |
|---|---|---|
| 268 | 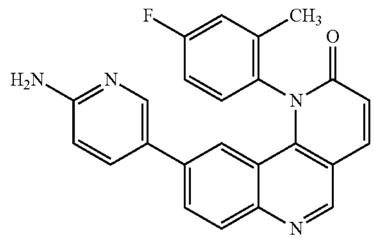 | C24H17FN4O<br>LC-MS (M + H): 397.00 |
| 269 | 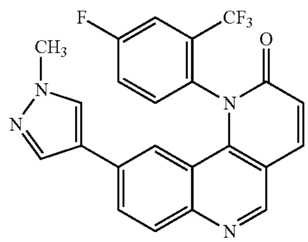 [SMILES: Cn1cc(-c2ccc3ncc4ccc(=O)n(-c5ccc(F)cc5C(F)(F)F)c4c3c2)cn1] | C23H14F4N4O<br>LC-MS (M + H): 438.93 |
| 270 | 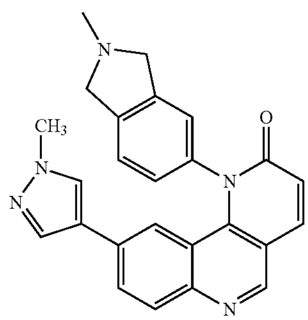 [SMILES: CN1Cc2ccc(-n3c(=O)ccc4cnc5ccc(-c6cnn(C)c6)cc5c43)cc2C1] | C25H21N5O<br>LC-MS (M + H): 407.88 |
| 271 | 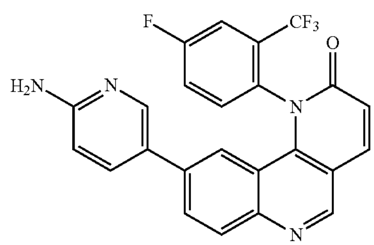 | C24H14F4N4O<br>LC-MS (M + H): 450.73 |
| 272 | 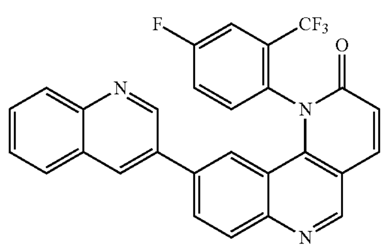 [SMILES: O=c1ccc2cnc3ccc(-c4cnc5ccccc5c4)cc3c2n1-c1ccc(F)cc1C(F)(F)F] | C28H15F4N3O<br>LC-MS (M + H): 485.68 |
| 273 | 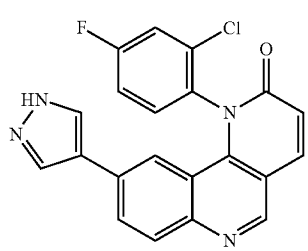 [SMILES: O=c1ccc2cnc3ccc(-c4cn[nH]c4)cc3c2n1-c1ccc(F)cc1Cl] | C21H12ClFN4O<br>LC-MS (M + H): 390.87 |

TABLE 4-continued

| Compound Number | Structure | Physical Data ¹H NMR 600 MHz and/or MS (m/z) |
|---|---|---|
| 274 | 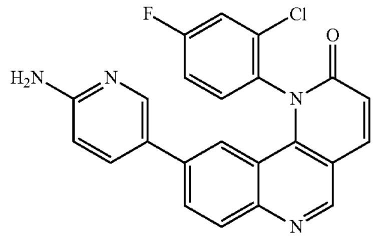 [SMILES: Nc1ccc(-c2ccc3ncc4ccc(=O)n(-c5ccc(F)cc5Cl)c4c3c2)cn1] | C23H14ClFN4O<br>LC-MS (M + H): 416.85 |
| 275 | 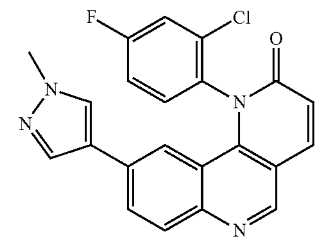 [SMILES: Cn1cc(-c2ccc3ncc4ccc(=O)n(-c5ccc(F)cc5Cl)c4c3c2)cn1] | C22H14ClFN4O<br>LC-MS (M + H): 404.72 |
| 276 | 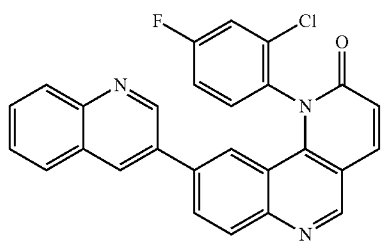 [SMILES: O=c1ccc2cnc3ccc(-c4cnc5ccccc5c4)cc3c2n1-c1ccc(F)cc1Cl] | C27H15ClFN3O<br>LC-MS (M + H): 451.72 |
| 277 | 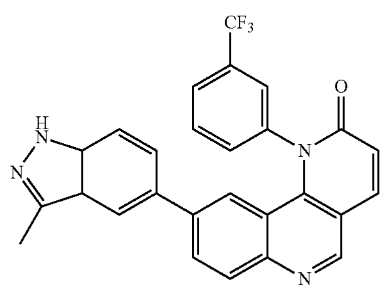 [SMILES: CC1=NNC2C=CC(c3ccc4ncc5ccc(=O)n(-c6cccc(C(F)(F)F)c6)c5c4c3)=CC12] | C27H19F3N4O<br>LC-MS (M + H): 470.87 |
| 278 | 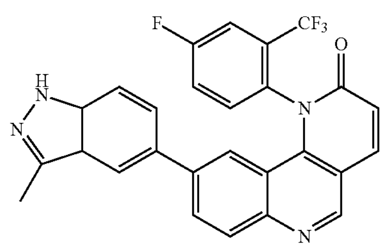 [SMILES: CC1=NNC2C=CC(c3ccc4ncc5ccc(=O)n(-c6ccc(F)cc6C(F)(F)F)c5c4c3)=CC12] | C27H18F4N4O<br>LC-MS (M + H): 488.90 |

One of ordinary skill in the art will appreciate that while certain compounds of formula I, II-a, II-b, II-c, II-d or III are shown above in Table 4, additional compounds in accordance with the present invention may be made according to the Examples and methods disclosed herein. Non-limiting examples of additional compounds include those comprising and an $R^1$ group of Table 1, an $R^2$ group of Table 2, and an $R^x$ group of Table 3. All combinations of said $R^1$, $R^2$ and $R^x$ groups are contemplated by the present disclosure.

Example 9 mTORC1/2 Purification

To produce soluble mTORC1 or mTORC2, we generated HEK-293T cell lines that stably express N-terminally FLAG-tagged Raptor, Rictor or mLST8. Stable low-expression of these components has the useful effect of maintaining stoichiometry with endogenous complex components. FLAG-Raptor expressing cell lines were used to specifically purify mTORC1, FLAG-Rictor expressing cell lines were used to purify mTORC2 and FLAG-mLST8 cell lines were used purify a mixture of mTORC1/2. Each cell line was produced by infecting HEK-293T cells with the respective VSVG-pseudotyped MSCV retrovirus.

The complex was purified by lysing cells using a 0.4% CHAPS-based lysis buffer: 50 mM Hepes pH 7.4, 100 mM NaCl, 0.5 mM EDTA, 0.5 mM EGTA 0.4% CHAPS. Concentrations of CHAPS above 5% disrupt complex integrity and concentrations below 0.1% result in inefficient protein extraction. Detergents such as Triton-X100 and NP-40 also disrupt complex integrity and are not optimal. Cells were lysed at 4° C. for 30 min, and the insoluble fraction was removed by microcentrifugation at 13,000 RPM for 10 min. Supernatants were incubated with FLAG-M2 mAb agarose for 1 h, and then washed 1 time with [50 mM Hepes pH 7.4, 100 mM NaCl, 3 mM DTT], once with [50 mM Hepes pH 7.4, 150 mM NaCl, 2 mM MgCl2, 2 mM ATP, 3 mM DTT], once with [50 mM Hepes pH 7.4, 100 mM NaCl, 0.5 mM EDTA, 0.5 mM EGTA, 0.05% CHAPS, 3 mM DTT]. Complex was eluted with 100 ug/ml 3×FLAG buffer in [50 mM Hepes pH 7.4, 500 mM NaCl, 0.05% CHAPS]. Eluate can be aliquoted and stored at −80° C.

Example 10

Substrate Purification

Full-length rat p70 S6K1 and mouse Akt1/PKB were cloned into an HA-GST pRK5 vector modified so as to contain a PreScission protease site (GE Healthcare) between the GST tag and the initiator codon of S6K1. The expression construct was transfected into HEK293T cells using FuGENE 6, and after 48 hr the cells were treated with 20 μM LY294002 for 1 hr prior to cell harvesting and lysis. HA-GST-PreSciss-S6K1 or Akt/PKB was purified using glutathione-agarose and the affinity tag removed with the PreScission protease. S6K1 or Akt/PKB was separated from free GST by gel filtration on a HiLoad 16/60 Superdex 200 column (GE Healthcare) and the purified protein stored at −80° C. in 20% glycerol.

Example 11

Rheb Purification

Rheb1 cDNA in HA-GST-pRK5 was transfected as above into HEK293T cells. Cells were lysed with lysis buffer described above, but without EDTA and containing 5 mM MgCl$_2$, and cleared lysates were incubated with immobilized glutathione for 2 hr at 4° C. Beads were washed twice with lysis buffer and once with storage buffer (20 mM HEPES pH 8.0, 200 mM NaCl, and 5 mM MgCl$_2$). GST-rheb1 was then eluted from the beads with 10 mM glutathione in storage buffer.

Example 12

High-Throughput Assay (Chemiluminescense)

Purified soluble mTORC1/2 was assayed in eppendorf tubes, standard 96-well and 384-well plate format as follows: purified mTORC1/2 was combined with purified S6K or Akt/PKB (and, optionally, Rheb) in reaction buffer (25 mM Hepes pH 7.4, 50 mM KCl, 10 mM MgCl2) and aliquoted into individual wells. 100 uM ATP and test compound were added to each well, and reactions were allowed to proceed at 25° C. for 30 min. Reactions were stopped by the addition of cold PBS and EDTA to a final concentration of 15 mM. Reaction mixture was then transferred to MaxiSorp (NUNC) 384-well high-protein binding plates and incubated for 1 h at 25° C. with gentle shaking. Wells were then aspirated and blocked with 5% BSA/PBST for 1 h at 25° C. Block was then aspirated and wells were incubated with primary antibody specific for phospho-Akt S473 or phospho-S6K T389 (Cell Signaling Technology) in 5% BSA/PBST for 1 h at 25° C. Antibody mix was aspirated, and plates were washed 4× with PBST. Goat anti-rabbit IgG HRP-conjugated antibody (Pierce) in 5% BSA/PBST was added and plates were incubated for 1 h at 25° C. Antibody mix was aspirated again and wells are washed 4×PBST and 2×PBS. Chemiluminescense reagent (Perkin Elmer, Western Lightning) was added and luminescence was read using a standard luminescence reader. As depicted in FIG. 1b, control compound PI-103 and test compound Kin001-084 (Kontopidis, G. et al. 2006. Chem. Biol. 13, 201; Wang, S. et al. 2004. J. Med. Chem. 47, 1662) were assayed at 8 concentrations to determine IC50s against mTORC1.

Example 13

High-Throughput Assay (LanthaScreen)

This assay is also compatible with other common high-throughput screen technologies, such as LanthaScreen (Invitrogen). C-terminal EGFP-tagged rat S6K and mouse Akt/PKB are cloned into an HA-GST pRK5 vector, GST-purified as described above, and used as substrates in kinase reactions. To measure substrate phosphorylation, terbium-labelled phospho-Akt S473 or phospho-S6K T389 IgG (Invitrogen, Cell Signaling Technology) are added to the terminated reaction. Following incubation, the amount of bound IgG is quantitated by TR-FRET.

Example 14

Figure 2:
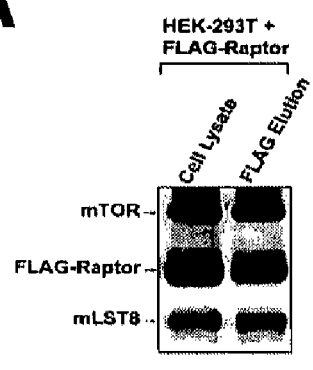
FIG. 2A depicts intact mTORC1 purified from FLAG-Raptor expressing HEK-293T cells. HEK-293T cells were engineered to stably express N-terminal FLAG-tagged Raptor. Total cell lysates and FLAG-purified eluate were then separated by gel electrophoresis and probed with antibodies specific for mTOR, FLAG-Raptor and mLST8, as indicated.
FIG. 2B shows FLAG-Raptor purifications that are highly enriched for mTORC1 components. FLAG-Raptor eluate was prepared as in FIG. 2A and separated by gel electrophoresis. Gel was then analyzed by silver stain. FLAG-Raptor, mTOR and mLST8 are indicated.
FIG. 2C depicts FLAG-purified mTORC1 and mTORC2 phosphorylation of p70 S6K and AKT1, respectively.
Figure 2:
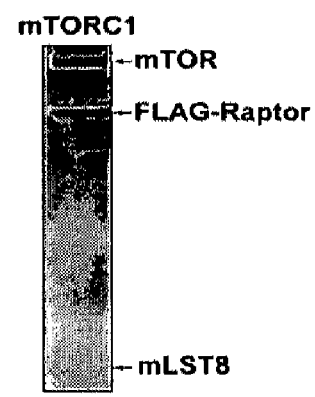
Figure 2:
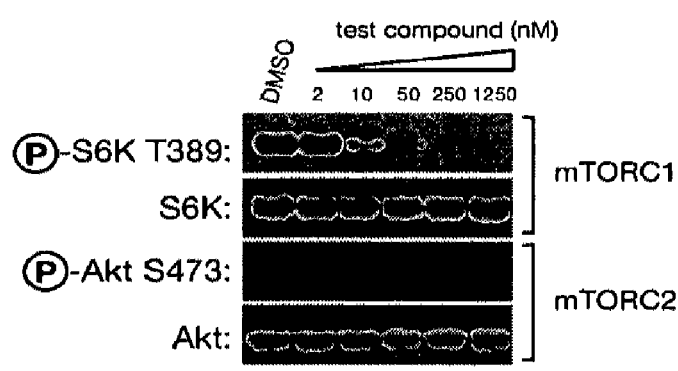
Figure 3:
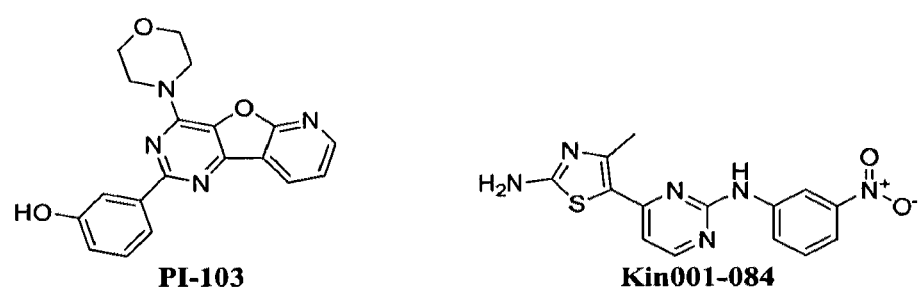
FIG. 3 depicts the structures of compounds PI-103 (3-(4-(4-Morpholinyl)pyrido[3',2':4,5]furo[3,2-d]pyrimidin-2-yl) phenol) and Kin001-084 (4-methyl-5-(2-(3-nitrophenylamino)pyrimidin-4-yl)thiazol-2-amine).

A selection of compounds of formula I were tested for activity against pure mTORC1 and mTORC2 complexes. FIG. 2C depicts FLAG-purified mTORC1 and mTORC2 phosphorylation of p70 S6K and AKT1, respectively, using a representative compound of formula I as a test compound. mTORC1/2 complexes were purified from cells expressing FLAG-Raptor or FLAG-Protor and used to phosphorylate p70 S6K or AKT1, respectively, in in vitro kinase assays. Reactions were conducted in the presence of increasing concentrations of a mTOR-specific inhibitor of formula I, as indicated. Reactions were then analyzed by western blot and probed using antibodies specific for phosphorylated and non-phosphorylated S6K and AKT1.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

What is claimed is:

1. A compound of formula I:

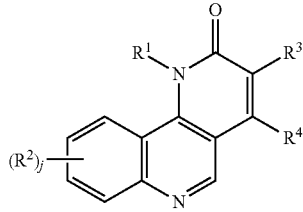

wherein:
- $R^1$ is an optionally substituted group selected from the group consisting of 6-10-membered aryl; $C_{7-15}$ arylalkyl; $C_{6-15}$ heteroarylalkyl; $C_{1-12}$ heteroaliphatic; $C_{1-12}$ aliphatic; 5-10-membered heteroaryl having 1-4 heteroatoms independently selected from the group consisting of nitrogen, oxygen, and sulfur; and 4-7-membered heterocyclic having 1-2 heteroatoms independently selected from the group consisting of nitrogen, oxygen, and sulfur;
- each occurrence of $R^2$ is independently halogen, —$NR_2$—OR, —SR, or an optionally substituted group selected from the group consisting of $C_{1-12}$ acyl; 6-10-membered aryl; $C_{7-15}$ arylalkyl; $C_{6-15}$ heteroarylalkyl; $C_{1-12}$ heteroaliphatic; $C_{1-12}$ aliphatic; 5-10-membered heteroaryl having 1-4 heteroatoms independently selected from the group consisting of nitrogen, oxygen, and sulfur; and 4-7-membered heterocyclic having 1-2 heteroatoms independently selected from the group consisting of nitrogen, oxygen, and sulfur;
- j is an integer from 1 to 4, inclusive;
- $R^3$ and $R^4$ are independently hydrogen, hydroxyl, alkoxy, halogen, or optionally substituted $C_{1-6}$ aliphatic, with the proviso that $R^3$ and $R^4$ are not taken together to form a ring; and
- each R is independently hydrogen, an optionally substituted group selected from the group consisting of $C_{1-12}$ acyl; 6-10-membered aryl; $C_{7-15}$ arylalkyl; $C_{6-15}$ heteroarylalkyl; $C_{1-12}$ aliphatic; 5-10-membered heteroaryl having 1-4 heteroatoms independently selected from the group consisting of nitrogen, oxygen, and sulfur; 4-7-membered heterocyclic having 1-2 heteroatoms independently selected from the group consisting of nitrogen, oxygen, and sulfur; and $C_{1-12}$ heteroaliphatic having 1-2 heteroatoms independently selected from the group consisting of nitrogen, oxygen, and sulfur; or:
  - two R on the same nitrogen atom are taken with the nitrogen to form a 4-7-membered heterocyclic ring having 1-2 heteroatoms independently selected from the group consisting of nitrogen, oxygen, and sulfur.

2. The compound according to claim 1, wherein $R^1$ is optionally substituted 6-membered aryl or optionally substituted 6-membered heteroaryl having 1-4 heteroatoms independently selected from the group consisting of nitrogen, oxygen, and sulfur.

3. The compound according to claim 2, wherein $R^1$ is optionally substituted phenyl or pyridyl.

4. The compound according to claim 1, wherein $R^2$ is —$NR_2$, optionally substituted 6-10-membered aryl, or optionally substituted 5-10-membered heteroaryl having 1-4 heteroatoms independently selected from nitrogen, oxygen, and sulfur.

5. The compound according to claim 4, wherein $R^2$ is optionally substituted 6-10-membered aryl.

6. The compound according to claim 4, wherein $R^2$ is optionally substituted 5-10-membered heteroaryl having 1-4 heteroatoms independently selected from the group consisting of nitrogen, oxygen, and sulfur.

7. The compound according to claim 1, wherein j is 1.

8. The compound according to claim 1, wherein $R^3$ and $R^4$ are both hydrogen.

9. The compound according to claim 1, wherein the compound is of formula II-a:

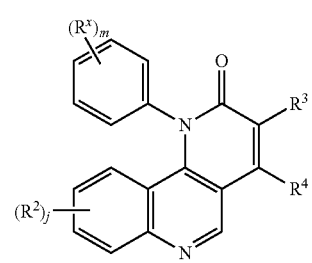

wherein:
- each occurrence of $R_x$ is independently halogen, —$NR_2$—OR, —SR, —$SO_2NR_2$, or an optionally substituted group selected from the group consisting of 6-10-membered aryl; $C_{7-15}$ arylalkyl; $C_{6-15}$ heteroarylalkyl; $C_{1-12}$ aliphatic; 5-10-membered heteroaryl having 1-4 heteroatoms independently selected from the group consisting of nitrogen, oxygen, and sulfur; and 4-7-membered heterocyclic having 1-2 heteroatoms independently selected from the group consisting of nitrogen, oxygen, and sulfur;
- m is an integer from 1 to 4; and when m is 2, 3, or 4, two $R^x$ substituents may join together to form a 5-7-membered cyclic group or a 5-7-membered heterocyclic group having 1-2 heteroatoms independently selected from the group consisting of nitrogen, oxygen, and sulfur; and wherein the 5-7-membered cyclic group or 5-7-membered heterocyclic group formed from two $R^x$ substituents is optionally substituted by one group selected from the group consisting of 6-10-membered aryl; 5-10-membered heteroaryl; $C_{7-15}$ arylalkyl; $C_{6-15}$ heteroarylalkyl; or $C_{1-12}$ aliphatic;
- each occurrence of $R^2$ is independently halogen, —$NR_2$—OR, —SR, or an optionally substituted group selected from the group consisting of $C_{1-12}$ acyl; 6-10-membered aryl; $C_{7-15}$ arylalkyl; $C_{6-15}$ heteroarylalkyl; $C_{1-12}$ heteroaliphatic; $C_{1-12}$ aliphatic; 5-10-membered heteroaryl having 1-4 heteroatoms independently selected from the group consisting of nitrogen, oxygen, and sulfur; and 4-7-membered heterocyclic having 1-2 heteroatoms independently selected from the group consisting of nitrogen, oxygen, and sulfur;
- j is an integer from 1 to 4, inclusive;
- $R^3$ and $R^4$ are independently hydrogen, halogen, or optionally substituted $C_{1-6}$ aliphatic, with the proviso that $R^3$ and $R^4$ are not taken together to form a ring; and
- each R is independently hydrogen, an optionally substituted group selected from the group consisting of $C_{1-12}$ acyl; 6-10-membered aryl; $C_{7-15}$ arylalkyl; $C_{6-15}$ heteroarylalkyl; $C_{1-12}$ aliphatic; 5-10-membered heteroaryl having 1-4 heteroatoms independently selected from the group consisting of nitrogen, oxygen, and sulfur; 4-7- membered heterocyclic having 1-2 heteroatoms independently selected from the group consisting of nitrogen, oxygen, and sulfur; and $C_{1-12}$ heteroaliphatic having 1-2 heteroatoms independently selected from the group consisting of nitrogen, oxygen, and sulfur; or:

two R on the same nitrogen atom are taken with the nitrogen to form a 4-7-membered heterocyclic ring having 1-2 heteroatoms independently selected from the group consisting of nitrogen, oxygen, and sulfur.

10. The compound according to claim 1, wherein $R^1$ is selected from the group consisting of:

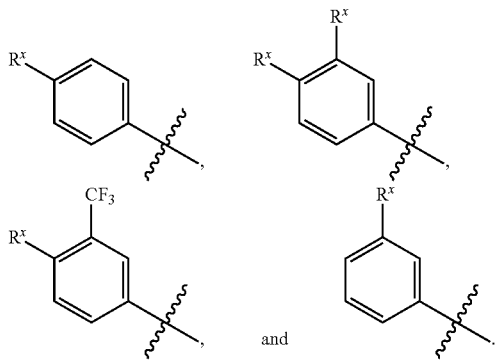

11. The compound according to claim 1, wherein the compound is of formula II-b, II-c, or II-d:

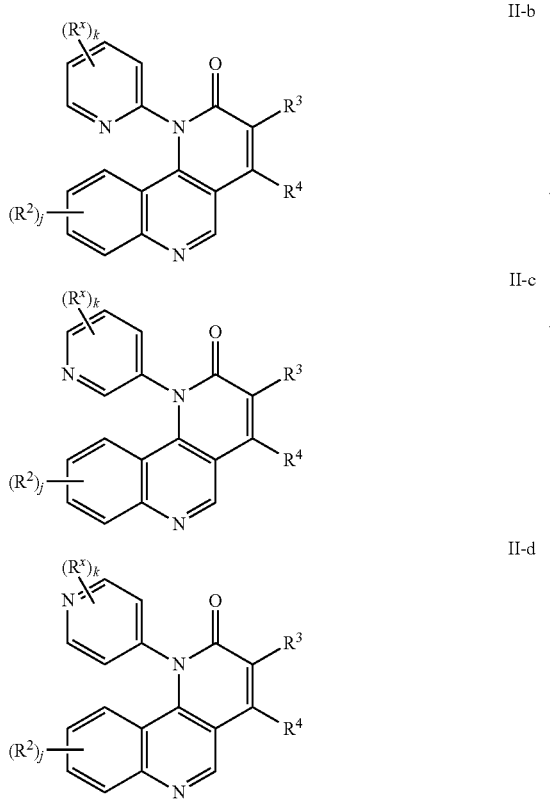

wherein:
each occurrence of $R^x$ is independently halogen, —$NR_2$— OR, —SR, —$SO_2NR_2$, or an optionally substituted group selected from the group consisting of 6-10-membered aryl; $C_{7-15}$ arylalkyl; $C_{6-15}$ heteroarylalkyl; $C_{1-12}$ aliphatic; 5-10-membered heteroaryl having 1-4 heteroatoms independently selected from the group consisting of nitrogen, oxygen, and sulfur; and 4-7-membered heterocyclic having 1-2 heteroatoms independently selected from the group consisting of nitrogen, oxygen, and sulfur;

k is an integer from 1 to 4; and when m is 2, 3, or 4, two $R^x$ substituents may join together to form a 5-7-membered cyclic group or a 5-7-membered heterocyclic group having 1-2 heteroatoms independently selected from the group consisting of nitrogen, oxygen, and sulfur; and wherein the 5-7-membered cyclic group or 5-7-membered heterocyclic group formed from two $R^x$ substituents is optionally substituted by one group selected from the group consisting of 6-10-membered aryl; 5-10-membered heteroaryl; $C_{7-15}$ arylalkyl; $C_{6-15}$ heteroarylalkyl; or $C_{1-12}$ aliphatic;

each occurrence of $R^2$ is independently halogen, —$NR_2$— OR, —SR, or an optionally substituted group selected from the group consisting of $C_{1-12}$ acyl; 6-10-membered aryl; $C_{7-15}$ arylalkyl; $C_{6-15}$ heteroarylalkyl; $C_{1-12}$ heteroaliphatic; $C_{1-12}$ aliphatic; 5-10-membered heteroaryl having 1-4 heteroatoms independently selected from the group consisting of nitrogen, oxygen, and sulfur; and 4-7-membered heterocyclic having 1-2 heteroatoms independently selected from the group consisting of nitrogen, oxygen, and sulfur;

j is an integer from 1 to 4, inclusive;

$R^3$ and $R^4$ are independently hydrogen, halogen, or optionally substituted $C_{1-6}$ aliphatic, with the proviso that $R^3$ and $R^4$ are not taken together to form a ring; and each R is independently hydrogen, an optionally substituted group selected from the group consisting of $C_{1-12}$ acyl; 6-10-membered aryl; $C_{7-15}$ arylalkyl; $C_{6-15}$ heteroarylalkyl; $C_{1-12}$ aliphatic; 5-10-membered heteroaryl having 1-4 heteroatoms independently selected from the group consisting of nitrogen, oxygen, and sulfur; 4-7-membered heterocyclic having 1-2 heteroatoms independently selected from the group consisting of nitrogen, oxygen, and sulfur; and $C_{1-12}$ heteroaliphatic having 1-2 heteroatoms independently selected from the group consisting of nitrogen, oxygen, and sulfur; or:

two R on the same nitrogen atom are taken with the nitrogen to form a 4-7-membered heterocyclic ring having 1-2 heteroatoms independently selected from the group consisting of nitrogen, oxygen, and sulfur.

12. The compound according to claim 9, wherein at least one $R^x$ is:

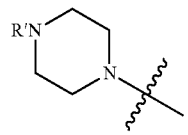

wherein $R^1$ is selected from the group consisting of hydrogen, acyl, sulphonyl, aliphatic, and heteroaliphatic.

13. The compound according to claim 9, wherein each $R^x$ is independently selected from:
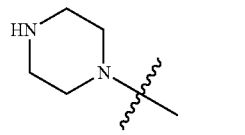 i
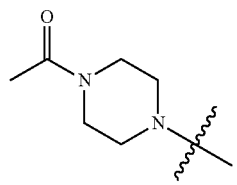 ii
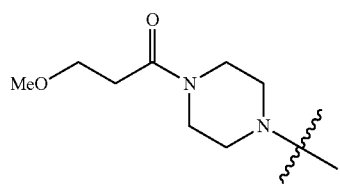 iii
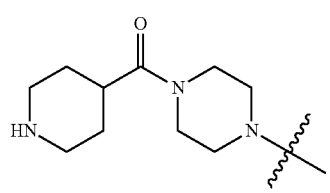 iv
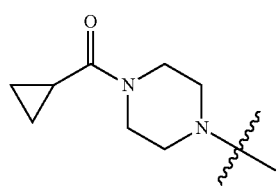 v
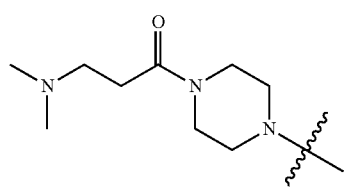 vi
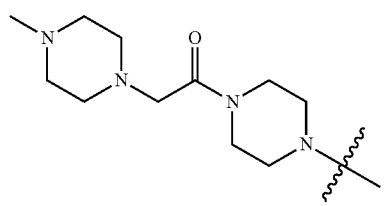 vii
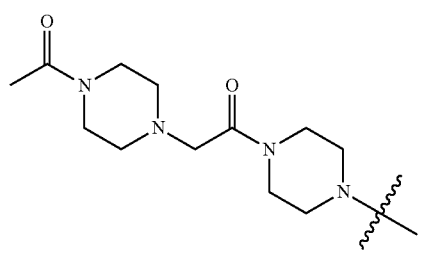 viii
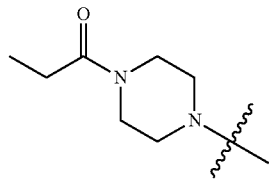 ix
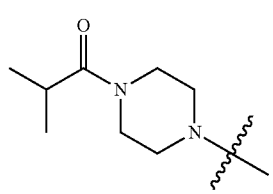 x
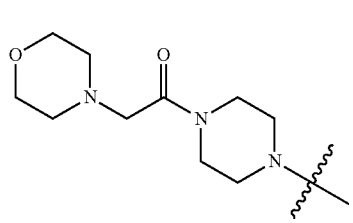 xi
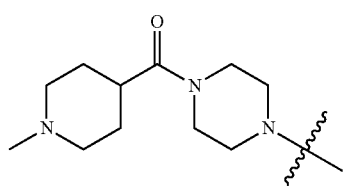 xii
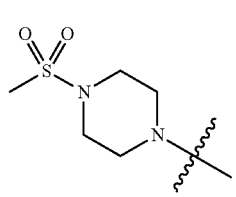 xiii
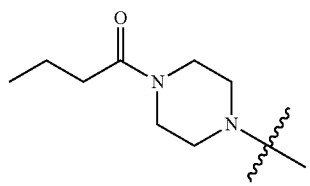 xiv
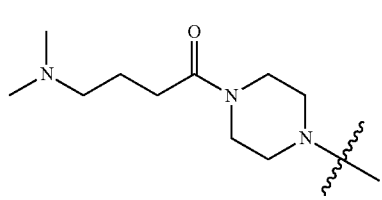 xv
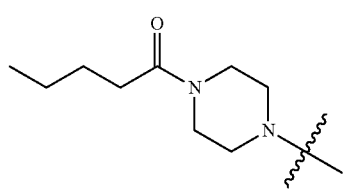 xvi

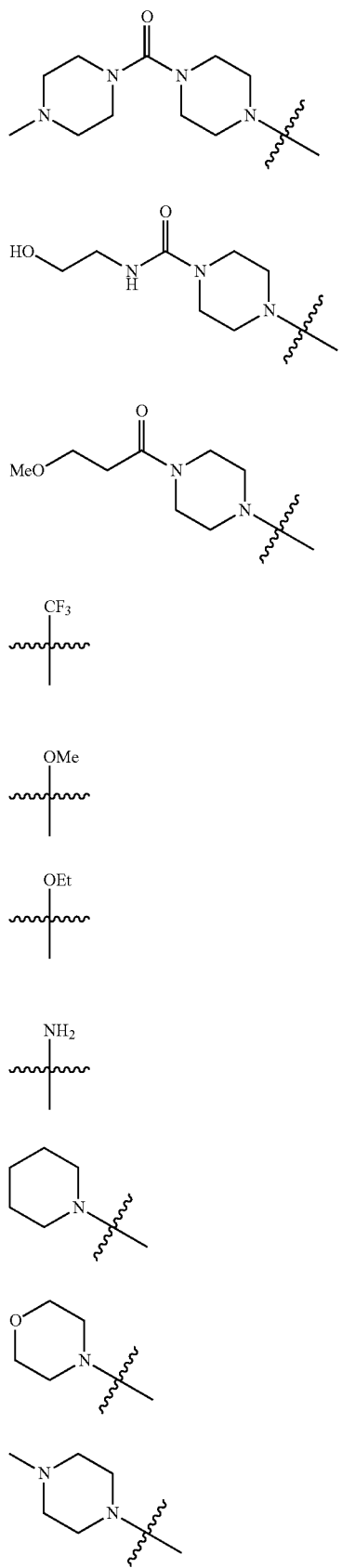
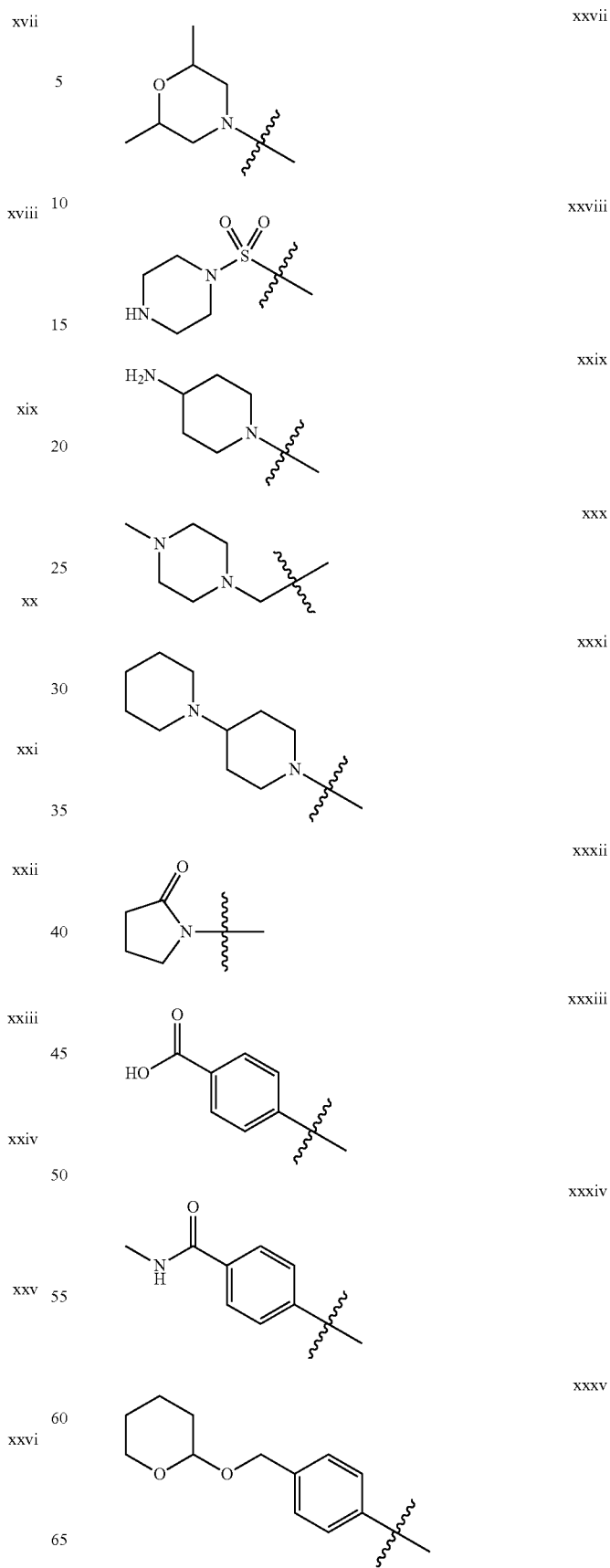

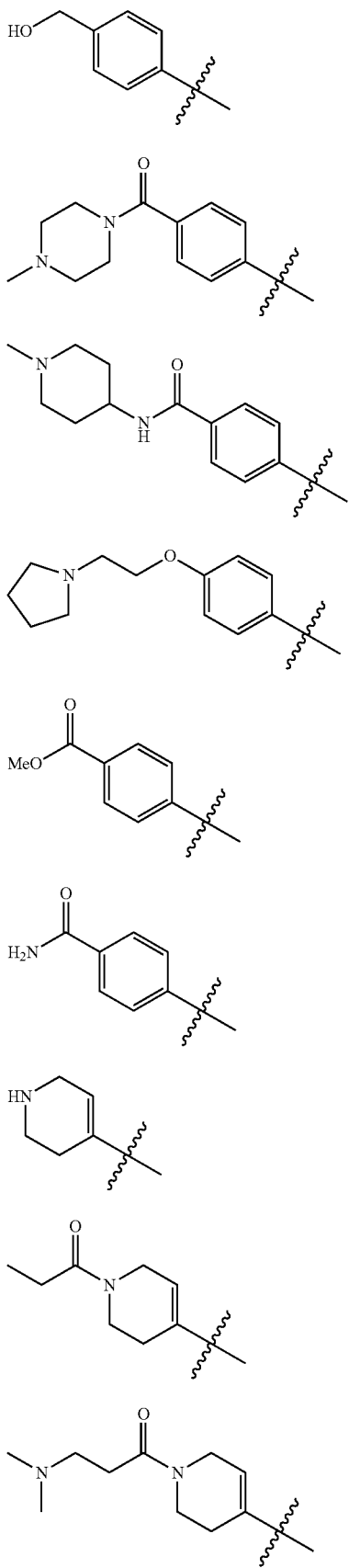
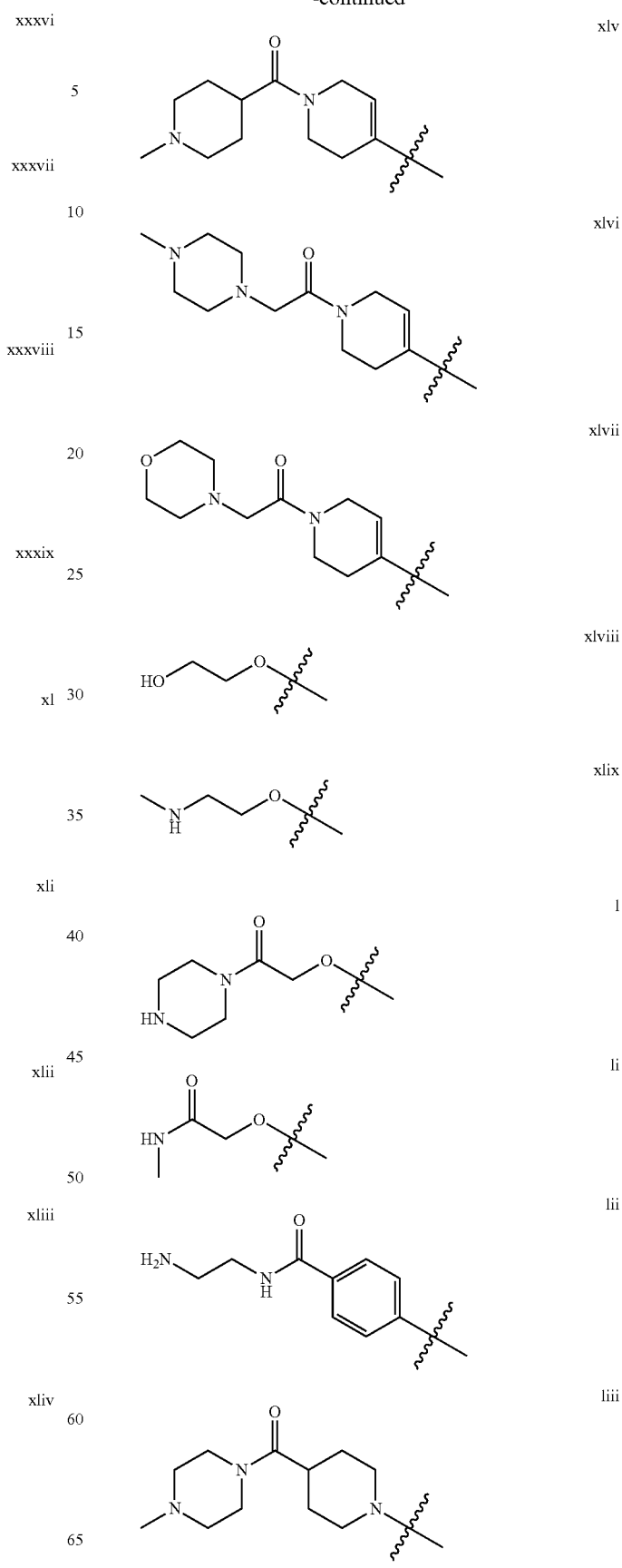

-continued

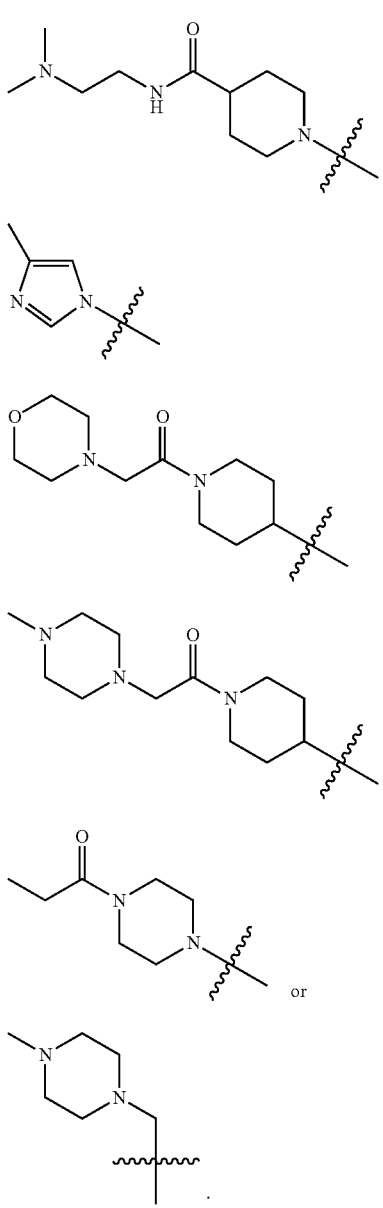

14. The compound according to claim 1, wherein the compound is of formula III-a:

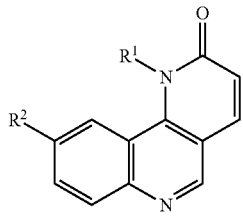

III-a wherein:
R¹ is an optionally substituted group selected from the group consisting of 6-10-membered aryl; $C_{7-15}$ arylalkyl; $C_{6-15}$ heteroarylalkyl; $C_{1-12}$ heteroaliphatic; $C_{1-12}$ aliphatic; 5-10-membered heteroaryl having 1-4 heteroatoms independently selected from the group consisting of nitrogen, oxygen, and sulfur; and 4-7-membered heterocyclic having 1-2 heteroatoms independently selected from the group consisting of nitrogen, oxygen, and sulfur;

R² is independently halogen, —NR₂—OR, —SR, or an optionally substituted group selected from the group consisting of $C_{1-12}$ acyl; 6-10-membered aryl; $C_{7-15}$ arylalkyl; $C_{6-15}$ heteroarylalkyl; $C_{1-12}$ heteroaliphatic; $C_{1-12}$ aliphatic; 5-10-membered heteroaryl having 1-4 heteroatoms independently selected from the group consisting of nitrogen, oxygen, and sulfur; and 4-7-membered heterocyclic having 1-2 heteroatoms independently selected from the group consisting of nitrogen, oxygen, and sulfur; and each R is independently hydrogen, an optionally substituted group selected from the group consisting of $C_{1-12}$ acyl; 6-10-membered aryl; $C_{7-15}$ arylalkyl; $C_{6-15}$ heteroarylalkyl; $C_{1-12}$ aliphatic; 5-10-membered heteroaryl having 1-4 heteroatoms independently selected from the group consisting of nitrogen, oxygen, and sulfur; 4-7-membered heterocyclic having 1-2 heteroatoms independently selected from the group consisting of nitrogen, oxygen, and sulfur; and $C_{1-12}$ heteroaliphatic having 1-2 heteroatoms independently selected from the group consisting of nitrogen, oxygen, and sulfur; or:

two R on the same nitrogen atom are taken with the nitrogen to form a 4-7-membered heterocyclic ring having 1-2 heteroatoms independently selected from the group consisting of nitrogen, oxygen, and sulfur.

15. The compound according to claim 14, wherein R² is 6-10-membered aryl.

16. The compound according to claim 14, wherein R² is 5-10-membered heteroaryl having 1-4 heteroatoms independently selected from the group consisting of nitrogen, oxygen, and sulfur.

17. The compound according to claim 14, wherein R² is selected from:

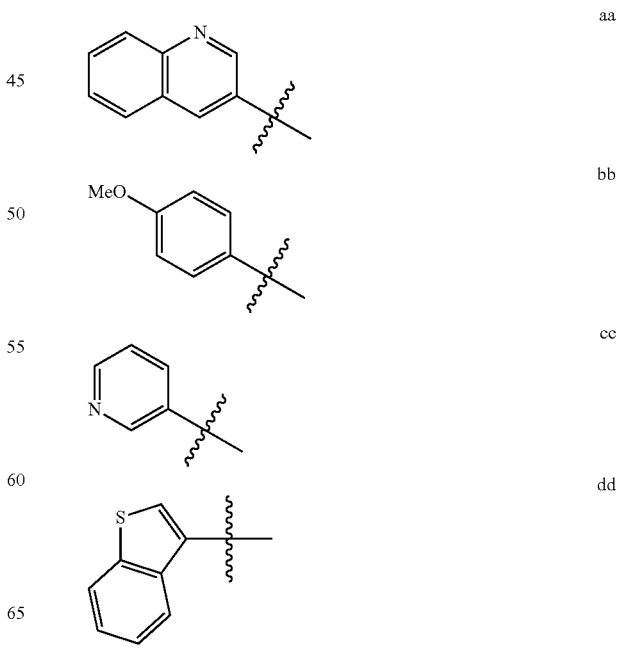

-continued
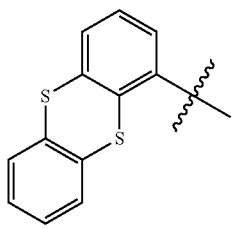
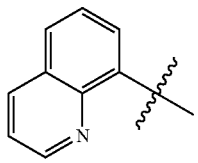
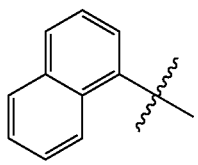
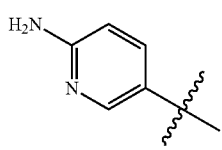
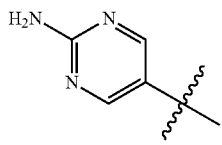
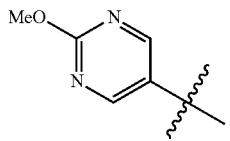
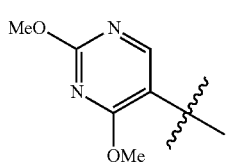
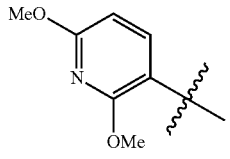
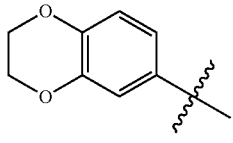
-continued
ee
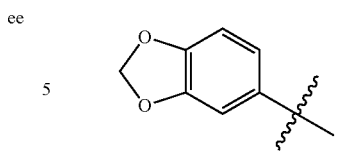
ff
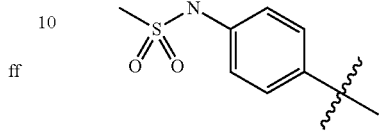
gg
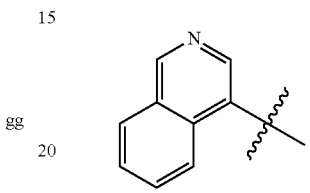
hh
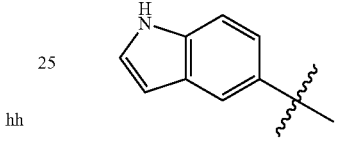
jj
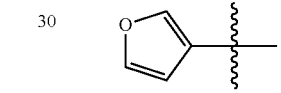
kk
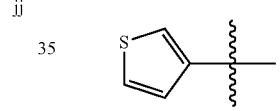
ll
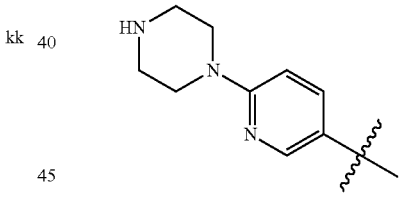
mm
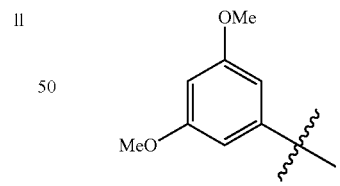
nn
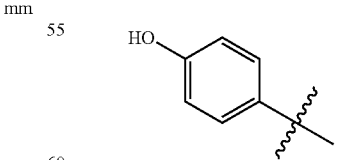
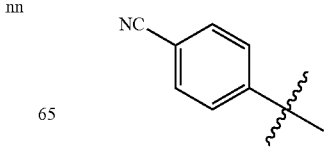
oo
pp
qq
rr
ss
tt
uu
vv
ww
xx

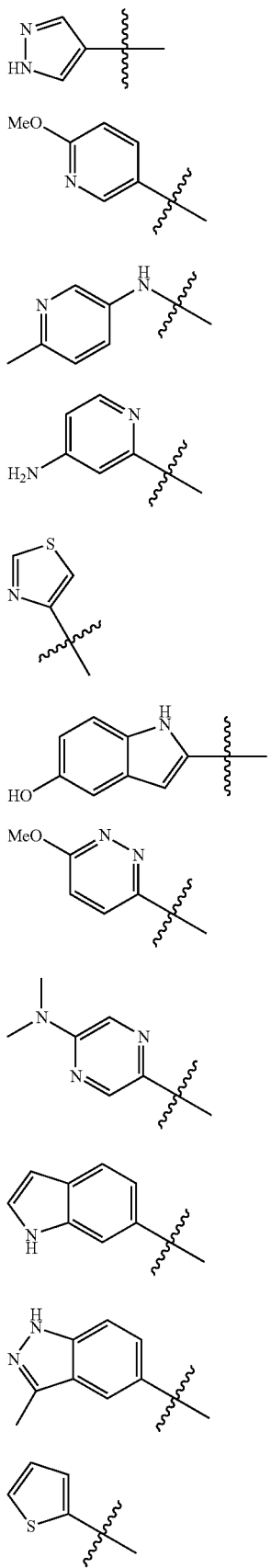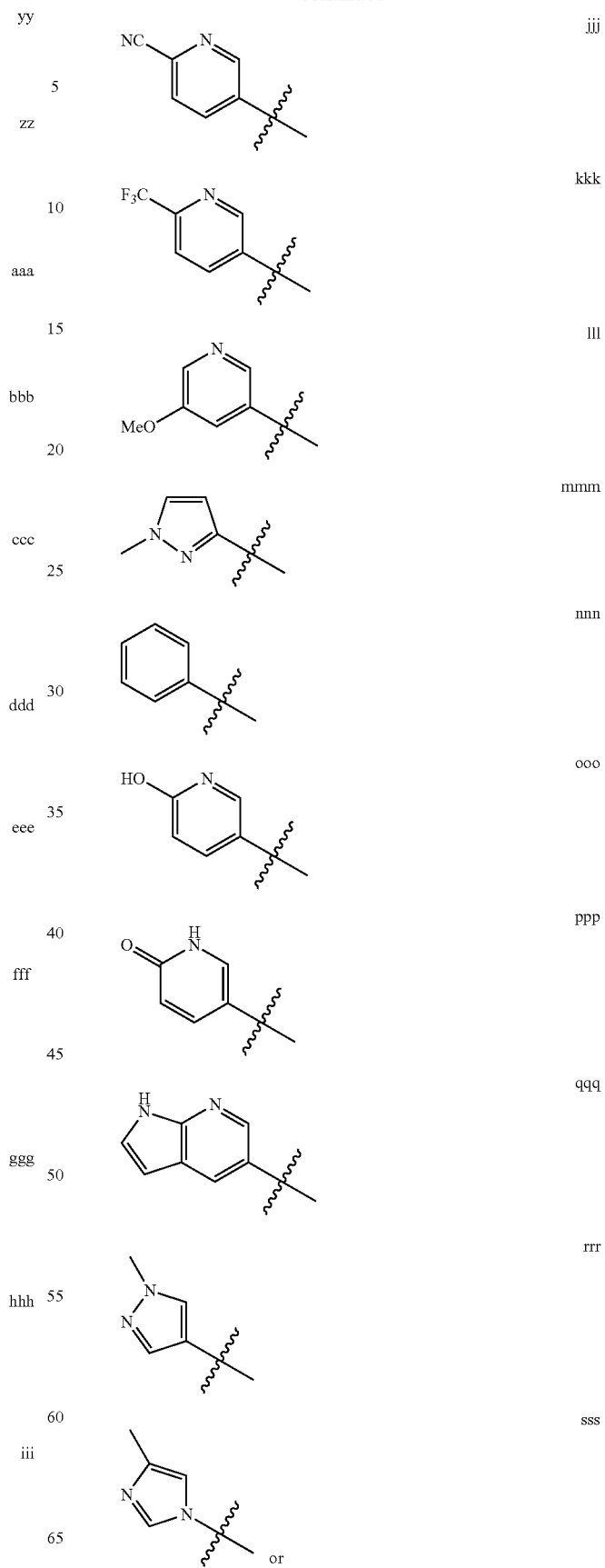

-continued

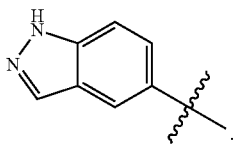
ttt

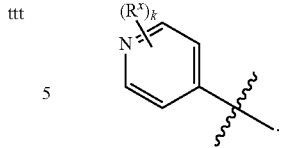

18. A pharmaceutical composition comprising a compound according to claim 1 and a pharmaceutically acceptable excipient.

19. The compound according to claim 1, wherein $R^1$ is optionally substituted 6-10-membered aryl or optionally substituted 5-10-membered heteroaryl having 1-4 heteroatoms independently selected from the group consisting of nitrogen, oxygen, and sulfur.

20. The compound according to claim 3, wherein $R^1$ is optionally substituted phenyl.

21. The compound according to claim 20, wherein $R^1$ is 3-trifluoromethylphenyl.

22. The compound according to claim 1, wherein $R^2$ is —NHR, wherein R is optionally substituted 6-10-membered aryl or optionally substituted 5-10-membered heteroaryl having 1-4 heteroatoms independently selected from the group consisting of nitrogen, oxygen, and sulfur.

23. The compound according to claim 1, wherein j is 1 or 2.

24. The compound according to claim 1, wherein one of $R^3$ and $R^4$ is hydrogen.

25. The compound according to claim 1, wherein $R^1$ is selected from the group consisting of:

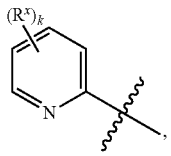, 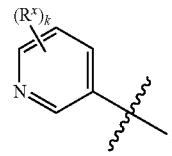, and

26. The compound according to claim 9 or 11, wherein each occurrence of $R^x$ is independently —$NR_2$, —OR, —$SO_2NR_2$, or an optionally substituted group selected from the group consisting of 6-10-membered aryl; $C_{1-6}$ aliphatic; 5-10-membered heteroaryl having 1-4 heteroatoms independently selected from the group consisting of nitrogen, oxygen, and sulfur; and 4-7-membered heterocyclic having 1-2 heteroatoms independently selected from the group consisting of nitrogen, oxygen, and sulfur.

27. The compound according to claim 26, wherein at least one occurrence of $R^x$ is $NR_2$, wherein two R on the same nitrogen atom are taken with the nitrogen to form a 5-6-membered heterocyclic ring having 1-2 heteroatoms independently selected from the group consisting of nitrogen, oxygen, and sulfur.

28. The compound according to claim 26, wherein at least one occurrence of $R^x$ is 4-7- membered heterocyclic having 1-2 heteroatoms independently selected from the group consisting of nitrogen, oxygen, and sulfur.

29. The compound according to claim 26, wherein each occurrence of $R^x$ is independently —$NH_2$, —OR, —$SO_2NR_2$, or an optionally substituted group selected from the group consisting of 6-membered aryl; $C_{1-4}$ aliphatic; and 5-6-membered heterocyclic having 1-2 heteroatoms independently selected from the group consisting of nitrogen, oxygen, and sulfur.

30. The compound according to claim 11, wherein k is 1 or 2.

31. The compound according to claim 26, wherein k is 2.

* * * * *